US008753604B2

(12) United States Patent
Ruoslahti et al.

(10) Patent No.: US 8,753,604 B2
(45) Date of Patent: Jun. 17, 2014

(54) METHODS AND COMPOSITIONS FOR SYNAPHICALLY-TARGETED TREATMENT FOR CANCER

(75) Inventors: Erkki Ruoslahti, Buellton, CA (US); Venkata Ramana Kotamraju, Goleta, CA (US); Priya Karmali, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 699 days.

(21) Appl. No.: 12/646,168

(22) Filed: Dec. 23, 2009

(65) Prior Publication Data

US 2010/0172835 A1     Jul. 8, 2010

Related U.S. Application Data

(60) Provisional application No. 61/140,127, filed on Dec. 23, 2008.

(51) Int. Cl.
*A61K 45/06* (2006.01)

(52) U.S. Cl.
USPC ......... 424/1.69; 977/773; 424/93.6; 424/649; 514/9; 514/12

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,585,277 A | 12/1996 | Bowie | |
| 5,767,071 A | 6/1998 | Palladino | |
| 5,780,426 A | 7/1998 | Palladino | |
| 5,789,542 A | 8/1998 | McLaughlin | |
| 5,891,646 A | 4/1999 | Barak | |
| 6,110,693 A | 8/2000 | Barak | |
| 6,365,619 B1 | 4/2002 | Shi | |
| 2004/0009122 A1 | 1/2004 | Klaveness | |
| 2004/0087499 A1 | 5/2004 | Laakkonen | |
| 2008/0267882 A1 | 10/2008 | Chen | |
| 2011/0053878 A1* | 3/2011 | Yang et al. | 514/34 |

OTHER PUBLICATIONS

Maltzahn et al ("In Vivo Tumor Cell Targeting with "Click" Nanoparticles," Bioconjugate Chem. 2008, 19, 1570-1578).*
Simberg et al ("Biomimetic amplification of nanoparticle homing to tumors," PNAS 104(3): 932-936 Jan. 16, 2007).*
Laakkonen et al ("Antitumor activity of a homing peptide that targets tumor lymphatics and tumor cells," PNAS 101(25): 9381-9386).*
Desai et al ("Increased antitumor activity, intratumor paclitaxel concentrations, and endothelial cell transport of cremophor-free, albumin-bound paclitaxel, ABI-007, compared with cremophor-based paclitaxel," Clin Cancer Res 2006;12:1317-1324. Published online Feb. 17, 2006.*

Laakkonen et al ("Antitumor activity of a homing peptide that targets tumor lymphatics and tumor cells," PNAS 101(25): 9381-9386) 2002.*
Arap, et al., "Chemotherapy targeted to tumor vasculature", Curr Opin Oncol., 10:560-5 (1998b).
Arap, et al. "The human vascular mapping project. Selection and utilization of molecules for tumor endothelial targeting", Haemostasis, 31 (Suppl1):30-1 (2001).
Boerner, et al., "Production of antigen-specific human monoclonal antibodies from in vitro-primed human splenocytes" , J. Immunol., 147(1):86-95 (1991).
Bruggermann, et al., "Designer mice: the production of human antibody repertoires in transgenic animals" , Year in Immunol., 7:33-40 (1993).
Chang, et al. "The discovery of small molecule carbamates as potent dual alpha(4)beta(1)/alpha(4)beta(7) integrin antagonists", Bioorg Med Chem Lett.,12:159-63 (2002).
Effert, et al., "Metabolic imaging of untreated prostate cancer by positron emission tomography with 18fluorine-labeled deoxyglucose" , J Urol., 155:994-8 (1996).
Hofer, et al., "Fluorine-18-fluorodeoxyglucose positron emission tomography is useless for the detection of local recurrence after radical prostatectomy" , Eur Urol, 36:31-5 (1999).
Williams,"Receptor binding in the drug discovery process", Med Res Rev., 11:147-84 (1991).
Akerman, et al., "Nanocrystal targeting in vivo" , PNAS, 99:12617-21 (2002).
Alirol and Martinou, "Mitochondria and cancer: is there a morphological connection" , Oncogene, 25, 4706-16 (2006).
Alitalo, et al., "Lymphangiogenesis and cancer: meeting report" , Cancer Res, 64:9225-9 (2004).
Allam, et al. "Cholera toxin triggers apoptosis in human lung cancer cell lines" Cancer Res., 57:2615-8 (1997).
Alvarez-Bravo et al. "Novel synthetic antimicrobial peptides effective against methicillin-resistant *Staphylococcus aureus*", Biochem J., 302:535-8 (1994).
Arap, et al., "Cancer treatment by targeted drug delivery to tumor vasculature in a mouse model", Science, 279:377-80 (1998).
Arap, et al., "Targeting the prostate for destruction through a vascular address", PNAS, 99: 1527-31 (2002).
Arleth, et al., "Detailed structure of hairy mixed micelles formed by phosphatidylcholine and PEGylated phospholipids in aqueous media", Langmuir, 21:3279-90 (2005).
Bessalle, et al., "All-D-magainin: chirality, antimicrobial activity and proteolytic resistance" FEBS Lett.,274:151-5 (1990).
Blancato, et al., "Correlation of amplification and overexpression of the c-myc oncogene in high-grade breast cancer: FISH, in situ hybridisation and immunohistochemical analyses", Br J Cancer, 90, 1612-9 (2004).
Blondelle and Houghten, "Design of model amphipathic peptides having potent antimicrobial activities" Biochem., 31:12688-94 (1992).
Borgstrom, et al. "Importance of VEGF for breast cancer angiogenesis in vivo: implications from intravital microscopy of combination treatments with an anti-VEGF neutralizing monoclonal antibody and doxorubicin", Anticancer Res., 19:4203-14 (1999).

(Continued)

*Primary Examiner* — Suzanne Ziska

(74) *Attorney, Agent, or Firm* — Pabst Patent Group LLP

(57) ABSTRACT

Disclosed are compositions and methods useful for targeting therapeutics to cancerous cells and tumors. The disclosed targeting is useful for delivering therapeutic and detectable agents to cancerous cells and tumors.

26 Claims, 69 Drawing Sheets

(56) References Cited

OTHER PUBLICATIONS

Braun, et al., "gC1q-R/p32, a C1q-binding protein, is a receptor for the InIB invasion protein of Listeria monocytogenes", Embo J, 19:1458-66 (2000).
Chan, et al. "Prospective randomized trial of docetaxel versus doxorubicin in patients with metastatic breast cancer", J Clin Oncol.,17:2341-54 (1999).
Christian, et al., "Nucleolin expressed at the cell surface is a marker of endothelial cells in angiogenic blood vessels", J Cell Biol., 163:871-8 (2003).
Crown, "The platinum agents: a role in breast cancer treatment", Seminars in Oncol, 28:28-37 (2001).
Davis, et al. "Isolation of angiopoietin-1, a ligand for the TIE2 receptor, by secretion-trap expression cloning", Cell, 87:1161-9 (1996).
Deb and Datta, "Molecular cloning of human fibroblast hyaluronic acid-binding protein confirms its identity with P-32, a protein co-purified with splicing factor SF2. Hyaluronic acid-binding protein as P-32 protein, co-purified with splicing factor SF2", J Biol Chem., 271: 2206-12 (1996).
Desai, et al., "Increased antitumor activity, intratumor paclitaxel concentrations, and endothelial cell transport of cremophor-free, albumin-bound paclitaxel, ABI-007, compared with cremophor-based paclitaxel", Clin Cancer Res, 12:1317-24 (2006).
Dvorak, et al., "Regulation of extravascular coagulation by microvascular permeability", Science, 227: 1059-61 (1985).
Ferrara and Alitalo, "Clinical applications of angiogenic growth factors and their inhibitors", Nat Med, 5:1359-64 (1999).
Fisher, et al. "Tamoxifen for prevention of breast cancer: report of the National Surgical Adjuvant Breast and Bowel Project P-1 Study", J Natl Cancer Instit., 90:1371-88 (1998).
Fitzpatrick and Garnett, "Design, synthesis and in vitro testing of methotrexate carrier conjugates linked via oligopeptide spacers", Anticancer Drug Des., 10:1-9 (1995).
Fogal, et al., "Mitochondrial/ Cell surface protein p32/gC1qR as a molecular target in tumor cells and tumor stroma", Cancer Res., 68(17):7210-8 (2008).
Folkman, "Addressing tumor blood vessels", Nature Biotechnol.,15:510 (1997).
Folkman and Shing "Angiogenesis" J Biol Chem., 267:10931-4 (1992).
Ghebrehiwet, et al., "Isolation, cDNA cloning, and overexpression of a 33-kD cell surface glycoprotein that binds to the globular "heads" of C1q", J Exp Med, 179:1809-21 (1994).
Gradishar, et al., "Phase III trial of nanoparticle albumin-bound paclitaxel compared with polyethylated castor oil-based paclitaxel in women with breast cancer", J Clin Oncol, 23: 7794-7803 (2005).
Guo, et al., "Up-regulation of endothelial cell binding proteins/receptors for complement component C1q by inflammatory cytokines", J Lab Clin Med., 133:541-50 (1999).
Hagedorn and Bikfalvi, "Target molecules for anti-angiogenic therapy: from basic research to clinical trials", Crit Rev Oncol Hematol., 34:89-110 (2000).
Hanahan and Weinberg, The hallmarks of cancer, Cell, 100: 57-70 (2000).
Heldin, et al., "High interstitial fluid pressure—an obstacle in cancer therapy", Nat Rev Cancer, 4:806-13 (2004).
Herwald, et al., "Isolation and characterization of the kininogen-binding protein p33 from endothelial cells. Identity with the gC1q receptor", J Biol Chem(1996).
Hirasawa, et al., "Regulation of subcellular localization of alpha1-adrenoceptor subtypes", Life Sci, 68:2259-67 (2001).
Hoffman, et al., "Progressive vascular changes in a transgenic mouse model of squamous cell carcinoma", Cancer Cell, 4:383-91 (2003).
Homandberg, et al. "Heparin-binding fragments of fibronectin are potent inhibitors of endothelial cell growth: structure-function correlations" Biophys Acta., 874:61-71 (1986).
Homandberg, et al. "Heparin-binding fragments of fibronectin are potent inhibitors of endothelial cell growth", Am J Path., 120:327-32 (1985).

Hoogenboom, et al., "By-passing immunisation: Human antibodies from synthetic repertoires of germline VH gene segments rearranged in vitro", J. Mol. Biol., 227:381-8 (1992).
Inoki, et al., "TSC2 mediates cellular energy response to control cell growth and survival", Cell, 115:577-90 (2003).
Isidoro, et al., "Breast carcinomas fulfill the Warburg hypothesis and provide metabolic markers of cancer prognosis", Carcinogenesis, 26:2095-2104 (2005).
Jain, "The next frontier of molecular medicine: delivery of therapeutics", Nat Med 4:655-7(1998).
Jain, "Vascular and interstitial barriers to delivery of therapeutic agents in tumors", Cancer Metastasis Rev, 9:253-66 (1990).
Jakobovits, et al., "Analysis of homozygous mutant chimeric mice: deletion of the immunoglobulin heavy-chain joining region blocks B-cell development and antibody production", PNAS, 90:2551 5 (1993a).
Jakobovits, et al., "Germ-line transmission and expression of a human-derived yeast artificial chromosome", Nature, 362:255 8 (1993b).
Javadpour, et al., "De novo antimicrobial peptides with low mammalian cell toxicity", J. Med. Chem., 39:3107-13 (1996).
Jin,et al., "Metabolic catastrophe as a means to cancer cell death", J Cell Sci., 120:379-83 (2007).
Jones, et al., "AMP-activated protein kinase induces a p53-dependent metabolic checkpoint", Mol Cell., 18:283-93 (2005).
Joseph, et al., "Identification of the zinc-dependent endothelial cell binding protein for high molecular weight kininogen and factor XII: Identity with the receptor that binds to the globular "heads" of C1q (gC1q-R)", PNAS, 93:8552-7 (1996).
Joyce, et al., "Stage-specific vascular markers revealed by phage display in a mouse model of pancreatic islet tumorigenesis", Cancer Cell, 4: 393-403 (2003).
Karmali, et al., "Targeting of Albumin-embedded paclitaxel nanoparticles to tumors", Nanaomedicine, 5(1):73-82 (2009).
Kerjaschki, et al., "Lymphatic endothelial progenitor cells contribute to de novo lymphangiogenesis in human renal transplants", Nat Med., 12:230-4 (2006).
Kirsch, et al. "Anti-angiogenic treatment strategies for malignant brain tumors" J Neurooncol., 50:149-63 (2000).
Kittlesen, et al., "Interaction between complement receptor gC1qR and hepatitis C virus core protein inhibits T-lymphocyte proliferation", J Clin Invest., 106:1239-49 (2000).
Kohler and Milstein, Continuous cultures of fused cells secreting antibody of predefined specificity\, Nature, 256:495 (1975).
Kreitman and Pastan "Recombinant toxins containing human granulocyte-macrophage colony-stimulating factor and either pseudomonas exotoxin or diphtheria toxin kill gastrointestinal cancer and leukemia cells", Blood, 90:252-9 (1997).
Laakkonen, et al., A tumor-homing peptide with a targeting specificity related to lymphatic vessels, Nat Med, 8:751-5 (2002).
Laakkonen, et al., "Antitumor activity of a homing peptide that targets tumor lymphatics and tumor cells", PNAS, 101: 9381-6 (2004).
Le, et al. "Hypoxic gene expression and metastasis" Cancer Metastasis Rev. 23:293-310 (2004).
Levine, "Cell biology: autophagy and cancer", Nature, 446:745-7 (2007).
Liao and Dickson, "c-Myc in breast cancer", Endocr Relat Cancer, 7:143-64 (2000).
Lim, et al., "The binding protein for globular heads of complement C1q, gC1qR. Functional expression and characterization as a novel vitronectin binding factor", J Biol Chem., 271: 26739-44 (1996).
Lin, et al., "Specific and dual antagonists of alpha(4)beta(1) and alpha(4)beta(7) integrins" Bioorg Med Chem Lett., 12:133-6 (2002).
Liu, "Fatty acid oxidation is a dominant bioenergetic pathway in prostate cancer", Prostate Cancer Prostatic Dis 9:230-4 (2006).
Maloy and Kari, "Structure-activity studies on magainins and other host defense peptides" Biopolymers, 37:105-22 (1995).
Mancheno, et al. "A peptide of nine amino acid residues from alpha-sarcin cytotoxin is a membrane-perturbing structure", J Peptide Res, 51:142-8 (1998).
Marks, et al., "By-passing immunization. Human antibodies from V-gene libraries displayed on phage", J. Mol. Biol., 222(3):581-97 (1991).

(56) References Cited

OTHER PUBLICATIONS

Martin, et al., "Cancer gene therapy by thyroid hormone-mediated expression of toxin genes", Cancer Res., 60:3218-24 (2000).
Maruyama, et al., "Inflammation-induced lymphangiogenesis in the cornea arises from CD11b-positive macrophages", J Clin Invest., 115:2363-72 (2005).
Maruyama, et al., "Decreased macrophage Number and activation lead to reduced lymphatic vessel formation and contribute to Impaired diabetic wound healing", Am J Pathol., 170 :1178-91 (2007).
Matthews and Russell, "Adenovirus core protein V interacts with p32—a protein which is associated with both the mitochondria and the nucleus",. J Gen Virol., 79(Pt7): 1677-85 (1998).
Morrison, et al., "Chimeric human antibody molecules: mouse antigen-binding domains with human constant region domains", PNAS, 81:6851 5 (1984).
Muta, et al., "p32 protein, a splicing factor 2-associated protein, is localized in mitochondrial matrix and is functionally important in maintaining oxidative phosphorylation", J Biol Chem., 272:24363-70 (1997).
O'Reilly, et al. "Angiostatin: a novel angiogenesis inhibitor that mediates the suppression of metastases by a Lewis lung carcinoma", Cell, 79:315-28 (1994).
O'Reilly, et al. "Antiangiogenic activity of the cleaved conformation of the serpin antithrombin", Science, 285:1926-8 (1999).
O'Reilly, et al. "Endostatin: an endogenous inhibitor of angiogenesis and tumor growth", Cell 88:277-85 (1997).
Oh, et al., "Subtractive proteomic mapping of the endothelial surface in lung and solid tumours for tissue-specific therapy", Nature, 429, 629-35 (2004).
Osborne and Coronado-Heinsohn, "Targeting the epidermal growth factor receptor in breast cancer cell lines with a recombinant ligand fusion toxin (DAB389EGF)", Cancer J Scie Am., 2:175-80 (1996).
Paridaens, et al. "Paclitaxel versus doxorubicin as first-line single-agent chemotherapy for metastatic breast cancer: a European Organization for Research and Treatment of Cancer Randomized Study with cross-over", J Clin Oncol., 18:724-33 (2000).
Park, et al., "Magnetic iron oxide nanoworms for tumor targeting and imaging", Adv. Mater., 20:1630-5 (2008).
Peerschke, et al., "Identification of a novel 33-kDa C1q-binding site on human blood platelets", J Immunol.,152:5896-5901 (1994).
Pilch, et al., "Peptides selected for binding to clotted plasma accumulate in tumor stroma and wounds", PNAS, 103:2800-4 (2006).
Porkka, et al., "A fragment of the HMGN2 protein homes to the nuclei of tumor cells and tumor endothelial cells in vivo", PNAS, 99:7444-9 (2006).
Robles-Flores, et al., "p32 (gC1qBP) is a general protein kinase C (PKC)-binding protein; interaction and cellular localization of P32-PKC complexes in ray hepatocytes", J Biol Chem., 277:5247-55 (2002).
Rozanov, et al., "The cytoplasmic tail peptide sequence of membrane type-1 matrix metalloproteinase (MT1-MMP) directly binds to gC1qR, a compartment-specific chaperone-like regulatory protein", FEBS Lett., 527:51-7 (2002).
Rubinsztein, et al., "Potential therapeutic applications of autophagy",. Nat Rev Drug Discov 6:304-12 (2007).
Ruoslahti, et al., "Vascular homing peptides with cell-penetrating properties", Curr Pharm Des,11:3655-60 (2005).
Ruoslahti, "Specialization of tumour vasculature", Nat Rev Cancer, 2:83-90 (2002).
Saberwal, et al., "Cell-lytic and antibacterial peptides that act by perturbing the barrier function of membranes: facets of their conformational features, structure-function correlations and membrane-perturbing abilities", Biochim. Biophys. Acta., 1197:109-31 (1994).
Schaerer, et al., "Interaction between GABA(A) receptor beta subunits and the multifunctional protein gC1q-R", J Biol Chem., 276:26597-604 (2001).
Schraa, et al. "Endothelial cells internalize and degrade RGD-modified proteins developed for tumor vasculature targeting", J Control Release, 83(2):241-51 (2002).
Shim, et al., "c-Myc transactivation of LDH-A: implications for tumor metabolism and growth", PNAS, 94:6658-63 (1997).
Simberg, et al., "Biomimetic amplification of nanoparticle homing to tumors", PNAS, 104: 932-6 (2007).
Slavin, et al., "Fibroblast growth factors: at the heart of angiogenesis", Cell Biol. Int., 19:431-4 (1995).
St Croix, et al., "Genes expressed in human tumor endothelium", Science, 289:1197-1202 (2002).
Stacker, et al., "Lymphangiogenesis and cancer metastasis", Nat Rev Cancer, 2:573-83 (2002).
Storz, et al., "Protein kinase C [micro] is regulated by the multifunctional chaperon protein p32", J Biol Chem., 275:24601-7 (2000).
Subarsky and Hill, "The hypoxic tumour microenvironment and metastatic progression", Clin Exp Metastasis, 20:237-50 (2003).
Sullivan and Graham, "Hypoxia-driven selection of the metastatic phenotype", Cancer Metastasis Rev,26:319-31 (2007).
Suri, et al. "Requisite role of angiopoietin-1, a ligand for the TIE2 receptor, during embryonic angiogenesis", Cell, 87:1171-80 (1996).
Sweetnam, et al. "The role of receptor binding in drug discovery", J Nat Prod.,56:441-55 (1993).
Tange, et al., "In vitro interaction between human immunodeficiency virus type 1 Rev protein and splicing factor ASF/SF2-associated protein, p32", J Biol Chem., 271:10066-72 (1996).
Tu and Tirrell, "Bottom-up design of biomimetic assemblies", Adv Drug Deliv Rev, 56:1537-63 (2004).
Vives, "Present and future of cell-penetrating peptide mediated delivery systems: is the Trojan horse too wild to go only to Troy?" J Control Release, 109:77-85 (2005).
von Maltzahn., et al, "In vivo Tumor Cell Targeting with "Click" Nanoparticles", Bioconjugate Chem., 19:1570-8 (2008).
Waggoner, et al. "gC1q receptor ligation selectively down-regulates human IL-12 production through activation of the phosphoinositide 3-kinase pathway", J Immunol.,175(7):4706-14 (2005).
White, et al. "Antibody-targeted immunotherapy for treatment of malignancy", Annu Rev Med., 52:125-41 (2001).
Wieboldt, et al., "Immunoaffinity Ultrafiltration with Ion Spray HPLC/MS for Screening Small-Molecule Libraries", Anal Chem., 69:1683-91 (1997).
Zhang, et al., "Lymphatic zip codes in premalignant lesions and tumors", Cancer Res., 66, 5696-706 (2006).
Zorko and Langel, "Cell-penetrating peptides: mechanism and kinetics of cargo delivery", Adv Drug Deliv Rev, 57: 529-45 (2005).

* cited by examiner

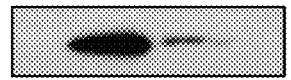
FIG. 4C continued

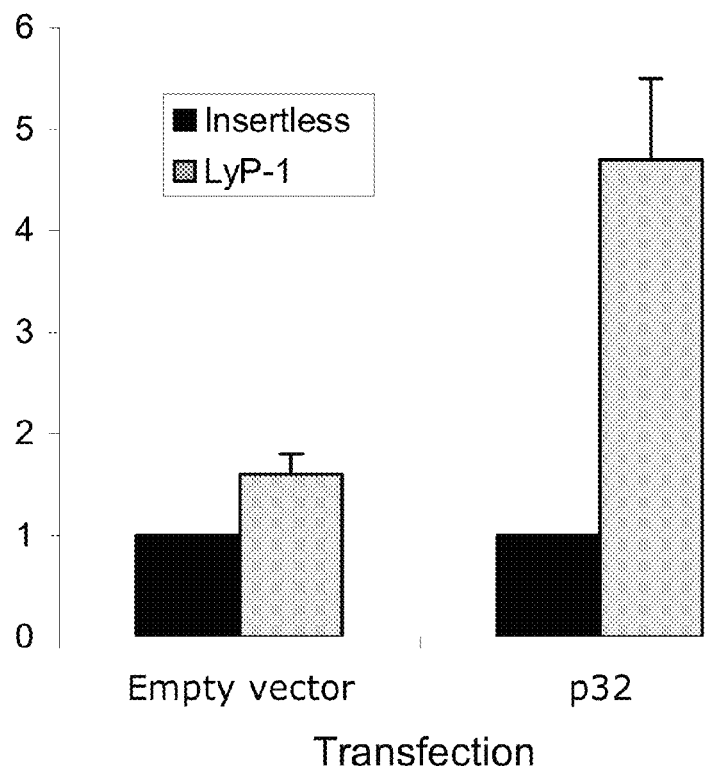
FIG. 5A

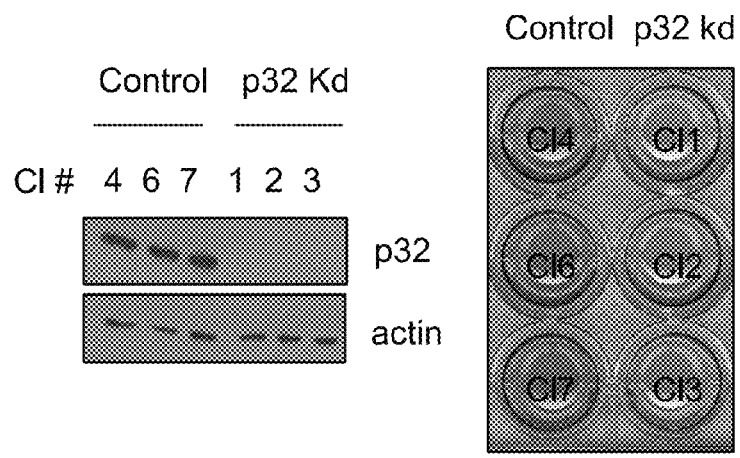
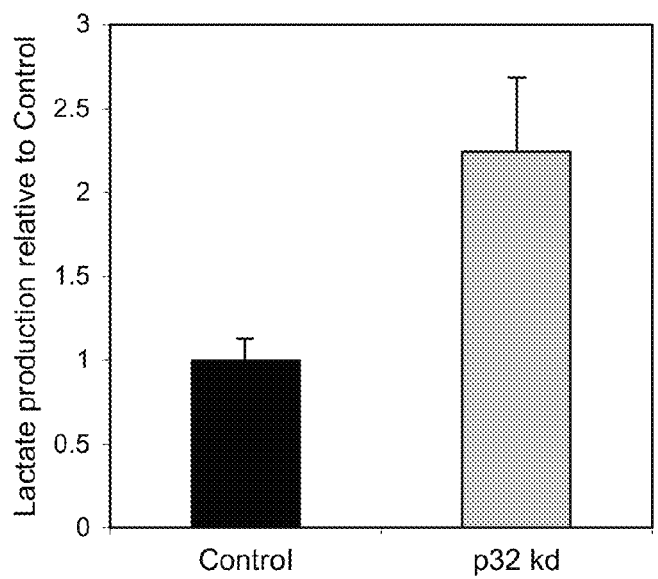
FIG. 7A

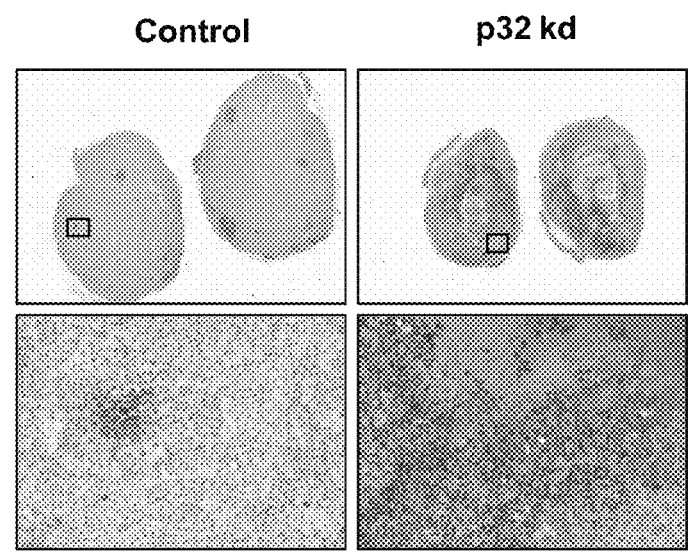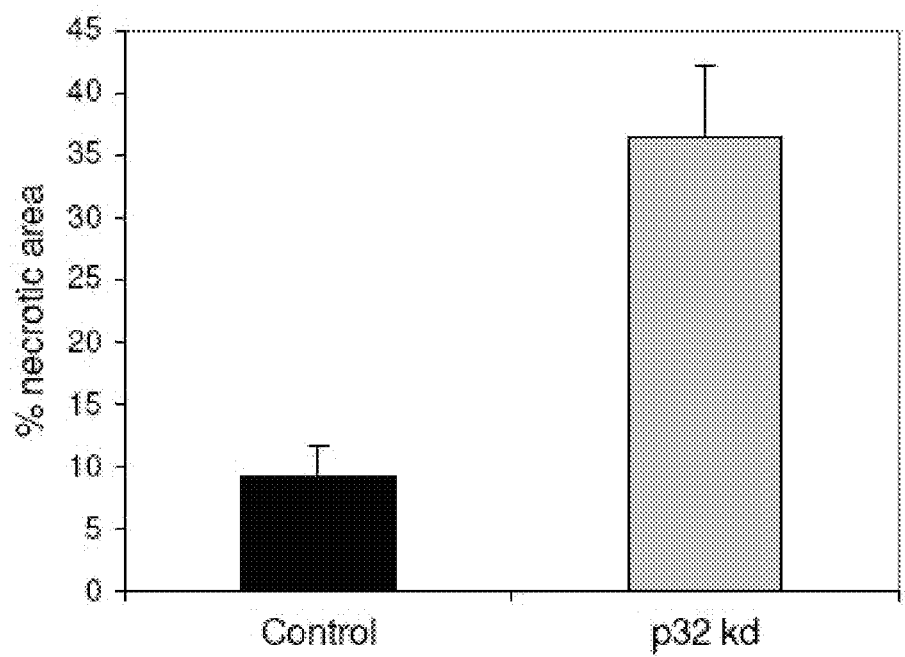
FIG. 9C

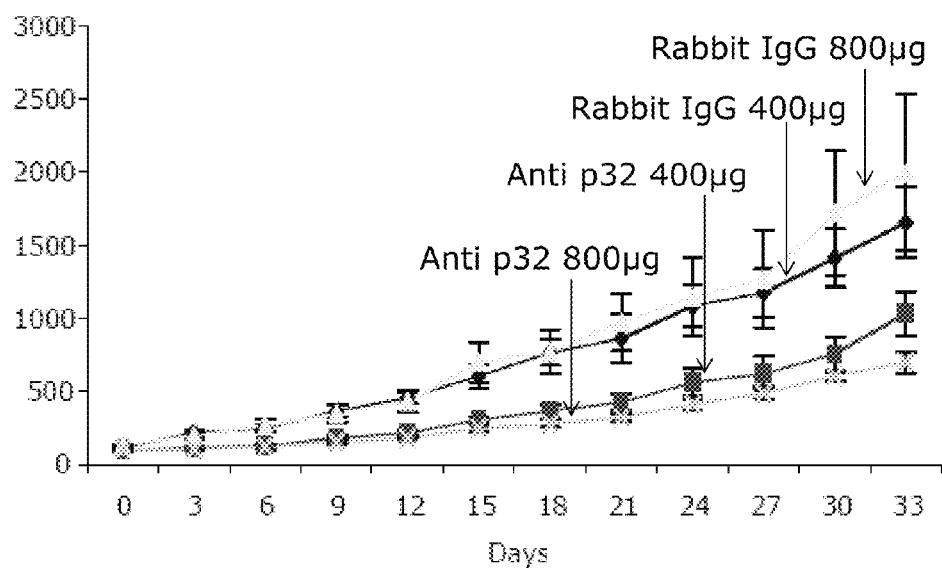
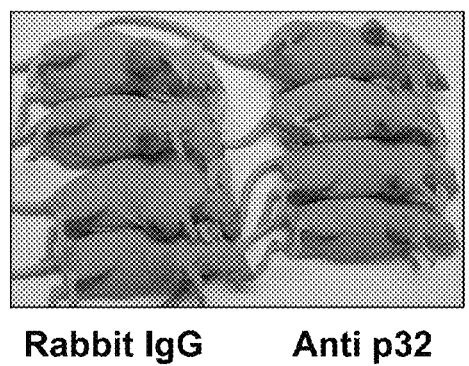
FIG. 10B

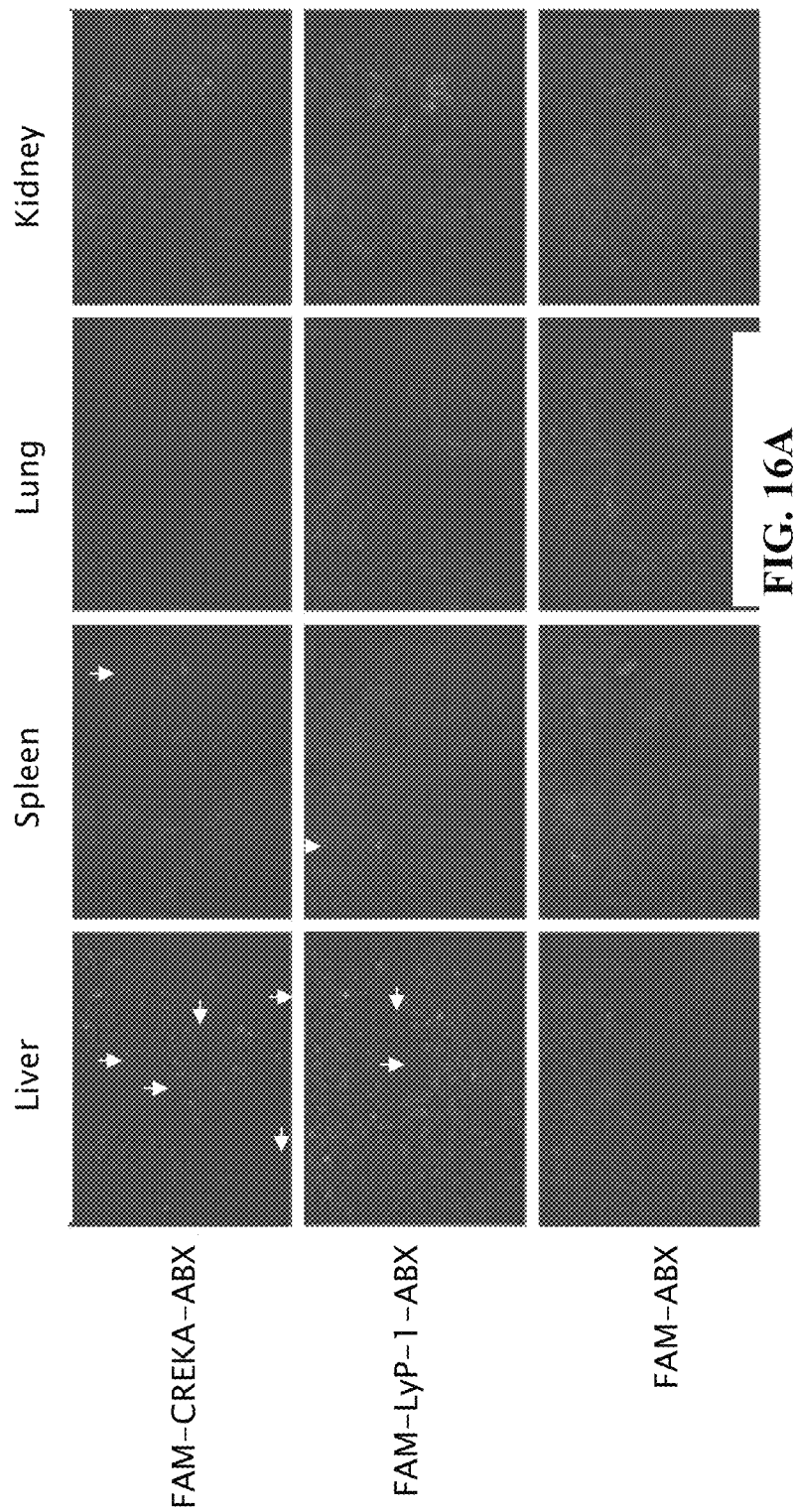

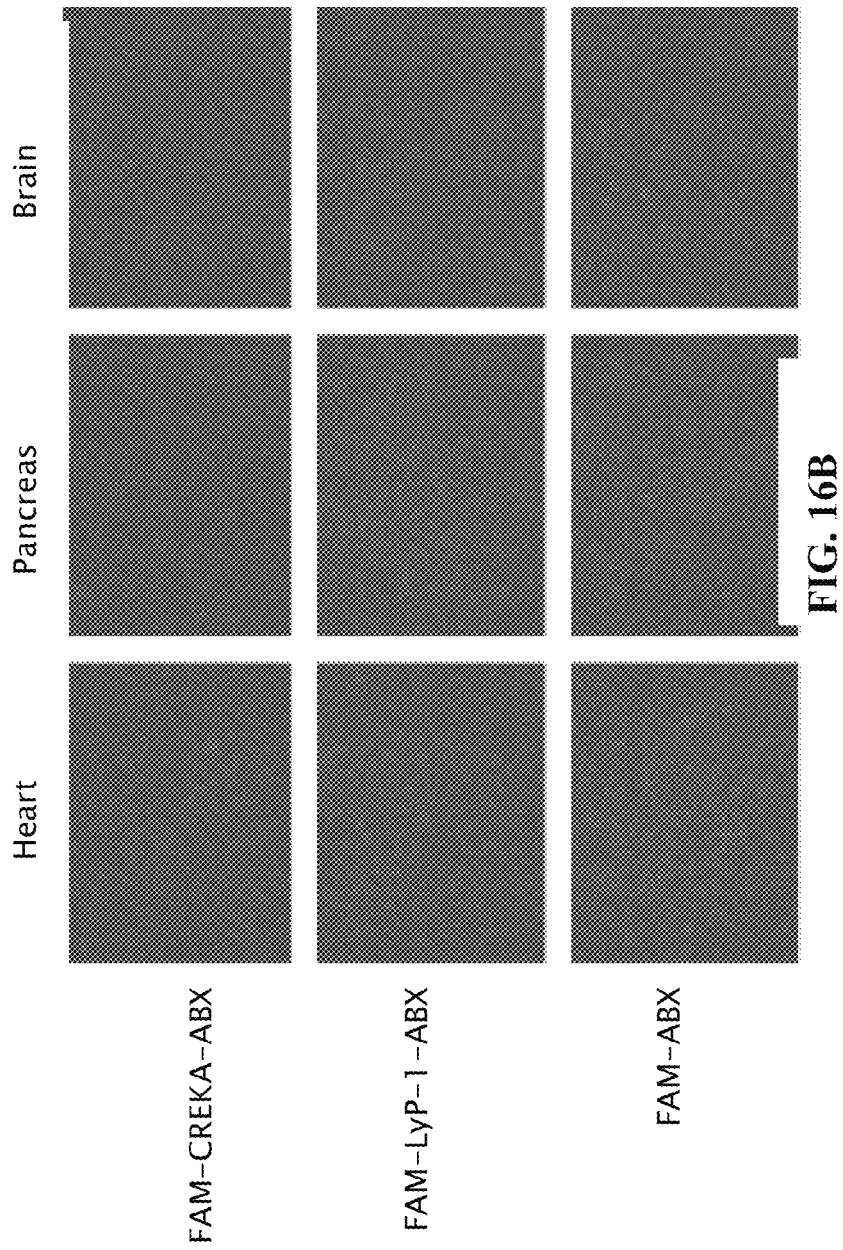

SEQUENCE LISTING

<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: PEPTIDE
<222> LOCATION: (1)..(9)

<400> SEQUENCE: 1

Cys Gly Asn Lys Arg Thr Arg Gly Cys
1               5

<210> SEQ ID NO 2
<211> LENGTH: 7
<212> TYPE: PRT
<213> ORGANISM: Artificial Sequence
<220> FEATURE:
<223> OTHER INFORMATION: homing peptide
<220> FEATURE:
<221> NAME/KEY: PEPTIDE
<222> LOCATION: (1)..(7)

<400> SEQUENCE: 2

Gly Asn Lys Arg Thr Arg Gly
1               5

<210> SEQ ID NO 3
<211> LENGTH: 5
<212> TYPE: PRT
<213> ORGANISM: Artificial Sequence
<220> FEATURE:
<223> OTHER INFORMATION: homing peptide
<220> FEATURE:
<221> NAME/KEY: PEPTIDE
<222> LOCATION: (1)..(5)

<400> SEQUENCE: 3

Cys Arg Glu Lys Ala
1               5

<210> SEQ ID NO 4
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 4

Cys Arg Val Arg Thr Arg Ser Gly Cys
1               5

<210> SEQ ID NO 5
<211> LENGTH: 10
<212> TYPE: PRT
<213> ORGANISM: Artificial Sequence
<220> FEATURE:
<223> OTHER INFORMATION: control peptide for Lyp-1 p32 binding
<220> FEATURE:
<221> NAME/KEY: peptide
<222> LOCATION: (1)..(10)

<400> SEQUENCE: 5

```
Ala Arg Ala Leu Pro Ser Gln Arg Ser Arg
1               5                   10
```

```
<210> SEQ ID NO 6
<211> LENGTH: 8
<212> TYPE: PRT
<213> ORGANISM: Artificial Sequence
<220> FEATURE:
<223> OTHER INFORMATION: antimicrobial peptide
<220> FEATURE:
<221> NAME/KEY: peptide
<222> LOCATION: (1)..(8)

<400> SEQUENCE: 6

Asp Lys Leu Ala Lys Leu Ala Lys
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 7

Cys Asn Arg Arg Thr Lys Ala Gly Cys
1               5
```

```
<210> SEQ ID NO 8
<211> LENGTH: 18
<212> TYPE: PRT
<213> ORGANISM: Artificial Sequence
<220> FEATURE:
<223> OTHER INFORMATION: antigen; amino acids 76-93 of mouse gC1qR/p32
      protein
<220> FEATURE:
<221> NAME/KEY: peptide
<222> LOCATION: (1)..(18)

<400> SEQUENCE: 8

Thr Glu Gly Asp Lys Ala Phe Val Glu Phe Leu Thr Asp Glu Ile Lys
1               5                   10                  15

Glu Glu
```

```
<210> SEQ ID NO 9
<211> LENGTH: 18
<212> TYPE: PRT
<213> ORGANISM: Artificial Sequence
<220> FEATURE:
<223> OTHER INFORMATION: antigen; amino acids 76-93 of human gC1qR/p32
      protein
<220> FEATURE:
<221> NAME/KEY: peptide
<222> LOCATION: (1)..(18)

<400> SEQUENCE: 9

Thr Asp Gly Asp Lys Ala Phe Val Asp Phe Leu Ser Asp Glu Ile Lys
1               5                   10                  15

Glu Glu
```

```
<210> SEQ ID NO 10
<211> LENGTH: 21
<212> TYPE: DNA
<213> ORGANISM: Artificial Sequence
<220> FEATURE:
```

```
<223> OTHER INFORMATION: shRNA
<220> FEATURE:
<221> NAME/KEY: Unsure
<222> LOCATION: (1)..(21)

<400> SEQUENCE: 10
ggatgaggtt ggacaagaag a                                              21

<210> SEQ ID NO 11
<211> LENGTH: 25
<212> TYPE: DNA
<213> ORGANISM: Artificial Sequence
<220> FEATURE:
<223> OTHER INFORMATION: shRNA
<220> FEATURE:
<221> NAME/KEY: unsure
<222> LOCATION: (1)..(25)

<400> SEQUENCE: 11
cccaatatcg tggttgatgt tataa                                          25

<210> SEQ ID NO 12
<211> LENGTH: 21
<212> TYPE: DNA
<213> ORGANISM: Artificial Sequence
<220> FEATURE:
<223> OTHER INFORMATION: shRNA
<220> FEATURE:
<221> NAME/KEY: unsure
<222> LOCATION: (1)..(21)

<400> SEQUENCE: 12
ggatgaggtt ggacaggagg a                                              21

<210> SEQ ID NO 13
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 13

Cys Gly Gln Lys Arg Thr Arg Gly Cys
1               5

<210> SEQ ID NO 14
<211> LENGTH: 9
<212> TYPE: PRT
<213> ORGANISM: Artificial Sequence
<220> FEATURE:
<223> OTHER INFORMATION: control peptide to compare to homing peptides
<220> FEATURE:
<221> NAME/KEY: peptide
<222> LOCATION: (1)..(9)

<400> SEQUENCE: 14

Cys Gly Gly Gly Gly Gly Gly Gly Cys
1               5

<210> SEQ ID NO 15
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
```

```
<222> LOCATION: (1)..(9)

<400> SEQUENCE: 15

Cys Arg Gly Asp Lys Gly Pro Asp Cys
1               5

<210> SEQ ID NO 16
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 16

Cys Arg Gly Asp Arg Gly Pro Asp Cys
1               5

<210> SEQ ID NO 17
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 17

Cys Arg Gly Asp Lys Gly Pro Glu Cys
1               5

<210> SEQ ID NO 18
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 18

Cys Arg Gly Asp Arg Gly Pro Glu Cys
1               5

<210> SEQ ID NO 19
<211> LENGTH: 4
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(4)
<220> FEATURE:
<221> NAME/KEY: peptide
<222> LOCATION: (1)..(4)
<223> OTHER INFORMATION: X can be any amino acid
<220> FEATURE:
<221> NAME/KEY: peptide
<222> LOCATION: (1)..(4)
<223> OTHER INFORMATION: X can be any amino acid

<400> SEQUENCE: 19

Arg Xaa Xaa Lys
1
```

```
<210> SEQ ID NO 20
<211> LENGTH: 4
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(4)
<220> FEATURE:
<221> NAME/KEY: peptide
<222> LOCATION: (1)..(4)
<223> OTHER INFORMATION: X can be any amino acid
<220> FEATURE:
<221> NAME/KEY: peptide
<222> LOCATION: (1)..(4)
<223> OTHER INFORMATION: X can be any amino acid

<400> SEQUENCE: 20

Arg Xaa Xaa Arg
1

<210> SEQ ID NO 21
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 21

Cys Arg Gly Asp Lys Thr Thr Asn Cys
1               5

<210> SEQ ID NO 22
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 22

Cys Arg Gly Asp His Ala Gly Asp Cys
1               5

<210> SEQ ID NO 23
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 23

Cys Arg Gly Asp His Gly Val Glu Cys
1               5

<210> SEQ ID NO 24
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
```

```
<222> LOCATION: (1)..(9)

<400> SEQUENCE: 24

Cys Gly Arg Gly Asp Asn Leu Pro Cys
1               5

<210> SEQ ID NO 25
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 25

Cys Gly Arg Gly Asp Asn Leu Ala Cys
1               5

<210> SEQ ID NO 26
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 26

Cys Glu Lys Arg Gly Asp Asn Leu Cys
1               5

<210> SEQ ID NO 27
<211> LENGTH: 9
<212> TYPE: PRT
<213> ORGANISM: Artificial Sequence
<220> FEATURE:
<223> OTHER INFORMATION: homing peptide

<400> SEQUENCE: 27

Cys Glu Lys Arg Gly Asp Ser Val Cys
1               5

<210> SEQ ID NO 28
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 28

Cys Ser Gly Arg Gly Asp Ser Leu Cys
1               5

<210> SEQ ID NO 29
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 29
```

```
Cys Gly Lys Arg Gly Asp Ser Ile Cys
1               5
```

<210> SEQ ID NO 30
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 30

```
Cys Thr Gly Arg Gly Asp Ala Leu Cys
1               5
```

<210> SEQ ID NO 31
<211> LENGTH: 7
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(7)

<400> SEQUENCE: 31

```
Cys Arg Gly Asp Ser Ala Cys
1               5
```

<210> SEQ ID NO 32
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 32

```
Cys Arg Gly Asp Lys Gly Glu Asn Cys
1               5
```

<210> SEQ ID NO 33
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 33

```
Cys Gly Arg Gly Asp Ser Pro Asp Cys
1               5
```

<210> SEQ ID NO 34
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 34

```
Cys Arg Gly Asp Lys His Ala Asp Cys
1               5

<210> SEQ ID NO 35
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 35

Cys Arg Gly Asp His Ala Ala Asn Cys
1               5

<210> SEQ ID NO 36
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 36

Cys Arg Gly Asp Ala Gly Ile Asn Cys
1               5

<210> SEQ ID NO 37
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 37

Cys Gly Arg Gly Asp Met Pro Ser Cys
1               5

<210> SEQ ID NO 38
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 38

Cys Glu Lys Arg Gly Asp Ser Leu Cys
1               5

<210> SEQ ID NO 39
<211> LENGTH: 9
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(9)

<400> SEQUENCE: 39
```

```
Cys Arg Gly Glu Lys Gly Pro Asp Cys
1               5
```

<210> SEQ ID NO 40
<211> LENGTH: 5
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(5)

<400> SEQUENCE: 40

```
Cys Arg Gly Asp Cys
1               5
```

<210> SEQ ID NO 41
<211> LENGTH: 7
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(7)

<400> SEQUENCE: 41

```
Arg Gly Asp Cys Cys Cys Cys
1               5
```

<210> SEQ ID NO 42
<211> LENGTH: 4
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(4)
<223> OTHER INFORMATION: X at locations 2 and 3 can be any amino acid

<400> SEQUENCE: 42

```
Lys Xaa Xaa Arg
1
```

<210> SEQ ID NO 43
<211> LENGTH: 4
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(4)
<223> OTHER INFORMATION: X at locations 2 and 3 can be any amino acid

<400> SEQUENCE: 43

```
Lys Xaa Xaa Lys
1
```

<210> SEQ ID NO 44
<211> LENGTH: 7
<212> TYPE: PRT
<213> ORGANISM: Artificial Sequence
<220> FEATURE:
<223> OTHER INFORMATION: blocking peptide that inhibits CRGDK binding to
      cells
<220> FEATURE:
<221> NAME/KEY: peptide

```
<222> LOCATION: (1)..(7)

<400> SEQUENCE: 44

Arg Pro Ala Arg Pro Ala Arg
1               5

<210> SEQ ID NO 45
<211> LENGTH: 8
<212> TYPE: PRT
<213> ORGANISM: Artificial Sequence
<220> FEATURE:
<223> OTHER INFORMATION: blocking peptide that inhibits CRGDK binding to
      cells
<220> FEATURE:
<221> NAME/KEY: peptide
<222> LOCATION: (1)..(8)

<400> SEQUENCE: 45

Arg Pro Ala Arg Pro Ala Arg Ala
1               5

<210> SEQ ID NO 46
<211> LENGTH: 5
<212> TYPE: PRT
<213> ORGANISM: Artificial Sequence
<220> FEATURE:
<223> OTHER INFORMATION: homing peptide
<220> FEATURE:
<221> NAME/KEY: peptide
<222> LOCATION: (1)..(5)

<400> SEQUENCE: 46

Cys Arg Gly Asp Lys
1               5

<210> SEQ ID NO 47
<211> LENGTH: 4
<212> TYPE: PRT
<213> ORGANISM: Artificial Sequence
<220> FEATURE:
<223> OTHER INFORMATION: cell internalization sequence
<220> FEATURE:
<221> NAME/KEY: peptide
<222> LOCATION: (1)..(4)

<400> SEQUENCE: 47

Arg Gly Asp Lys
1

<210> SEQ ID NO 48
<211> LENGTH: 9
<212> TYPE: PRT
<213> ORGANISM: Artificial Sequence
<220> FEATURE:
<223> OTHER INFORMATION: homing peptide with no internalization sequence
<220> FEATURE:
<221> NAME/KEY: peptide
<222> LOCATION: (1)..(9)

<400> SEQUENCE: 48

Cys Arg Gly Asp Gly Gly Pro Asp Cys
1               5

<210> SEQ ID NO 49
<211> LENGTH: 9
<212> TYPE: PRT
<213> ORGANISM: Artificial Sequence
<220> FEATURE:
<223> OTHER INFORMATION: homing peptide
<220> FEATURE:
```

-continued

```
<221> NAME/KEY: peptide
<222> LOCATION: (1)..(9)

<400> SEQUENCE: 49

Cys Gly Asn Lys Arg Thr Arg Gly Cys
1               5

<210> SEQ ID NO 50
<211> LENGTH: 5
<212> TYPE: PRT
<213> ORGANISM: Artificial Sequence
<220> FEATURE:
<223> OTHER INFORMATION: integrin binding peptide
<220> FEATURE:
<221> NAME/KEY: peptide
<222> LOCATION: (1)..(5)

<400> SEQUENCE: 50

Cys Arg Asp Gly Cys
1               5

<210> SEQ ID NO 51
<211> LENGTH: 5
<212> TYPE: PRT
<213> ORGANISM: Artificial Sequence
<220> FEATURE:
<223> OTHER INFORMATION: internalization peptide that can transport
      cargo inside a cell
<220> FEATURE:
<221> NAME/KEY: peptide
<222> LOCATION: (1)..(5)

<400> SEQUENCE: 51

Cys Arg Gly Asp Arg
1               5

<210> SEQ ID NO 52
<211> LENGTH: 4
<212> TYPE: PRT
<213> ORGANISM: Artificial Sequence
<220> FEATURE:
<223> OTHER INFORMATION: aids in internalization of peptide but is
      eventually discarded and does not enter cell
<220> FEATURE:
<221> NAME/KEY: peptide
<222> LOCATION: (1)..(4)

<400> SEQUENCE: 52

Gly Pro Asp Cys
1
```

METHODS AND COMPOSITIONS FOR SYNAPHICALLY-TARGETED TREATMENT FOR CANCER

CROSS-REFERENCE TO RELATED APPLICATIONS

This application claims benefit of U.S. Provisional Application No. 61/140,127, filed Dec. 23, 2008. Application No. 61/140,127, filed Dec. 23, 2008, is hereby incorporated herein by reference in its entirety.

STATEMENT REGARDING FEDERALLY SPONSORED RESEARCH

This invention was made with government support under National Cancer Institute grants CA119335, CA124427, CA115410, CA104898; National Heart, Lung and Blood Institute grant HL080718; and MRSEC Program of the National Science Foundation under Award DMR05-20415. The government has certain rights in the invention.

REFERENCE TO SEQUENCE LISTING

The Sequence Listing submitted Mar. 5, 2010 as a text file named "24520_40_8402_2010_03_05_AM-D_AFD_Edited$_{13}$ Sequence_Listing_in$_{13}$ Response$_{13}$ to$_{13}$ Notice. txt," created on Feb. 24, 2010, and having a size of 12,708 bytes is hereby incorporated by reference pursuant to 37 C.F.R. §1.52(e)(5).

FIELD OF THE INVENTION

The present invention relates generally to the fields of molecular medicine and cancer biology and, more specifically, to targeting of therapeutic molecules to cancer cells and tumors.

BACKGROUND OF THE INVENTION

C1q is a component of the CI complex of the classical complement pathway (R. B. Sim and K. B. M. Reid, Immunology Today 1991; 12:307-311). The biological functions of C1q are diverse, including initiation of the complement cascade for opsonization and cytolysis, and mediation of several different functions depending on the cell types expressing the C1q receptor. C1q enhances FcR and CR1-mediated phagocytosis in monocytes/macrophages (D. A. Bobak et al., Eur. J. Immunol. 1988; 18:2001-2007; D. A. Bobak et al., J. Immunol. 1987; 138:1150-1156), stimulates immunoglobulin production by B cells (K. R. Young et al., J. Immunol. 1991; 146:3356-3364), activates platelets to express αIIb/β3 integrins, P-selectin, and procoagulant activity (E. I. B. Peerschke et al., J. Exp. Med. 1993; 178:579-587; E. I. B. Peerschke et al., J. Immunol. 1994; 152:5896-5901), activates tumor cytotoxicity of macrophages (R. W. Leu et al., J. Immunol. 1990; 144:2281-2286), exerts anti-proliferative effects on T cell growth (A. Chen et al., J. Immunol. 1994; 153:1430-1440), and serves as a receptor for the *Listeria* monocytogenes invasion protein InIB Braun et al., EMBO J, 2000; 19: 1458-1466).

A 33 kilodalton (kD) receptor, designated gC1qR/p32 (and alternatively referred to as p32, and referred to herein as gC1qR/p32), which binds to the globular head of C1q molecules has been identified, cloned and sequenced (B. Ghebrehiwet al., J. Exp. Med. 1994; 179:1809-1821; E. I. B. Peerschke et al., J. Immunol. 1994; 152:5896-5901; A. Chen et al., J. Immunol. 1994; 153: 1430-1440). The crystal structure of gC1qR/p32 has also been solved (Jiang et al. PNAS, 1999; 96, 3572-3577). Another 60 kD receptor, designated cC1qR, binds to the amino-terminal collagen-like region of C1q (B. Ghebrehiwet, Behring Inst. Mitt. 1989; 84:204-215; A. Chen et al., J. Immunol. 1994; 153:1430-1440). Based on the detection of gC1q-R mRNA by polymerase chain reaction (PCR) amplification and gC1q-R protein expression by immunochemical methods, this receptor was found to exist on a large number of different cell types, e.g. B cells, T cells, monocytes/macrophages, neutrophils, eosinophils, fibroblasts, platelets, endothelial cells, liver cells, neural cells and smooth muscle cells. The gC1q-R protein is over-expressed in tumor cells and tumors (Rubinstein et al., Int J Cancer, 2004; 110: 741-750).

The endothelial lining of blood vessels is highly diversified. Many, and perhaps all, normal tissues impart a tissue-specific "signature" on their vasculature, and tumor vessels differ from normal vessels both in morphology and molecular composition (Ruoslahti E. Specialization of tumor vasculature. Nat Rev Cancer 2002; 2:83-90). Tumors induce angiogenesis to support expansive growth (Hanahan D, Weinberg R A. The hallmarks of cancer. Cell 2000; 100:57-70) and many of the changes in tumor vessels are angiogenesis related (Brooks P G et al. J Reprod Med 1994; 39:755-60; Christian et al. J Cell Biol 2003; 163:871-8; Ferrara et al. Nat Med 1999; 5: 1359-64; Pasqualini et al Cancer Res 2000; 60: 722-7). Moreover, tumor blood vessels have tumor type-specific and, in some stages, stage-specific characteristics; in vivo screening of phage libraries has yielded distinct sets of homing peptides selectively recognizing angiogenic signatures in two transgenic mouse models of organ-specific tumorigenesis. Homing peptides can also distinguish the angiogenic blood vessels of premalignant lesions from those of fully malignant lesions in the same tumor. Lymphatic vessels in tumors also carry specific markers that distinguish tumor lymphatics from lymphatics in normal tissues (Laakkonen et al., Nat Med 2002; 8: 751-755; Laakkonen et al., Proc Natl Acad Sci USA, 2004; 101: 9381-9386: Zhang et al., Cancer Res, 2006; 66: 5696-9706). Tumor blood vessels and lymphatics provide important targets for tumor therapy. Destroying tumor blood vessels or preventing their growth suppresses tumor growth, whereas tumor lymphatics are not essential for tumor growth, but destroying them reduces metastasis (Saharinen et al. Trends Immunol 2004; 25:387-95).

The elevated expression of gC1qR/p32 in tumors and the findings reported here show there is a need for new therapeutic strategies for selectively targeting gC1q receptors (gC1qR, alternatively referred to in the art and herein as p32, and throughout as gC1qR/p32). The present invention satisfies this need by providing molecules that selectively interact with gC1qR/p32, and which are suitable for selectively targeting chemotherapeutic drugs, gene therapy vectors or other agents to the appropriate tissue. Related advantages also are provided.

BRIEF SUMMARY OF THE INVENTION

Disclosed herein are methods of treating cancer comprising administering to a subject having cancer a composition comprising a tumor- or cancer-homing compound coupled to a paclitaxel-loaded albumin nanoparticle. Also disclosed are the compositions comprising a tumor- or cancer-homing compound coupled to a paclitaxel-loaded albumin nanoparticle. The composition can further comprise one or more different tumor- or cancer-homing compounds coupled to the nanoparticle.

Also disclosed herein are methods of treating cancer comprising administering to a subject having cancer a composition comprising a Lyp-1 peptide coupled to a paclitaxel-loaded albumin nanoparticle. Also disclosed are the compositions comprising a Lyp-1 peptide coupled to a paclitaxel-loaded albumin nanoparticle. The composition can further comprise a CREKA peptide coupled to the nanoparticle.

Also disclosed herein are methods of treating cancer comprising administering to a subject having cancer a composition comprising a CREKA peptide coupled to a paclitaxel-loaded albumin nanoparticle. Also disclosed are the compositions comprising a CREKA peptide coupled to a paclitaxel-loaded albumin nanoparticle.

The paclitaxel-loaded albumin nanoparticle can be abraxane.

The Lyp-1 peptide can comprise, for example, SEQ ID NO:1 or SEQ ID NO:13. The Lyp-1 peptide can consist essentially of SEQ ID NO:1 or SEQ ID NO:13. The Lyp-1 peptide can be SEQ ID NO:1, SEQ ID NO:13, or a variant of SEQ ID NO:1 or SEQ ID NO:13 with one or more conservative amino acid substitutions. The Lyp-1 peptide can be SEQ ID NO:1 or SEQ ID NO:13.

The composition can further comprise a therapeutic moiety. The therapeutic moiety can target a DNA-associated process. The therapeutic moiety can be selected from the group consisting of, for example, a cytotoxic agent, an alkylating agent, an anti-tumor antibiotic, a sequence-selective agent, an anti-angiogenic agent, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

The method can further comprise identifying the subject as having a cancer associated with gC1q/p32 receptor. Identifying the subject as having a cancer associated with gC1q/p32 receptor can be accomplished by, for example, bringing into contact a cancer cell of the subject and a composition that selectively interacts with gC1q/p32 receptor; and detecting interaction between gC1q/p32 receptor and the composition that selectively interacts with gC1q/p32 receptor, thereby detecting the presence or level of gC1q/p32, wherein the presence or level of gC1q/p32 receptor identifies the subject as having a cancer associated with a gC1q/p32 receptor. The composition that selectively interacts with gC1q/p32 receptor can be a Lyp-1 composition, wherein the Lyp-1 composition comprises a moiety linked to a Lyp-1 peptide. The level of the composition that selectively interacts with gC1q/p32 receptor interacting with gC1q/p32 receptor is detected. The level of gC1q/p32 receptor in the subject can be compared to a previous measurement in the same subject. The level of gC1q/p32 receptor in the subject can be compared to a control level or standard level. The moiety can be, for example, a detectable agent, a polypeptide, a nucleic acid molecule, or a small molecule. The composition that selectively interacts with gC1q/p32 receptor can comprise a virus. The composition that selectively interacts with gC1q/p32 receptor can comprise a phage. The detectable agent can be a small molecule, a fluorophore, fluorescein, rhodamine, a radionuclide, indium-111, technetium-99, carbon-11, carbon-13, or a combination thereof.

The method can further comprise administering to the subject one or more second compositions each comprising a different tumor- or cancer-homing compound coupled to a paclitaxel-loaded albumin nanoparticle. The method can further comprise administering to the subject a second composition comprising a CREKA peptide coupled to a paclitaxel-loaded albumin nanoparticle.

Also disclosed are methods of treating a disease associated with gC1q/p32 receptor comprising identifying a subject having a disease associated with the gC1q/p32 receptor; and administering to the subject a composition comprising SEQ ID NO:1.

Also disclosed are methods of treating a disease associated with gC1q/p32 receptor comprising identifying a subject having a disease associated with the gC1q/p32 receptor; and administering to the subject a composition that specifically interacts with gC1q/p32 receptor.

Also disclosed are methods of detecting the presence of gC1q/p32 receptor, comprising bringing into contact a cell and a composition, wherein the composition comprises a moiety linked to a composition that specifically interacts with gC1q/p32 receptor; and detecting interaction between gC1q/p32 receptor and the composition, thereby detecting the presence of gC1q/p32 receptor.

Further disclosed are methods of detecting interaction between a gC1q/p32 receptor and a composition, wherein the composition comprises a moiety linked to a composition that specifically interacts with gC1q/p32 receptor, the method comprising: selecting a cell for its potential to comprise a gC1q/p32 receptor; bringing into contact the composition and the cell; and detecting interaction between the gC1q/p32 receptor and the composition.

Also disclosed are methods of delivering a composition to a gC1q/p32 receptor, wherein the composition comprises a moiety linked to a composition that specifically interacts with gC1q/p32 receptor; wherein the method comprises bringing into contact the composition and a cell, thereby delivering the composition to the gC1q/p32 receptor.

Disclosed are methods of delivering a composition to a gC1q/p32 receptor, wherein the composition comprises a moiety linked to a composition that specifically interacts with gC1q/p32 receptor; comprising: selecting a cell for its potential to comprise a gC1q/p32 receptor; and bringing into contact the composition and the cell, thereby delivering the composition to the gC1q/p32 receptor.

Further disclosed are methods of determining and/or assessing gC1q/p32 receptor level in a cell of a subject, comprising: bringing into contact a cell of the subject and a composition comprising a detectable agent linked to a composition that specifically interacts with gC1q/p32 receptor; and detecting the level of composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a composition, wherein the composition comprises a moiety linked to a composition that specifically interacts with gC1q/p32 receptor; and detecting interaction between gC1q/p32 receptor and the composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of detecting the presence of gC1q/p32 receptor, comprising bringing into contact a cell and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence of gC1q/p32 receptor.

Further disclosed are methods of detecting interaction between a gC1q/p32 receptor and a Lyp-1 composition, wherein the Lyp-1 composition comprises a moiety linked to a composition comprising SEQ ID NO:1, the method comprising: selecting a cell for its potential to comprise a gC1q/p32 receptor; bringing into contact the Lyp-1 composition and the cell; and detecting interaction between the gC1q/p32 receptor and the Lyp-1 composition.

Also disclosed are methods of delivering a Lyp-1 composition to a gC1q/p32 receptor, wherein the Lyp-1 composition comprises a moiety linked to a composition comprising SEQ ID NO:1; wherein the method comprises bringing into contact the Lyp-1 composition and a cell, thereby delivering the Lyp-1 composition to the gC1q/p32 receptor.

Disclosed are methods of delivering a Lyp-1 composition to a gC1q/p32 receptor, wherein the Lyp-1 composition comprises a moiety linked to a composition comprising SEQ ID NO:1; comprising: selecting a cell for its potential to comprise a gC1q/p32 receptor; and bringing into contact the Lyp-1 composition and the cell, thereby delivering the Lyp-1 composition to the gC1q/p32 receptor.

Further disclosed are methods of determining and/or assessing gC1q/p32 receptor level in a cell of a subject, comprising: bringing into contact a cell of the subject and a Lyp-1 composition comprising a detectable agent linked to a composition comprising SEQ ID NO:1; and detecting the level of Lyp-1 composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence or level of gC1q/p32 on the cell, wherein the presence or level of gC1q/p32 receptor on the cell identifies the subject as having a disease associated with a gC1q/p32 receptor.

Further disclosed are methods of screening for a compound that interacts with a gC1q/p32 receptor, comprising: bringing into contact a test compound, a Lyp-1 composition, and a gC1q/p32 receptor, wherein the Lyp-1 composition comprises SEQ ID NO:1; and detecting unbound Lyp-1 composition, wherein a given amount of unbound Lyp-1 composition indicates a compound that interacts with gC1q/p32 receptor.

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as Lyp-1, thereby treating a disease associated with the gC1q/p32 receptor.

The gC1q/p32 receptor can be, for example, on or in a cell. The cell can be in any context, such as in an organism, in situ, ex vivo, in culture, and/or in vitro.

Also disclosed is a method of treating or preventing a disease in a subject associated with gC1q/p32 receptor, the method comprising administering to the subject a composition that modulates gC1q/p32 receptor expression or activity, thereby treating or preventing a disease in a subject associated with the gC1q/p32 receptor. The disease can be cancer. Expression or activity of the gC1q/p32 receptor can be inhibited. This can occur by the use of interfering nucleic acid, such as shRNA or siRNA. Activity of the gC1q/p32 receptor can be inhibited by the LyP-1 peptide, an antibody, or a small molecule mimic of Lyp-1.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 10 shows inhibition of tumor growth by anti p32 treatment. A polyclonal antibody directed against aa 76-93 of both human and mouse p32 was produced and tested for homing to tumors in vivo. FIG. 10B-M*ice* bearing MDA-MB-435 tumor xenografts were i.v. injected every three days with 400 and 800 μg of polyclonal anti p32 or rabbit IgG (n=4 mice per group) for a total of 33 days. In the graph are shown the kinetics of tumor growth in anti p32 and rabbit IgG treated mice. Both doses of antibody significantly inhibited tumor growth (Student's t test, p<0.001) without exhibiting any toxic effect as indicated by the constant body weight of the mice throughout the treatment.

FIGS. 16A and 16B show tissue distribution of abraxane conjugates. Normal tissues were collected from tumor mice injected with abraxane conjugates as in FIGS. 11 and 12, and analyzed for the presence of fluorescence. Nuclei were stained with DAPI. Some liver and spleen uptake was observed with the CREKA and LyP-1 conjugates. The results are representative of three independent experiments. Magnification: 200×.

FIG. 32A shows in vitro tumor cell treatment with various abraxane conjugates. Cultured 22Rv1 cells were treated for 30 min at room temperature with non-targeted abraxane (ABX), or abraxane conjugated with iRGD (iRGD-ABX) or CRGDC(CRGDC-ABX). The cells were incubated for 48 hrs and cell death was quantified by MTT assays (n=3). Statistical analyses were performed with Student's t-test. Error bars, s.e.m.; single asterisk, $p<0.05$; double asterisk, $p<0.01$; triple asterisk, $p<0.001$. FIG. 32B shows in vivo tumor homing of abraxane conjugates. Confocal microscopy images of 22Rv1 orthotopic tumors from mice injected with the indicated abraxane conjugates at a paclitaxel equivalent of 3 mg/kg. The particles were allowed to circulate for 3 hrs. Representative images from three tumors for each conjugate are shown. There is CD31 staining in all images although it is much harder to see in the iRGD-ABX due to the intense ABX staining. Bright staining seen surrounding the black areas, abraxane; light staining that appears to outline the black area (best seen in FAM-ABX), CD31; small gray spheres, DAPI. Scale bars=100 µm.

FIGS. 33A and C show abraxane quantification in orthotopic 22Rv1 (A) and BT474 (C) xenograft models. Abraxane was intravenously injected into tumor mice 3 hr earlier and captured from tumor extracts with a taxol antibody, followed by detection with a human albumin antibody. N=3 for each group. FIGS. 33B and D show long-term treatment of tumor mice with targeted abraxane conjugates. Mice bearing orthotopic 22Rv1 (B) or BT474 (D) xenografts were intravenously injected with peptide-coated abraxanes every other day at 3 mg paclitaxel/kg/injection. The treatment was continued for 14 days in (B) and 20 days in (D). (B) shows one of three experiments, which all gave similar results. The total number of mice (B) was as follows: untargeted abraxane (ABX; n=18), abraxane coated with CRGDC (CRGDC-ABX; n=10) or iRGD (iRGD-ABX; n=19), iRGD peptide alone as a control (iRGD peptide; n=10), or PBS (n=18). The number of mice per group was eight in (D). Statistical analyses were performed with Student's t-test in (A) and (C) and ANOVA in (B) and (D). Error bars, SEM; n.s., not significant; *$p<0.05$; $p<0.01$; *$p<0.001$.

DETAILED DESCRIPTION OF THE INVENTION

Figure 1A:
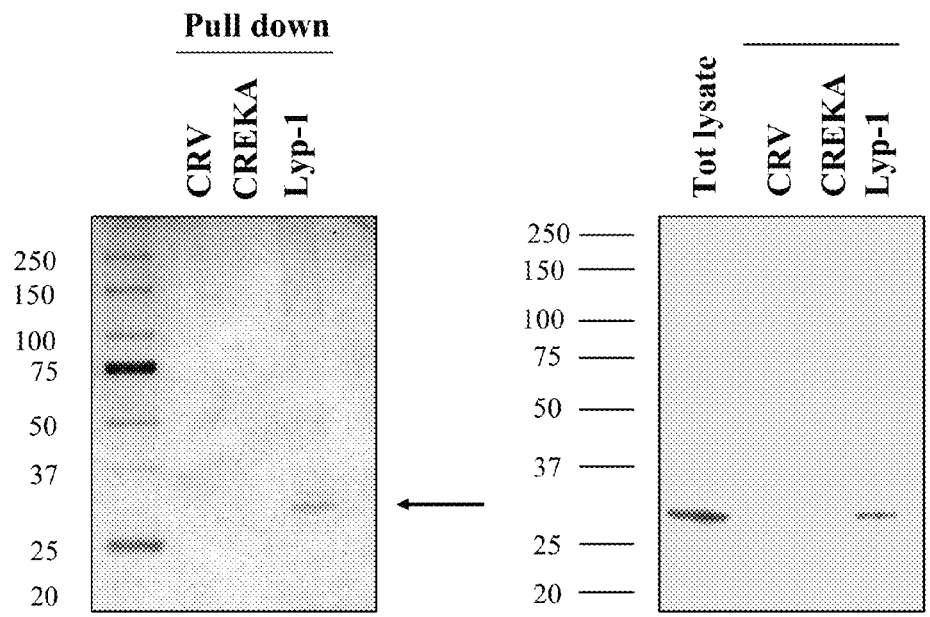
FIG. 1 shows gC1q/p32R binds Lyp-1 peptide in pull down assay. Pull down assays are shown with biotinylated Lyp-1 peptide (SEQ ID NO:1, CGNKRTRGC) from protein extracts derived from MDA-MB-435 cultured cells (a) or MDA-MB-435 tumor xenografts (b). A tumor homing peptide, CREKA (SEQ ID NO:3), and a peptide CRV which resembles Lyp-1 in its amino acid composition and cyclic structure (SEQ ID NO:4, CRVRTRSGC), were used as negative controls. (a) Left panel: silver staining of Lyp-1 bound proteins. The arrow indicates a specific 33 kD band, which was identified as gC1q/p32R by mass spectrometry. Right panel: immunoblot of total cell extract (Tot lysate) and proteins bound to Lyp-1 and control peptides using a monoclonal antibody against gC1q/p32 receptor. The antibody recognizes a band of 33 kD in the total proteins lysate and in the Lyp-1 pull down. Anti gC1q/p32 receptor reactive bands are not detected in the pull downs from both control peptides. Silver staining of proteins pulled down from MDA-MB-435 tumor xenografts by Lyp-1 peptide, revealed an additional 75 kD band (b-left panel), which was also identified as gC1q/p32 receptor by mass spectrometry. The monoclonal antibody against gC1qR/p32 recognized a 75 kD and a 33 kD band only in the Lyp-1 peptide pull down (b-right panel).

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "multiwell plate" refers to a two dimensional array of addressable wells located on a substantially flat surface. Multiwell plates can include any number of discrete addressable wells, and include addressable wells of any width or depth. Common examples of multiwell plates include 96 well plates, 384 well plates and 3456 well Nanoplates™. Such multiwell plates can be constructed of any suitable material. Examples of suitable material include plastic, glass, or any essentially electrically nonconductive material By "knockdown" is meant a decrease in detectable mRNA expression. Nucleic acids are generally used to knockdown gene expression and generally comprise a sequence capable of hybridizing to the target sequence, such as mRNA. Examples of such functional nucleic acids include antisense molecules, ribozymes, triplex forming nucleic acids, external guide sequences (EGS), and small interfering RNAs (siRNA).

The term "gene knockout" as used herein, refers to the targeted disruption of a gene in vivo with complete loss of function that has been achieved by any transgenic technology familiar to those in the art. In one example, transgenic animals having gene knockouts are those in which the target gene has been rendered nonfunctional by an insertion targeted to the gene to be rendered non-functional by homologous recombination.

The term "hit" refers to a test compound that shows desired properties in an assay.

The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The term "transgenic" is used to describe an organism that includes exogenous genetic material within all of its cells. The term includes any organism whose genome has been altered by in vitro manipulation of the early embryo or fertilized egg or by any transgenic technology to induce a specific gene knockout.

The term "transgene" refers to any piece of DNA which is inserted by artifice into a cell, and becomes part of the genome of the organism (i.e., either stably integrated or as a stable extrachromosomal element) which develops from that cell. Such a transgene can include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes disclosed herein can include DNA sequences that encode the fluorescent or bioluminescent protein that may be expressed in a transgenic non-human animal.

The term "activity" as used herein refers to a measurable result of the interaction of molecules. Some exemplary methods of measuring these activities are provided herein.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "treating" as used herein refers to administering a compound after the onset of clinical symptoms.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

The idea of an antibody type "magic bullet" for targeted cancer treatment has been around for 100 years, but the application of this concept to the treatment of solid tumors has proven challenging. The main reason for the limited success is that tumor tissue is not readily penetrable to compounds introduced through the blood stream (Jain 1990). Targeting tumor vasculature obviates this limitation, as tumor blood vessels are fully accessible to agents in the blood and express numerous marker molecules that are not present, or are expressed only at low levels in normal resting blood vessels. Many of these molecules are linked to angiogenesis, the growth of new blood vessels from existing ones, a process that is needed for tumor growth (Ferrara and Alitalo 1999; Hanahan and Weinberg 2000; Ruoslahti 2002).

Markers that are functionally important in angiogenesis can be targeted with agents that inhibit the angiogenesis related function. Another way of utilizing vascular markers is to have a probe such as an antibody or peptide bind to a specific vascular marker and carry a diagnostic or therapeutic payload with it, so that the payload becomes concentrated at the target site (Arap et al. 1998). The term "synaphic" (affinity-based) targeting was introduced to distinguish this approach from activity-based targeting that is based on the specificity of drug action.

Any tumor-homing or cancer-homing compound can be used in the disclosed compositions. A battery of tumor-homing peptides that selectively recognize tumor blood vessels or tumor lymphatics have been assembled (Ruoslahti 2002; Hoffman et al. 2003; Joyce et al. 2003; Laakkonen et al. 2002; Pilch et al. 2006; Ruoslahti et al. 2005; Simberg et al. 2007; Zhang et al. 2006). Two peptides from this collection are particularly relevant here: CREKA (cysteine-arginine-glutamic acid-lysine-alanine; SEQ ID NO:3) is a pentapeptide that binds to clotted plasma proteins and homes to tumors because interstitial tissue of tumors (Dvorak et al. 1985) and the vessels wall (Simberg et al. 2007) contain clotted plasma proteins, while the vessels in normal tissues do not. LyP-1 is a cyclic 9-amino-acid peptide (Cys-Gly-Gln-Lys-Arg-Thr-Arg-Gly-Cys; SEQ ID NO:1) that provided the first demonstration that lymphatic vessels in tumors can differ molecularly from normal lymphatics (Laakkonen et al. 2002). A protein known as p32 or gC1qR receptor (Ghebrehiwet et al. 1994) is the target molecule for the LyP-1 peptide and, in addition to overexpression in tumors, it also exhibits aberrant cell surface expression in tumor lymphatics, tumor cells, and, a subset of myeloid cells which contributes to the tumor specificity of LyP-1 homing (Fogal et al. 2008).

Iron oxide nanoparticles coated with the CREKA peptide bind to clotted plasma proteins in tumor vessels and induce additional clotting thus amplifying their own homing (Simberg et al. 2007). Quantum dots coated with the LyP-1 peptide specifically target tumor cells and lymphatic vessels upon intravenous injection in mice bearing MDA-MB-435 tumors (Akerman et al. 2002). LyP-1 coated Iron oxide nanoparticles extravasate into the tumor and specifically bind p32 expressing tumor cells (Von Maltzahn et al. 2008). These peptides were used in tumor targeting of an anti-tumor nanoparticle drug.

Abraxane is a 130-nm, albumin-based nanoparticle formulation of paclitaxel that is clinically used for the treatment of metastatic breast cancer (Gradishar et al 2005). Abraxane obviates cremaphor, the emulsifier used to solubilize paclitaxel, eliminating the need for pre-medication with steroids and anti-histamines and a long infusion. Moreover, a higher dose of paclitaxel ($260 \text{ mg/m}^2$) can be administered as abraxane than in cremaphor ($175 \text{ mg/m}^2$). The disclosed compositions can comprise abraxane nanoparticles where the surface of abraxane nanoparticles are coated with tumor homing peptides. Such coating further increases the accumulation of albumin bound paclitaxel in tumors. This, in turn, will improve the therapeutic efficacy of the drug.

Disclosed herein are methods of treating cancer comprising administering to a subject having cancer a composition comprising a tumor- or cancer-homing compound coupled to a paclitaxel-loaded albumin nanoparticle. Also disclosed are the compositions comprising a tumor- or cancer-homing compound coupled to a paclitaxel-loaded albumin nanoparticle. The composition can further comprise one or more different tumor- or cancer-homing compounds coupled to the nanoparticle.

Also disclosed herein are methods of treating cancer comprising administering to a subject having cancer a composition comprising a Lyp-1 peptide coupled to a paclitaxel-loaded albumin nanoparticle. Also disclosed are the compositions comprising a Lyp-1 peptide coupled to a paclitaxel-loaded albumin nanoparticle. The composition can further comprise a CREKA peptide coupled to the nanoparticle.

Also disclosed herein are methods of treating cancer comprising administering to a subject having cancer a composition comprising a CREKA peptide coupled to a paclitaxel-loaded albumin nanoparticle. Also disclosed are the compositions comprising a CREKA peptide coupled to a paclitaxel-loaded albumin nanoparticle.

The paclitaxel-loaded albumin nanoparticle can be abraxane.

The Lyp-1 peptide can comprise, for example, SEQ ID NO:1 or SEQ ID NO:13. The Lyp-1 peptide can consist essentially of SEQ ID NO:1 or SEQ ID NO:13. The Lyp-1 peptide can be SEQ ID NO:1, SEQ ID NO:13, or a variant of SEQ ID NO:1 or SEQ ID NO:13 with one or more conservative amino acid substitutions. The Lyp-1 peptide can be SEQ ID NO:1 or SEQ ID NO:13.

The composition can further comprise a therapeutic moiety. The therapeutic moiety can target a DNA-associated process. The therapeutic moiety can be selected from the group consisting of, for example, a cytotoxic agent, an alkylating agent, an anti-tumor antibiotic, a sequence-selective agent, an anti-angiogenic agent, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

The method can further comprise identifying the subject as having a cancer associated with gC1q/p32 receptor. Identifying the subject as having a cancer associated with gC1q/p32 receptor can be accomplished by, for example, bringing into contact a cancer cell of the subject and a composition that selectively interacts with gC1q/p32 receptor; and detecting interaction between gC1q/p32 receptor and the composition that selectively interacts with gC1q/p32 receptor, thereby detecting the presence or level of gC1q/p32, wherein the presence or level of gC1q/p32 receptor identifies the subject as having a cancer associated with a gC1q/p32 receptor. The composition that selectively interacts with gC1q/p32 receptor can be a Lyp-1 composition, wherein the Lyp-1 composition comprises a moiety linked to a Lyp-1 peptide. The level of the composition that selectively interacts with gC1q/p32 receptor interacting with gC1q/p32 receptor is detected. The level of gC1q/p32 receptor in the subject can be compared to a previous measurement in the same subject. The level of gC1q/p32 receptor in the subject can be compared to a control level or standard level. The moiety can be, for example, a detectable agent, a polypeptide, a nucleic acid molecule, or a small molecule. The composition that selectively interacts with gC1q/p32 receptor can comprise a virus. The composition that selectively interacts with gC1q/p32 receptor can comprise a phage. The detectable agent can be a small molecule, a fluorophore, fluorescein, rhodamine, a radionuclide, indium-111, technetium-99, carbon-11, carbon-13, or a combination thereof.

The method can further comprise administering to the subject one or more second compositions each comprising a different tumor- or cancer-homing compound coupled to a paclitaxel-loaded albumin nanoparticle. The method can further comprise administering to the subject a second composition comprising a CREKA peptide coupled to a paclitaxel-loaded albumin nanoparticle.

Also disclosed are methods of treating a disease associated with gC1q/p32 receptor comprising identifying a subject having a disease associated with the gC1q/p32 receptor; and administering to the subject a composition comprising SEQ ID NO:1.

Also disclosed are methods of treating a disease associated with gC1q/p32 receptor comprising identifying a subject having a disease associated with the gC1q/p32 receptor; and administering to the subject a composition that specifically interacts with gC1q/p32 receptor.

Also disclosed are methods of detecting the presence of gC1q/p32 receptor, comprising bringing into contact a cell and a composition, wherein the composition comprises a moiety linked to a composition that specifically interacts with gC1q/p32 receptor; and detecting interaction between gC1q/p32 receptor and the composition, thereby detecting the presence of gC1q/p32 receptor.

Further disclosed are methods of detecting interaction between a gC1q/p32 receptor and a composition, wherein the composition comprises a moiety linked to a composition that specifically interacts with gC1q/p32 receptor, the method comprising: selecting a cell for its potential to comprise a gC1q/p32 receptor; bringing into contact the composition and the cell; and detecting interaction between the gC1q/p32 receptor and the composition.

Also disclosed are methods of delivering a composition to a gC1q/p32 receptor, wherein the composition comprises a moiety linked to a composition that specifically interacts with gC1q/p32 receptor; wherein the method comprises bringing into contact the composition and a cell, thereby delivering the composition to the gC1q/p32 receptor.

Disclosed are methods of delivering a composition to a gC1q/p32 receptor, wherein the composition comprises a moiety linked to a composition that specifically interacts with gC1q/p32 receptor; comprising: selecting a cell for its potential to comprise a gC1q/p32 receptor; and bringing into contact the composition and the cell, thereby delivering the composition to the gC1q/p32 receptor.

Further disclosed are methods of determining and/or assessing gC1q/p32 receptor level in a cell of a subject, comprising: bringing into contact a cell of the subject and a composition comprising a detectable agent linked to a composition that specifically interacts with gC1q/p32 receptor; and detecting the level of composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a composition, wherein the composition comprises a moiety linked to a composition that specifically interacts with gC1q/p32 receptor; and detecting interaction between gC1q/p32 receptor and the composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of detecting the presence of gC1q/p32 receptor, comprising bringing into contact a cell and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence of gC1q/p32 receptor.

Further disclosed are methods of detecting interaction between a gC1q/p32 receptor and a Lyp-1 composition, wherein the Lyp-1 composition comprises a moiety linked to a composition comprising SEQ ID NO:1, the method comprising: selecting a cell for its potential to comprise a gC1q/p32 receptor; bringing into contact the Lyp-1 composition and the cell; and detecting interaction between the gC1q/p32 receptor and the Lyp-1 composition.

Also disclosed are methods of delivering a Lyp-1 composition to a gC1q/p32 receptor, wherein the Lyp-1 composition comprises a moiety linked to a composition comprising SEQ ID NO:1; wherein the method comprises bringing into contact the Lyp-1 composition and a cell, thereby delivering the Lyp-1 composition to the gC1q/p32 receptor.

Disclosed are methods of delivering a Lyp-1 composition to a gC1q/p32 receptor, wherein the Lyp-1 composition comprises a moiety linked to a composition comprising SEQ ID NO:1; comprising: selecting a cell for its potential to comprise a gC1q/p32 receptor; and bringing into contact the Lyp-1 composition and the cell, thereby delivering the Lyp-1 composition to the gC1q/p32 receptor.

Further disclosed are methods of determining and/or assessing gC1q/p32 receptor level in a cell of a subject, comprising: bringing into contact a cell of the subject and a Lyp-1 composition comprising a detectable agent linked to a composition comprising SEQ ID NO:1; and detecting the level of Lyp-1 composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence or level of gC1q/p32 on the cell, wherein the presence or level of gC1q/p32 receptor on the cell identifies the subject as having a disease associated with a gC1q/p32 receptor.

Further disclosed are methods of screening for a compound that interacts with a gC1q/p32 receptor, comprising: bringing into contact a test compound, a Lyp-1 composition, and a gC1q/p32 receptor, wherein the Lyp-1 composition comprises SEQ ID NO:1; and detecting unbound Lyp-1 composition, wherein a given amount of unbound Lyp-1 composition indicates a compound that interacts with gC1q/p32 receptor.

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as Lyp-1, thereby treating a disease associated with the gC1q/p32 receptor.

The gC1q/p32 receptor can be, for example, on or in a cell. The cell can be in any context, such as in an organism, in situ, ex vivo, in culture, and/or in vitro.

Also disclosed is a method of treating or preventing a disease in a subject associated with gC1q/p32 receptor, the method comprising administering to the subject a composition that modulates gC1q/p32 receptor expression or activity, thereby treating or preventing a disease in a subject associated with the gC1q/p32 receptor. The disease can be cancer. Expression or activity of the gC1q/p32 receptor can be inhibited. This can occur by the use of interfering nucleic acid, such as shRNA or siRNA. Activity of the gC1q/p32 receptor can be inhibited by the LyP-1 peptide, an antibody, or a small molecule mimic of Lyp-1.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

A. Tumor- and Cancer-Homing Compounds

Any tumor-homing or cancer-homing compound can be used in the disclosed compositions. A battery of tumor-homing peptides that selectively recognize tumor blood vessels or tumor lymphatics have been assembled (Ruoslahti 2002; Hoffman et al. 2003; Joyce et al. 2003; Laakkonen et al. 2002; Pilch et al. 2006; Ruoslahti et al. 2005; Simberg et al. 2007; Zhang et al. 2006). Any of these can be used alone or in combination coupled to paclitaxel-loaded albumin nanoparticles. Ruoslahti 2002; Hoffman et al. 2003; Joyce et al. 2003; Laakkonen et al. 2002; Pilch et al. 2006; Ruoslahti et al. 2005; Simberg et al. 2007; and Zhang et al. 2006 are each incorporated herein by reference in their entirety and specifically for their description of tumor-homing peptides and the described tumor-homing peptides.

The tumor- or cancer-homing compound can bind to a receptor or ligand on the surface of the cancer cell or can bind to an intracellular target of cancer cell provided that the target is accessible to the agent. Accessibility to intracellular cancer cell targets can arise in cancer cells that have a compromised plasma membrane such as cells which are undergoing apoptosis, necrosis, and the like. For example, certain tumor- or cancer-homing compounds can bind intracellular portions of a cell that does not have a compromised plasma membrane. See e.g., Porkka et al., Proc Natl Acad Sci USA. (2002) 99(11): 7444-9.

Tumor- or cancer-homing compounds also can bind to a molecule that is present in the tumor. As used herein "tumor" includes cancer cells, necrosis, as well as stroma. Stroma includes cells such as fibroblasts and endothelial cells of vessels and capillaries and extracellular matrix, which is composed of fibrillar and non-fibrillar components. The major fibrillar proteins are collagen and elastin. A tumor- or cancer-homing compound can target to the tumor by binding to the stroma which surrounds the cancer cells in the tumor. Thus, a tumor- or cancer-homing compound can target in the vicinity of a cancer by binding to a stromal component such as a fibroblast or endothelial cell or a component of the extracellular matrix. See, e.g. Schraa et al. Control Release (2002) 83(2): 241-51; Arap et al. Haemostasis (2001) 31 Suppl 1: 30-1.

Tumor- or cancer-homing compounds can include those that bind to tumor specific or tumor associated antigens. The term "tumor associated antigen" (TAA) as used herein refers to a protein which is present on tumor cells, and on normal cells during fetal life (onco-fetal antigens), after birth in selected organs, or on normal cells, but at much lower concentration than on tumor cells. A TAA also can be present in the stroma in the vicinity of the cancer cell but be expressed at lower amounts in the stroma elsewhere in the body. A variety of TAA have been described including BRCA-1 and BRCA-2 proteins, the HER-2-neu, mucins such as MUC1, integrins, cytokines, and the like. In contrast, tumor specific antigen (TSA) (aka. "tumor-specific transplantation antigen" or TSTA) refers to a tumor cell expressed protein absent from normal cells. TSA usually appear when an infecting virus has caused the cell to become immortal and to express virus antigens. Exemplary viral TSAs are the E6 or E7 proteins of HPV type 16. TSAs not induced by viruses can be idiotypes of the immunoglobulin on B cell lymphomas or the T cell receptor (TCR) on T cell lymphomas.

Cancers treatable using the disclosed methods include carcinomas, sarcomas, and leukemias and lymphomas and other types of cancer. Carcinomas include those of lung, breast, colon, ovarian, prostate, and the like. These cancers can be primary or metastatic. In the case of leukemias and lymphomas, the cancer cells treatable with the invention methods include those in the form of a tumor as well as cancer cells in the bone marrow and in the circulation.

Tumor- or cancer-homing compounds include small molecule compounds such as drugs, organic compounds, peptides, peptidomimetics, as well as larger molecules such as glycoproteins, proteoglycans, lipids glycolipids, phospholipids, lipopolysaccharide, nucleic acids, proteoglycans, carbohydrates, and the like. Small molecule tumor- or cancer-homing compounds can be about 5,000 daltons or less in size. Tumor- or cancer-homing compounds can include well known therapeutic compounds including anti-neoplastic agents. Anti-neoplastic targeting molecules can include paclitaxel, daunorubicin, doxorubicin, caminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin A2, dideazatetrahydrofolic acid, aminopterin, methotrexate, cholchicine and cisplatin, and the like. Tumor- or cancer-homing compounds also can include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

Tumor- or cancer-homing compounds can be a protein or peptide. "Polypeptide," "peptide," and "protein" are used interchangeably to refer to a polymer of amino acid residues linked by amide bonds. As used herein, these terms apply to amino acid polymers in which one or more amino acid residue is an artificial chemical analogue of a corresponding naturally occurring amino acid. Thus, proteins can include natural and non-natural amino acids. Amino acids can be in the L or D form as long as the binding function of the peptide is maintained. Peptides can be of variable length, but are generally between about 4 and 200 amino acids in length. Peptides can be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

The tumor- or cancer-homing compound can be an antagonist or agonist of an integrin. Integrin is a heterodimeric transmembrane glycoprotein complex that functions in cellular adhesion events and signal transduction processes. Integrins, which comprise and alpha and a beta subunit, include numerous types. Integrin $\alpha_v\beta_3$ is expressed on a variety of cells and has been shown to mediate several biologically relevant processes, including adhesion of osteoclasts to bone matrix, migration of vascular smooth muscle cells, and angiogenesis. Suitable targeting molecules for integrins include RGD peptides or peptidomimetics or non-RGD peptides or peptidomimetics (see, e.g., U.S. Pat. Nos. 5,767,071 and 5,780,426) as well as for other integrins such as $\alpha_4\beta_1$ (VLA-4), $\alpha_4\beta_7$ (see, e.g., U.S. Pat. No. 6,365,619; Chang et al., Bioorganic & Medicinal Chem Lett, 12:159-163 (2002); Lin et al., Bioorganic & Medicinal Chem Lett, 12:133-136 (2002)), and the like. The tumor- or cancer-homing compound can be an antibody.

By "homing" is meant that a stated compound or material can preferentially interact with a stated target compared with non-targets. Thus, for example, in vivo, Lyp-1 can preferentially interact with the gC1qR/p32 as compared to non-target. Therefore, when gC1qR/p32 is associated with a cancerous cell, or a site of inflammation, Lyp-1 will interact with the cancerous cell or site of inflammation preferentially, as compared to a non-cancerous cell, or a site without inflammation. Homing to, or selective or preferential interaction with, for example, tumors, generally is characterized by at least a two-fold or greater localization at the tumor site. Homing to, or selective or preferential interaction with, for example, cancer, generally is characterized by at least a two-fold or greater localization at the cancer site. A compound can be characterized by 5-fold, 10-fold, 20-fold or more preferential localization to cancerous sites such as tumors, as compared to several or many tissue types of non-tumoral tissue, or as compared to most or all non-tumoral tissue. Thus, it is understood that, in some cases, tumor- or cancer-homing compounds interact with, in part, one or more normal organs in addition to cancerous sites such as tumors. Homing can also be referred to as targeting or selective interaction.

As discussed above, selectively interacting with, including preferential and/or selective homing, does not mean that the homing compound does not bind to any normal and/or non-targeted areas. In some embodiments, interaction selectivity can be, for example, at least about 20-fold, at least about 30-fold, at least about 50-fold, at least about 75-fold, at least about 100-fold, at least about 150-fold, or at least about 200-fold selective for a corresponding target. Selective interaction or homing can be, for example, in terms of relative amounts or in terms of relative $K_i$ over other non-target components. In some embodiments, the homing compound can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, the homing compound can have a $K_i$ value against a target of less than about 200 nM, less than about 150 nM, less than about 100 nM, or less than about 75 nM. In some preferred embodiments, the homing compound can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the homing compound binds its target with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

B. Lyp-1 and gC1qR/p32

Lyp-1 is a useful example of a tumor- or cancer-homing compound that can be used in the disclosed compositions. It has been discovered that the Lyp-1 (SEQ ID NO:1, CGNKRTRGC; SEQ ID NO:13, CGQKRTRGC) selectively interacts with the gC1q receptor (gC1qR/p32, which has been described in the literature by one of the alternative terms gC1qR and p32, and is described herein as either gC1qR, gC1q receptor, or p32, or as "gC1qR/p32" which refers to the protein known in the literature as gC1qR and as p32). gC1qR/p32 is associated with tumor lymphatic vasculature, for example, the lymphatic vasculature of breast cancer tumors, squamous carcinomas, and osteosarcomas. gC1qR/p32 is also associated with inflammation (Waggoner et al., J. Immunol. 2005 Oct. 1; 175(7):4706-14, herein incorporated by reference in its entirety for its teaching concerning gC1q/p32 receptors and inflammation).

As disclosed herein, the interaction of peptide Lyp-1 (SEQ ID NO:1) and gC1qR/p32 was identified by pull down assays with biotinylated Lyp-1 peptide from protein extracts (FIG. 1). A tumor homing peptide, CREKA (SEQ ID NO:3), and a peptide (CRV) which resembles Lyp-1 in its amino acid composition and cyclic structure (CRVRTRSGC, SEQ ID NO:4), were used as negative controls. Anti gC1qR/p32 reactive bands were not detected in the pull downs from both control peptides. The monoclonal antibody against gC1qR/p32 recognized a 75 kD and a 33 kD band only in the Lyp-1 peptide pull down.

Figure 2A:
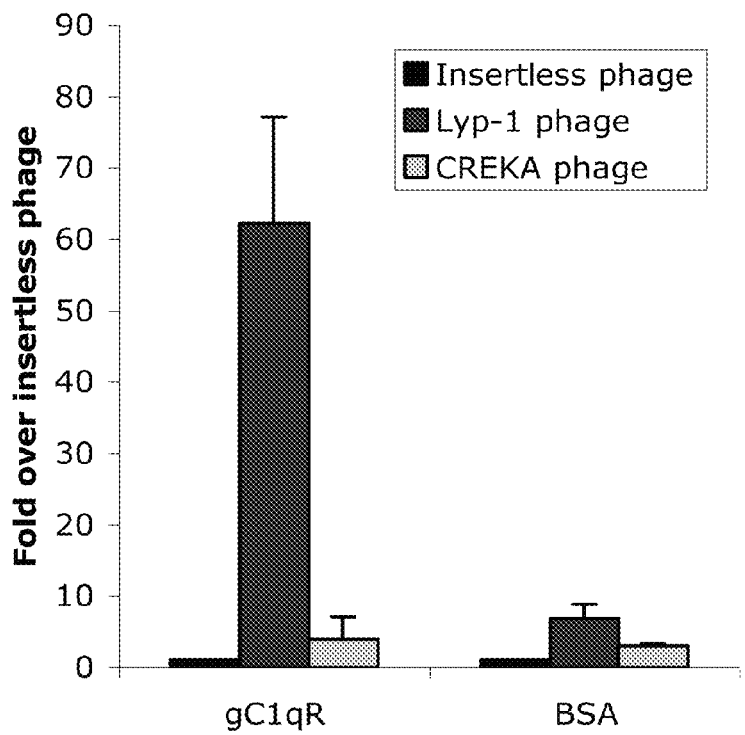
FIG. 2 shows Lyp-1 phage specifically binds to purified gC1qR/p32 protein. (a) Purified gC1qR or BSA, as a control, were coated onto microtiter wells (5 µg/ml) and targeted for binding with 108 pfu of insertless phage, Lyp-1 phage, or control phage carrying another tumor homing peptide (CREKA, SEQ ID NO:3). After 16 hours of incubation at 37° C., bound phages were eluted and quantified by plaque assay. Results are expressed as fold of Lyp-1 and CREKA (SEQ ID NO:3) phages recovered over insertless phage and are representative of five independent experiments. (b) An antibody against the N-terminus of gC1qR inhibits Lyp-1 phage binding to purified gC1qR/p32. Left panel: Diagram of precursor (aa 1-282) and mature (aa 74-282) gC1qR/p32 protein. Boxes indicate the amino acid residues recognized by the monoclonal antibodies, mAb 60.11 and mAb 74.5.2, respectively at the N-terminus (aa 76-93) and C-terminus (aa 204-282) of the mature protein. The amino acid sequence recognized by mAb 60.11 is also indicated. Right panel: $1.5 \times 10^7$ pfu of insertless and Lyp-1 phages were allowed to bind for 6 hours at 37° C. to gC1qR/p32 protein coated onto microtiter plates in the presence or absence of 20 µg/ml of either mAbs 60.11, 74.5.2 or purified mouse IgG1 (mIgG). The results are representative of three independent experiments and are expressed as percentage of phage binding, with Lyp-1 phage binding alone as 100%.
Figure 2B:
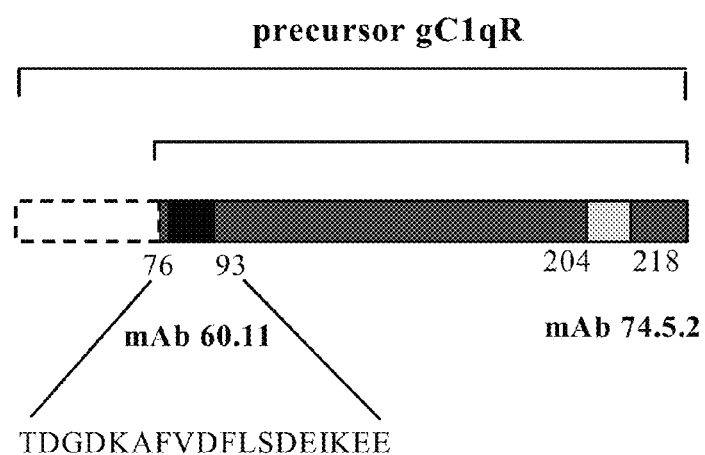
Figure 4A:
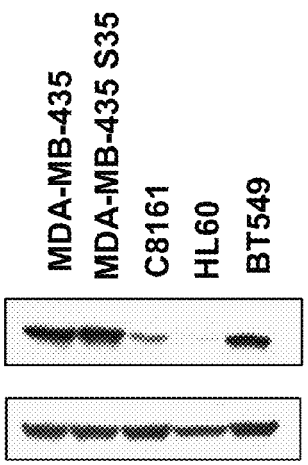
FIG. 4 shows expression and cell surface localization of p32 in tumor cells. A. Immunoblot of endogenous p32 in extracts of the indicated cultured tumor cell lines. p32 was detected with mAb 60.11, and β-actin was used as loading control. B and C. FACS analysis to detect cell surface expression of p32 in tumor cell cultures (B) and primary cell suspensions from MDA-MB-435 and C8161 tumor xenografts (C, left panel). Rabbit IgG or a polyclonal antibody against full-length p32 were applied to live cells and detected with an Alexa 488-labeled secondary antibody. Propidium iodide-negative (living) cells were gated for the analysis. The total expression level of p32 in lysates from tumor xenografts was detected by immunoblot (C, right panel).

Furthermore, Lyp-1 phage specifically bound to purified gC1qR/p32 protein. Purified gC1qR/p32 or BSA, as a control, were coated onto microtiter wells and targeted for binding with insertless phage, Lyp-1 phage, or control phage carrying another tumor homing peptide (CREKA, SEQ ID NO:3). As can be seen in FIG. 2a, the Lyp-1 phage bound gC1qR/p32, while the insertless and control phages showed essentially no interaction. Furthermore, an antibody against the N-terminus of gC1qR/p32 inhibited Lyp-1 phage binding to purified gC1qR/p32 (FIG. 2B).

gC1qR/p32 protein levels and cell surface expression are also shown in cultured tumor cells and tumor xenografts. FIG. 4A shows gC1qR/p32 western blot analysis from lysates of different tumor cell lines. C8161 melanoma cells and HL-60 promyelocitic leukemia cells, both low binders of Lyp-1 phage (Laakkonen et al., 2002), express low levels of gC1qR/ p32 compared to MDA-MB-435 and BT549 breast cancer cells which exhibit higher Lyp-1 phage binding ability. FACS analysis was used to detect the cell surface expression of gC1qR/p32 in tumor cell cultures or primary cell suspensions from MDA-MB-435 tumor xenografts. Propidium iodide negative (living) cells were gated for the analysis. In cell suspensions from MDA-MB-435 tumor xenografts, polyclonal anti-gC1qR/p32 antibody caused a significant shift of the FACS peak compared with the rabbit IgG control. The cell surface expression of gC1qR/p32 was low in cultured MDA-MB-435 and BT549 cells. There was not cell surface expression of gC1qR/p32 in C8161 cells.

Figure 5B:
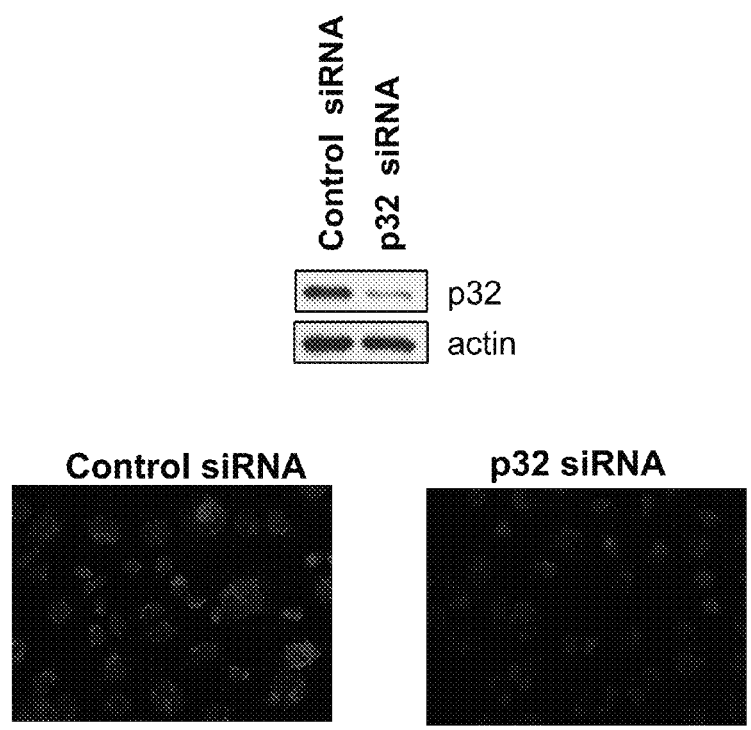
FIG. 5 shows LyP-1 binds to p32 at the cell surface. A. C8161 cells were transiently transfected with pEGFP together with either empty pcDNA3.1 vector or p32 pcDNA3.1 vector. Transfected cells were sorted for EGFP expression and the sorted populations were used for phage binding assay and immunoblot analysis with anti-p32. LyP-1 phage binding to cells transfected with the empty vector or p32 vector is expressed as fold binding over insertless phage. The graph represents the mean of binding in two independent experiments performed in duplicate (LyP-1 vs insertless phage in p32-transfected cells p<0.05; Student's t test). B. MDA-MB-435 S35 cells were transiently transfected with p32-specific or control siRNAs. 48 hours after transfection, inhibition of p32 expression was checked by immunoblot analysis and immunostaining (upper panels). β-actin was used as a control. (Lower panels) cells transfected with p32 siRNA or control siRNA were incubated for 1 h at 4° C. in the presence of 10 μM FITC conjugated LyP-1 peptide or a control peptide, ARALPSQRSR (ARAL, SEQ ID NO:5), which has same overall charge as LyP-1. Cells incubated in the absence of peptide served as negative control. Down-regulation of p32 expression reduced LyP-1 binding to the cells (left panel), but control peptide fluorescence was unaffected (right panel). A representative experiment out of three is shown. C. LyP-1 phage binding in Raji cells in the presence of 40 μg/ml of mIgG1 (control), mAb 60.11, or mAb 74.5.2. Insertless phage was used to determine background phage binding. The results are representative of three independent experiments and are expressed as percentage of phage binding (±SD), with binding of LyP-1 phage in the presence of mIgG1 set as 100%.
Figure 5B:
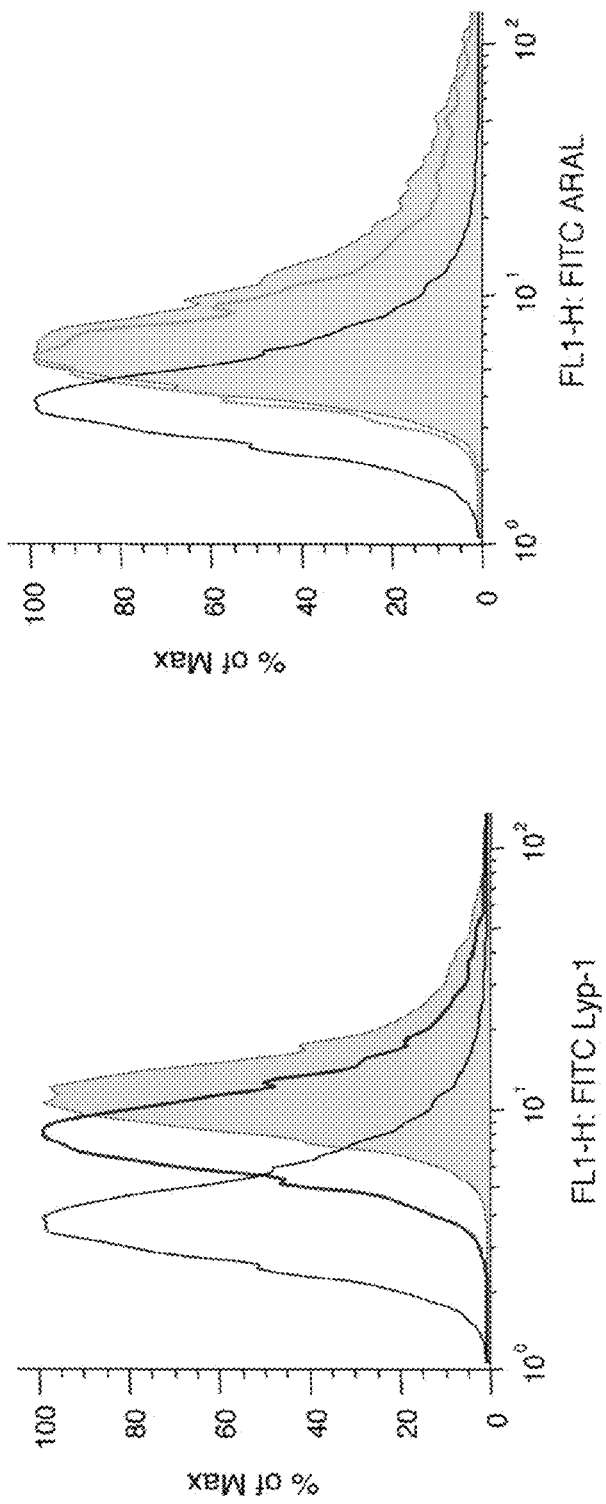

Furthermore, gC1qR/p32 overexpression enhanced Lyp-1 phage binding to C8161 melanoma cells (FIG. 5). A phage binding assay and western blot analysis were used to detect gC1qR/p32 overexpression. Lyp-1 phage binding to gC1qR/p32 was much greater than to empty vector. RNAi-mediated gC1qR/p32 silencing also decreases Lyp-1 peptide binding to the cell surface. MDA-MB-435 cells were transiently transfected with gC1qR/p32-specific or control siRNAs. Cells incubated in the absence of peptide served as FITC negative control. Compared to control siRNA transfected cells, downregulation of gC1qR/p32 expression caused a shift in the peak of Lyp-1, but not control peptide fluorescence.

FIG. 3 shows tumor localization of gC1qR/p32 and Lyp-1 peptide. Staining of gC1qR/p32 and lymphatic or blood vessels, podoplanin and Meca32/CD31, respectively, in MDA-MB-435 tumor xenografts was done. Polyclonal anti-gC1qR/p32 antibody recognized cell clusters that lack blood vessels but contain lymphatics, or cells lining vessel-like structures positive for Podoplanin but not CD31 or Meca32. Lyp-1 peptide localized in gC1qR/p32-positive patches within the tumor.

Based on these findings, disclosed herein are Lyp-1 compositions useful in diseases and disorders associated with gC1qR/p32. For example, the Lyp-1 compositions disclosed herein are useful for reducing or preventing tumor metastasis in cancer patients having a primary tumor. The Lyp-1 compositions can be administered, for example, to a subject having pre-metastatic breast or bone cancer or to a subject having early or late stage metastatic breast or bone cancer. Lyp-1 polypeptides can also be useful, for example, for imaging tumor lymphatic vasculature, such as breast cancer or osteosarcoma lymphatic vasculature. The disclosed compositions are also useful for reducing or preventing inflammation in patients in need thereof.

Thus, disclosed herein are isolated peptides or peptidomimetic containing the amino acid sequence GNKRTRG (SEQ ID NO:2), or a peptidomimetic thereof. The invention further provides an isolated peptide or peptidomimetic containing the amino acid sequence CGNKRTRGC (SEQ ID NO:1) or a peptidomimetic thereof.

Disclosed are compositions, such as those comprising Lyp-1, that selectively interact with tumors and sites of inflammation, as well as other diseases and disorders associated with gC1qR/p32. A variety of homing compositions can be used in the disclosed methods. Such compositions include, without limitation, peptides as disclosed herein. The disclosed compounds, compositions, molecules and methods can include or use the disclosed homing compositions in various forms, including peptides and peptidomimetics as disclosed. For convenience of expression, in many places herein the use or inclusion of peptides will be recited. It is understood that, in such cases, it is considered homing compositions in various forms can also be used or included in the same or similar ways as is described in terms of peptides, and such use and inclusion is specifically contemplated and disclosed thereby.

There are multiple diseases and disorders associated with the gC1q/p32 receptor. Examples include, but are not limited to, cancer and inflammation.

The composition comprising SEQ ID NO:1 can further comprise a moiety. Examples of moieties include, but are not limited to, therapeutic or diagnostic moieties. Therapeutic moieties can include anti-angiogenic agents or cytotoxic agents. The therapeutic moiety can target a DNA-associated process. The therapeutic moiety can be selected from the group consisting of an alkylating agent, an anti-tumor antibiotic and a sequence-selective agent. Other examples of therapeutic moieties include cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286. The moiety can also be a nanoparticle. Use of Lyp-1 is described in Akerman, M. E., Chan, W. C. W., Laakkonen, P., Bhatia, S. N., and Ruoslahti, E. Nanocrystal targeting in vivo. *Proc. Natl. Acad. Sci. USA.* 99:12617-12621 (2002), and von Maltzahn G, Ren Y, Park J-H, Min D-H., Kotamraju V R., Jayakumar J, Fogal V, Sailor M, Ruoslahti E, and Bhatia, S. In vivo Tumor Cell Targeting with "Click" Nanoparticles, Bioconjugate Chem., 2008, 19: 1570-1578 (2008).

Disclosed are methods of detecting the presence of gC1q/p32 receptor, the method comprising bringing into contact a cell and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence of gC1q/p32 receptor. The gC1q/p32 receptor can be, for example, on or in a cell. The cell can be in any context, such as in an organism, in situ, ex vivo, in culture, and/or in vitro.

The moiety can be a detectable moiety. Examples of such moieties include, but are not limited to, a polypeptide, a nucleic acid molecule, a small molecule, a fluorophore, fluorescein, rhodamine, a radionuclide, indium-111, technetium-99, carbon-11, carbon-13, or a combination thereof.

The homing composition being brought into contact with the cell described above can comprise a virus in one example. The homing composition can also comprise a phage.

Lyp-1 can selectively interacts with (or home to) gC1qR/p32 as compared to non-target. Therefore, when gC1qR/p32 is associated with a cancerous cell, or a site of inflammation, Lyp-1 will interact with the cancerous cell or site of inflammation preferentially, as compared to a non-cancerous cell, or a site without inflammation. Selective or preferential interaction with, for example, tumors, generally is characterized by at least a two-fold or greater localization at the cancerous site. A Lyp-1 peptide can be characterized by 5-fold, 10-fold, 20-fold or more preferential localization to cancerous sites such as tumors, as compared to several or many tissue types of non-tumoral tissue, or as compared to most or all non-tumoral tissue. Thus, it is understood that, in some cases, Lyp-1 interacts with, in part, one or more normal organs in addition to those with gC1qR/p32 present. Selective interaction can also be referred to as targeting or homing.

As discussed above, selectively interacting with, including preferential and/or selective homing, does not mean that Lyp-1 does not bind to any normal and/or non-targeted areas. In some embodiments, interaction selectivity can be, for example, at least about 20-fold, at least about 30-fold, at least about 50-fold, at least about 75-fold, at least about 100-fold, at least about 150-fold, or at least about 200-fold selective for a corresponding target. Selective interaction can be, for example, in terms of relative amounts or in terms of relative $K_i$ over other non-target components. In some embodiments, Lyp-1 can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, Lyp-1 can have a $K_i$ value against a target of less than about 200 nM, less than about 150 nM, less than about 100 nM, or less than about 75 nM. In some preferred embodiments, Lyp-1 can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the Lyp-1 binds its target with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

C. p32/gC1q Receptor

It has been found that knocking down gC1qR/p32 expression in tumor cells shift their metabolism toward glycolysis and that, surprisingly, the glycolytic phenotype is associated with impaired tumor cell survival and growth, especially under adverse growth conditions (Example 2). At the same time, tumorigenicity of the gC1qR/p32 knockdown cells is reduced. Therefore, disclosed herein are methods of targeting the gC1q/p32 receptor in order to treat gC1q/p32 receptor-related disorders and diseases, as described herein. An example of such a disease is cancer.

Also disclosed herein is a method of treating a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. Expression or activity of the gC1q/p32 receptor can be inhibited. This can occur by the use of interfering nucleic acid, such as shRNA or siRNA. Activity of the gC1q/p32 receptor can be inhibited by LyP-1 peptide, an antibody, or a small molecule mimic of Lyp-1. The methods of treating cancer disclosed herein can be used in conjunction with other treatment therapies as well, as described below in the section relating to moieties.

Disclosed herein are subjects having a disease associated with the gC1q/p32 receptor. By this is meant that the subject has either an increased level of gC1q/p32 receptor, a decreased level of gC1q/p32 receptor, or that the gC1q/p32 receptor can be targeted to treat or ameliorate the symptoms of a disease or disorder. By an "increased level of gC1q/p32 receptor" is meant that the number of gC1q/p32 receptors in the subject as a whole is increased over normal, basal, or standard levels accepted by those of skill in the art. It can also mean that the number of gC1q/p32 receptors present in a given cell are increased over a basal, normal, or standard amount. By a "decreased level of gC1q/p32 receptor" is meant that the number of gC1q/p32 receptors in the subject as a whole is deceased over normal, basal, or standard levels accepted by those of skill in the art. It can also mean that the number of gC1q/p32 receptors present in a given cell are decreased over a basal, normal, or standard amount. One of skill in the art would be able to determine gC1q/p32 levels in a subject as a whole, as well as in individual cells, using the methods disclosed herein and those known to those of skill in the art. One method of doing so involves using Lyp-1, as disclosed herein. Diseases associated with the gC1q/p32 receptor include cancer, for example.

D. Peptides and Peptidomimetics

Disclosed are compositions related to isolated peptides comprising specific amino acids sequences. The isolated peptides can comprise, for example, a specific amino acid sequence, an amino acid sequence at least about 90% identical to the specific amino acid sequence, or the specific amino acid sequence having one or more conservative amino acid substitutions. The peptide can be at least about 90%, 80%, 70%, or 60% identical to the specific amino acid sequence. The specific amino acid sequence can have one, two, three, four, five, six, seven, eight, or nine conservative amino acid substitutions, for example. The peptide can comprise a chimera of the specific amino acid sequence. Such a chimera can be additive, where sequence of one sequence is added to another sequence, substitutional, where sequence of one sequence is substituted for sequence of another sequence, or a combination. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

Also disclosed are compositions related to an isolated peptide comprising, for example, SEQ ID NO:1 (Lyp-1). The isolated peptides can comprise, for example, SEQ ID NO:1, an amino acid sequence at least about 90% identical to SEQ ID NO:1, or the amino acid sequence of SEQ ID NO:1 having one or more conservative amino acid substitutions. The peptide can be at least about 90%, 80%, 70%, or 60% identical to the amino acid sequence of SEQ ID NO:1. The amino acid sequence of SEQ ID NO:1 can have one, two, three, four, five, six, seven, eight, or nine conservative amino acid substitutions, for example. The peptide can comprise a chimera of the amino acid sequence SEQ ID NO:1. Such a chimera can be additive, where sequence of one sequence is added to another sequence, substitutional, where sequence of one sequence is substituted for sequence of another sequence, or a combination. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

The amino acid sequence can be linear, circular or cyclic. The amino acid segment can be circularized or cyclized via any suitable linkage, for example, a disulfide bond. The peptide can have any suitable length, such as a length of less than 100 residues. The peptide can have a length of less than 50 residues. The peptide can have a length of less than 20 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH) $CH_2$—, and —$CHH_2SO$—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C (OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing a specific amino acid sequence (the amino acid sequence SEQ ID NO:1, for example), or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides, which contain a tumor- or cancer-homing peptide (such as Lyp-1, for example) fused to a second peptide having a separate function. Such bifunctional peptides have at least two functions conferred by different portions of the full-length molecule and can, for example, display anti-angiogenic activity or pro-apoptotic activity in addition to the ability to selectively interact with tumors or cancerous sites.

Also disclosed are isolated multivalent peptides that include at least two subsequences each independently containing a peptide (for example, the amino acid sequence SEQ ID NO:1, or a conservative variant or peptidomimetic thereof). The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. In a further embodiment, the multivalent peptide can contain identical subsequences, such as repeats of SEQ ID NO:1. In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an $N^\alpha$—$C^\alpha$ cyclized amino acid; an $N^\alpha$.- methylated amino acid; a β- or γ-amino cycloalkane carboxylic acid; an α,β-unsaturated amino acid; a β,β-dimethyl or β-methyl amino acid; a β-substituted-2,3-methano amino acid; an N—C$^ε$ or C$^α$—C$^Δ$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

If desired, an isolated peptide such as Lyp-1 can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl) benzoic acid (Mamb). Cyclization additionally can be effected, for example, through the formation of a lysinonor-leucine bond between lysine (Lys) and leucine (Leu) residues or a dityrosine bond between two tyrosine (Tyr) residues. The skilled person understands that these and other bonds can be included in a cyclic peptide.

E. Antibodies i. Antibodies Generally

Figure 10A:
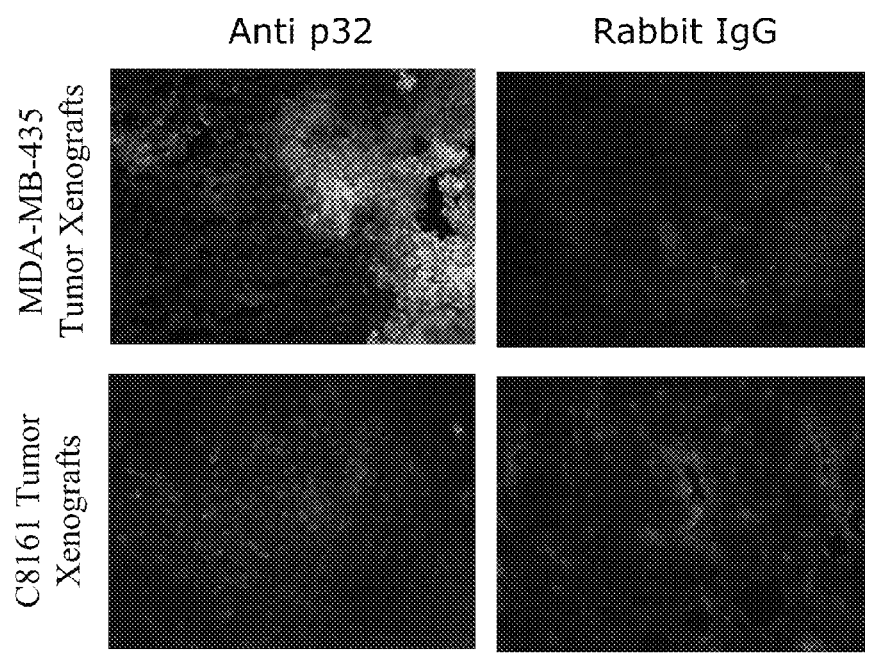
FIG. 10A—Affinity purified anti N-terminus p32 polyclonal antibody or rabbit IgG, as a control, was injected into the tail vein of mice bearing MDA-MB-435 or C8161 tumor xenografts. The tumor and various organs were removed 1 hour after the injection, sectioned, and examined for the presence of rabbit IgG using Alexa 488 anti rabbit IgG secondary antibody. The antibody recognizes clusters of cells similar to those visualized after i.v. injection of FITC LyP-1 or by p32 staining of tumor sections (FIG. 10A left panel). Homing to MDA-MB-435 xenografts is more efficient than to C8161 tumors, which express high and low levels of p32 respectively (FIG. 10A-right panel).
Figure 10B:
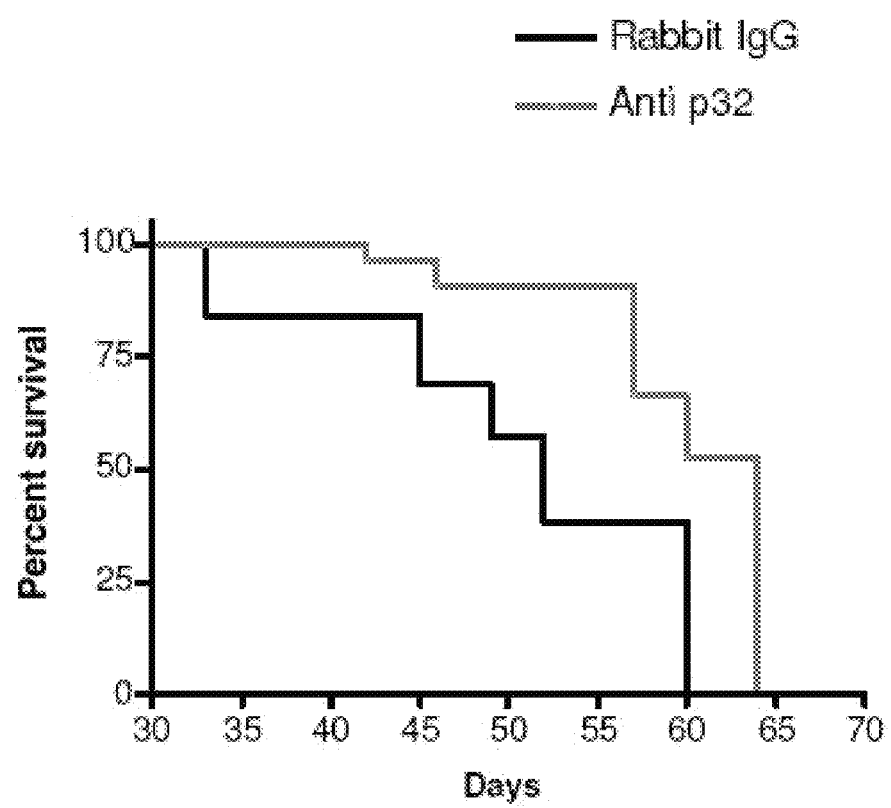

Disclosed herein are antibodies that can be used to modulate the gC1q/p32 receptor, or Lyp-1. Examples of such antibodies can be found in FIG. 10. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with gC1qR/p32. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

ii. Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

iii. Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

iv. Administration of Antibodies

Administration of the antibodies can be done as disclosed herein. Nucleic acid approaches for antibody delivery also exist. The broadly neutralizing anti DES-1 antibodies, for example, and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

F. Homing Compositions

Disclosed are homing compositions comprising a homing compound, and optionally also comprising a moiety. The moiety can be any molecule. For example, disclosed are moieties containing a therapeutic agent linked to a homing compound such as SEQ ID NO:1. Preferably the moiety is a molecule that is usefully targeted to tumors and cancers. For example, the homing composition can be targeted to the gC1q/p32 receptor. For example, moieties that affect the target, such as moieties with therapeutic effect, or that facilitate detection, visualization or imaging of the target, such as fluorescent molecule or radionuclides. In particular, the moiety can be a paclitaxel-loaded albumin nanoparticle such as abraxane. The disclosed homing compounds (such as the disclosed peptides, such as SEQ ID NO:1 and SEQ ID NO:13, that selectively interact with gC1qR/p32) can be usefully combined with, for example, moieties that can, for example, affect tumors and cancer, reduce or eliminate inflammation or infection, and/or promote wound healing. A variety of therapeutic agents are useful in the homing compositions, including, without limitation, cancer chemotherapeutic agents, cytotoxic agents, anti-angiogenic agents, polypeptides, nucleic acid molecules and small molecules. In particular, the moiety can be a paclitaxel-loaded albumin nanoparticle such as abraxane. A homing composition comprising a Lyp-1 peptide as the homing compound can be referred to as a Lyp-1 composition.

A homing composition can comprise, for example, two or more, three or more, five or more, ten or more, twenty or more, thirty or more, forty or more, fifty or more, 100 or more, 200 or more, 300 or more, 400 or more, 500 or more, or 1000 or more copies of a homing compound such as, for example, Lyp-1 peptide (SEQ ID NO:1 or SEQ ID NO:13, for example). A homing composition with a peptide as the homing compound can comprise peptides that all have an identical amino acid sequence. In another embodiment, such a homing composition can comprise two or more non-identical amino acid sequences. For example, SEQ ID NO:1 and another targeting peptide can be used separately or together. As another example, any mixture of two or more different peptides such as, for example, peptides comprising SEQ ID NO:1 or SEQ ID NO:13, peptide consisting essentially of SEQ ID NO:1 or SEQ ID NO:13, peptides that are a variant of SEQ ID NO:1 or SEQ ID NO:13 with one or more conservative amino acid substitutions, or peptides that are SEQ ID NO:1 or SEQ ID NO:13. Moieties useful in a homing composition incorporating multiple peptides include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A homing composition can contain, for example, a liposome or other polymeric matrix linked to at least two peptides. If desired, the liposome or other polymeric matrix can be linked to at least ten, at least 100 or at least 1000 homing compounds such as Lyp-1 peptides (SEQ ID NO:1 or SEQ ID NO:13, for example). Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule.

Components of the disclosed homing compositions can be combined, linked and/or coupled in any suitable manner. For example, moieties and peptides can be associated covalently or non-covalently, directly or indirectly, with or without a linker moiety.

1. Moieties

Disclosed are compositions useful for directing a moiety to a target. For example, the moiety can be incorporated into a homing composition. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

i. Therapeutic Agents

The moiety can be a therapeutic agent. As used herein, the term "therapeutic agent" means a molecule which has one or more biological activities in a normal or pathologic tissue. A variety of therapeutic agents can be used as a moiety.

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in homing compositions. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000). In particular, the moiety can be a paclitaxel-loaded albumin nanoparticle such as abraxane.

A cancer chemotherapeutic agent useful in a homing composition also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine or a derivative thereof can be a useful cancer chemotherapeutic agent.

A platinum agent also can be a useful cancer chemotherapeutic agent. Such a platinum agent can be, for example, cisplatin or carboplatin as described, for example, in Crown, Seminars in Oncol. 28:28-37 (2001). Other useful cancer chemotherapeutic agents include, without limitation, methotrexate, mitomycin-C, adriamycin, ifosfamide and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu. Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB389EGF, ricinus communis toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon .alpha. (IFN-α); interferon .gamma. (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, Pseudomonas exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The homing compositions disclosed herein can also be used to site of inflammation. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites. Thus, for example, also disclosed are homing compositions comprising an antimicrobial peptide, where the homing composition is selectively internalized and exhibits a high toxicity to the targeted area. Useful antimicrobial peptides can have low mammalian cell toxicity when not incorporated into the homing composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:151-155 (1990).); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into a homing composition can have low mammalian cell toxicity linked to Lyp-1. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, disclosed are homing compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, (SEQ ID NO:6) for example, is an antimicrobial peptide which induces marked mitochondrial swelling at a concentration of 10 μM, significantly less than the concentration required to kill eukaryotic cells.

An antimicrobial peptide that induces significant mitochondrial swelling at, for example, 50 μM, 40 μM, 30 μM, 20 μM, 10 μM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed compositions and methods. Thus, it is understood that a homing composition can contain one or more of such therapeutic agents and that additional components can be included as part of the composition, if desired. As a non-limiting example, it can be desirable in some cases to utilize an oligopeptide spacer between Lyp-1 and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed homing compositions can use any of these or similar agents.

ii. Detectable Agents

The moiety in the disclosed homing compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011, 686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or T1-201.

The use of Technitium-99m (Tc-99m) is preferable and has been described in other applications, for example, see U.S. Pat. Nos. 4,418,052 and 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraaza-cyclododecane-N—,N',N",N'"-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbiurn(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to Lyp-1 in such a way so as not to interfere with the ability of Lyp-1 to interact with gC1qR/p32. In some embodiments, the detectable agent can be chemically bound to Lyp-1. In some embodiments, the detectable agent can be chemically bound to a moiety that is itself chemically bound to Lyp-1, indirectly linking the imaging and targeting moieties.

G. Pharmaceutical Compositions and Carriers

The disclosed compositions can be administered in vivo in a pharmaceutically acceptable carrier. By "pharmaceutically acceptable" is meant a material that is not biologically or otherwise undesirable, i.e., the material can be administered to a subject, along with the homing composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

H. Combinatorial Chemistry/Screening Methods

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NO:1 or portions thereof, are used as the target in a combinatorial or screening protocol.

It is understood that when using the disclosed compositions in combinatorial techniques or screening methods, molecules, such as macromolecular molecules, will be identified that have particular desired properties, such as interaction with gC1qR/p32. The molecules identified and isolated when using the disclosed compositions, such as Lyp-1, are also disclosed. Thus, the products produced using the combinatorial or screening approaches that involve the disclosed compositions, such as Lyp-1, are also considered herein disclosed.

Disclosed herein are methods of screening for a compound that interacts with a gC1q/p32 receptor, comprising: bringing into contact a test compound, a Lyp-1 composition, and a gC1q receptor, wherein the Lyp-1 composition comprises SEQ ID NO:1; and detecting unbound Lyp-1 composition, wherein a given amount of unbound Lyp-1 composition indicates a compound that interacts with gC1q/p32 receptor.

Also disclosed is a method of screening for a test compound that modulates gC1q/p32 receptor activity, comprising: contacting a cell that comprises the gC1q/p32 receptor with a test compound; and detecting altered gC1q/p32 receptor activity; wherein altered levels of gC1q/p32 receptor activity indicate a compound that modulates gC1q/p32 receptor activity.

By "altered levels of activity" is meant that the gC1q/p32 receptor can display an increase or decrease in activity. The increase in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% increase, or a 1, 2, 3, 4, 5, 6, 7, 8, 9, 10, 20, 25, 30, 35, 40, 45, 50, 75, or 100 fold or more increase in activity, as compared to a standard, control, or basal level. The decrease in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease in activity as compared to a standard, control, or basal level. For example, a test compound can interact with the gC1q/p32 receptor in such as way as to decrease the ability of the gC1q/p32 receptor to interact with another compound, thereby decreasing its activity. In another example, a test compound can prevent the synthesis of the gC1q/p32 receptor, thereby decreasing its activity in that way.

Disclosed is a method of screening for a test compound that interacts with the gC1q/p32 receptor, comprising: contacting a cell that comprises the gC1q/p32 receptor with a test compound; and detecting interaction between the gC1q/p32 receptor and the test compound. After the test compound has been shown to interact with the gC1q/p32 receptor, it can further be tested for its ability to modulate gC1q/p32 receptor activity, including the ability to treat a gC1q/p32 receptor-related disorder.

Further disclosed is a method of screening for a test compound that can be used to treat a gC1q/p32 receptor-related disorder, such as cancer, comprising: contacting a cell that comprises the gC1q/p32 receptor with a test compound; and detecting altered gC1q/p32 receptor activity; wherein altered levels of gC1q/p32 receptor activity indicate a compound that can modulate gC1q/p32 receptor activity. After the test compound has been shown to modulate gC1q/p32 receptor activity, the test compound can then be tested for its ability to treat a gC1q/p32 receptor-related disorder.

The modulation can comprise a decrease in gC1q/p32 receptor activity, expression, or the ability to treat a gC1q/p32 receptor-related disease. By a "decrease" is meant that the activity is less in the presence of the test compound than not in the presence of the test compound. The modulation can comprise an increase in gC1q/p32 receptor activity or related activity. By an "increase" is meant that the activity is greater in the presence of the test compound than not in the presence of the test compound.

The response of the gC1q/p32 receptor can be measured in the presence of various concentrations of test compound. The measuring steps can also comprise measuring the response at various concentrations of the test compound. For example, the concentration of the test compound can range from 1 nM to 1000 μM.

Assays contemplated by the invention include both binding assays and activity assays; these assays may be performed in conventional or high throughput formats. Modulator screens are designed to identify stimulatory and inhibitory agents. The sources for potential agents to be screened include natural sources, such as a cell extract (e.g., invertebrate cells including, but not limited to, bacterial, fungal, algal, and plant cells) and synthetic sources, such as chemical compound libraries or biological libraries such as antibody substance or peptide libraries. Agents are screened for the ability to either stimulate or inhibit the activity. Binding assays are used to detect activity levels. Both functional and binding assays of activity are readily adapted to screens for modulators such as agonist (stimulatory) and antagonist (inhibitory) compounds.

Contemplated herein are a multitude of assays to screen and identify modulators, such as agonists and antagonists, of the gC1q/p32 receptor (and downstream activity). In one example, the cell is immobilized and interaction with a candidate modulator is detected. In another example, the test compound is immobilized. In yet another example, interaction between gC1q/p32 receptor and the test compound is assessed in a solution assay. Another contemplated assay involves a variation of the di-hybrid assay wherein a modulator of protein/protein interactions is identified by detection of a positive signal in a transformed or transfected host cell.

Candidate modulators for screening according to contemplated by the invention include any chemical compounds, including libraries of chemical compounds. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, or analogs of known compounds, or analogs of compounds that have been identified as "hits" or "leads" in prior drug discovery screens, some of which may be derived from natural products or from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of modulators through use of the various libraries described herein permits modification of the candidate "hit" (or "lead") to optimize the capacity of the "hit" to modulate activity.

Candidate modulators contemplated by the invention can be designed and include soluble forms of binding partners, as well as chimeric, or fusion, proteins thereof. A "binding partner" as used herein broadly encompasses non-peptide modulators, peptide modulators (e.g., neuropeptide variants), antibodies (including monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide as disclosed herein), antibody fragments, and modified compounds comprising antibody domains that are immunospecific for the expression product.

Assays that measure binding or interaction of compounds with target proteins include assays that identify compounds that inhibit unfolding or denaturation of a target protein, assays that separate compounds that bind to target proteins through affinity ultrafiltration followed by ion spray mass spectroscopy/HPLC methods or other physical and analytical methods, capillary electrophoresis assays and two-hybrid assays.

One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Alternatively, such binding interactions are evaluated indirectly using the yeast two-hybrid system described in Fields et al., Nature, 340:245-246 (1989), and Fields et al., Trends in Genetics, 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene.

The literature is replete with examples of the use of radiolabeled ligands in HTS binding assays for drug discovery (see Williams, Med. Res. Rev. 11:147-184 (1991); Sweetnam et al., J. Nat. Prod. 56:441-455 (1993) herein incorporated by reference in their entirety for their teaching concerning high throughput screens). It is also possible to screen for novel neuroregeneration compounds with radiolabeled ligands in HTS binding screens. Other reasons that recombinant receptors are preferred for HTS binding assays include better specificity (higher relative purity) and ability to generate large amounts of receptor material (see Hodgson, Bio/Technology 10:973-980 (1992)).

A variety of heterologous systems are available for expression of recombinant proteins and are well known to those skilled in the art. Such systems include bacteria (Strosberg et al., Trends in Pharm. Sci. 13:95-98 (1992)), yeast (Pausch, Trends in Biotech. 15:487-494 (1997)), several kinds of insect cells (Vanden Broeck, Intl. Rev. Cytol. 164:189-268 (1996)), amphibian cells (Jayawickreme et al., Curr. Opin. Biotechnol. 8:629-634 (1997)) and several mammalian cell lines (CHO, HEK293, COS, etc.; see Gerhardt et al., Eur. J. Pharmacol. 334:1-23 (1997); Wilson et al., Brit. J. Pharmacol. 125:1387-1392 (1998)). These examples do not preclude the use of other possible cell expression systems, including cell lines obtained from nematodes (WO 98/37177).

Inhibition of gC1qR/p32, or downstream products or genes related thereto, can result in a variety of biological responses, which are typically mediated by proteins expressed in the host cells. The proteins can be native constituents of the host cell or can be introduced through well-known recombinant technology. They can be mutants of native varieties as well. The proteins can be intact or chimeric.

Fluorescence changes can also be used to monitor ligand-induced changes in membrane potential or intracellular pH; an automated system suitable for HTS has been described for these purposes (Schroeder et al., J. Biomol. Screening 1:75-80 (1996)). Among the modulators that can be identified by these assays are natural ligand compounds; synthetic analogs and derivatives of natural ligands; antibodies, antibody fragments, and/or antibody-like compounds derived from natural antibodies or from antibody-like combinatorial libraries; and/or synthetic compounds identified by high throughput screening of libraries; and other libraries known in the art. All modulators that interact with gC1qR/p32 are useful for identifying Lyp-1-like polypeptides (e.g., for diagnostic purposes, pathological purposes, and other purposes known in the art). Agonist and antagonist modulators are useful for up-regulating and down-regulating gC1qR/p32 activity, respectively, for purposes described herein.

The assays may be performed using single putative modulators; they may also be performed using a known agonist in combination with candidate antagonists (or visa versa). Detectable molecules that may be used include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the biological function of the molecule and must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the GRK protein by methods as described in Barak et al. (U.S. Pat. Nos. 5,891,646 and 6,110,693). The detectable molecule may be conjugated at the front-end, at the back-end, or in the middle.

I. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as Lyp-1, are also disclosed. Thus, the products produced using the molecular modeling approaches that involve the disclosed compositions, such as Lyp-1, are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

J. Compositions with Similar Functions

It is understood that the compositions disclosed herein have certain functions, such as interacting with gC1qR/p32. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

K. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include Lyp-1 and gC1q/p32 receptors.

L. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

M. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

N. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

O. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO:1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Methods

Disclosed herein are methods of treating cancer comprising administering to a subject having cancer a composition comprising a tumor- or cancer-homing compound coupled to a paclitaxel-loaded albumin nanoparticle. The composition can further comprise one or more different tumor- or cancer-homing compounds coupled to the nanoparticle.

Also disclosed herein are methods of treating cancer comprising administering to a subject having cancer a composition comprising a Lyp-1 peptide coupled to a paclitaxel-loaded albumin nanoparticle.

Also disclosed herein are methods of treating cancer comprising administering to a subject having cancer a composition comprising a CREKA peptide coupled to a paclitaxel-loaded albumin nanoparticle. The paclitaxel-loaded albumin nanoparticle can be abraxane.

The Lyp-1 peptide can comprise SEQ ID NO:1 or SEQ ID NO:13. The Lyp-1 peptide can consist essentially of SEQ ID NO:1 or SEQ ID NO:13. The Lyp-1 peptide can be SEQ ID NO:1, SEQ ID NO:13, or a variant of SEQ ID NO:1 or SEQ ID NO:13 with one or more conservative amino acid substitutions. The Lyp-1 peptide can be SEQ ID NO:1 or SEQ ID NO:13.

The composition can further comprise a therapeutic moiety. The therapeutic moiety can target a DNA-associated process. The therapeutic moiety can be selected from the group consisting of, for example, a cytotoxic agent, an alkylating agent, an anti-tumor antibiotic, a sequence-selective agent, an anti-angiogenic agent, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

The method can further comprise identifying the subject as having a cancer associated with gC1q/p32 receptor. Identifying the subject as having a cancer associated with gC1q/p32 receptor can be accomplished by, for example, bringing into contact a cancer cell of the subject and a composition that selectively interacts with gC1q/p32 receptor; and detecting interaction between gC1q/p32 receptor and the composition that selectively interacts with gC1q/p32 receptor, thereby detecting the presence or level of gC1q/p32, wherein the presence or level of gC1q/p32 receptor identifies the subject as having a cancer associated with a gC1q/p32 receptor. The composition that selectively interacts with gC1q/p32 receptor can be a Lyp-1 composition, wherein the Lyp-1 composition comprises a moiety linked to a Lyp-1 peptide. The level of the composition that selectively interacts with gC1q/p32 receptor interacting with gC1q/p32 receptor is detected. The level of gC1q/p32 receptor in the subject can be compared to a previous measurement in the same subject. The level of gC1q/p32 receptor in the subject can be compared to a control level or standard level. The moiety can be, for example, a detectable agent, a polypeptide, a nucleic acid molecule, or a small molecule. The composition that selectively interacts with gC1q/p32 receptor can comprise a virus. The composition that selectively interacts with gC1q/p32 receptor can comprise a phage. The detectable agent can be a small molecule, a fluorophore, fluorescein, rhodamine, a radionuclide, indium-111, technetium-99, carbon-11, carbon-13, or a combination thereof.

The composition can further comprise a CREKA peptide coupled to the nanoparticle. The method can further comprise administering to the subject one or more second compositions each comprising a different tumor- or cancer-homing compound coupled to a paclitaxel-loaded albumin nanoparticle. The method can further comprise administering to the subject a second composition comprising a CREKA peptide coupled to a paclitaxel-loaded albumin nanoparticle.

Also disclosed are methods of interacting compositions with gC1qR/p32. Such interactions can be, for example, selective, targeted or homing. Interaction with gC1qR/p32 can be mediated by Lyp-1 and can involve any Lyp-1 or Lyp-1 composition as described herein. Interaction with gC1qR/p32 can be useful for detecting and/or treating diseases and conditions, such as diseases and/or conditions associated with gC1qR/p32.

Disclosed herein are methods of treating a disease associated with gC1q/p32 receptor comprising identifying a subject having a disease associated with the gC1q/p32 receptor; and administering to the subject a composition comprising SEQ ID NO:1 (Lyp-1).

Also disclosed are methods of treating a disease associated with gC1q/p32 receptor comprising identifying a subject having a disease associated with the gC1q/p32 receptor; and administering to the subject a composition that specifically interacts with gC1q/p32 receptor.

Also disclosed are methods of detecting the presence of gC1q/p32 receptor, comprising bringing into contact a cell and a composition, wherein the composition comprises a moiety linked to a composition that specifically interacts with gC1q/p32 receptor; and detecting interaction between gC1q/p32 receptor and the composition, thereby detecting the presence of gC1q/p32 receptor.

Further disclosed are methods of detecting interaction between a gC1q/p32 receptor and a composition, wherein the composition comprises a moiety linked to a composition that specifically interacts with gC1q/p32 receptor, the method comprising: selecting a cell for its potential to comprise a gC1q/p32 receptor; bringing into contact the composition and the cell; and detecting interaction between the gC1q/p32 receptor and the composition.

Also disclosed are methods of delivering a composition to a gC1q/p32 receptor, wherein the composition comprises a moiety linked to a composition that specifically interacts with gC1q/p32 receptor; wherein the method comprises bringing into contact the composition and a cell, thereby delivering the composition to the gC1q/p32 receptor.

Disclosed are methods of delivering a composition to a gC1q/p32 receptor, wherein the composition comprises a moiety linked to a composition that specifically interacts with gC1q/p32 receptor; comprising: selecting a cell for its potential to comprise a gC1q/p32 receptor; and bringing into contact the composition and the cell, thereby delivering the composition to the gC1q/p32 receptor.

Further disclosed are methods of determining and/or assessing gC1q/p32 receptor level in a cell of a subject, comprising: bringing into contact a cell of the subject and a composition comprising a detectable agent linked to a composition that specifically interacts with gC1q/p32 receptor; and detecting the level of composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a composition, wherein the composition comprises a moiety linked to a composition that specifically interacts with gC1q/p32 receptor; and detecting interaction between gC1q/p32 receptor and the composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as Lyp-1, thereby treating a disease associated with the gC1q/p32 receptor. The composition that interacts with the gC1q/p32 receptor can be, for example, an antibody, protein, or chemical.

Disclosed are methods of delivering a Lyp-1 composition to a gC1q/p32 receptor, wherein the Lyp-1 composition comprises a moiety linked to a composition comprising SEQ ID NO:1; wherein the method comprises bringing into contact the Lyp-1 composition and a cell, thereby delivering the Lyp-1 composition to the gC1q/p32 receptor.

In one example, the cell is in a subject. When the cell is in a subject, the cell can be selected for its potential to comprise a gC1q/p32 receptor by detecting the presence of gC1q/p32 receptor on another cell of the subject.

Also disclosed are methods of delivering a Lyp-1 composition to a gC1q/p32 receptor, wherein the Lyp-1 composition comprises a moiety linked to a composition comprising SEQ ID NO:1; comprising: selecting a cell for its potential to comprise a gC1q/p32 receptor; and bringing into contact the Lyp-1 composition and the cell, thereby delivering the Lyp-1 composition to the gC1q/p32 receptor.

Also disclosed are methods of detecting interaction between a gC1q/p32 receptor and a Lyp-1 composition, wherein the Lyp-1 composition comprises a moiety linked to a composition comprising SEQ ID NO:1, the method comprising: selecting a cell for its potential to comprise a gC1q/p32 receptor; bringing into contact the Lyp-1 composition and the cell; and detecting interaction between the gC1q/p32 receptor and the Lyp-1 composition.

Disclosed are methods of determining and/or assessing gC1q/p32 receptor level in a cell of a subject, comprising: bringing into contact a cell of the subject and a Lyp-1 composition comprising a detectable agent linked to a composition comprising SEQ ID NO:1; and detecting the level of Lyp-1 composition interacting with gC1q/p32 receptor, thereby determining and/or assessing gC1q/p32 receptor level in the cell. The level of gC1q/p32 receptor in the subject is compared to a previous measurement in the same subject, or can be compared to a control level or standard level.

Also disclosed are methods of identifying a subject having a disease associated with gC1q/p32 receptor, the method comprising bringing into contact a cell of the subject and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of screening for a compound that interacts with a gC1q/p32 receptor, comprising bringing into contact a test compound, a Lyp-1 composition, and a gC1q/p32 receptor, wherein the Lyp-1 composition comprises SEQ ID NO:1; and detecting unbound Lyp-1 composition, wherein a given amount of unbound Lyp-1 composition indicates a composition that interacts with gC1q/p32 receptor. The Lyp-1 composition can comprise a moiety, wherein the moiety comprises SEQ ID NO:1. In one example, the moiety can be a detectable agent. Methods of screening are discussed in more detail below.

Further disclosed herein is a method of treating or preventing a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. The composition can have a therapeutic effect on the cancer. The size of a tumor can be reduced. The growth of a tumor can be reduced, stopped or reversed.

Expression or activity of the gC1q/p32 receptor can be inhibited. This can occur by the use of interfering nucleic acid, such as shRNA or siRNA. Activity of the gC1q/p32 receptor can be inhibited by LyP-1 peptide, an antibody, or a small molecule mimic of Lyp-1. Examples of these can be found in FIG. 10 and Example 2. The methods of treating or preventing cancer disclosed herein can be used in conjunction with other treatment therapies as well.

The therapeutic effect of the composition disclosed above can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The gC1q/p32 receptor involved in the disclosed methods can be, for example, on or in a cell. The cell can be in any context, such as in an organism, in situ, ex vivo, in culture, and/or in vitro.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

EXAMPLES

A. Example 1

Lyp-1 and gC1qR/p32

Figure 1B:
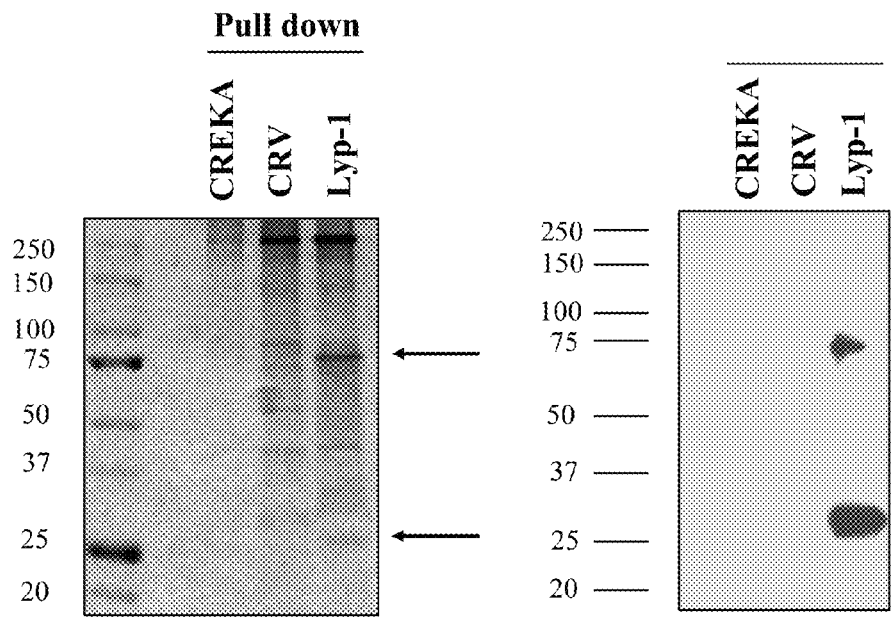

Interaction of Lyp-1 with gC1qR/p32 was demonstrated in a pull down assay. Pull down assays were performed with biotinylated Lyp-1 peptide (SEQ ID NO:1, CGNKRTRGC) from protein extracts derived from MDA-MB-435 cultured cells or MDA-MB-435 tumor xenografts. A tumor homing peptide, CREKA (SEQ ID NO:3), and a peptide CRV which resembles Lyp-1 in its amino acid composition and cyclic structure (SEQ ID NO:4, CRVRTRSGC), were used as negative controls. The Lyp-1 bound proteins were visualized using silver staining and immunoblotting. The left panel of FIG. 1(a) shows the results of silver staining. The arrow indicates a specific 33 kD band, which was identified as gC1qR/p32 by mass spectrometry. The right panel of FIG. 1(a) shows the results of immunoblotting of total cell extract (Tot lysate) and proteins bound to Lyp-1 and control peptides using a monoclonal antibody against gC1qR/p32. The antibody recognizes a band of 33 kD in the total proteins lysate and in the Lyp-1 pull down. Anti gC1qR/p32 reactive bands are not detected in the pull downs from both control peptides. The left panel of FIG. 1(b) shows the results of silver staining of proteins pulled down from MDA-MB-435 tumor xenografts by Lyp-1 peptide, revealed an additional 75 kD band, which was also identified as gC1qR/p32 by mass spectrometry. The right panel of FIG. 1(b) shows the results of immunoblotting. The monoclonal antibody against gC1qR/p32 recognized a 75 kD and a 33 kD band only in the Lyp-1 peptide pull down.

Lyp-1 expressing phage was shown to specifically bind to purified gC1qR/p32 protein. Purified gC1qR/p32 or BSA, as a control, were coated onto microtiter wells (5 µg/ml) and targeted for binding with 10⁸ pfu of insertless phage, Lyp-1 phage, or control phage carrying another tumor homing peptide (CREKA, SEQ ID NO:3). After 16 hours of incubation at 37° C., bound phages were eluted and quantified by plaque assay. The results are show in FIG. 2(a). Results are expressed as fold of Lyp-1 and CREKA (SEQ ID NO:3) phages recovered over insertless phage and are representative of five independent experiments.

An antibody against the N-terminus of gC1qR/p32 was shown to inhibit Lyp-1 phage binding to purified gC1qR/p32. The left panel of FIG. 2(b) shows a diagram of precursor (aa 1-282) and mature (aa 74-282) gC1qR/p32 protein. Boxes indicate the amino acid residues recognized by the monoclonal antibodies, mAb 60.11 and mAb 74.5.2, respectively at the N-terminus (aa 76-93) and C-terminus (aa 204-282) of the mature protein. The amino acid sequence recognized by mAb 60.11 is also indicated. $1.5 \times 10^7$ pfu of insertless and Lyp-1 phages were allowed to bind for 6 hours at 37° C. to gC1qR/p32 protein coated onto microtiter plates in the presence or absence of 20 µg/ml of either mAbs 60.11, 74.5.2 or purified mouse IgG1 (mIgG). The results are shown in the right panel of FIG. 2(b). The results are representative of three independent experiments and are expressed as percentage of phage binding, with Lyp-1 phage binding alone as 100%.

gC1qR/p32 protein levels and cell surface expression was measured in cultured tumor cells and tumor xenografts. Lysates of different tumor cell lines were subjected to Western blot analysis for gC1qR/p32. Actin was used as loading control. C8161 melanoma cells and HL-60 promyelocitic leukemia cells, both low binders of Lyp-1 phage (Laakkonen et al., 2002), express low levels of gC1qR/p32 compared to MDA-MB-435 and BT549 breast cancer cells which exhibit higher Lyp-1 phage binding ability (see FIG. 4(a)). (b-c) FACS analysis was used to detect the cell surface expression of gC1qR/p32 in tumor cell cultures (FIG. 4(b)) or primary cell suspensions from MDA-MB-435 tumor xenografts (FIG. 4(c)). Propidium iodide negative (living) cells were gated for the analysis. In cell suspensions from MDA-MB-435 tumor xenografts, polyclonal anti-gC1qR/p32 antibody causes a significant shift of the FACS peak compared with the rabbit IgG control (see FIG. 4(c)). The cell surface expression of gC1qR/p32 is low in cultured MDA-MB-435 and BT549 cells (see FIG. 4(b)). MDA-MB-435 S35, a MDA-MB-435 subclone with higher Lyp-1 phage binding ability, exhibits a bigger shift of the FACS peak compared to the parental MDA-MB-435 cells. gC1qR/p32 is not expressed on the cell surface in C8161 cells.

gC1qR/p32 overexpression was shown to enhance Lyp-1 phage binding to C8161 melanoma cells. C8161 cells were transiently transfected with pEGFP (2 µg) together with either pcDNA3 or pcDNA3gC1qR/p32 (10 µg). 22 hours post transfection cells were sorted for EGFP expression. The two sorted populations were used for phage binding assay and Western blot analysis to detect gC1qR/p32 overexpression. The results are shown in FIG. 5. Lyp-1 phage binding to empty vector or gC1qR/p32 transfected cells is expressed as fold of binding over insertless phage. The graph represents the mean fold of binding of two independent experiments performed in duplicate.

RNAi-mediated gC1qR/p32 silencing was shown to decrease Lyp-1 peptide binding to the cell surface. MDA-MB-435 cells were transiently transfected with gC1qR/p32-specific or control siRNAs. 48 hours after transfection, inhibition of gC1qR/p32 expression was checked by Western blot analysis and immunostaining. β-actin was used as a control. gC1qR/p32 silencing visibly reduced gC1qR/p32 in both the Western blot and in immunostaining. gC1qR/p32 cell surface expression in control and gC1qR/p32-siRNA transfected cells was determined by FACS analysis on living (propidium iodide negative) cells. Rabbit IgG were used as staining control. gC1qR/p32 silencing reduced cell surface expression to be the same as the control. gC1qR/p32 or control siRNA transfected cells were incubated for 1 hour at 4° C. in the presence of 10 µM FITC conjugated Lyp-1 peptide or a control peptide-ARAL-which has same amino acid charge (ARALPSQRSR, SEQ ID NO:5) and exhibits less binding ability (first graft on the left). The amount of fluorescence in living cells was analyzed by FACS. Cells incubated in the absence of peptide served as FITC negative control. Compared to control siRNA transfected cells, down-regulation of gC1qR/p32 expression (in the presence of gC1qR/p32 siRNA) caused a shift in the peak of Lyp-1 fluorescence but not control peptide fluorescence. Detection of the control peptide showed no difference in the cells exposed to the gC1qR/p32 siRNA and the control siRNA.

Tumor localization of gC1qR/p32 and Lyp-1 peptide were visualized. gC1qR/p32, lymphatic or blood vessels, podoplanin and Meca32/CD31 were stained with fluorescently-labeled antibodies in MDA-MB-435 tumor xenografts. Polyclonal anti-gC1qR/p32 antibody recognizes cell clusters that lack blood vessels but contain lymphatics, or cells lining vessel-like structures positive for Podoplanin but not CD31 or Meca32. Fluorescein-conjugated Lyp-1 peptide was i.v. injected into mice bearing MDA-MB-435 tumors and allowed to circulate for 1 hour before removal of the tumor for gC1qR/p32 immunohistochemical analysis. Lyp-1 peptide localizes in gC1qR/p32-positive patches within the tumor.

B. Example 2

The Mitochondrial/Cell Surface Protein p32/gC1qR Regulates the Balance Between Glycolysis and Oxidative Phosphorylation in Tumor Cells 1. Introduction A tumor homing peptide, LyP-1, selectively binds to tumor-associated lymphatic vessels and tumor cells in certain tumors and exhibits an anti-tumor effect. It is herein shown that the multi-ligand, multi-compartmental protein p32/gC1qR is the receptor for LyP-1. The LyP-1 peptide specifically bound gC1qR/p32 from extracts of cultured tumor cells, and gC1qR/p32 co-localized with intravenously injected LyP-1 in tumor lymphatics and in cells positioned adjacent to these vessels. Immunohistochemical analysis of human tissues revealed greatly elevated expression of gC1qR/p32 in several cancers relative to corresponding normal tissues. Knocking down gC1qR/p32 expression with shRNA elevated glycolysis and decreased mitochondrial respiration in MDA-MB-435 tumor cells. Surprisingly, the knockdown compromised the ability of the tumor cells to survive and proliferate in low glucose conditions and severely diminished their tumorigenicity in vivo. Restored expression of gC1qR/p32 reversed these changes.

Tumors can be distinguished from their non-malignant counterparts by specific molecular signatures expressed in malignant cells and tumor vasculature. Tumor associated antigens such as certain growth factor and cytokine receptors, membrane-type matrix metalloproteinases, and cell adhesion molecules are highly expressed in many tumors. Similarly, biochemical features that distinguish tumor vasculature from the vasculature of normal tissues include the expression of various angiogenesis-related molecules (Ruoslahti, 2002; St Croix et al., 2000). Tumor lymphatics are also specialized, since they express markers that are not present in the lymphatics of normal tissues (or in tumor blood vessels) (Laakkonen et al., 2002; Zhang et al., 2006). The markers in tumor blood vessels and lymphatics can vary between tumor types, and the marker profile of the vessels changes as tumorigenesis advances from premalignant lesions to fully malignant tumors (Hoffman et al., 2003; Joyce et al., 2003; Zhang et al., 2006).

The distinct protein profile of tumor vessels and tumor cells can be exploited in ligand-directed (synaphic) targeting of diagnostic therapeutic agents. Targeting can improve the specificity and efficacy of a compound while reducing side effects (Arap et al., 2002; Arap et al., 1998b; Jain, 1998). This partial success emphasizes the need to find new molecules that recognize selectively expressed markers in tumors.

In vivo screening of phage libraries that display random peptide sequences on their surface has yielded a number of specific homing peptides for tumor vasculature and tumor cells (Arap et al., 1998a; Porkka et al., 2002). Identification of receptors for homing peptides provides new tumor markers, and may also reveal signaling pathways that, if interrupted, affect tumor growth/malignancy. LyP-1, a cyclic nonapeptide that specifically recognizes lymphatic vessels in certain tumors (Laakkonen et al., 2002), is a case in point. Lymphatic vessels are an important conduit for the spread of solid tumors, and their abundance in and around tumors correlates with propensity to metastasize (Alitalo et al., 2004; Stacker et al., 2002).

The LyP-1 peptide provides a marker for these vessels, but also binds to tumor cells, offering the ability to selectively target both tumor lymphatics and tumor cells. Moreover, the target molecule (receptor) for the LyP-1 peptide appears to be involved in tumor growth because systemic administration of LyP-1 inhibits tumor growth in mice (Laakkonen et al., 2004). LyP-1 appears to be cytotoxic against tumor cells undergoing stress, as LyP-1 accumulation coincides with hypoxic areas in tumors and tumor starvation enhances its binding and internalization in cultured tumor cells (Laakkonen et al., 2004). These unique properties of the LyP-1 system prompted the search for the tumor cell receptor for this peptide.

In this study, p32/p33/gC1qR/HABP1 (p32) has been identified as the cellular receptor for LyP-1. This protein was originally isolated based on its co-purification with the nuclear splicing factor SF-2 (Krainer et al., 1991). It was also found to bind to the globular heads of the C1q protein and was therefore designated the gC1q/p32 receptor (gC1qR/p32) (Ghebrehiwet et al., 1994). Plasma proteins and extracellular matrix components, such as kininogen, factor XII, vitronectin and hyaluronic acid, have been also reported to bind to gC1qR/p32 (Deb and Datta, 1996; Herwald et al., 1996; Joseph et al., 1996; Lim et al., 1996). In addition, gC1qR/p32 interacts with several bacterial and viral proteins, showing its possible role in microbial pathogenesis (Braun et al., 2000; Kittlesen et al., 2000; Matthews and Russell, 1998; Tange et al., 1996).

The gC1qR/p32 protein can be present in diverse cellular compartments depending on the cell type and physiological conditions. This protein has been variously located in mitochondria (Dedio et al., 1998; Matthews and Russell, 1998; Muta et al., 1997), nucleus (Krainer et al., 1991; Majumdar et al., 2002), and at the cell surface (Ghebrehiwet et al., 1994; Gupta et al., 1991; Soltys et al., 2000). It may also be secreted and bound to the extracellular matrix (Herwald et al., 1996; Lim et al., 1996; Rozanov et al., 2002a). The disparate observations on its multiple protein interactions and cellular localization, have left the physiological role(s) of gC1qR/p32 in mammalian cells unclear. In the yeast, the gC1qR/p32 homologue has been reported to regulate oxidative phosphorylation (Muta et al., 1997).

It is herein shown that knocking down gC1qR/p32 expression in tumor cells shift their metabolism toward glycolysis and that, surprisingly, the glycolytic phenotype is associated with impaired tumor cell survival and growth, especially under adverse growth conditions. At the same time, tumorigenicity of the gC1qR/p32 knockdown cells is reduced.

2. Results i. LyP-1 Peptide Binds to gC1qR/p32 Protein

To identify the receptor for the LyP-1 peptide, biotin-labeled LyP-1 and control peptides were incubated with extracts of MDA-MB-435 cells, a cell line that binds and internalizes LyP-1 (Laakkonen et al., 2004). LyP-1 bound a specific band in the 30 kDa range that was not seen in the controls (FIG. 3A, left panel), which were the pentapeptide CREKA (SEQ ID NO:3) (Simberg et al., 2007) and the nonapeptide CRVRTRSGC (SEQ ID NO:4), which resembles LyP-1 in its amino acid composition and cyclic structure. Two independent MALDI-TOF analyses indicated that the specific band represents the mature form of a protein known as gC1qR/p32, a receptor for the globular head of complement component C1q (Ghebrehiwet et al., 2002; Ghebrehiwet et al., 1994). LyP-1 affinity isolation also yielded gC1qR/p32 from cultured BT549 breast carcinoma cells and from extracts of MDA-MB-435 xenograft tumors.

Figure 3A:
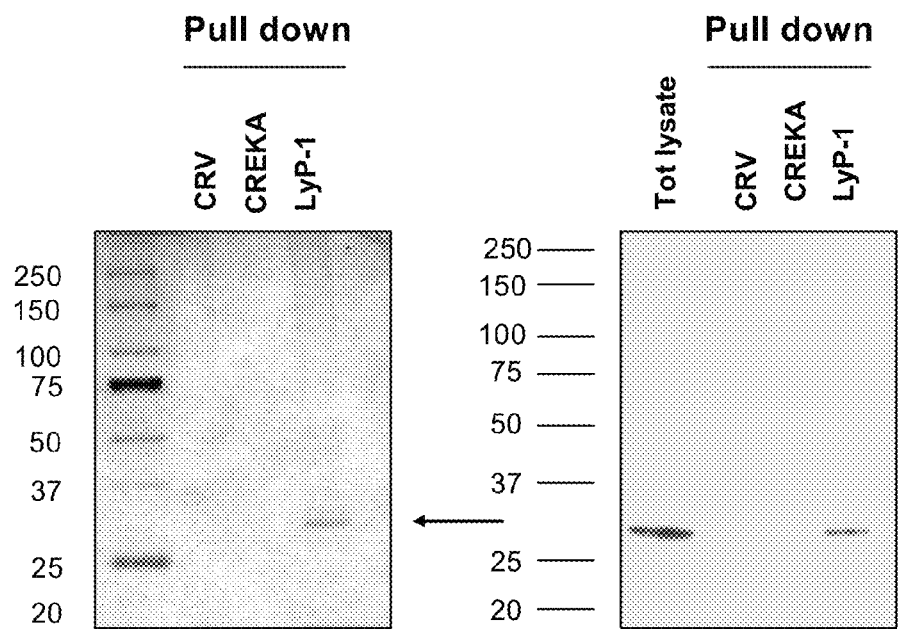
FIG. 3 shows LyP-1 peptide binds to p32 protein in tumor cell extracts. A. Proteins bound to biotinylated LyP-1 peptide (CGNKRTRGC, SEQ ID NO:1) from extracts of cultured MDA-MB-435 cells. Peptides with the sequences CREKA (SEQ ID NO:3) and CRVRTRSGC(CRV, SEQ ID NO:4) were used as negative controls in the pull down. Left panel: silver staining of LyP-1 bound proteins. The arrow indicates a specific band that was identified as p32 by mass spectrometry. Right panel: Anti-p32 immunoblot of total cell extract (lysate) and proteins bound to the LyP-1 and control peptides. B. Phage binding to p32. Purified p32, or BSA as a control, were coated onto microtiter wells and binding of LyP-1 phage, insertless phage, and phage clones displaying the tumor homing peptides CREKA (SEQ ID NO:3) and LyP-2 (CNRRTKAGC, SEQ ID NO:7) to the wells was tested. Results are expressed as fold of bound peptide phage over insertless phage (±SD) and are representative of five independent experiments. C. Diagrammatic representation of precursor (amino acids 1-282) and mature (amino acids 74-282) forms of p32 protein. Boxes indicate the amino acid residues recognized by the monoclonal antibodies, mAb 60.11 and mAb 74.5.2, respectively, at the N-terminus (amino acids 76-93) and C-terminus (amino acids 204-282) of the mature protein. The amino acid sequence recognized by mAb 60.11 is also shown. D. Inhibition of LyP-1 phage binding to purified p32 by mAb 60.11. Anti-p32 mAb 74.5.2 and purified mouse IgG1 (mIgG; negative control) do not inhibit the binding. The results are representative of three independent experiments and are expressed as percentage of phage binding (±SD), with LyP-1 phage binding alone as 100%.
Figure 3B:
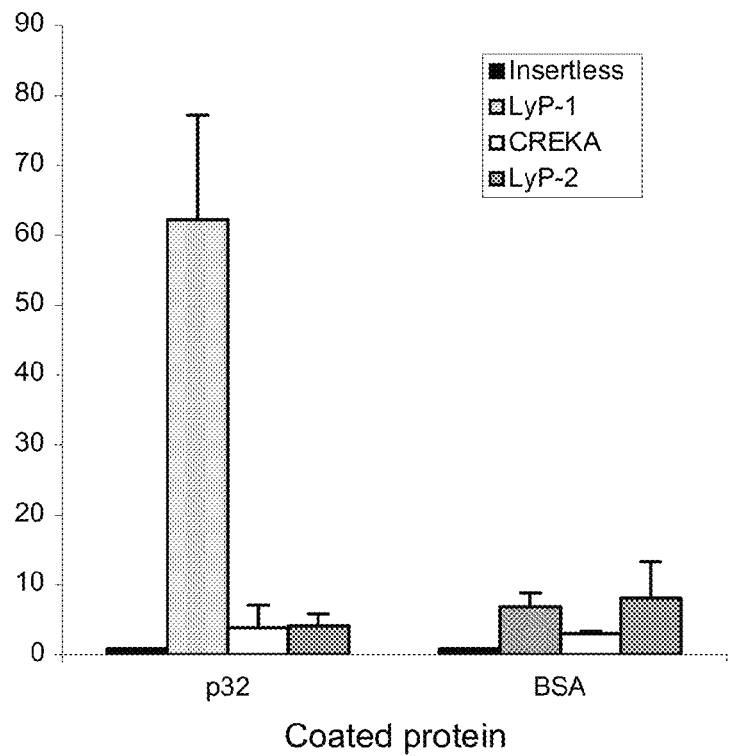
Figure 3C:
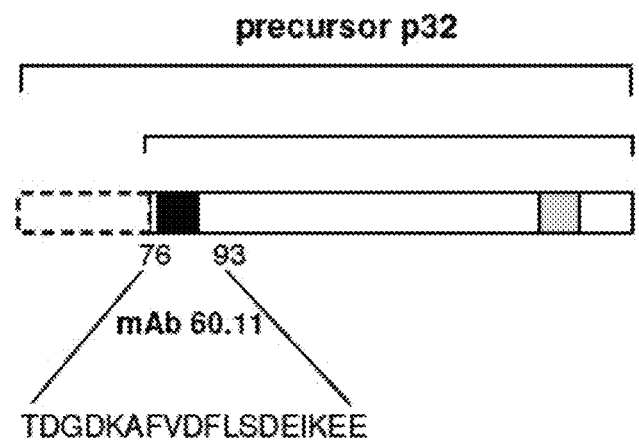
Figure 3D:
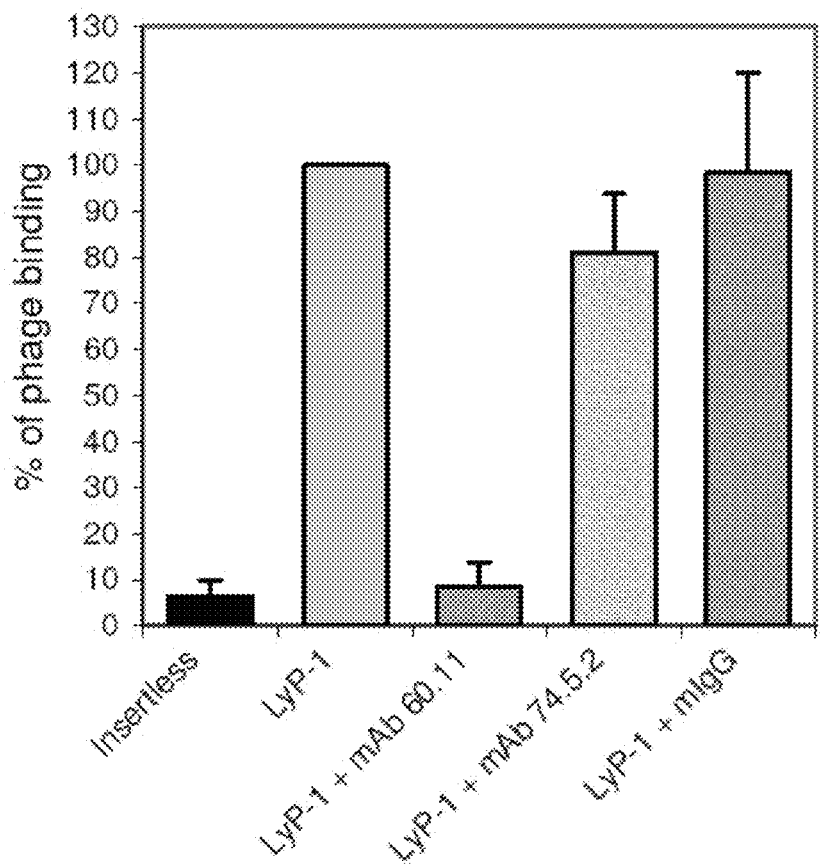

The identification of the LyP-1-binding protein as gC1qR/p32 was confirmed by immunoblotting and phage binding assays. A monoclonal antibody directed against gC1qR/p32 specifically recognized the band (FIG. 3A right panel). No detectable gC1qR/p32 was pulled down by the control peptides. The LyP-1 phage bound to purified gC1qR/p32 protein an average of 60-fold more than insertless control phage, while only marginal binding of either phage to plates coated with BSA was seen (FIG. 3B). LyP-2, a peptide, which shares a consensus sequence with LyP-1 but binds a different spectrum of tumor lymphatics (Zhang et al., 2006), did not significantly bind to gC1qR/p32. A monoclonal antibody, mAb 60.11, which binds to gC1qR/p32 near the N-terminus (amino acids 76-93), reduced LyP-1 phage binding to gC1qR/p32 by 90% (FIG. 3C). In contrast, mAb 74.5.2, which recognizes the C-terminal end of gC1qR/p32 (amino acids 204-218), did not inhibit the phage binding. These results indicate that the interaction between LyP-1 and gC1qR/p32 is specific and that the N-terminus of gC1qR/p32 between amino acids 76 and 93 plays an important role in the interaction.

Figure 4B:
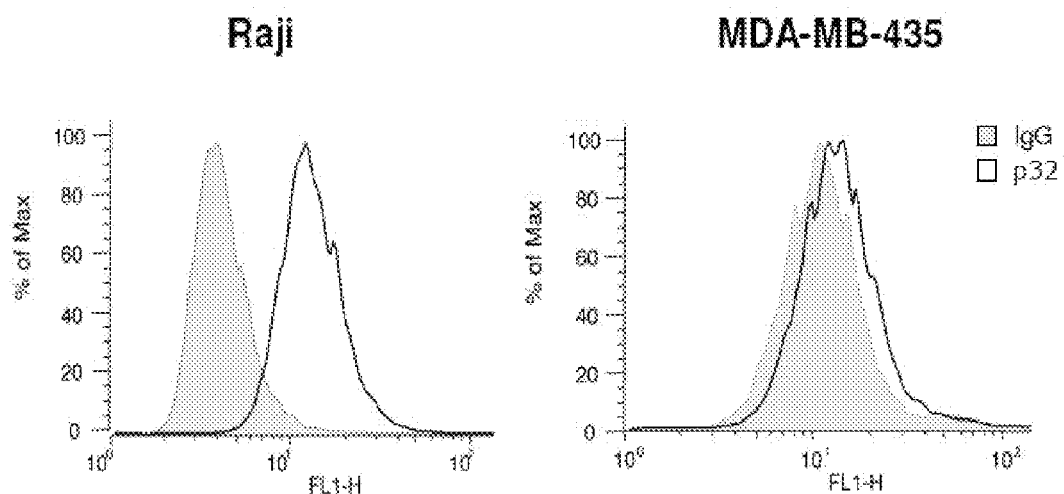
Figure 4B:
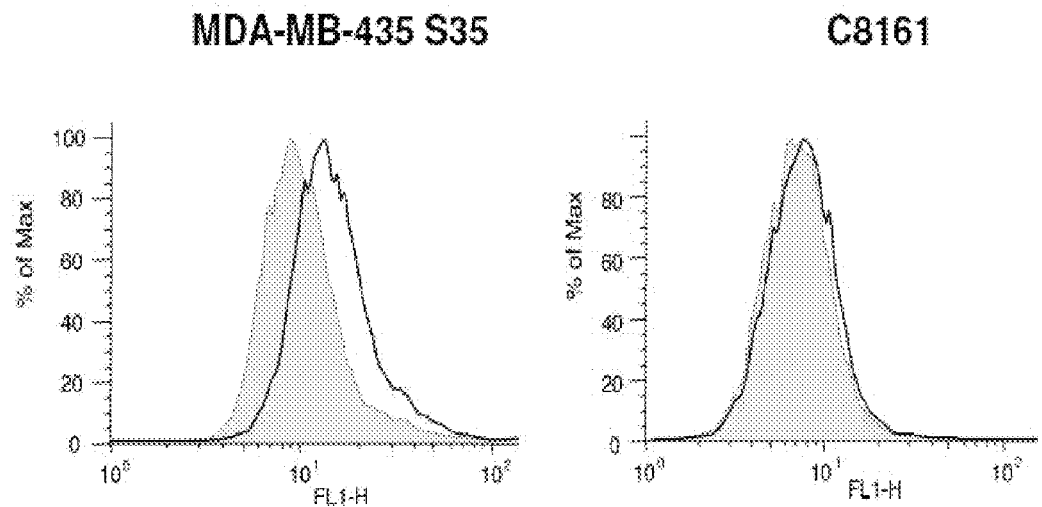
Figure 4C:
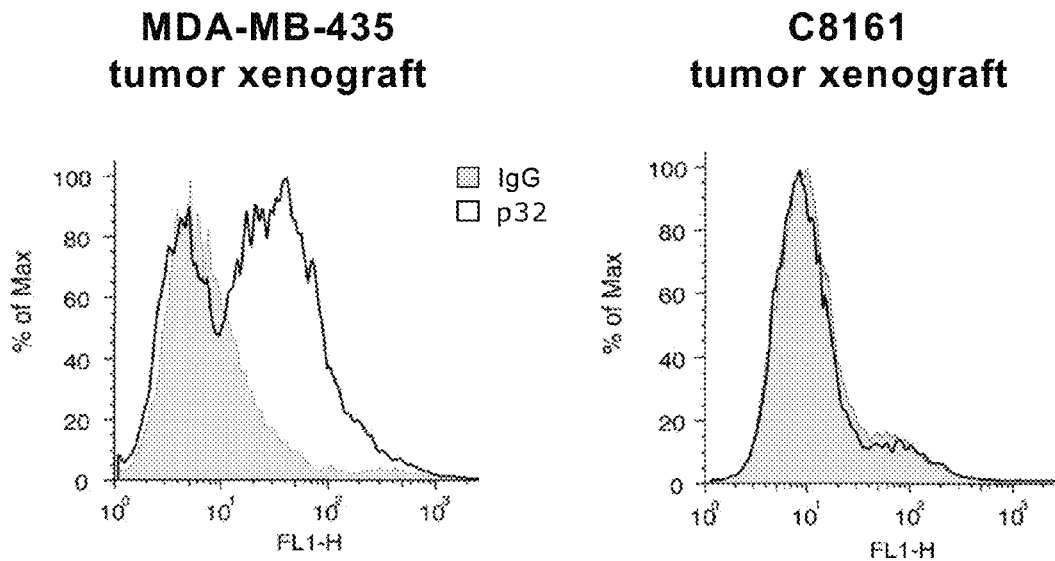

Immunoblotting revealed a correlation between gC1qR/p32 expression and LyP-1 binding in a number of tumor cell lines; HL-60 leukemia cells and C8161 melanoma cells, previously shown not to significantly bind LyP-1 (Laakkonen et al., 2002), expressed low levels of gC1qR/p32 protein, whereas two strong LyP-1 binders, MDA-MB-435 and BT549 ((Laakkonen et al., 2002), expressed abundant gC1qR/p32 (FIG. 4A).

ii. The gC1qR/p32 Protein is Expressed at the Cell Surface and Mediates LyP-1 Binding For gC1qR/p32 to act as a LyP-1 receptor, it would have to be expressed at the cell surface. While primarily localized in intracellular compartments (mitochondria, nucleus and cytoplasm), gC1qR/p32 has also been reported to be present at cell surface (Ghebrehiwet et al., 1994; Guo et al., 1999; Peerschke et al., 1994). gC1qR/p32 was also found at the cell surface. A polyclonal anti-gC1qR/p32 antibody produced a small but consistent shift in FACS analysis of live MDA-MB-435 cells (FIG. 4B). A greater shift was obtained in an MDA-MB-435 subclone (S35), which binds LyP-1 with higher efficiency than the parental cell line. Raji Burkitt lymphoma cells were even more strongly positive. Interestingly, the total gC1qR/p32 expression level was similar in the parental MDA-MB-435 and the S35 variant cells (FIG. 4A). Single cell suspensions from MDA-MB-435 tumor xenografts were more strongly positive for cell surface gC1qR/p32 protein than cultured MDA-MB-435 cells, whereas C8161 cells remained essentially negative for LyP-1 binding even as primary tumor cells (FIG. 4C).

Figure 5C:
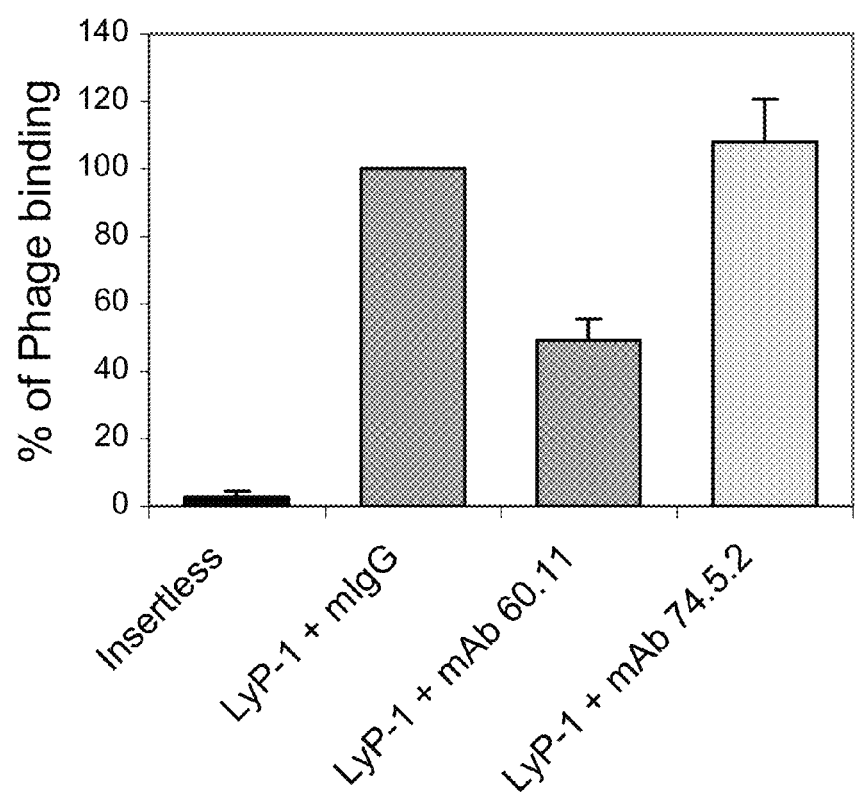

The effect of forced expression and knockdown of gC1qR/p32 on LyP-1 binding was next studied. Transient transfection of C8161 cells with gC1qR/p32 cDNA increased LyP-1 phage binding to 5-fold over control phage (FIG. 5A). A less than 2-fold binding was obtained upon transfection with the empty vector. Transfection with a gC1qR/p32 siRNA construct markedly reduced expression in MDA-MB-435 cells (FIG. 5B, upper left panel), with an accompanying reduction in the binding of FITC-LyP-1 peptide to the cells (FIG. 5B lower left panel). Controls showed that an unrelated siRNA did not affect gC1qR/p32 expression or LyP-1 binding, and neither siRNA changed the expression of β-actin. Also, a control peptide, which like LyP-1 has three basic residues but does not significantly bind to the MDA-MB-435 cells (Laakkonen et al., 2002), gave the same amount of background fluorescence in the gC1qR/p32 knockdown and control cells (FIG. 5B, lower right panel). Finally, blocking gC1qR/p32 with mAb 60.11 in Raji cells (which express high levels of cell surface gC1qR/p32) reduced LyP-1 binding to these cells by 50%, while the phage binding was unaffected by mAb 74.5.2 (FIG. 5C). These results are consistent with those obtained with purified gC1qR/p32 protein (FIG. 3C) and indicate that the gC1qR/p32 level expression at the cell surface dictates LyP-1 binding to the cells. They also suggest that cell surface localization of gC1qR/p32 is regulated independently of total gC1qR/p32 expression, and that tumor microenvironment may enhance the cell surface expression.

iii. Expression of gC1qR/p32 in MDA-MB-435 Tumor Xenografts and Human Cancers

Figure 6A:
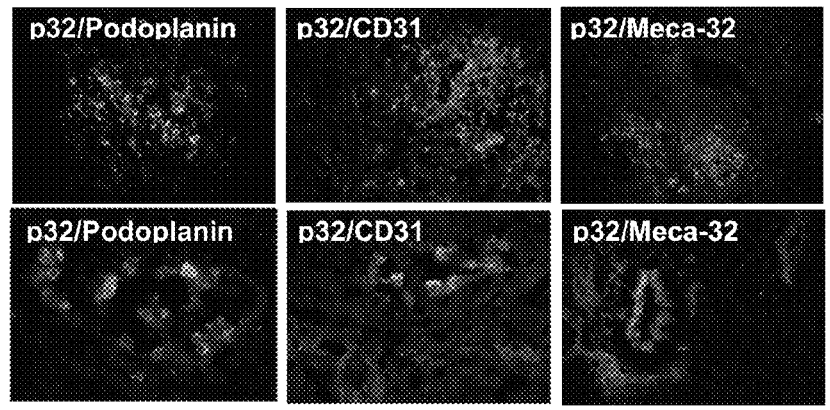
FIG. 6 shows expression of p32 in tumor xenografts and human cancers. A. Double staining of sections from MDA-MB-435 xenograft tumors for p32 and podoplanin as a marker for lymphatic vessels, or CD31 and Meca-32 as markers for blood vessels. Polyclonal anti-p32 antibody recognizes cell clusters in podoplanin-positive areas. Cells that are positive both for p32 and podoplanin frequently line vessel-like structures that are negative for the blood vessel markers (lower panels). B. Co-localization of LyP-1 peptide and p32 in tumors. Fluorescein-conjugated LyP-1 peptide was intravenously injected into mice bearing MDA-MB-435 tumors and allowed to circulate for 1 hour before removal of the tumor for p32 immunohistochemical staining and analysis of LyP-1 fluorescence. C. Partial tumor co-localization of intravenously injected FITC-LyP-1 peptide (upper panel) and p32 protein (lower panels) with the macrophages markers CD11b and Gr-1. D and E. Immunohistochemical detection of p32 in human tissue arrays. Anti-p32 mAb 60.11 was used for the staining. (D) Sequential tissue sections were stained separately for p32 and epithelial membrane antigen (EMA). (E) Comparison of p32 expression in tumors and the corresponding normal tissues. Parallel sections of all tissues examined were incubated with mIgG instead of mAb60.11 and showed no staining.
Figure 6B:
Figure 6C:
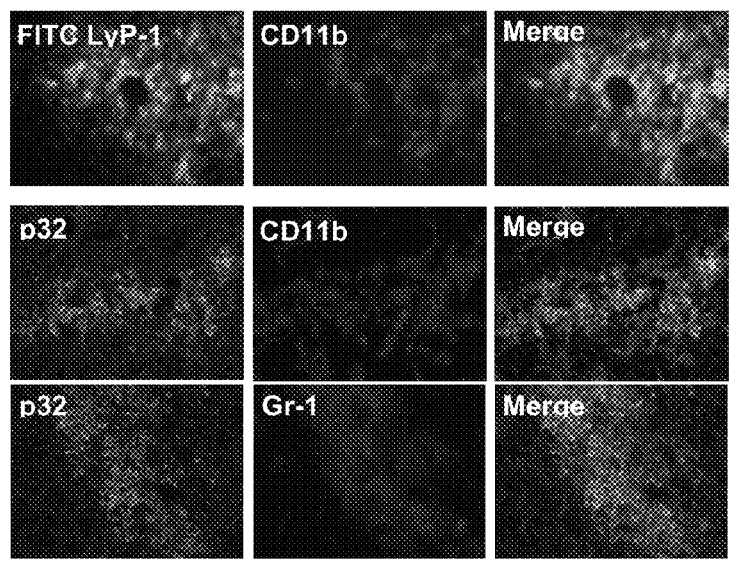

To investigate the localization of gC1qR/p32 in tumors, sections of MDA-MB-435 tumor xenografts were stained for gC1qR/p32 and podoplanin (a lymphatic/macrophage marker). Clusters of cells strongly positive for gC1qR/p32 were found in close proximity to tumor lymphatics, whereas there was no association with blood vessels as visualized by staining for CD31 or Meca-32 (FIG. 6A, upper panels). Cells expressing gC1qR/p32 were also found lining vessel-like structures that were also positive for podoplanin, but not for CD31 or Meca-32 (FIG. 6A, lower panels). Normal tissues and C8161 tumor xenografts showed much less gC1qR/p32 staining than the MDA-MB-435 tumors. Intravenously injected FITC-LyP-1 peptide accumulated in tumor areas with high expression levels of gC1qR/p32 and closely associated with vessel lumens (FIG. 6B). There was a good degree of co-localization of the gC1qR/p32/LyP-1 positive cells and the macrophage markers DC11b and Gr-1 (FIG. 6C). The localization of gC1qR/p32 in the lymphatic areas of tumors confirms the previously noted association of LyP-1 with MDA-MB-435 tumor lymphatics. The gC1qR/p32-positive cells integrated into the lymphatics in these tumors are likely tumor macrophages and/or macrophage-like precursors of lymphatic endothelial cells.

Figure 6D:
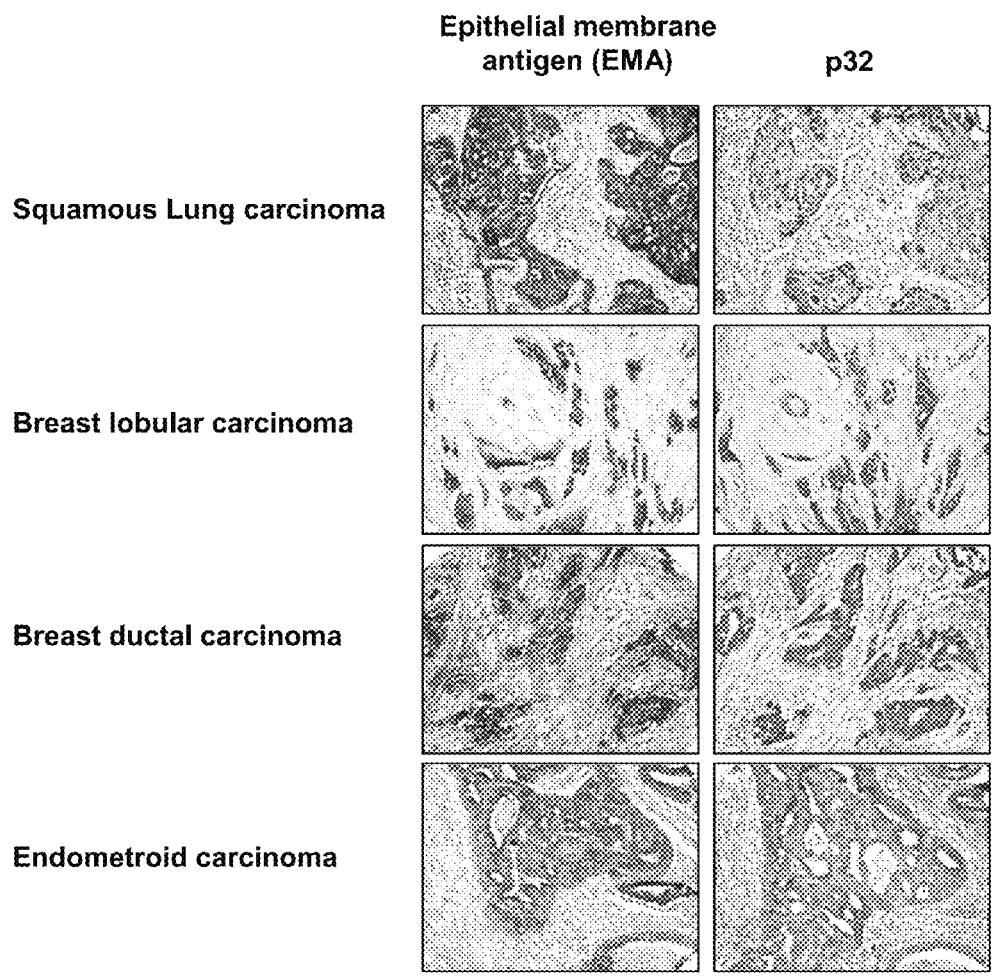
Figure 6E:
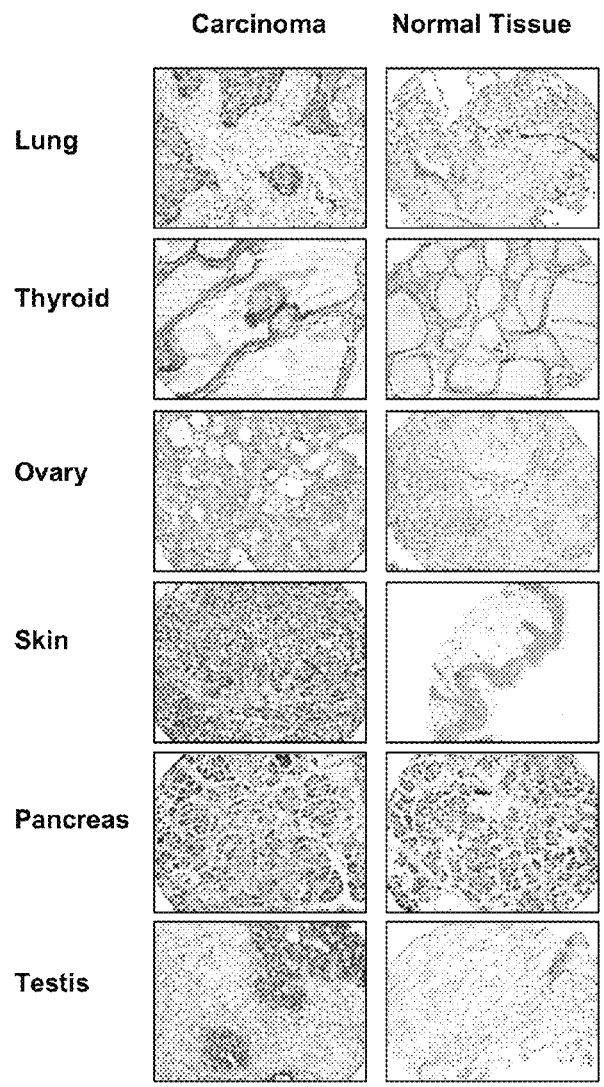

Next, the levels of gC1qR/p32 expression in a variety of human carcinomas were compared by immunohistochemical staining for gC1qR/p32 in clinical samples. The intensity of the staining (FIG. 6D, right panel) was visually scored and compared with a parallel staining for an epithelial membrane antigen in tumor cells (6D, left panel). An immuno-score was assigned to each sample based on the percentage of tumor cells within the tissue and their intensity of gC1qR/p32 staining (Table 1). Compared to non-malignant tissues, several tumor types showed elevated gC1qR/p32 expression levels (FIG. 6E). In particular, breast lobular carcinoma, endometroid adenocarcinoma, melanoma, and carcinomas of the colon and testis, as well as squamous cell carcinomas of the lung, exhibited markedly elevated gC1qR/p32 expression. None of the nine prostate carcinomas examined contained significant gC1qR/p32 levels. The expression of gC1qR/p32 was high in cancers of stomach, pancreas and kidney, but the corresponding non-malignant tissues also expressed gC1qR/p32 at substantial levels. These results confirm and extend previous reports showing preferential expression of gC1qR/p32 by adenocarcinoma cells.

iv. Stable Knockdown of gC1qR/p32 Alters Tumor Cell Metabolism and Growth

Figure 7A:
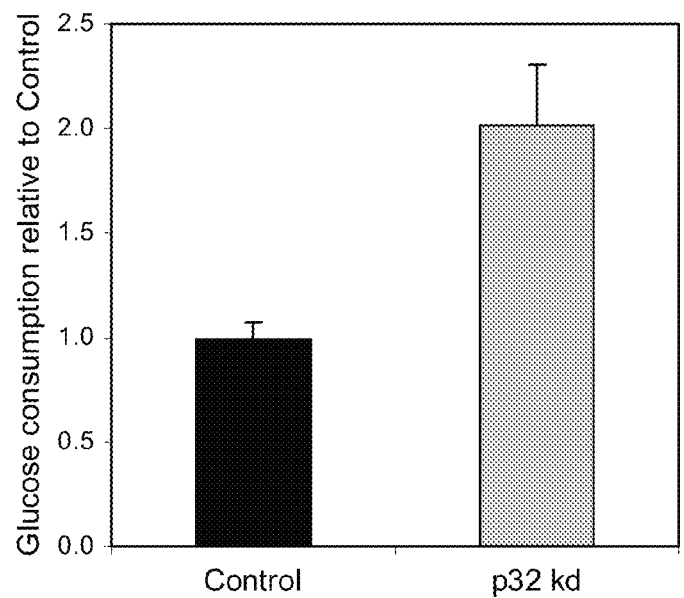
FIG. 7 shows knockdown of p32 in MDA-MB-435 tumor cells. A. Upper left panel, immunoblot analysis on whole cell lysates from three MDA-MB-435 clones stably expressing ShRNA for p32 (p32 kd; Cl 1,2, and 3) and three clones expressing a base mismatch control ShRNA (Control, Cl 4,5, and 6). Upper right panel—acidification of the culture media in p32 knockdown clones, as indicated by the color change of the phenol red indicator in the media to orange/yellow. Lower panels: lactate production and glucose consumption 4 days post cells seeding calculated as described in materials and shown as relative to control (p<0.001). B. Cellular ATP from lysates of p32 knockdown and control cells grown for 4 days in media with the indicated glucose concentrations. The ATP present in each lysate was normalized for the ATP production of control clones grown in 25 mM glucose. The result is the average (±SEM) of two independent experiments performed with three p32 kd and three control clones. (*=p<0.03, =p<0.002). C. Oxygen consumption. Shown are the values for p32 knockdown clones relative to control clones. The results come from three independent experiments (±SD) performed in triplicate (=p<0.001, *=p<0.05). D. Confocal analysis of p32 localization in cells. p32 knockdown and control cells were stained with anti-N-terminal p32 polyclonal antibody and anti-cytochrome c monoclonal antibody, followed by Alexa 488 and Alexa 594 anti-rabbit and anti-mouse secondary antibodies, respectively. The panels on the right are high magnification of the white-framed areas in the merge panels.

To delineate the role of gC1qR/p32 in tumor physiology shRNA-based knockdown of gC1qR/p32 expression was employed in tumor with subsequent analysis of the cells in vitro and in vivo. shRNAs complementary to gC1qR/p32 or a two-base-pair mismatch control shRNA were expressed in MDA-MB-435 tumor cells. A series of gC1qR/p32 and control shRNA stable clones were screened for gC1qR/p32 expression. Three gC1qR/p32 shRNA clones, with undetectable gC1qR/p32 expression, and three control shRNA clones were selected for analysis (FIG. 7A, upper left panel). Each of the gC1qR/p32 knockdown clones showed markedly reduced uptake of FITC-LyP-1 peptide compared to control clones. Strikingly, gC1qR/p32 knockdown induced acidification of the culture medium, as indicated by a phenol red color change 3-4 days after cell seeding (FIG. 7A upper right panel). Consistent with a decrease in pH, lactate production was significantly increased in gC1qR/p32 knockdown compared to control cells (FIG. 7A lower left panel).

Lactic acid is a byproduct of glycolysis and can accumulate under anaerobic conditions or in cases of mitochondrial dysfunction. The ensuing reliance on glycolysis for ATP production is associated with a high rate of conversion of glucose to lactate and a high rate of glucose uptake. It was found that gC1qR/p32 knockdown cells consumed more glucose than the control clones, indicating increased glycolysis (FIG. 7A lower right panel). However, the elevated glycolytic rate and lactate production was not related to increased cell growth of the gC1qR/p32 knockdown cells, as these cells grew more slowly than the control cells (see FIG. 8 below).

Figure 7B:
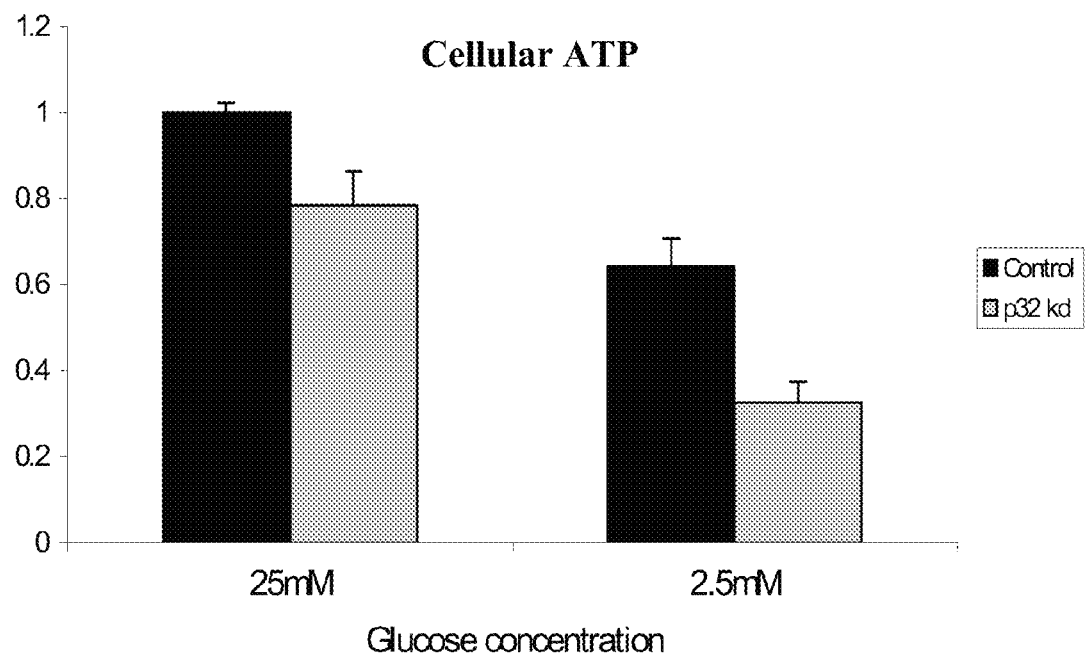
Figure 7C:
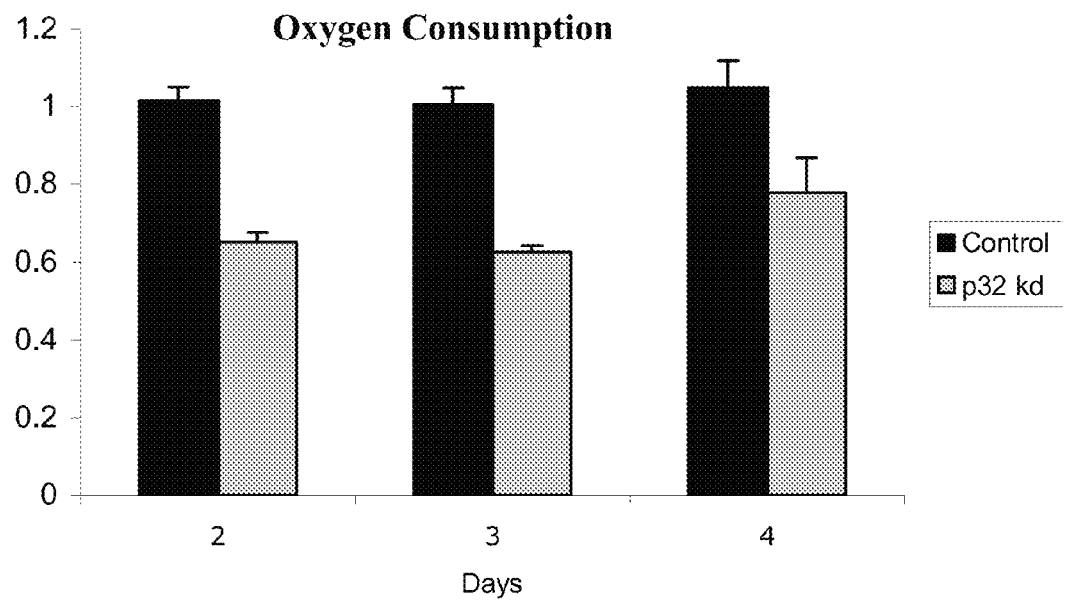

The gC1qR/p32 protein has been found to be present in each of the main cellular compartments, but it is predominantly a mitochondrial protein (Dedio et al., 1998; Jiang et al., 1999; Muta et al., 1997; Soltys et al., 2000; van Leeuwen and O'Hare, 2001). Consistent with a mitochondrial role of gC1qR/p32, a growth defect in yeast lacking the gC1qR/p32 homolog has been linked to an abnormality in maintaining mitochondrial ATP synthesis (Muta et al., 1997). The gC1qR/p32 knockdown cells, when grown in normal media containing high (25 mM) glucose, produced 20% less total ATP than control cells (FIG. 7B). The decrease in mitochondrial ATP production may have been greater than that, as increased ATP production via glycolysis may have compensated for some of the lost mitochondrial ATP synthesis. Reducing glucose concentration in the media to 2.5 mM was more detrimental to cellular ATP production in gC1qR/p32 knockdown (50% reduction) compared to control clones. These data show that gC1qR/p32 can be required for efficient ATP production through oxidative phosphorylation (OXPHOS). Consistent with such a role, gC1qR/p32 knockdown cells consumed less oxygen than control clones (FIG. 7C). Thus, loss of gC1qR/p32 shifts energy metabolism toward glycolysis, likely via perturbation of mitochondrial function.

Figure 7D:
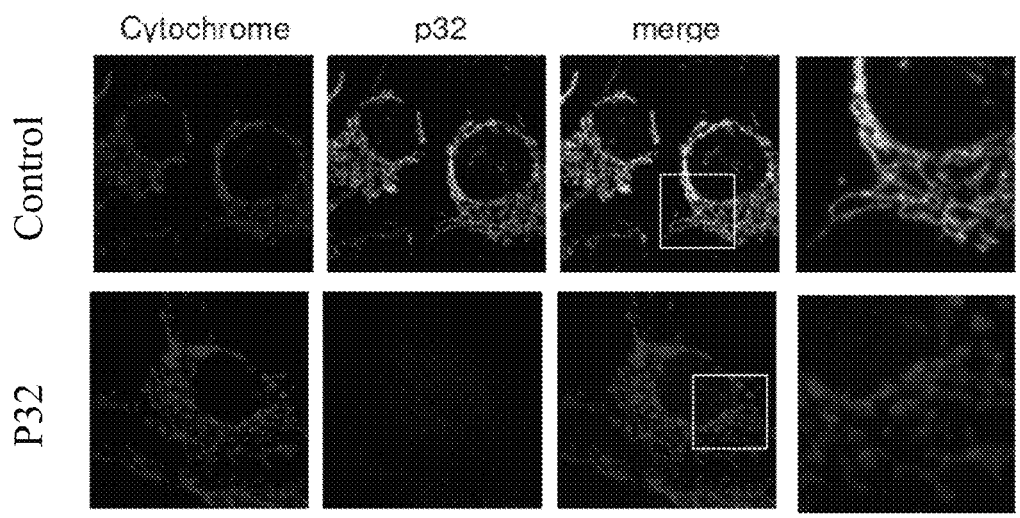

Mitochondrial morphology is closely linked to energy metabolism. Enhanced respiration correlates with an interconnected mitochondrial network and enlarged cristae compartment, while reduced OXPHOS and enhanced glycolysis correlates with fragmented mitochondria and matrix expansion (Alirol and Martinou, 2006). Confocal analysis of mitochondria in gC1qR/p32 knockdown and control clones showed that the mitochondrial network was fragmented rather than fibrillar when gC1qR/p32 was not expressed (FIG. 7D). Taken together, these data support the view that gC1qR/p32 is critical for mitochondrial function, and its inactivation alters energy metabolism in favor of glycolysis.

v. Loss of gC1qR/p32 Impairs Cell Growth and Increases Cell Death

Figure 8A:
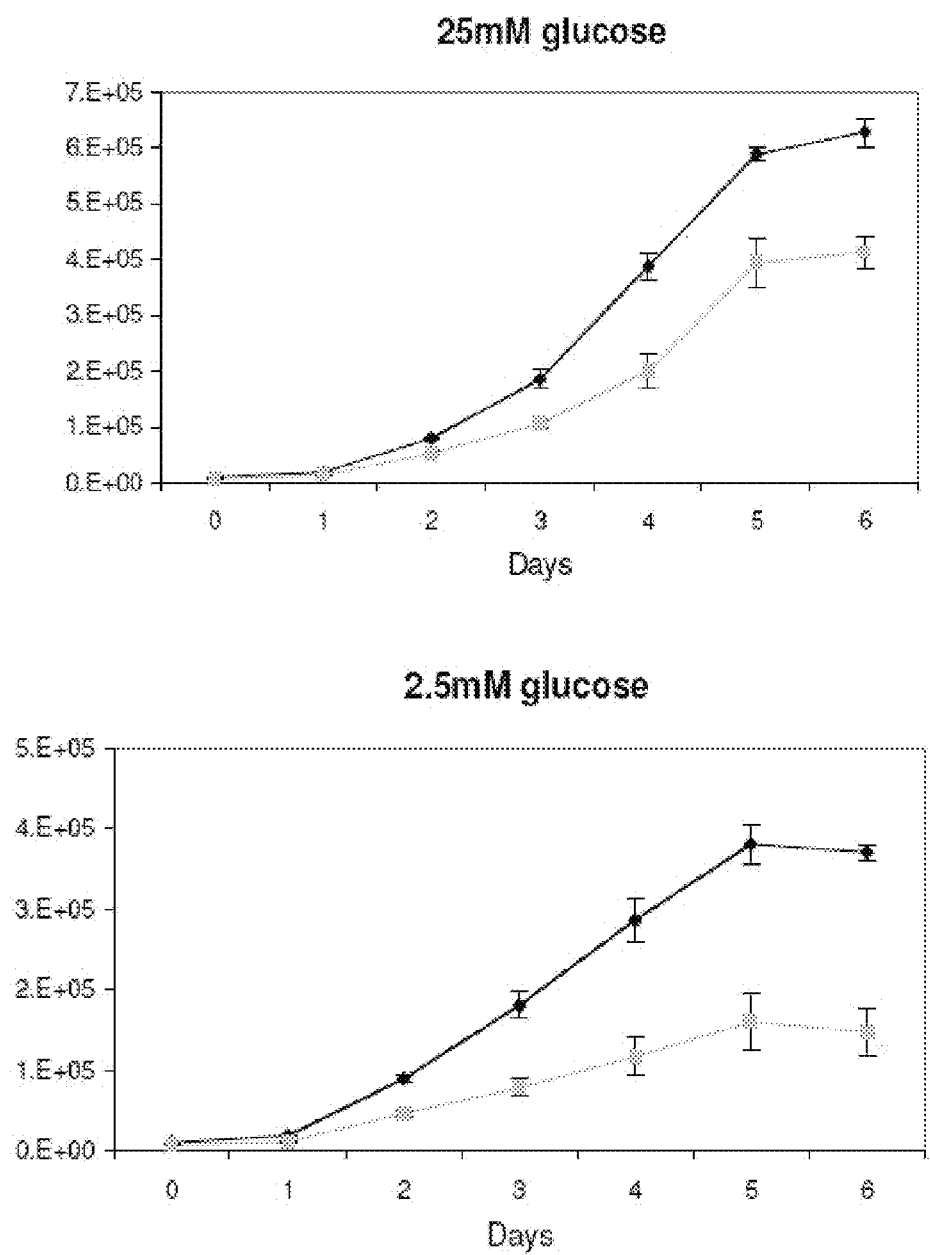
FIG. 8 shows the effect of p32 knockdown on growth and survival of tumor cells in vitro. A. Proliferation of MDA-MB-435 p32 knockdown (kd) and control cells under high (25 mM) and low (2.5 mM) glucose conditions. Average cell number at each time point was determined by counting absolute cell number in duplicate wells of three p32 knockdown and control clones (p<0.0002). The panel on the right shows the color media of two control and p32 kd clones after 6 days in 25 mM or 2.5 mM glucose. B. Left panel—Microscopic analysis of p32 knockdown and control cells after 3 days in medium containing the indicated glucose concentration. The p32 kd clones show morphological changes in 2.5 mM glucose and cell death becomes pronounced in 0.5 mM glucose. Cell death was quantified by FACS analysis of cells that bind FITC-annexin V (right panel; *=<0.05). C. Upper left panel, immunoblot analysis of a parental p32 kd clone and single clones derived from it that express p32 from a cDNA resistant to the p32 shRNA silencing (Cl #3,8,14) or that were transfected with empty cDNA vector (Cl #9,10,18). A clone expressing control ShRNA (Control) was used to detect the endogenous level of p32. The lower left panel shows the restoration of culture medium pH by reintroduction of p32. The middle panels and the panel on the right show lactate production, glucose consumption, and growth rate in control, p32 kd and p32-restored (p32 kd+p32) clones.
Figure 8A:
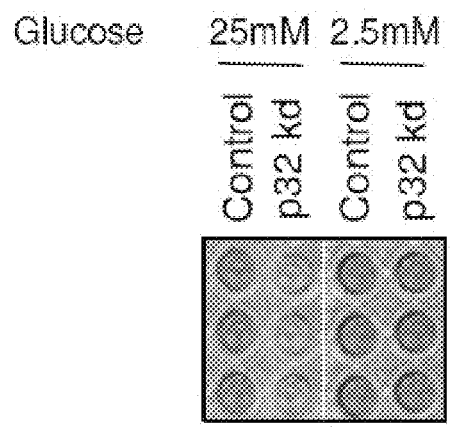

The gC1qR/p32 knockdown cells grew more slowly than control cells (FIG. 8A, left and middle panels). The difference was particularly striking in medium containing only 2.5 mM glucose. Under these low glucose conditions, the medium in the gC1qR/p32 knockdown cells did not become acidic (FIG. 8A, right panel), indicating that the cells were not able to carry out glycolysis at a level that would support cell growth.

Figure 8B:
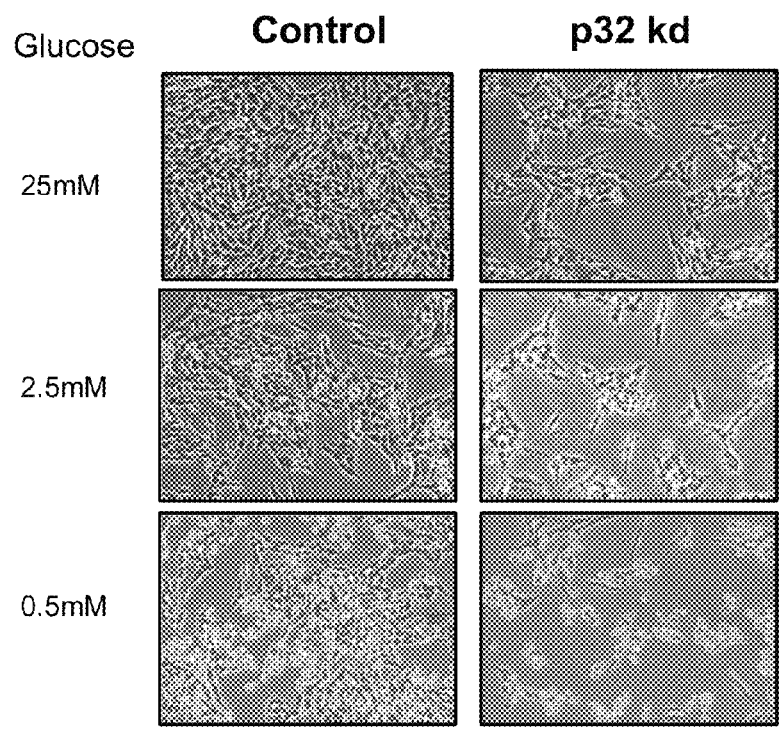
Figure 8B:
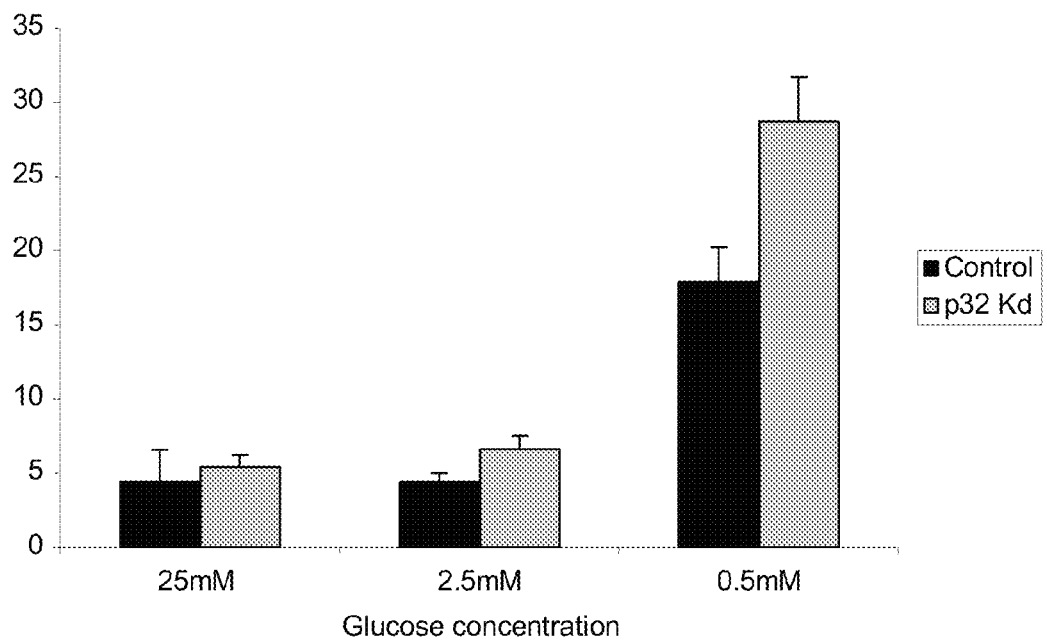

Tumor cells have a tendency to undergo cell death under low glucose conditions (Inoki et al., 2003; Jones et al., 2005). It was next determined whether loss of gC1qR/p32 would confer this trait to the MDA-MB-435 cells. The percentage of annexin V-positive cells in the gC1qR/p32 knockdown and control cells was similar in high glucose media, but a greater sensitivity of the knockdown cells became evident in low glucose media (FIG. 8B).

Figure 8C:
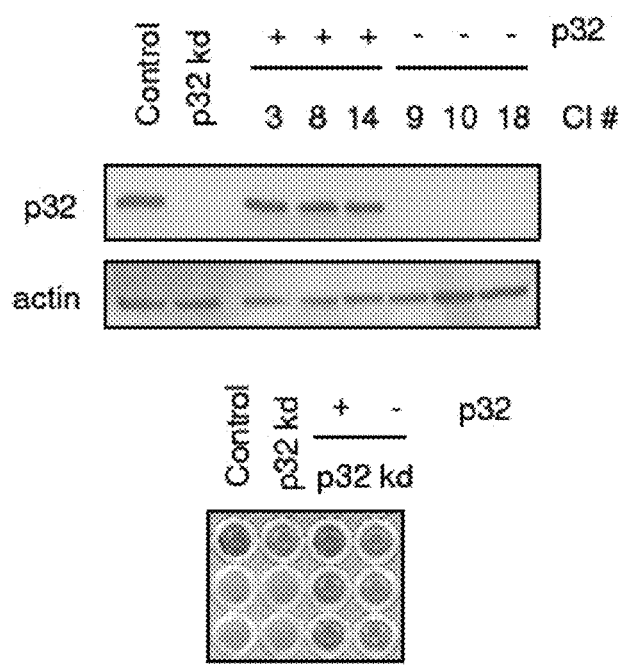
Figure 8C:
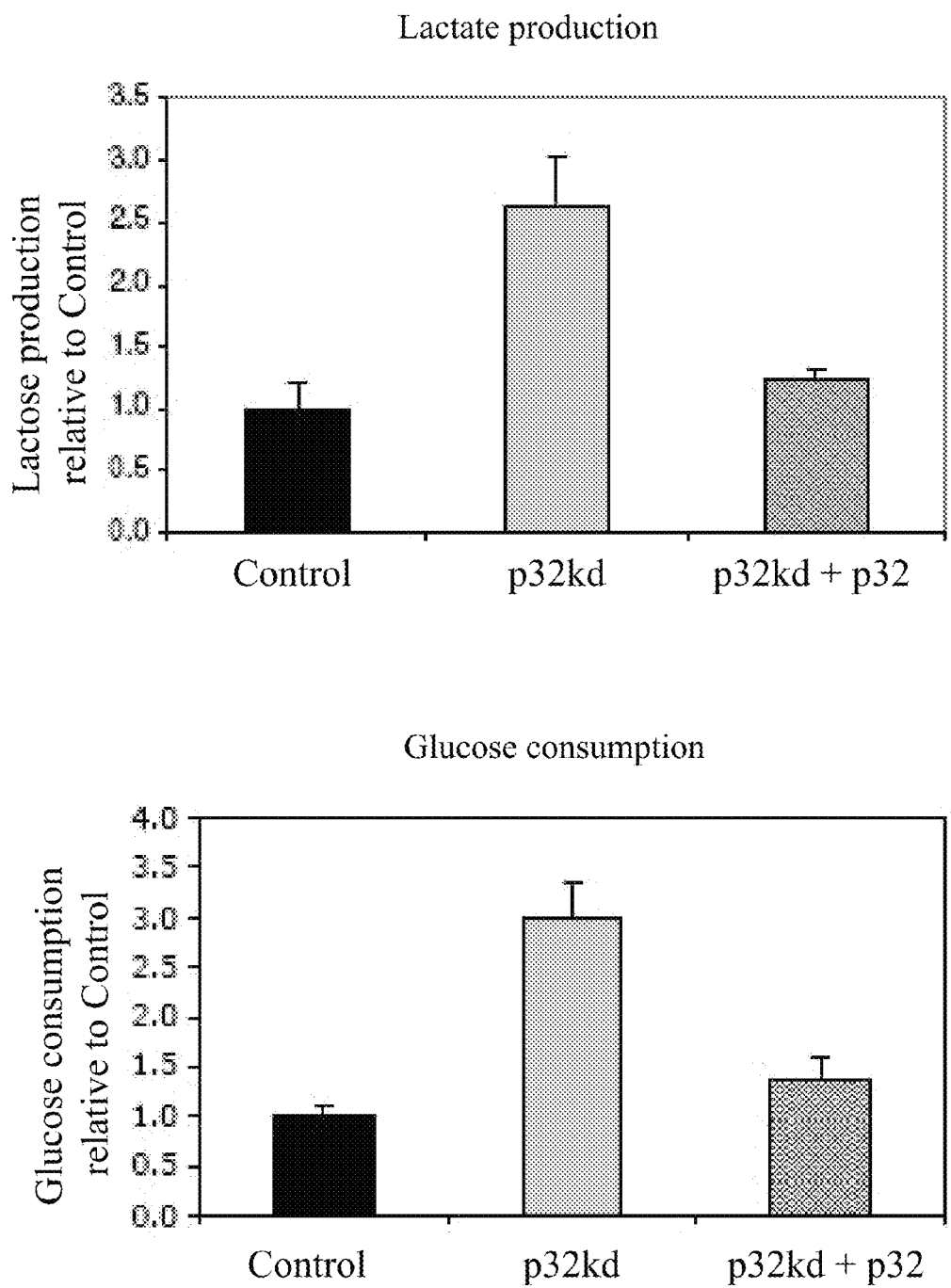
Figure 8C:
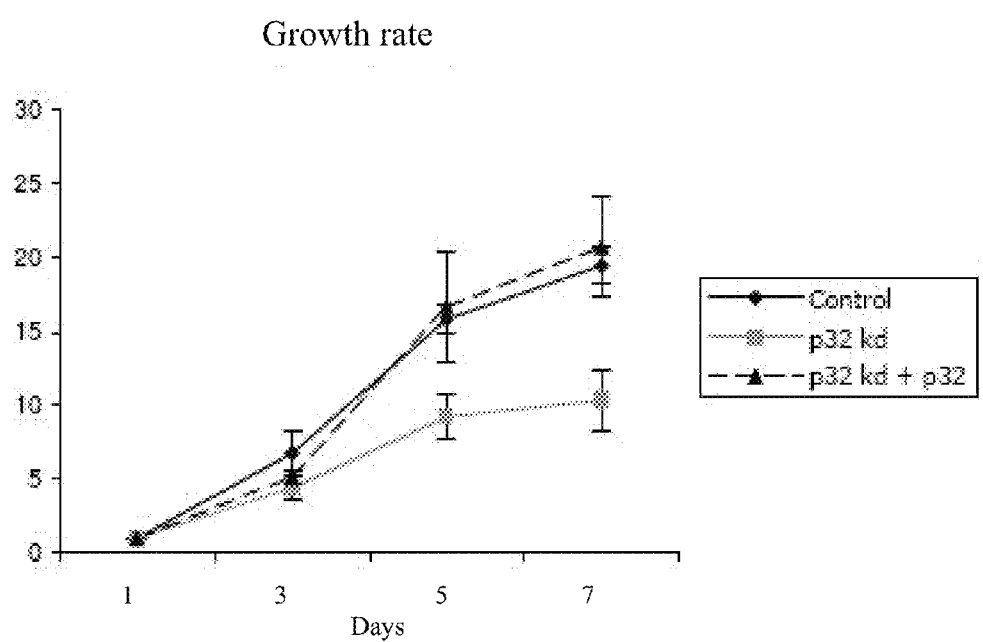

To show the specificity of the shRNA knockdown, gC1qR/p32 production was restored in knockdown cells. A gC1qR/p32 cDNA in which silent mutations confer resistance to inhibition by the gC1qR/p32 shRNA was employed to bring gC1qR/p32 expression to the original level (FIG. 8C). This treatment normalized lactate accumulation, glucose consumption, and proliferation of the knockdown cells (FIG. 8C). These results show that off-target effects are not responsible for the phenotypic effects of the knockdown.

vi. Loss of gC1qR/p32 Suppresses Malignancy of Tumor Cells

Figure 9A:
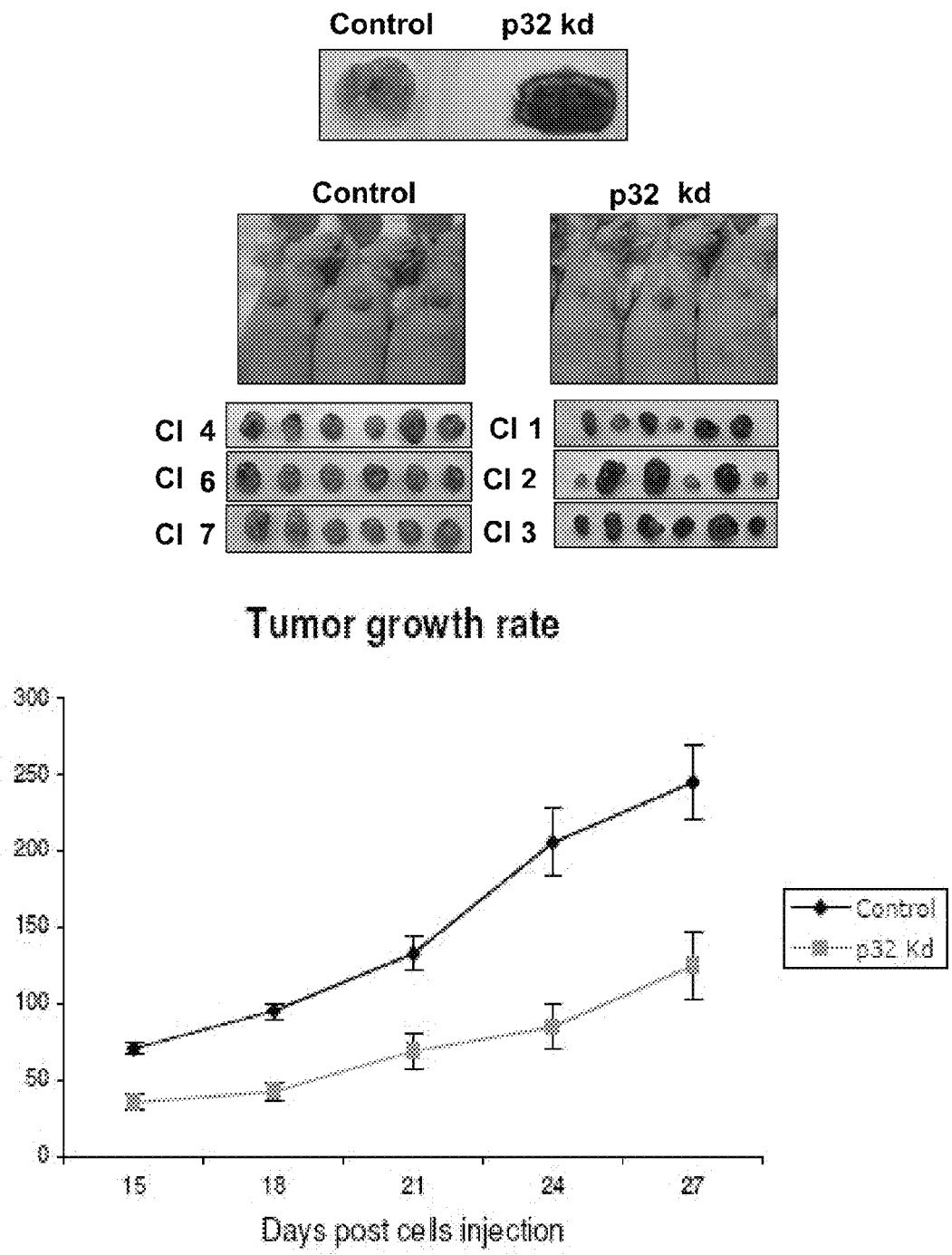
FIG. 9 shows growth properties of tumors derived from p32 knockdown cells. Tumors were grown from three p32 kd and control clones (6 mice per clone) in the mammary fat pad of nude mice. A. Control tumors are homogenous in size, while p32 kd tumors are either significantly smaller than the control cell tumors, or swollen and hemorrhagic. The middle panel shows an example of a knockdown cell tumor with extensive necrosis accompanied by hemorrhage. The right panel shows average of tumor volume as a function of time (±SEM, p<0.001). B. BrdU incorporation in tumor cells. Mice were administered a pulse of BrdU 24 h prior to sacrifice. The graph indicates the number of cells per field that scored positive for BrdU staining. The data were derived by counting via Image-J software the number of BrdU positive cells in 4 random fields per tumor (N=14 tumors per group); p<0.003. C. Hematoxylin/eosin staining of tumors derived from p32 kd and control cell clones. Dark areas in p32 kd tumors are indicative of extensive necrosis. The upper images were taken with a 10× magnification, the lower images correspond to the indicated framed areas at 200× magnification. The percentage of necrotic areas was calculated via Image-J software (p<0.001).
Figure 9B:
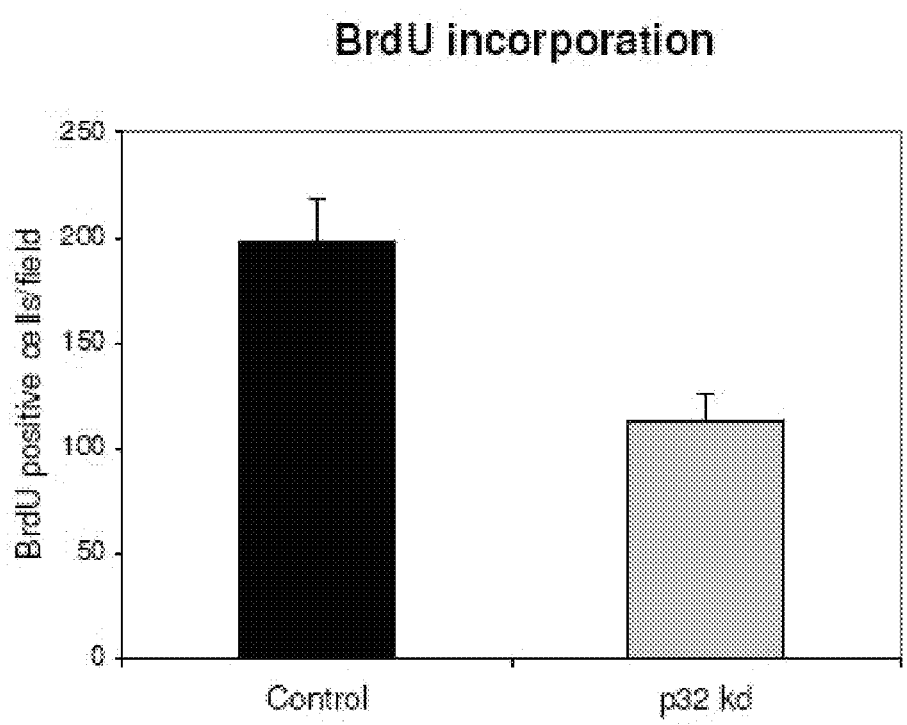

The elevated gC1qR/p32 expression in tumors and impaired proliferation and survival of gC1qR/p32 knockdown cells, prompted the investigation of the role of gC1qR/p32 in tumorigenesis. Control and gC1qR/p32 knockdown cell clones were orthotopically injected into the mammary gland fat pad of nude mice, and tumor growth was monitored. The gC1qR/p32 knockdown cells produced smaller tumors than controls or the tumors were swollen and soft, and purple color and release of blood upon cutting indicated intratumoral hemorrhage (FIG. 9A, left and middle panels). Even with the hemorrhage contributing to the size of the knockdown tumors, the growth rate of these tumors was significantly lower than that of control tumors (p<0.001). Assessment of cell proliferation in the tumors by BrdU incorporation showed significantly reduced number of BrdU-positive cells in the gC1qR/p32 knockdown tumors (FIG. 9B), which is consistent with the slow proliferation rate of the knockdown cells in vitro. Histopathological analysis of tumor sections revealed extensive necrosis in the gC1qR/p32 knockdown compared to control tumors (FIG. 9C). Some necrosis was evident even in small gC1qR/p32 knockdown tumors, indicating that necrosis is an early event in tumors produced by gC1qR/p32-deficient cells. Taken together these data establish an important role for gC1qR/p32 in tumor growth and maintenance.

3. Discussion

It is herein shown that a mitochondrial/cell surface protein, p32/gC1qR, is the receptor for a tumor-homing peptide, LyP-1, which specifically recognizes an epitope in tumor lymphatics and tumor cells in certain cancers. It is shown that knocking down gC1qR/p32 expression with shRNA elevates glycolysis, decreases mitochondrial respiration, and reduces tumorigenicity in MDA-MB-435 tumor cells. As the expression of gC1qR/p32 is frequently up-regulated in experimental and human cancers, the results show that elevated glycolysis (the Warburg effect) is not necessarily advantageous to tumor growth.

Several lines of evidence show that the LyP-1 peptide specifically binds a protein known as gC1qR/p32 or the receptor for the C1q component of the complement, gC1qR/p32. First, LyP-1 phage binds purified gC1qR/p32 protein and the interaction was inhibited by an antibody directed against the N-terminus of gC1qR/p32. Second, endogenous expression levels and cell surface localization of gC1qR/p32 correlated with the ability of different cell lines to bind LyP-1. Third, overexpression of gC1qR/p32 enhanced and RNAi silencing decreased LyP-1 binding to cells. Finally, intravenously injected FITC-LyP-1 peptide homed in vivo to the areas in tumors where gC1qR/p32 expression was high. The identification of gC1qR/p32 as the LyP-1 receptor prompted the further study of the expression and role of gC1qR/p32 in cancer.

The gC1qR/p32 protein is primarily mitochondrial, but it can be found in the cytoplasm, nuclei, and most importantly for the LyP-1 binding, at the cell surface (Ghebrehiwet et al., 1994; Guo et al., 1999; Peerschke et al., 1994). Several other mitochondrial proteins are also found in extra-mitochondrial locations (Soltys and Gupta, 1999). For example, the mitochondrial chaperone proteins HSP60 and HSP70 have also been observed at the cell surface (Soltys and Gupta, 1997) and endoplasmic reticulum (Singh et al., 1997; Soltys and Gupta, 1996). HSP60 found at the surface of tumor cells and stressed cells (Kaur et al., 1993; Xu et al., 1994) can function as a chaperone for certain proteins (Khan et al., 1998). Interestingly, a chaperone-like function has also been suggested for gC1qR/p32 (Hirasawa et al., 2001; Kittlesen et al., 2000; Robles-Flores et al., 2002; Rozanov et al., 2002b; Schaerer et al., 2001; Storz et al., 2000). FACS data corroborate the earlier findings on the cell surface localization of gC1qR/p32 and indicate that the tumor microenvironment may enhance the cell surface expression of gC1qR/p32.

The amount of gC1qR/p32 at the surface did not necessarily correlate with the total amount of gC1qR/p32 in the cell, showing that the localization is separately controlled. Interestingly, two ubiquitous intracellular proteins, nucleolin (Christian et al., 2003) and annexin 1 (Oh et al., 2004) have been shown to be aberrantly expressed at the cell surface in tumor blood vessels, where they serve as specific markers of angiogenesis. The expression of gC1qR/p32 in tissues is much more restricted than that of nucleolin or annexin 1, but its cell surface expression may add a further degree of tumor specificity, as the LyP-1 peptide (Laakkonen et al., 2004; Laakkonen et al., 2002) and anti-gC1qR/p32 (this study) are strikingly specific in their tumor accumulation upon systemic administration.

Antibody staining of tissue sections with anti-gC1qR/p32 antibody, and intravenously injected anti-gC1qR/p32, confirmed the previously reported association of LyP-1 with specific areas in tumors. Similar to the LyP-1 peptide (Laakkonen et al., 2004; Laakkonen et al., 2002), the antibody outlined two main locations within tumors: cell clusters in areas that were rich in lymphatics, but sparsely populated with blood vessels, and vessel-like structures that apparently represent lymphatics. Bone marrow-derived macrophages that contribute to lymphagiogenesis have been described (Kerjaschki et al., 2006; Maruyama et al., 2007; Maruyama et al., 2005), and it was found that a significant number of intensely gC1qR/p32-positive cells within tumors were also positive for macrophage markers. It was hypothesized that the LyP-1/anti-gC1qR/p32-positive cells represent a rare macrophage population that can serve as a precursor to lymphatic endothelial cells.

The findings with shRNA-mediated knockdown of gC1qR/p32 show an important role of gC1qR/p32 in tumor cells. In vitro, the knockdown resulted in a striking increase in the utilization of the glycolytic pathway of glucose metabolism by tumor cells. These metabolic changes are similar to those caused by mutations that disable the gC1qR/p32 homologue in yeast (Muta et al., 1997). The gC1qR/p32 knockdown was also associated with impaired cell growth, increased cell death, and compromised tumorigenicity. These changes were specifically caused by the knockdown, as an shRNA-resistant gC1qR/p32 construct reversed them.

It was found that breast cancers and some other adenocarcinomas up-regulate gC1qR/p32, but some other cancers, notably prostate cancers, do not express gC1qR/p32 at detectable levels. The mouse and human genomes appear to contain only one gC1qR/p32-related gene, making it unlikely that a related gene would serve in the same role in tumors that lack gC1qR/p32. Interestingly, in contrast to most malignancies, a majority of prostate cancers are not highly glycolytic (Effert et al., 1996; Hofer et al., 1999; Liu, 2006). Hence, they may not need the offsetting activity of gC1qR/p32.

One factor that drives the glycolytic response in tumors is the myc oncogene (Shim et al., 1997). It is noteworthy that c-myc changes are common in breast cancers (Blancato et al., 2004; Liao and Dickson, 2000) which exhibit high glycolytic activity (Isidoro et al., 2005). Thus, the role of gC1qR/p32 can be to counteract excessive glycolysis-promoting activities of c-myc, while allowing its tumor-promoting effects to remain intact.

There can also exist a link between mitochondrial metabolism, autophagy and gC1qR/p32. Autophagy is a dynamic process of subcellular degradation. By mobilizing nutrients that result from macromolecular degradation, autophagy acts to buffer metabolic stress in organisms from yeast to mammals (Levine, 2007; Rubinsztein et al., 2007). A role for gC1qR/p32 protein in autophagy has been previously suggested (Sengupta et al., 2004) and recently gC1qR/p32 has been reported to interact with and stabilize the autophagic inducer protein smARF in mitochondria (Reef et al., 2007). Moreover, deletion of the genes for various autophagy-related proteins in yeast resulted in abnormal mitochondrial morphology and lowered oxidative phosphorylation, along with a growth defect (Zhang et al., 2007). This phenocopies observations in tumor cells with knocked down gC1qR/p32, as these cells also displayed altered mitochondria, a shift from oxidative phosphorylation to glycolysis, and poor growth.

Autophagy can act as a tumor suppressor, but it can also enhance tumor growth (Degenhardt et al., 2006; Levine, 2007). The tumor suppressor function can relate to the role of autophagy in removal of sources of oxygen radicals that would cause DNA damage, with the resulting accumulation of mutations that can accelerate tumor progression. The other side of the coin is that autophagy is a survival mechanism for cells under stress. Tumors often outgrow their blood supply, which results in local areas of hypoxia and nutrient depletion; turning on autophagy provide a cannibalistic mechanism for survival under such stress.

These results agree well with the assumption that gC1qR/p32 expression is involved in the autophagy response. First, the LyP-1 peptide accumulated in hypoxic (and presumably also nutrient-deficient) regions in tumors (Laakkonen et al., 2004), and it is demonstrated in the present work with anti-gC1qR/p32 antibodies that these regions preferentially express gC1qR/p32. Second, tumors that lack the autophagy response are prone to necrosis through a process dubbed metabolic catastrophe (Jin et al., 2007). This is exactly what was observed with tumors grown from gC1qR/p32 knockdown cells; these tumors often contained a large necrotic and hemorrhagic core. Moreover, LyP-1 peptide treatment induced TUNEL-positive lesions in tumors in vivo (Laakkonen et al., 2004), indicating apoptosis or incipient necrosis at these sites.

Given the dual effect of autophagy (and by extension presumably of gC1qR/p32 expression) on tumorigenesis, the question arises as to whether suppressing autophagy would be helpful in treating tumors, or that might be harmful. Partial tumor necrosis resulting from suppression of autophagy is one mechanism that could produce a harmful result, as necrosis causes inflammation, and inflammatory mediators can promote tumor growth (Degenhardt et al., 2006). The results show that necrosis elicited by autophagy suppression can be beneficial as a treatment modality. Extensive necrosis was observed in a majority of the gC1qR/p32 knockdown tumors, yet the tumors grew more slowly than the wild type tumors. The results show that gC1qR/p32 represents a new target for tumor therapy; RNAi, or human monoclonal antibodies and small molecular weight compounds that mimic the LyP-1 peptide, for example, can be used for harnessing this potential.

4. Experimental Procedures i. Reagents

Mouse monoclonal 60.11 and 74.5.2 anti-gC1qR/p32 antibodies were purchased from Chemicon (Temecula, Calif.). Rat monoclonal anti-mouse CD-31, rat anti-MECA-32, rat anti mouse CD-11b and R-Phycoerythrin (R-PE)-conjugated rat anti-mouse Gr-1 were from BD-PharMingen (San Jose, Calif.), the anti-epithelial membrane antigen (clone E29) was from Chemicon and anti β-actin from Sigma-Aldrich (St. Louis, Mo.). Monoclonal anti-cytochrome c was purchased from BD-PharMingen. Rat anti-podoplanin antibody was kindly provided by Drs. T. Petrova and K. Alitalo (University of Helsinki, Helsinki, Finland). ChromPure Rabbit IgG (whole molecule) was from Jackson ImmunoResearch Laboratories (West Grove, Pa.) and purified Mouse IgG1 (mIgG) from BD-Pharmingen. Purified polyclonal anti-full-length gC1qR/p32 was a generous gift from Dr. B. Ghebrehiwet (Stony Brook University, NY). Polyclonal antibody anti-gC1qR/p32 NH2-terminal antibody was generated in New Zealand White rabbits against a mixture of peptides corresponding to amino acids 76-93 of mouse (TEGDKAFVEFLTDEIKEE, SEQ ID NO:8) and human (TDGDKAFVDFLSDEIKEE, SEQ ID NO:9) gC1qR/p32 protein. The peptides were coupled to keyhole limpet hemocyanin (Pierce, Rockford, Ill.) via a cysteine residue added at their N-termini and the conjugate was used to immunize the rabbits according to instructions of the hemocyanine manufacturer. The antibody was affinity purified on the peptides coupled to Sulfolink Gel (Pierce) via the N-terminal cysteine. Dr. A. Strongin (Burnham Institute for Medical Research, La Jolla, Calif.) kindly provided human gC1qR/p32 cDNA in pcDNA3.1 Zeo and pET-15b vectors. Oligonucleotide duplexes for transient siRNA knock-down of gC1qR/p32 (C1QBP-HSS101146-47-48 Stealth RNAi) and negative control duplexes (Stealth RNAi control low GC and medium GC) were purchased from Invitrogen (Carlsbad, Calif.). Tissue Arrays (core diameter 0.6 mm) of paraformaldehyde fixed and paraffin-embedded tumor and normal tissue samples were from Applied Phenomics LLC (Tartu, Estonia).

ii. Cell Culture and Generation of Stable Cell Lines

MDA-MB-435, C8161, BT549, HL60, and Raji cells were maintained in DMEM containing 4500 mg/ml (25 mM) of glucose (without sodium pyruvate) and supplemented with 10% FBS and 1% Glutamine Pen-Strep (Omega Scientific, Tarzana, Calif.) at 37° C./5% CO2. For experiments in high and low glucose conditions, cells were first adapted for a few days to DMEM (25 mM glucose) supplement with 10% dialized FBS (dFBS; glucose≤5 mg/dl, Invitrogen).

Stable expression of control and gC1qR/p32 shRNA in MDA-MB-435 cells was achieved through the BLOCK-iT Lentiviral RNAi Expression system (Invitrogen). The design of shRNAs sequences complementary to gC1qR/p32 (GeneBank NM_001212) was carried out using Invitrogen's RNAi Designer. The double-stranded oligonucleotides were first cloned into the pENTRTM/U6 vector and tested for gC1qR/p32 silencing by transient transfection. The optimal gC1qR/p32 shRNA sequence (targeting nucleotides 5'-GGATGAGGTTGGACAAGAAGA-3', SEQ ID NO:10) was subsequently transferred into the pLenti6/BLOCK-iTTM-DEST vector for lentiviral RNAi production in 293FT cell line according to the manufacturer's instructions. As a control shRNA, a two-base-pair mismatched shRNA was used targeting a different region of gC1qR/p32 cDNA (5'-CCCAATaTCGTGGTTGAtGTTATAA-3', SEQ ID NO 11) lowercase nucleotides indicate the base pair mismatch). MDA-MB-435 cells were transduced with gC1qR/p32 and control RNAi lentiviral stocks. Selection of stably transduced clones was done in medium containing Blasticidin (5 µg/ml, Invitrogen).

To produce a gC1qR/p32 construct resistant to the selected shRNA, the quick Change II site-directed mutagenesis kit (Stratagene; Cedar Creek, Tex.) was used to introduce two silent mutations within the gC1qR/p32 sequence targeted by the shRNA (5'-GGATGAGGTTGGACAgGAgGA-3', SEQ ID NO:12, lowercase nucleotides indicate silent mutations). The pcDNA3.1Zeo gC1qR/p32 construct was used as a template. The resulting construct was transfected into an MDA-MB-435 cell clone stably expressing the gC1qR/p32 shRNA, and Zeocin (600 µg/ml, Invitrogen) was used to select clones with restored gC1qR/p32 expression.

iii. Pull-Down Assays and Mass Spectrometry

Streptavidin agarose beads (Sigma-Aldrich) were resuspended in 2 volumes of phosphate buffer saline (PBS) and conjugated to 3 µg/10 µl beads of biotynilated peptides for 2 h on ice. After incubation, beads were washed three times with PBS/50 mM n-octyl-β-D glucopyranoside (Calbiochem; San Diego, Calif.) to remove free peptides. Cells at 80-90% of confluence were pelleted and lysed in cold PBS/200 mM n-octyl-β-D glucopyranoside and 1% protease inhibitor cocktail (Sigma-Aldrich). The lysate was incubated on ice for 30 min before centrifugation at 14000 rpm for 30 min. An aliquot of the supernatant containing 1 mg of protein was pre-cleared with 40 µl of streptavidin beads for 2 h at 4° C. and subsequently incubated with streptavidin beads loaded with biotinylated peptides over night at 4° C. After 6 washes with PBS/50 mM n-octyl-β-D glucopyranoside, the beads were boiled for 5 min in 40 µl of SDS-PAGE-loading buffer, and the eluted material was separated on a 4-20% polyacrylamide gel and visualized by silver staining (Invitrogen). Bands that appeared in the LyP-1 but not control peptide pull down were cut out, digested with trypsin, and the resulting peptides were analyzed by matrix-assisted laser desorption ionization-time of flight (MALDI-TOF) mass spectrometry. The information was queried against a protein sequence data via Profound software.

iv. In vitro Phage Binding Assays

Microtiter wells (Costar, Corning, N.Y.) were coated overnight at 4° C. with 5 µg/ml of either purified gC1qR/p32 or BSA (Sigma-Aldrich) in 100 µl/well of carbonate buffer (15 mM sodium carbonate, 35 mM sodium bicarbonate). Wells were washed three times with TBS and blocked with Pierce Superblock buffer according to the manufactures instructions. 108 pfu of LyP-1 and control phages were added to the wells in 100 µl/well of TBS/0.05% tween-20 and incubated for 16 h at 37° C. After 6 washes in TBS/0.05% tween-20, bound phages were eluted with 200 µl of Tris-HCl 1M pH 7.5/0.5% SDS for 30 min and subsequently quantified by plaque assay. For inhibition of phage binding by anti gC1qR/p32 antibodies the assay was performed as described above with the difference that 1.5×107 pfu of LyP-1 or insertless phages were allowed to bind for 6 h at 37° C. to gC1qR/p32 protein in the presence of 20 µg/ml of mAb anti gC1qR/p32 antibodies or mIgG. When the assay was performed with cells, 2×106 Raji cells were resuspended in 500 µl of PBS/1% BSA and pre-incubated for 1 h at 4° C. with 40 µg/ml of mAb anti gC1qR/p32 antibodies or mIgG. 108 pfu of insertless or LyP-1 phages were subsequently added to the cells and incubated at 4° C. for 3 h. Cells were washed 5 times with PBS/1% BSA and bound phages were quantified by plaque assay.

v. Immunoblotting and Immunohistology

Cells grown in tissue culture plates were rinsed with PBS and lysed with NET buffer 1% NP40 (150 mM NaCl, 50 mM Tris-HCl pH 7.5, 5 mM EDTA pH 8, 1% NP40) containing complete protease inhibitor cocktail. Unbound material was removed by centrifugation at 14,000 rpm for 20 min. Protein concentration of the supernatant was determined by Bio-Rad protein assay. To prepare tumor lysates, tumors were removed, minced, and dissociated in DMEM (1:4 weight to volume) supplemented with 1 mg/ml collagenase (Sigma-Aldrich) for 30 min at 37° C. The cell suspension was centrifuged at 1000 rpm for 5 min and the cell pellet was washed 3 times with PBS/1% BSA prior to lysis in NET buffer containing 1% NP40. An aliquot of each lysate containing equivalent amounts of protein was separated by SDS-PAGE on 4-20% gradient gels and proteins were transferred to nitrocellulose membrane (Invitrogen). Immunoblots were prepared with 1 µg/ml of primary antibodies 60.11 monoclonal anti-gC1qR/p32, polyclonal anti-gC1qR/p32 and anti-β-actin and goat anti-rabbit or rabbit anti-mouse IgG-HRP (diluted 1:1000, Dako Cytomation; Carpinteria, Calif.). The blots were developed using SuperSignal West Pico Chemiluminescent Substrate (Pierce, Rockford, Ill.).

Immunohistochemical staining of frozen tissue sections was carried out using acetone fixation and reagents from Molecular Probes (Invitrogen). The secondary antibodies were: AlexaFluor-594 goat anti-rat or rabbit IgG, AlexaFluor-488 goat anti rabbit IgG. The slides were washed with PBS, incubated for 5 min with DAPI (1 µg/ml) and mounted with ProLong Gold anti-fade reagent. Cytochrome c and gC1qR/p32 were detected in cultured cells fixed in 4% PFA for 20 min at room temperature, followed by permeabilization with 0.2% Triton-X-100 in PBS for 5 min. Paraffin-embedded normal and malignant human tissue array sections were deparaffinized and then treated with Target Retrieval Solution (Dako-Cytometion). The tissue array sections were stained as described above, except gC1qR/p32 and epithelial membrane antigen, which were detected with biotinylated anti-mouse IgG and Vectastain ABC kit (Vector Laboratories Inc, Burlingame, Calif.). To prevent non-specific staining due to endogenous biotin, sections were treated with DAKO Biotin Blocking system prior to antibody incubation.

vi. FACS Analysis

Cultured cells were detached with cell enzyme-free dissociation buffer (Gibco/Invitrogen) and collected in PBS containing 1% BSA (PBSB). Single cells suspensions from tumors were obtained as indicated above. For FACS staining, $2.5 \times 10^5$ cells were resuspended in 100 µl of PBSB and incubated with polyclonal anti-full-length gC1qR/p32 or rabbit IgG (20 µg/ml) in PBSB for 30 min at 4° C. The cells were washed in PBSB and stained with goat anti rabbit Alexa 488 (2.5 µg/ml) for 30 min at 4° C. For FACS analysis of bound FITC-peptides, cultured cells were detached as above and incubated with 10 µM of FITC-peptides in 10% FCS/DMEM for 1 hour at 4° C. After washes with PBSB, the cells were resuspended in PBS containing 2 µg/ml of propidium iodide (PI, Molecular Probes/Invitrogen) to distinguish between live and dead cells, and 10,000 cells per sample were analyzed using a BD Biosciences FACSort.

vii. Quantification of Growth Rates and Cell Death

MDA-MB-435 clones were seeded in DMEM (25 mM glucose)/10% dialyzed FBS in duplicate at a density of $2.5 \times 10^4$ cells per well in 12-well plates and allowed to adhere overnight. The medium was removed by washing and substituted with glucose-free DMEM supplement with 10% dialyzed FBS and either 25 or 2.5 mM glucose (Mediatech, Inc., Herndon, Va.). The absolute cell count in each well at each time point was quantified by flow cytometry using CountBright absolute counting beads (Molecular Probes/Invitrogen). For cell death quantification, cells were grown for 3 days in either 25, 2.5, or 0.5 mM glucose, and the Annexin V-FITC kit from BioVision (Mountain View, Calif.) was used to quantify dead cells by flow cytometry.

viii. Quantification of Lactate Production and Glucose Consumption

The amount of lactate present in the culture media was determined by generally following the Sigma Diagnostic procedure No 836-UV. All the components were purchased separately from Sigma. Nicotinamide adenine dinucleotide (10 mg) was dissolved in 2 ml glycine buffer, 4 ml of water and 100 µl lactate dehydrogenase (1000 U/ml). In a 96-well plate, 5 µl of media sample was added to 145 µl of the enzyme mixture and incubated at room temperature for 30 min. Increased absorbance at 340 nm due to NADH production was used as measure of lactate originally present in the media. Lactate production/well at a given time point (Tx) was determined from: (A340 nm of cells media at Tx−A340 nm of media only [To]) divided by cell number at Tx. The amount of glucose present in the media was determined using the Glucose Assay Kit (K606-100) from BioVision. Glucose consumption/well was calculated as: (nmol glucose in media only (To)−nmol glucose in cell media at Tx) divided by cell number at Tx.

ix. Measurement of Cellular ATP

Cellular ATP levels were determined by a luciferin-luciferase-based assay using the ATP Bioluminescence Assay Kit CLS II (Roche; city, state). Cells ($2.5 \times 10^6$) were seeded in 6-well plates in DMEM (25 mM glucose)/10% dFCS. The day after cells were washed, and fresh medium containing 25 or 2.5 mM glucose was added. Four days later, the cells were lysed in 300 µl of NET buffer containing 1% NP40. Supernatants were diluted 4 times in 100 mM Tris, 4 mM EDTA, pH 7.75, and 50 µl samples were assayed with 50 µl of luciferase reagent in duplicate on a Spectra Max Gemini plate reader. The light signal was integrated for 10 s after a delay of 1 s. The bioluminescence units were normalized for the protein concentration determined by Bio-Rad protein assay (Bio-Rad Laboratories, Hercules, Calif.).

x. Quantification of Oxygen Consumption

Oxygen consumption rates of cells in culture were measured using the BD Oxygen Biosensor Systems (OBS) from BD Bioscience. Triplicate samples of 12,000 cells seeded onto 96-well OBS plates in final media volume of 200 µl were used for the measurement. The number of cells at each time point was determined using CountBright absolute counting beads by sampling cells seeded onto side-by-side plates. Fluorescence was measured every 24 h on a Spectra Max Gemini plate reader (excitation 485 nm and emission 630 nm) using the bottom plate reading configuration. Each measurement was normalized by factoring in a blank reading from the same well prior to the addition of the cells and the number of cells in the well at the time of the measurement (Guarino et al., 2004).

xi. Mice and Tumors

To produce tumors, BALB/c nude mice were orthotopically injected into the mammary fat pad with $2 \times 10^6$ MDA-MB-435 cells/100 µl of PBS. All animal experimentation received approval from the Animal Research Committee of Burnham Institute for Medical Research. The sizes of tumors were monitored and measured every three days. For in vivo BrdU labeling of tumor cells, tumor-bearing mice were intraperitoneally injected with 1 mg of BrdU (Sigma-Aldrich). The mice were sacrificed 24 h later, and the tumors were removed and fixed in Bouin's solution (Ricca Chemical Company, Arlington, Tex.) for 72 h prior to processing for paraffin embedding.

TABLE 1

Immuno-score of gC1qR/p32 expression in malignant and normal tissues.

| Carcinoma | Type | Score | Cases | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| Breast | Ductal | I | 1 | 1.5 | 2.5 | 1 | 1 | 1.5 | 1 | 1 | 2 | 1 | 1.5 |
| | | % | 60 | 70 | 100 | 60 | 70 | 80 | 50 | 60 | 100 | 60 | 80 |
| | | IS | 60 | 105 | 250 | 60 | 70 | 123 | 50 | 60 | 200 | 60 | 120 |

TABLE 1-continued

Immuno-score of gC1qR/p32 expression in malignant and normal tissues.

|  |  |  |  |  |  |  |  |  |  |  |
|---|---|---|---|---|---|---|---|---|---|---|
|  | Lobular | I | 2.5 | 2.5 | 0 | 2.5 | 2 |  | 1.5 | 1 |
|  |  | % | 90 | 90 |  | 80 | 100 | NT | 70 | 40 |
|  |  | IS | 225 | 225 | 0 | 200 | 200 |  | 105 | 40 |
|  | Mutinous | I | 1 | 1 |  |  |  |  |  |  |
|  |  | % | 60 | 20 |  |  |  |  |  |  |
|  |  | IS | 60 | 20 |  |  |  |  |  |  |
| Endometroid | Adenocarcinoma | I | 2 | 1.5 | 1.5 | 3 | 1 |  |  |  |
|  |  | % | 60 | 90 | 100 | 90 | 90 |  |  |  |
|  |  | IS | 120 | 135 | 150 | 270 | 90 |  |  |  |
| Ovarial | Adenocarcinoma | I | 1.5 | 1 | 1 | 1 | 1 |  |  |  |
|  |  | % | 50 | 15 | 10 | 40 | 30 |  |  |  |
|  |  | IS | 75 | 15 | 10 | 40 | 30 |  |  |  |
| Colon | Adenocarcinoma | I | 2.5 | 2 | 2.5 | 3 | 2 |  |  |  |
|  |  | % | 100 | 40 | 100 | 80 | 90 |  |  |  |
|  |  | IS | 250 | 80 | 250 | 240 | 180 |  |  |  |
| Stomac | Adenocarcinoma | I | 2 | 2 | NT | 3 | 3 |  |  |  |
|  |  | % | 70 | 90 |  | 100 | 100 |  |  |  |
|  |  | IS | 140 | 280 |  | 300 | 300 |  |  |  |
| Pancreas |  | I | 1(NT islet) | 2.5 (NT) | NT | 2 | 0 |  |  |  |
|  |  | % | 40 | 80 |  | 90 |  |  |  |  |
|  |  | IS | 40 | 200 |  | 180 | 0 |  |  |  |
| Kidney | Clear cells | I | 1.5 | 1.5 | 2 | 2 | 1 |  |  |  |
|  | carcinoma | % | 90 | 70 | 70 | 80 | 10 |  |  |  |
|  |  | IS | 135 | 105 | 140 | 160 | 10 |  |  |  |
| Melanoma | Skin | I | 2.5 | 2 |  |  |  |  |  |  |
|  |  | % | 80 | 40 |  |  |  |  |  |  |
|  |  | IS | 200 | 80 |  |  |  |  |  |  |
|  | Metastasis | I | 2 | 1.5 |  |  |  |  |  |  |
|  |  | % | 70 | 30 |  |  |  |  |  |  |
|  |  | IS | 140 | 45 |  |  |  |  |  |  |
| Liver |  | I | 0 |  |  |  |  |  |  |  |
|  |  | % |  |  |  |  |  |  |  |  |
|  |  | IS | 0 |  |  |  |  |  |  |  |
| Testis |  | I | 3 | 3 | 3 |  |  |  |  |  |
|  |  | % | 100 | 100 | 90 |  |  |  |  |  |
|  |  | IS | 300 | 300 | 270 |  |  |  |  |  |
| Lung | Squamous cells | I | 2.5 | $1_{(necr)}$ | $1_{(necr)}$ | NT |  |  |  |  |
|  |  | % | 50 | 15 | 10 |  |  |  |  |  |
|  |  | IS | 125 | 15 | 10 |  |  |  |  |  |
| Sarcoma |  | I | $0_{(necr)}$ |  |  |  |  |  |  |  |
|  |  | % |  |  |  |  |  |  |  |  |
|  |  | IS | 0 |  |  |  |  |  |  |  |
| Glioblastoma |  | I | 1 | 1 | 1 |  |  |  |  |  |
|  |  | % | 30 | 30 | 20 |  |  |  |  |  |
|  |  | IS | 30 | 30 | 20 |  |  |  |  |  |
| Spleen | Histiocytoma | I | 1.5 |  |  |  |  |  |  |  |
|  |  | % | 80 |  |  |  |  |  |  |  |
|  |  | IS | 120 |  |  |  |  |  |  |  |
| Prostate |  | I | 0 | $0_{(stroma\,2+)}$ | 1 | $0_{(stroma+)}$ | $3_{(stroma+)}$ | $0_{(stroma+)}$ | 0 | 0 | 1.5 |
|  |  | % |  |  | 10 |  | 10 |  |  |  | 15 |
|  |  | IS | 0 | 0 | 10 | 0 | 30 | 0 | 0 | 0 | 22.5 |
| Bladder |  | I | 1 |  |  |  |  |  |  |  |
|  |  | % | 10 |  |  |  |  |  |  |  |
|  |  | IS | 10 |  |  |  |  |  |  |  |

| NORMAL TISSUE | INTENSITY | TYPE OF CELLS POSITIVE |
|---|---|---|
| frontal lobe (gray matter) | 1-2+ | microglia |
| frontal lobe (white matter) | 1-2+ | microglia |
| cerebellum (cortex) | 1+ | Purkinje cells |
| Peripheral nerve | − |  |
| Adrenal gland | 2+ | cortex |
| Liver | 1-2+ |  |
| Pancreas | 3+ |  |
| Ovary | − |  |
| Testis | +/− | gonia cells |
|  | 2+ | Leydig cells |
| Thyroid | 1-2+ | epithelium |
| Spleen | +/− | small lymphocytes |
|  | + |  |
| Lung | 2+/3+ | macrophages |
| Myocard | 1+ |  |
| Aorta | +/− |  |
| Salivary gland | 1+/2+ |  |
| Liver | 1/2+ |  |

TABLE 1-continued

Immuno-score of gC1qR/p32 expression in malignant and normal tissues.

| | | |
|---|---|---|
| Esophagus | 1+ | Musc. Mucosa |
| Stomac (antrum) | 1-2+ | |
| Small Intestine (Ileum) | 3+ | |
| Cecum | 1+ | ! no epithelium, sm muscle |
| Kidney (cortex) | 2-3+ | distal ducts |
| Kidney (medulla) | 2+/3+ | |
| Bladder | +/− | ! no epithelium, sm muscle |
| Uterus | − | |
| Oviduct | 3+ | Ephithelium |
| Prostate | 2-3+ | |
| Skeletal muscle | +/− | |
| Skin | − | Dermis |
| | 1+ | Epidermis |
| Lymph node | | ! Not considered: Smoker |
| Adipose tissue | − | |
| Ependymis | − | |
| Tongue | +/− | |
| Thymus | − | stroma |
| | +/− | Hassal bodies |
| Placenta | 1-2+ | |
| Fetal Membranes | − | |
| Umbilical cord | − | |

I = staining intensity (scale 1-3), % = percentage of tumor cells (EMA positive) with a given gC1qR/p32 intensity of staining (scale 0-100). IS = immuno-score: I × % (scale 0-300). NT (non-tumor) was used to indicate samples where tumor cells were not identified.

C. Example 3

Peptide-Dependent Targeting and Localization of Moieties to Tumor Sites in Mice and Increased Effectiveness of Targeted Abraxane In this example, tumor-homing peptides were used to target abraxane, a clinically approved paclitaxel-albumin nanoparticle, to tumors in mice. The targeting was accomplished with two peptides, CREKA (SEQ ID NO:3), and LyP-1 (CGQKRTRGC; SEQ ID NO:13). Fluorescein (FAM)-labeled CREKA-abraxane, when injected intravenously into mice bearing MDA-MB-435 human cancer xenografts, accumulated in tumor blood vessels, forming aggregates that contained red blood cells and fibrin. FAM-LyP-1-abraxane co-localized with extravascular islands expressing its receptor, p32. Self-assembled mixed micelles carrying the homing peptide and the label on different subunits accumulated in the same areas of tumors as LyP-1-abraxane, showing that Lyp-1 can deliver intact nanoparticles into extravascular sites. Untargeted, FAM-abraxane was detected in the form of a faint meshwork in tumor interstitium. LyP-1-abraxane produced a statistically highly significant inhibition of tumor growth compared to untargeted abraxane. These results show that nanoparticles can be effectively targeted into extravascular tumor tissue and that targeting can enhance the activity of a therapeutic nanoparticle.

This example shows that the biodistribution of abraxane nanoparticles can be changed by conjugating the particles with tumor-homing peptides, and that the localization of the conjugates within tumor tissue is dictated by the specificity of the peptide. Using a modular nanoparticle system, self-assembled mixed micelles, a homing peptide was shown to effectively deliver intact nanoparticles into the extravascular compartment in tumors. Finally, a targeted abraxane was shown to be more effective in inhibiting tumor growth than unmodified abraxane.

1. Results
   i. Peptide-Abraxane Conjugates

The CREKA and LyP-1 peptides were coupled to the surface of abraxane particles through a cysteine sulfhydryl group. The CREKA peptide contains a cysteine residue, which can be used for conjugation to nanoparticles without loss of homing activity (Simberg et al. 2007). LyP-1 is a cyclic peptide with a disulfide bond. A free cysteine was added to this peptide using the chemistries described below in Methods.

Figure 11:
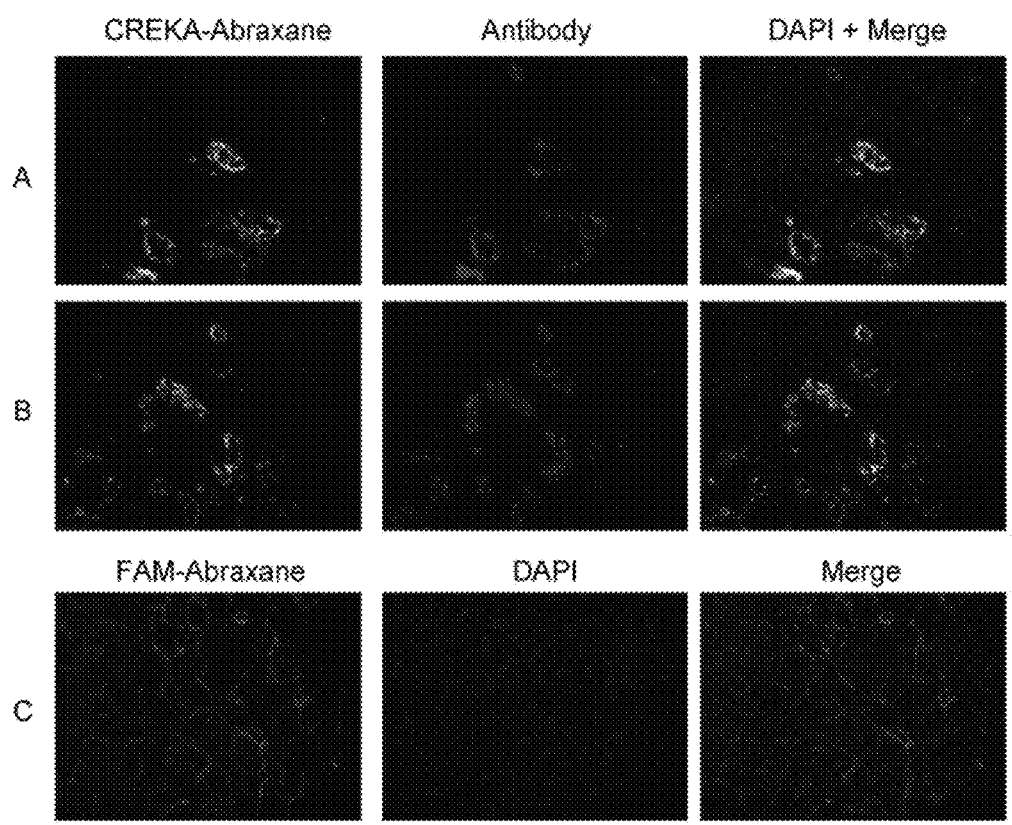
FIGS. 11A, 11B and 11C show localization of CREKA-abraxane in tumor tissue. Balb/c nude mice bearing MDA-MB-435 tumors (~0.5 cm³) were intravenously injected with abraxane conjugated to labeled CREKA peptide (CREKA-abraxane) or to fluorescein (FAM-abraxane), and adjusted to 20 mg/kg of paclitaxel equivalent. The mice were sacrificed by perfusion through the heart 3 hours later and tissues sections were examined for fluorescence. CREKA-abraxane accumulates in tumor blood vessels (A; anti-CD31) and co-localizes with anti-fibrin(ogen) staining (B). FAM-abraxane showed some accumulation in tumor interstitium (C). Nuclei were counterstained with DAPI. The results are representative of three independent experiments. Magnification: 200×.

The integrity of the cyclic structure was ascertained by mass spectrometry and activity was confirmed by in vitro cell-binding and internalization assays (Laakkonen et al. 2004). Both peptides had a fluorescein label on their N-terminus and the C-terminus was blocked as an amide. The peptides were coupled to abraxane particles through a sulfo-SMCC crosslinker Fluorescence measurements revealed one peptide moiety per molecule of albumin in the final conjugate. Fluorescein-labeled abraxane particles were also prepared and used as a control. Abraxane particles conjugated with fluorescein-labeled peptides or with fluorescein exhibited only a small increase in hydrodynamic diameter (~130 to ~150 nm) as measured by dynamic light scattering. To further confirm the presence of paclitaxel in these modified particles, they were digested with proteinase K and the released paclitaxel was extracted in chloroform. Mass spectrometric analysis of the chloroform extract demonstrated the presence of paclitaxel (see Methods).

ii. CREKA-Abraxane and LyP-1-Abraxane Target Different Structures in MDA-MB-435 Tumors The peptide-coated abraxane preparations were tested for in vivo homing to MDA-MB-435 xenograft tumors grown in nude mice. CREKA-abraxane, LyP-1-abraxane and FAM-abraxane at a dose of 20 mg/kg of paclitaxel equivalent were injected and allowed to circulate for 3 hours. CREKA-abraxane mostly accumulated in the tumor blood vessels as evident from its co-localization with CD31 staining (FIG. 11A). Some of the blood vessels appeared to have their lumens filled with a fluorescent mass that also contained trapped erythrocytes. This fluorescent material was positive for anti-fibrin (ogen) staining, indicating the presence of clotted plasma proteins (FIG. 11B). These results suggest that CREKA-abraxane induces a clotting event similar to what has been previously shown with CREKA-coated iron oxide nanoparticles (Simberg et al. 2007), and that the nascent clot may then trap circulating erythrocytes. In addition to its vascular homing, CREKA-abraxane was also present in a faint meshwork pattern throughout the tumor. This meshwork in tumors was also present in tumors of mice injected with FAM-abraxane (FIG. 11C). Among the tissues most likely to trap nanoparticles, there was modest uptake of CREKA-abraxane in the liver and in the spleen, while the lungs and kidneys showed no fluorescence. The heart, pancreas and brain also contained no detectable CREKA-abraxane fluorescence; FAM-abraxane was not detected in any normal organ. In agreement with what has been shown for CREKA-coated iron oxide nanoparticles (Simberg et al. 2007), no occluded vessels were seen in any of the non-tumor tissues examined (FIG. 16).

Figures 12A, 12B, 12C:
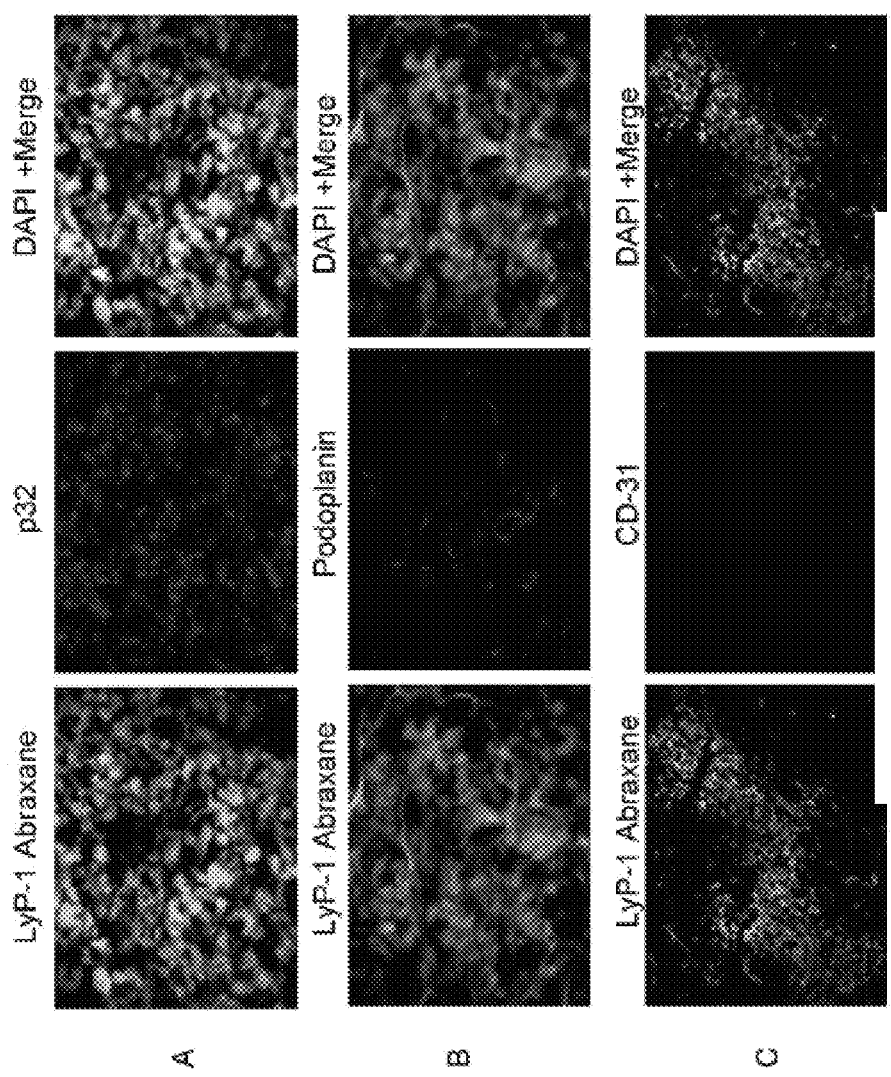
FIGS. 12A-12F show localization of LyP-1-abraxane in tumor tissue. LyP-1-abraxane was injected into nude mice bearing MDA-MB-435 tumors as described in the legend of FIG. 11. LyP-1-abraxane co-localizes with p32, the receptor for LyP-1 (A). Cell clusters positive for LyP-1-abraxane are interspersed with podoplanin-positive structures, presumed to be lymphatic vessels (B), but these areas are mostly devoid of blood vessels (C). LyP-1-abraxane exhibits increased accumulation in extravascular tissue compared to FAM-abraxane (D, E, F). Blood vessels were stained with anti-CD31 and lymphatic vessels with anti-podoplanin. Nuclei were counterstained with DAPI. The results are representative of three independent experiments. Magnification: 600× (A & B), 200× (C, D & E). Quantification of fluorescence (F) in tumor micrographs (FAM-abraxane, CREKA-abraxane and LyP-1-abraxane) and liver micrographs (LyP-1-abraxane) was performed using Image J (NIH, USA). Five random fields were quantified per tumor and liver for LyP-1-abraxane (n=3), four random fields per tumor for CREKA-abraxane (n=3) and five random fields per tumor for FAM-abraxane (n=3). Error bars represent S.E.M.
Figures 12D, 12E:
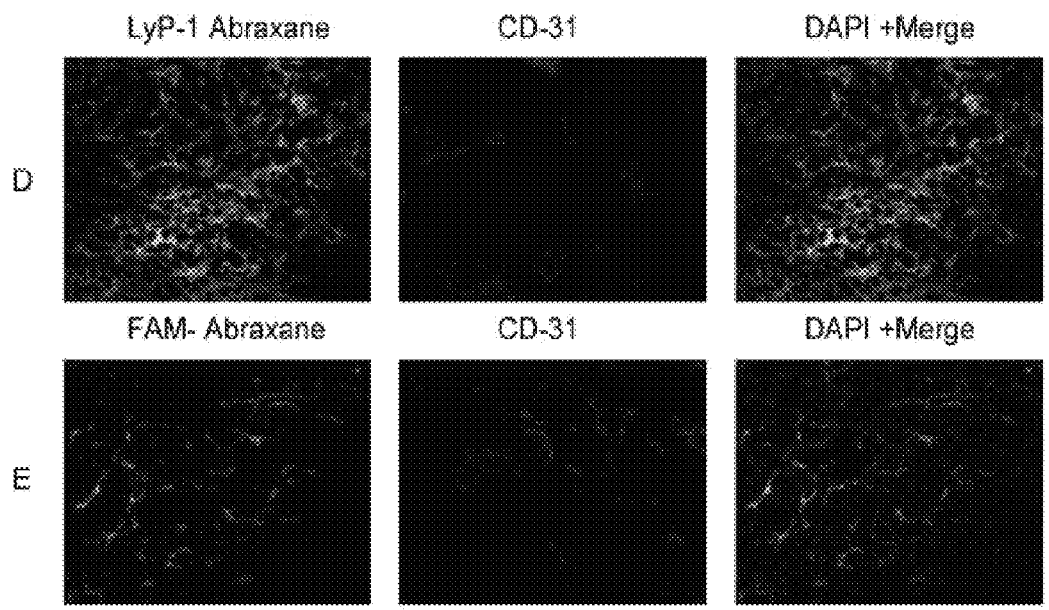
Figure 12F:
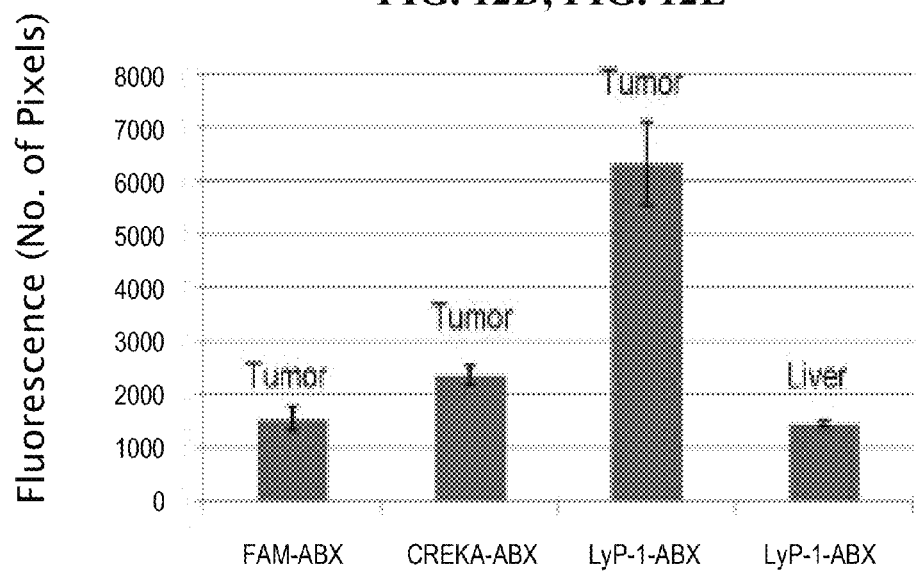

LyP-1-abraxane showed greatly enhanced accumulation in extravascular tumor tissue compared with CREKA-abraxane or FAM-abraxane. This conjugate homed to tumor cell clusters that were positive for p32 (FIG. 12A), the receptor for the LyP-1 peptide (Fogal et al. 2008). These cell clusters were typically located in regions that had interspersed podoplanin-positive structures, presumably lymphatic vessels (FIG. 12B), but few blood vessels (FIG. 12C). Similar distribution has been previously noted for the LyP-1 peptide (Laakkonen et al. 2002; Laakkonen et al. 2004). LyP-1-abraxane was also detected in tumor stroma in a meshwork pattern similar to, but more strongly fluorescent than that seen with FAM-abraxane. The presence of faint fluorescent meshwork in tumor tissue with untargeted FAM abraxane and CREKA abraxane could be due to an albumin dependent transport mechanism (Desai et al. 2006). However, the enhanced accumulation observed with LyP-1-abraxane shows that the LyP-1 peptide causes increased extravasation of abraxane compared to untargeted or CREKA targeted abraxane. LyP-1-abraxane was not detectable in the control tissues examined, with the exception of the liver and spleen, which like CREKA-abraxane, showed some uptake (FIG. 16). The liver uptake could be due to the presence of basic amino acids in the peptide sequences. Quantification of fluorescence intensities showed that FAM-LyP-1-abraxane delivered 4-fold more fluorescence into the tumors than FAM-abraxane (FIG. 12F, p<0.01), whereas FAM-CREKA-abraxane was not significantly different from FAM-abraxane. LyP-1 abraxane delivered 4-fold more fluorescence into tumors than to the liver (FIG. 12F, p<0.01).

iii. LyP-1 Phage and Micelles Extravasate into Tumor Tissue

The strong accumulation of fluorescence from LyP-1-abraxane in locations away from blood vessels suggested that LyP-1 can carry a nanoparticle payload into extravascular tumor tissue. However, since the fluorescent label was attached to the peptide, the formal possibility remained that the abraxane particle had disintegrated, and that the labeled peptide without its payload was actually being observed. As there was no practical way of designing an abraxane particle where the label and the peptide were uncoupled, phage (a 50 nm particle) and micelles (Arleth et al. 2005; Tu and Tirrell 2004) were used to study the ability of LyP-1 to deliver an intact particle outside the confines of blood vessels.

Figure 13:
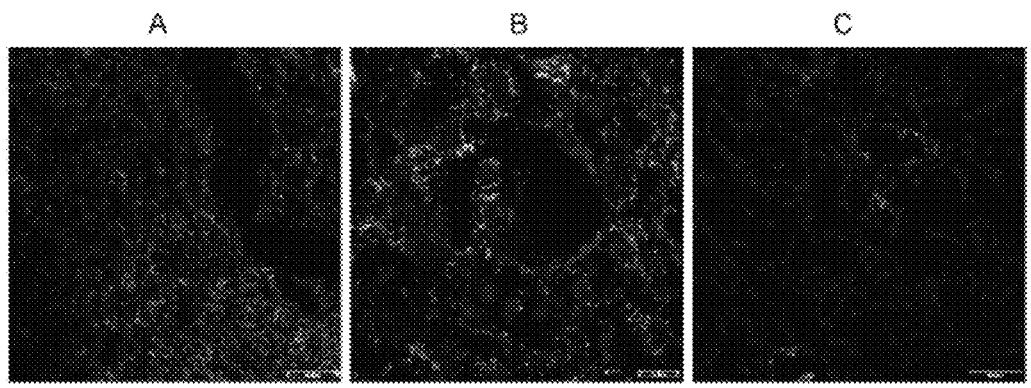
FIGS. 13A, 13B and 13C show rapid extravasation of LyP-1 phage. Nude mice with MDA-MB-435 tumors were intravenously injected with 100 μl of 2×10$^{10}$ plaque forming units (p.f.u.) of T7 phage displaying 415 copies of LyP-1 peptide (Cys-Gly-Gln-Lys-Arg-Thr-Arg-Gly-Cys) (A and B) or CG7C peptide (Cys-Gly-Gly-Gly-Gly-Gly-Gly-Gly-Cys) (C) on the phage capsid protein. The mice were sacrificed 15 minutes post-injection by perfusion with PBS and tissues were collected for histology. The T7 phage was detected by immunostaining with polyclonal rabbit anti-T7. Blood vessels were stained with anti-CD31 and nuclei were counterstained with DAPI. The images are representative of 2 independent experiments. Scale bar: 50 μm.

Immunohistochemical staining tumor sections with antibodies against T7 phage coat protein showed extensive staining for the LyP-1 phage as early as 10-15 minutes after an intravenous injection (FIGS. 13A and 13B). Co-staining with anti-CD31 showed no co-localization of the phage coat protein with tumor blood vessels, indicating extravascular localization of the phage. A control phage displaying the sequence Cys-Gly-Gly-Gly-Gly-Gly-Gly-Gly-Cys (SEQ ID NO:14)) was not detected in the tumor tissue (FIG. 13C). As the T7 phage is highly resistant to disassembly, for example, it remains infective after treatment with denaturing agents such as 1% SDS, 4M urea, and 2M guanidine-HCl (Rosenberg et al. 1996), this result suggests that the intact LyP-1 phage particle had extravasated and penetrated the tumor interior.

Figure 14:
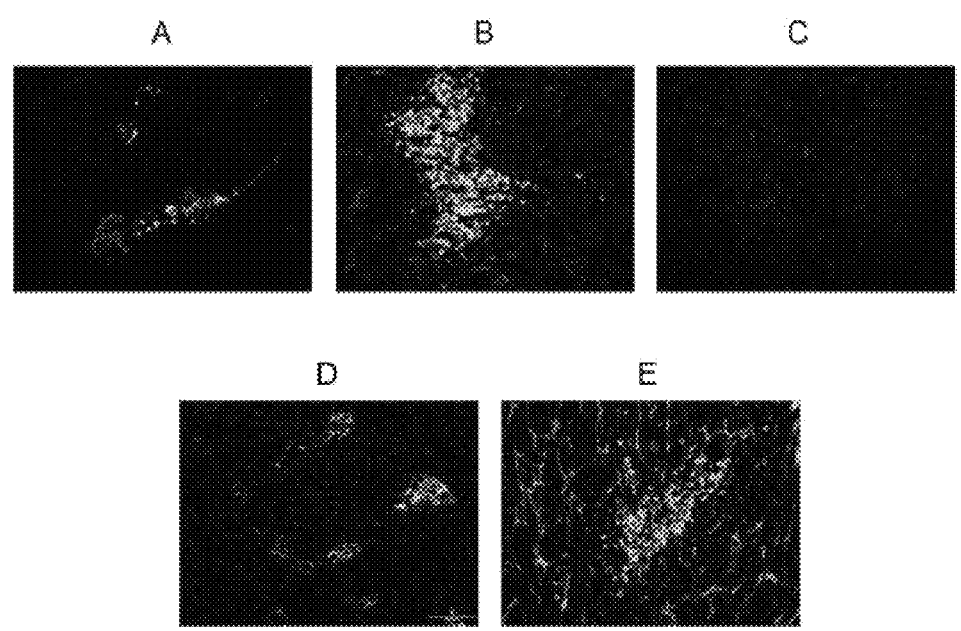
FIGS. 14A-14E show peptide-targeted micelles are delivered intact to tumor tissue. Nude mice bearing MDA-MB-435 tumors (~0.5 cm³ in diameter) were intravenously injected with 100 μl of 1 mM solution of DSPE-PEG$_{2000}$-FAM-CREKA micelles (A), DSPE-PEG$_{2000}$-FAM-LyP-1 micelles (B), DSPE-PEG$_{2000}$-FAM micelles (C), mixed CREKA micelles, (D) or mixed LyP-1 micelles (E). (The mixed micelles were prepared from DSPE-PEG$_{2000}$-CREKA (unlabeled) and DSPE-PEG$_{2000}$-FAM or DSPE-PEG$_{2000}$-LyP-1 (unlabeled) and DSPE-PEG$_{2000}$-FAM). The mice were sacrificed 3 hours post-injection by perfusion through heart with PBS and tissues were collected for histology. Blood vessels were visualized by staining with anti-CD31. Nuclei were counterstained with DAPI (small gray spheres). The images are representative of 3 experiments. Magnification: 200× (A, B, C, E). Scale bar: 50 μm (D).

To further test for peptide-guided extravasation of LyP-1-coated nanoparticles, micelles displaying the targeting peptides on their surface were constructed. The peptide or fluorophore was separately conjugated to 1,2-distearoyl-sn-glycero-3-phosphoethanolamine-N-[maleimide (polyethylene glycol)$_{2000}$] (DSPE-PEG), and mixed micelles composed of unlabeled lipopeptide and labeled lipid were prepared. Upon intravenous injection into mice bearing MDA-MB-435 tumors, the mixed micelles showed the same localization in tumors as the corresponding abraxane conjugates; LyP-1 micelles accumulated extravascularly, whereas CREKA based micelles accumulated in tumor blood vessels (FIG. 14). Micelles labeled on the peptide were also tested and found the same homing pattern as with the lipid-labeled compounds. Micelles prepared from a FAM-labeled lipid did not show any tumor homing. These results strongly support that LyP-1 peptide can deliver intact nanoparticles into extravascular locations, and that this process only takes minutes.

iv. LyP-1 Coating Increases the Anti-Tumor Activity of Abraxane

Figure 15:
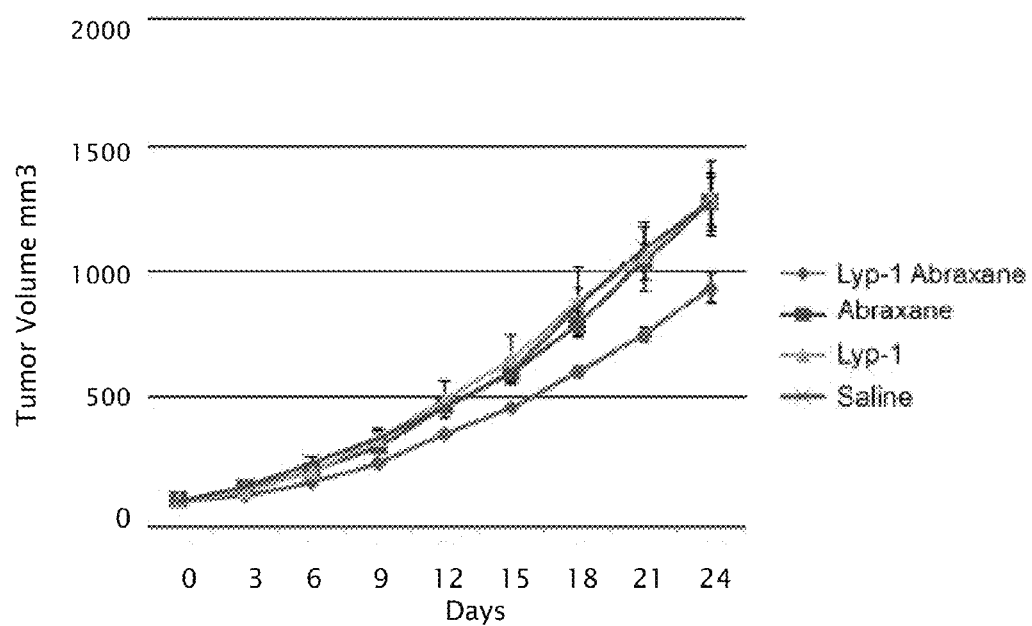
FIG. 15 shows the effect on tumor growth by LyP-1-abraxane conjugate. Nude mice bearing MDA-MB-435 xenograft tumors were treated with LyP-1-conjugated abraxane, and unmodified abraxane, free LyP-1 peptide, or saline four times a week for 3 weeks (at a paclitaxel equivalent of 3 mg/kg/day for LyP-1-abraxane and unmodified abraxane). The total cumulative dose was 30 mg/kg. LyP-1 peptide was used at a dose equivalent to what was injected on the particles. There were 10 mice per group and the treatment started when the mean tumor volume for each group was about 100 mm³. Two independent experiments were performed and gave similar results; one is shown here. LyP-1-abraxane was significantly more effective in inhibiting tumor growth than unmodified abraxane (p=0.013), LyP-1 alone (p<0.01) and saline (p<0.01). Error bars represent S.E.M.

Next, MDA-MB-435 tumors were treated with these conjugates. Initial experiments were performed to find the highest dose level at which unmodified abraxane had no effect on the growth of the tumors. The peptide-abraxane conjugates were then compared to unmodified abraxane at this dose level. CREKA-abraxane treatment resulted in a modest inhibition in tumor growth compared to unmodified abraxane, but the difference was not statistically significant. In contrast, treatment with LyP-1-abraxane resulted in a significant (p=0.013) inhibition of tumor growth (FIG. 15).

2. Discussion

It is shown in this example that the clinically used nanoparticle drug, abraxane, can be modified with homing peptides, and that peptides with different tumor-targeting specificities deliver abraxane to their target sites. A peptide-targeted abraxane is demonstrated to be more effective than untargeted abraxane in tumor treatment.

The two homing peptides used in this work both selectively target tumors, but with a very different specificity. The CREKA peptide recognizes clotted plasma proteins in tumor vessels and tumor stroma. Iron oxide nanoparticles delivered to tumors bind to the walls of tumor vessels and cause clotting in them. As this additional clotting creates new binding sites for the CREKA peptide, the homing of the nanoparticles becomes self-amplifying (Simberg et al. 2007). The CREKA-coated abraxane nanoparticles and micelles studied also accumulated in tumor vessels and caused clotting in them as shown by co-localization of the particles with fibrin staining and trapping of red blood cells inside the clots.

Iron oxide particles, even when coated with PEG, tend to accumulate in the liver (although they do not cause any detectable clotting in the liver (Simberg et al. 2007; Park et al. 2008). CREKA-abraxane or CREKA micelles showed only modest uptake into the liver. Abraxane that was modified only by FAM without a peptide was not detectable in the liver, indicating that adding the CREKA peptide causes liver binding. However, the increase obtained with CREKA coating in tumor accumulation of abraxane outweighs the slight diversion of some of the CREKA-abraxane into the liver. The LyP-1 peptide also caused some liver uptake of abraxane and micelles. The presence of basic amino acids in both the peptides might favor some liver uptake but the liver accumulation of the peptide-coated abraxane particles may not be entirely charge-based, as the net charge is +1 for CREKA and +3 for LyP-1, and the liver uptake of abraxane coated with these peptides appeared to be equal.

The distribution of LyP-1 abraxane and LyP-1 micelles within tumors was very different from that of the CREKA-coated particles. The LyP-1 particles were not detectable in blood vessels, and instead accumulated outside the blood vessels in islands of cells that were positive for the known receptor for this peptide, p32 (Fogal et al. 2008). The vessels in these areas are primarily lymphatics, and there are few blood vessels, which may be the reason why these areas are hypoxic (Laakkonen et al. 2004). Tumor cells in these hypoxic (and apparently also nutrient-deficient) areas tend to be resistant to chemotherapeutic agents, which generally target dividing cells. There is also growing evidence indicating that these cells are genetically unstable, and a significant source of metastasis (Le et al. 2004; Subarsky and Hill 2003; Sullivan and Graham 2007). Thus, the ability of LyP-1 to deliver payloads to these otherwise difficult-to-access sites opens up new modes for tumor therapy.

LyP-1 is a cell-penetrating peptide with activity similar to that of widely used cell-penetrating peptides such as Tat and penetratin (Langel 2002; Zorko and Langel 2005), except that LyP-1 is cell type-specific. The ability of LyP-1 to penetrate into tumor tissue and take payloads with it may be related to the cell type specificity of its binding and internalization. Non-selective cell-penetrating peptides are taken up by all cells in all tissues (Vives 2005) and will concentrate in the cells that are in or close to blood vessels, whereas LyP-1 is not consumed by these cells and can accumulate in the specific targets cells. The tumor homing of LyP-1 may have an active tissue-penetrating element.

Nanoparticles do not readily extravasate, and their penetration into tumor tissue beyond the vicinity of blood vessels is particularly problematic because of the high interstitial pressure in tumors (Jain 1990; Heldin et al. 2004). Importantly, the results in this example show that synthetic particles coated with LyP-1 extravasate and spread into tumor tissue. As the abraxane nanoparticles did not lend themselves to determining whether the particles were still intact when they reached the p32-rich extravascular sites, this question was studied by using mixed micelles that have the label on one amphiphile and the peptide on another. The presence of the label at the sites the peptide homes to indicates that LyP-1 can deliver intact micelles and other nanoparticles to extravascular sites.

Synaphic targeting makes it possible to change the pharmacokinetics of a drug such that more of the drug is delivered into the tumor, rendering it more effective and thereby reducing the toxicity. Although toxicity studies were not performed, the targeted abraxane nanoparticles fulfilled two of these expectations: non-targeted, FAM-labeled abraxane was detectable as a fluorescent network in tumor tissue, but this network was stronger when FAM-LyP-1-abraxane was injected, and p32-rich islands were intensely positive.

The tumor treatment results with the 3 abraxane compounds were in good agreement with the bio-distribution results. The CREKA compound was not significantly different from non-targeted abraxane. In contrast, LyP-1-abraxane improved the efficacy of abraxane in a statistically highly significant matter ($p=0.001$ and $0.013$ in two independent experiments; combined $p=0.007$). The reason for the difference may be that, although the accumulation of CREKA-abraxane in tumor blood vessels was impressive, the diffuse spread into the tumor was similar to unmodified abraxane. The accumulation in the blood vessels alone may not be sufficient to exert an enhanced anti-tumor effect compared to untargeted abraxane. However, there was an indication that CREKA-abraxane could have been slightly more active than non-targeted abraxane. LyP-1 abraxane and CREKA-abraxane together can increase effectiveness since the two peptides deliver abraxane to largely non-overlapping sites in tumor tissue and combining them can result in a broader distribution of the drug than either one alone.

3. Methods i. Reagents, Cell Lines and Tumors:

Abraxane (Abraxis Biosciences, Los Angeles, Calif., USA) was obtained from the Cancer Center Pharmacy at University of California, San Diego. Sulfo-SMCC (Sulfosuccinimidyl 4-[N-maleimidomethyl]cyclohexane-1-carboxylate) and NHS-Fluorescein 5-(and 6-) carboxyfluorescein succinimidyl ester were from Pierce, Rockford, Ill., USA. All the lipids were purchased from Avanti Polar Lipids, Alabaster, Ala., USA. MDA-MB-435 cells were maintained in DMEM supplemented with 10% FBS and 1% Glutamine Pen-Strep at 37° C./5% $CO_2$. To induce MDA-MB-435 tumors, Balb/c nude mice were injected with $2\times10^6$ MDA-MB-435 cells in PBS into the mammary fat pad region.

ii. Peptides

Peptides were synthesized with an automatic Microwave assisted peptide synthesizer (Liberty; CEM Corporation, USA) using standard solid-phase Fmoc/t-Bu chemistry. During synthesis, the peptides were labeled with 5(6)-Carboxyfluorescein (FAM) with a 6-aminohexanoic acid spacer separating the dye from sequence. The synthesis of LyP-1 peptide used for the chemoselective ligation described with an extra N-terminus cysteine were prepared using the following chemistries.

Synthesis of FAM-Cys-X-{CGNKRTRGC}-$NH_2$. Peptide was synthesized by Solid Phase Peptide Synthesis using the Fmoc/t-Bu strategy on a Microwave-assisted automated Peptide Synthesizer (Liberty, CEM corporation, Matthews, N.C.). The amino acids were coupled using HBTU-HOBt reagent system in the presence of diisopropyl amine (alternatively, collidine). N,N'-dimethyl formamide, DMF, (alternatively, N-methylpyrrolidinone, NMP) was used as the solvent. Fmoc deprotection was brought about using 5% piperazine in DMF or NMP. The peptide was synthesized on rink amide resin with Fmoc-Cys(Mmt) on the C-terminus and Fmoc-Cys-(St-Bu) on the N-terminus. Further, the additional third cysteine was introduced on the N-terminus with Fmoc-Cys(trt)-OH, spaced from the rest of the sequence by 6-aminohexanoic acid. The other residues had standard Fmoc-synthesis compatible protecting groups. The fluorescein (5(6)-fluorescein carboxylate) was coupled to the amine of third cysteine. The thio butyl protection on the N-terminal cysteine was removed using tributyl phosphine (alternately-2-mercaptoethanol) to liberate free thiol, which was activated using 2,2-dithiobis 2,2-dinitro pyridine. The peptide was cyclized using 1% TFA in DCM. Upon cleavage with TFA:TIS:water (95%:2.5%:2.5%) the title peptide was obtained in 20-30% yields after purification with acetonitrile and water gradient containing 0.1% TFA.

Alternate method: The cysteines in the sequence were incorporated into the sequence with Fmoc-Cys(Acm)-OH derivatives and subsequently cyclized using thallium(III)trifluoro acetate. Upon the cleavage with 95% TFA the title peptide was obtained in 5-20% yields.

This synthesis method is applicable for any peptides containing Disulfides and their synthesis with high efficiency has not been reported in the literature. The alternative method is compatible with Boc-strategy.

The integrity of the cyclic structure was ascertained by mass spectrometry and activity was confirmed by in vitro cell-binding and internalization assays (Laakkonen et al. 2004). Both peptides had a fluorescein label on their N-terminus and the C-terminus was blocked as an amide. The peptides were coupled to abraxane particles through a sulfo-SMCC crosslinker Fluorescence measurements revealed one peptide moiety per molecule of albumin in the final conjugate.

iii. Peptide-Nanoparticle Conjugates

Peptide-abraxane conjugates were prepared by coupling peptides to abraxane through their cysteine sulfhydryl group using a sulfo-SMCC cross-linker. Abraxane was suspended in nitrogen-purged sterile PBS at a concentration of 5 mg per ml and 0.3 mg of sulfo-SMCC was added. After incubation at room temperature for 30 minutes, the excess crosslinker was removed by filtration through a Nap-10 column (GE Healthcare, UK). Peptide labeled with FAM was dissolved in sterile nitrogen-purged water and added to the abraxane-sulfo-SMCC conjugate in small aliquots over a period of 1 hour. The peptide was used at 3-fold molar excess relative to albumin. Excess peptide was removed by repeated washing in ultracentrifugal devices (Amicon; MWCO 10K). Fluorescence measurements revealed approximately one peptide per albumin molecule in the final conjugate. FAM-abraxane was prepared by directly coupling of NHS-Fluorescein (Pierce) to abraxane in PBS for 1 hour at room temperature. Particle integrity was confirmed by hydrodynamic diameter measurements using dynamic light scattering (Brookhaven Instruments). The measurements were performed in deionized water at an angle of 90°. To further confirm the presence of paclitaxel in these modified particles, they were digested with proteinase K (Qiagen, Valencia, Calif., USA) for 1 hour at 60° C. The released paclitaxel was then extracted in chloroform and analyzed by mass spectrometry. Separately, chloroform was removed by evaporation, the residue was dissolved in methanol and absorbance measured at 227 nm. The concentration of paclitaxel was calculated from the slope of standard curve generated with pure paclitaxel (Sigma, St. Louis, Mo., USA) in methanol.

Lipopeptides were prepared by coupling unlabeled or FAM-labeled peptides to 1,2-distearoyl-sn-glycero-3-phosphoethanolamine-N-[maleimide(polyethylene glycol)$_{2000}$; DSPE-PEG$_{2000}$-maleimide] (Avanti Polar Lipids) at a 1:1 molar ratio by making use of a free cysteine sulfhydryl group on the peptide The reaction was performed in aqueous solution at room temperature for 4 hours. The resulting DSPE-PEG$_{2000}$ lipopeptides were lyophilized and stored at −20° C. until used. DSPE-PEG$_{2000}$-FAM was either purchased (Avanti polar lipids) or prepared by coupling 1,2-Distearoyl-sn-Glycero-3-Phosphoethanolamine-N-[Amino(Polyethylene Glycol)2000; (DSPE-PEG$_{2000}$-amine) with NHS-Fluorescein (Pierce) at a 1:1 molar ratio in PBS for 1 h at room temperature. Excess NHS-Fluorescein was removed by overnight dialysis against water using slide-a-lyzer dialysis cassettes (3.5K MWCO, Pierce). The dialyzed product was then lyophilized and stored at −20° C. until used.

To prepare micelles, lyophilized DSPE-PEG$_{2000}$-peptide and DSPE-PEG$_{2000}$-FAM were dissolved in methanol and transferred to a glass tube at appropriate molar ratios. Methanol was evaporated under nitrogen flow. Residual solvent was removed by storing the film under vacuum for 12 hours. The film was then hydrated for 15 minutes in MilliQ water (18 MΩ-cm) heated to 80° C. After the solution cooled to room temperature, it was filtered through a polyvinylidene fluoride centrifuge filter (100 nm nominal pore size, Amicon Bioseparations) and washed with PBS using the ultracentrifugal devices (Amicon; MWCO 10K). Dynamic light scattering system (Brookhaven Instruments Corporation, Holtsville, N.Y., USA) was used to confirm spherical shape and to measure the hydrodynamic diameter of the micelles. The first cumulant ($\Gamma$) of the first order autocorrelation function was measured as a function of scattering vector, q in the range of 0.013 to 0.024 nm$^{-1}$. The quantity, $\Gamma/q^2$, which corresponds to the translational diffusion coefficient was found to be independent of q, confirming the presence of isotropic spherical particles Thus, the Stokes-Einstein relation was used to calculate a hydrodynamic diameter of 12.5±0.5 nm for the micelles.

iv. Nanoparticle Injections

To analyze nanoparticle biodistribution, tumor-bearing mice were anesthetized with intraperitoneal Avertin, and abraxane nanoparticles (20 mg of paclitaxel per kg body weight) or micelles (100 µl of a 1 mM solution) were injected into the tail vein. The mice were sacrificed 3 hours postinjection by cardiac perfusion with PBS under anesthesia, and organs were dissected and analyzed for particle homing. In tumor treatment experiments, nude mice bearing MDA-MB-435 tumors of approximately 100 mm$^3$ were treated with LyP-1-conjugated abraxane, unmodified abraxane, free LyP-1 peptide, or saline four times a week for 3 weeks (at a paclitaxel equivalent of 3 mg/kg/day for LyP-1-abraxane and unmodified abraxane). The total cumulative dose was 30 mg/kg. LyP-1 peptide was used at a dose equivalent to what was injected on the particles. There were 10 mice per group. Tumor volume was calculated using the following formula: volume (mm$^3$)=(d$^2$×D)/2 where d and D are the smallest and biggest tumor diameters respectively. Similar treatment studies were conducted with CREKA-abraxane. All animal experiments were reviewed and approved by the Institutional Animal Care and Use Committee (IACUC) of UCSB and animal research committee of Burnham Institute for Medical Research. For humane reasons, mice were sacrificed when the tumor volumes became more than 2000 mm$^3$.

v. Immunohistochemistry

Tissues from mice injected with nanoparticles were fixed in 4% Paraformaldehyde (PFA) overnight at 4° C., cryoprotected in 30% sucrose for 10 hours and frozen in OCT embedding medium. For histological analysis, 5 µm sections were cut. For immunostaining, tissue sections were first incubated with 10% serum from the species in which secondary antibody is generated for 1 hour at room temperature followed by incubation with the primary antibody overnight at 4° C. The following antibodies were used: rat monoclonal anti-mouse CD31 (10 µg/ml; BD Pharmingen, San Jose, Calif., USA), hamster monoclonal anti-mouse podoplanin (10 µg/ml; Abcam, Cambridge, Mass., USA) and rabbit polyclonal anti-p32 (10 µg/ml). The p32 antibody was produced against a peptide from the p32 sequence near the N-terminus and extensively characterized by immunoblotting and tissue staining. The details will be published elsewhere (Fogal et al. 2008). T7 phage was detected by immunostaining with a polyclonal rabbit anti-T7 antibody (Laakkonen et al. 2002). The primary antibodies were detected with Alexa 594 goat anti-rat, Alexa 594 goat anti-rabbit and Alexa 594 goat anti-hamster secondary antibodies (1:1000; Molecular Probes, Eugene, Oreg., USA). Each staining experiment included sections stained with secondary antibodies only as negative controls. Nuclei were counterstained with DAPI (5 µg/mL; Molecular Probes, Eugene, Oreg., USA). The sections were mounted in gel/mount mounting medium (Biomeda, Foster city, CA) and visualized under an inverted fluorescent (Leica Microsystems, Weltzer, Germany) or confocal microscope (Olympus, Melville, N.Y.).

vi. Statistical Analysis

Differences between the various treatments were statistically tested using two tailed Student's unpaired t-test. P values of less than 0.05 were considered statistically significant.

D. Example 4

Analysis of iRGD Homing and Internalization

Peptides containing the RGD integrin recognition motif (Pierschbacher and Ruoslahti, E. Cell attachment activity of fibronectin can be duplicated by small synthetic fragments of the molecule. *Nature* 309, 30-33 (1984); Ruoslahti, The RGD story: a personal account. *Matrix Biol.* 22, 459-465 (2003)) and its mimics have been used to deliver drugs, biologicals, imaging agents, and nanoparticles to αv-integrins expressed in tumor blood vessels (Eliceiri and Cheresh, Adhesion events in angiogenesis. *Curr. Opin. Cell Biol.* 13, 563-568 (2001); Ruoslahti, Specialization of tumor vasculature. *Nature Rev. Cancer* 2, 83-90 (2002); Arap et al., Cancer treatment by targeted drug delivery to tumor vasculature in a mouse model. *Science* 279, 377-380 (1998); Curnis et al., Coupling tumor necrosis factor-α with $α_v$ integrin ligands improves its antineoplastic activity. *Cancer Res.* 64, 565-571 (2004); Sipkins et al., Detection of tumor angiogenesis in vivo by $α_vβ_3$-targeted magnetic resonance imaging. *Nature Med.* 4, 623-626 (1998); Murphy et al., Nanoparticle-mediated drug delivery to tumor vasculature suppresses metastasis. *Proc. Natl. Acad. Sci. USA* 105, 9343-9348 (2008)). However, a major obstacle has been the limited capability of such RGD-targeted agents to penetrate tumor parenchyma and accumulate therein (Jain, Vascular and interstitial barriers to delivery of therapeutic agents in tumors. *Cancer Metastasis Rev.* 9, 253-266 (1990)), despite evident expression of the target integrins. Disclosed is a cyclic RGD peptide, iRGD (sequence: CRGDK/RGPD/EC; SEQ ID NOs:15, 16, 17, and 18) that is exceptionally effective in orchestrating extravasation and spreading of linked payloads within tumor tissue, and subsequently internalizing within tumor cells. The peptide incorporates two functional elements: the RGD motif that gives tumor specificity (Pierschbacher and Ruoslahti, E. Cell attachment activity of fibronectin can be duplicated by small synthetic fragments of the molecule. *Nature* 309, 30-33 (1984); Ruoslahti (2003); Eliceiri and Cheresh (2001); Ruoslahti (2002); Arap et al. (1998); Curnis et al. (2004); Sipkins et al. (1998); Murphy et al. (2008)), and an RXXK/R motif (CendR motif; SEQ ID NOs:19 and 20) that mediates penetration. iRGD readily adhered to cultured cells expressing αv integrins, and was internalized far more effectively than other RGD peptides. Internalization was dependent on expression of neuropilin-1, the receptor for the CendR motif. In all seven tumor models tested, iRGD coupled to a payload of fluorescein, phage, or artificial nanoparticles, accumulated around tumor vessels in vivo, spread through the tumor interstitium, and became internalized within tumor cells. Systemic administration of iRGD micelles labeled with a near infrared dye produced a strong and specific tumor signal in whole body imaging of mice. The tissue-penetrating properties of iRGD present a new tool for synaphic (docking-based) tumor targeting of nanoscale payloads for diagnostic imaging and therapy.

Mouse models of prostate cancer were used as targets in phage library selection (Hoffman et al., Progressive vascular changes in a transgenic mouse model of squamous cell carcinoma. *Cancer Cell* 4, 383-391 (2003)) to identify peptides that bind to tumor blood vessels. Phage that contained the RGD motif (Pierschbacher and Ruoslahti (1984); Ruoslahti (2003)) within three related sequences, CRGDKGPDC (SEQ ID NO:15), CRGDRGPDC (SEQ ID NO:16), and CRGDKGPEC (SEQ ID NO:17), dominated in the selected pools (Table 2). CRGDKGPDC ("iRGD" for 'internalizing-RGD'; SEQ ID NO:15) was most frequent and was chosen for further analysis.

TABLE 2

RGD peptides selected in the screenings

| Screening 1 | | Screening 2 | | Screening 3 | |
| --- | --- | --- | --- | --- | --- |
| Sequence | (%) | Sequence | (%) | Sequence | (%) |
| CRGDKGPDC | 15.2 | CRGDKGPDC | 13.6 | CRGDKGPEC | 10.0 |
| CRGDRGPDC | 9.1 | CRGDKGENC | 4.5 | CRGDKHADC | 5.0 |
| CRGDKGPEC | 6.1 | CGRGDSPDC | 4.5 | CRGDHAANC | 5.0 |
| CRGDKTTNC | 3.0 | | | CRGDAGINC | 5.0 |
| CRGDHAGDC | 6.1 | | | CGRGDMPSC | 5.0 |
| CRGDHGVEC | 3.0 | | | CEKRGDSLC | 5.0 |
| CGRGDNLPC | 3.0 | | | | |
| CGRGDNLAC | 3.0 | | | | |
| CEKRGDNLC | 3.0 | | | | |
| CEKRGDSVC | 6.1 | | | | |
| CSGRGDSLC | 3.0 | | | | |
| CGKRGDSIC | 3.0 | | | | |
| CTGRGDALC | 3.0 | | | | |
| CRGDSAC | 3.0 | | | | |
| Total RGD peptides | 69.6 | Total RGD peptides | 22.6 | Total RGD peptides | 35.0 |

Figures 17A, 17B:
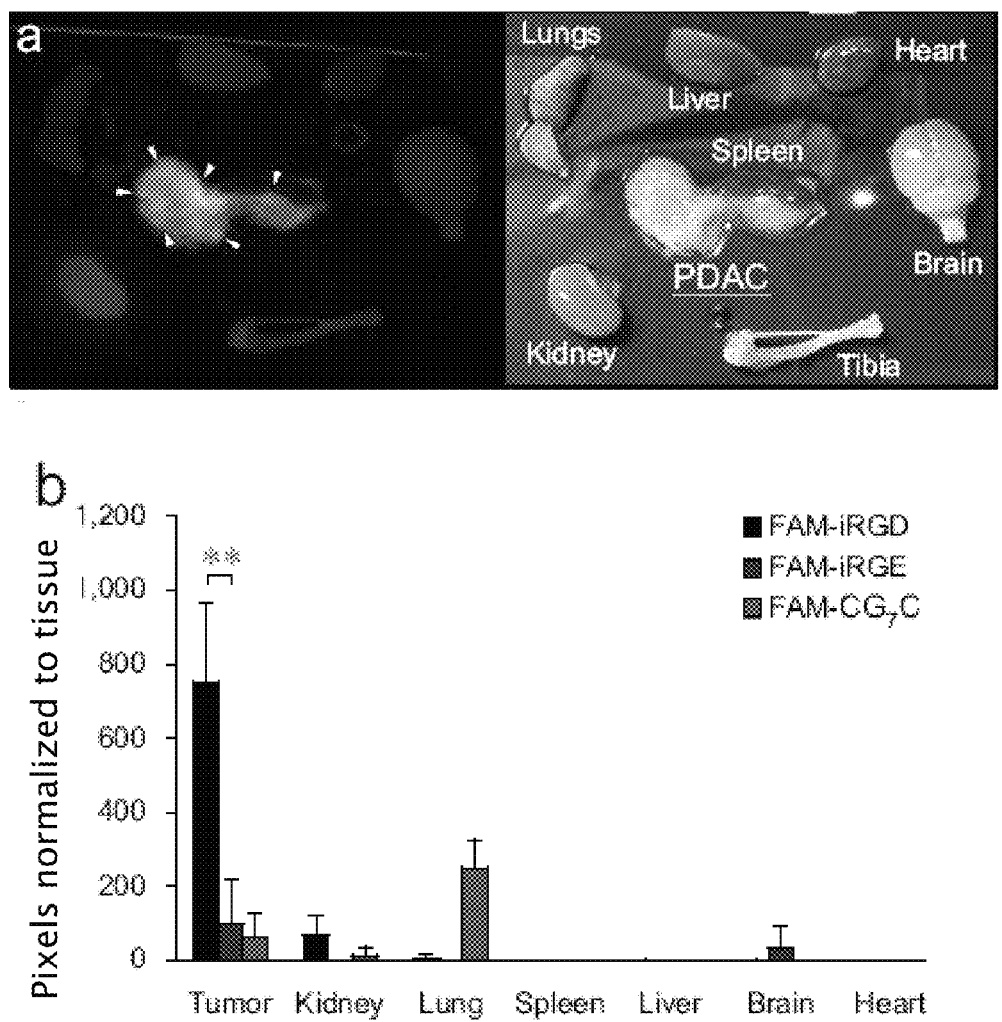
FIGS. 17A-17E show in vivo tumor homing of iRGD peptide. a, Approximately 200 μg of FAM-iRGD or control peptide in PBS was intravenously injected into LSL-Kras, p53-fl/+, p48-Cre mice bearing de novo pancreatic ductal adenocarcinoma (PDAC) (Bardeesy and DePinho, Pancreatic cancer biology and genetics. *Nature Rev. Cancer* 2, 897-909 (2002)). The peptides were allowed to circulate for 2 hrs and organs were collected and viewed under UV light (left panel) or white light (right panel). Arrowheads point to the tumors. b, c, Quantification of the in vivo distribution of iRGD and control peptides. FAM-iRGD; a non-integrin-binding iRGD mutant, FAM-CRGEKGPDC (SEQ ID NO:291) (FAM-iRGE); and a FAM-labeled cyclic polyglycine peptide (FAM-CG$_7$C) were injected into PDAC mice (Bardeesy and DePinho, Pancreatic cancer biology and genetics. *Nature Rev. Cancer* 2, 897-909 (2002)) as described elsewhere herein (b). In some cases, a 10-fold excess of unlabelled iRGD peptide or iRGE peptide was injected 30 min before FAM-iRGD (c). Fluorescence in each tissue was quantified with Image J software. Statistical analysis was performed with Student's t-test. FAM-iRGD homing without injection of unlabelled peptide was considered as 100% in c. n=3; error bars, s.d.; double asterisk, p<0.01. d, Confocal images of orthotopic 22Rv-1 human prostate cancer xenografts from mice injected with the indicated peptides, phage, and micelles. iRGD was compared to a similar integrin-binding but non-internalizing peptide, CRDGC (SEQ ID NO:50). The circulation time for the free peptides was 2 hrs, 15 min for the peptide-displaying phage, and 3 hrs for the peptide-coupled micelles. Arrows point to FAM-CRGDC (SEQ ID NO:40) peptide or CRGDC (SEQ ID NO:40) phage in or just outside the vessel walls, illustrating its homing to the tumor vasculature but not dispersion and internalization. Representative fields from multiple sections of each of three tumors are shown. Scale bars=50 μm. e, Whole body imaging of PDAC mice (Bardeesy and DePinho (2002)) injected with FAM-iRGD micelles or FAM control micelles labeled with Cy7. Images were taken 3 hrs after the injection of the micelles. Only the shaved areas of the skin delineated by the dotted lines are shown. Light staining, 800 nm (Cy7); darker staining, 700 nm (background fluorescence). The saw tooth appearance of the fluorescent organs is caused by the mouse's breathing.
Figure 17C:
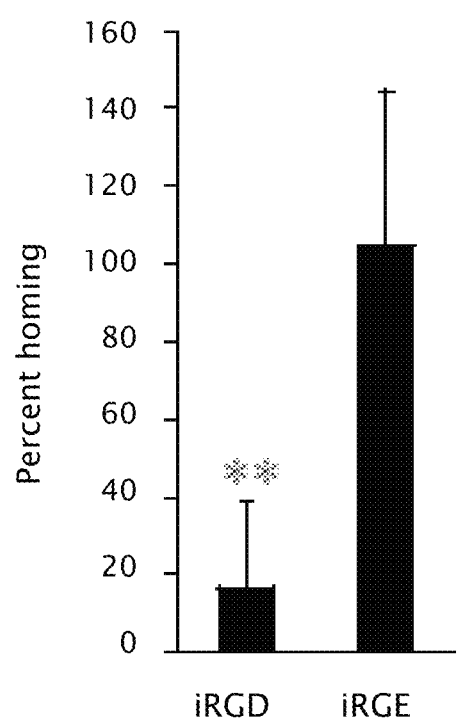
Figures 21A, 21B:
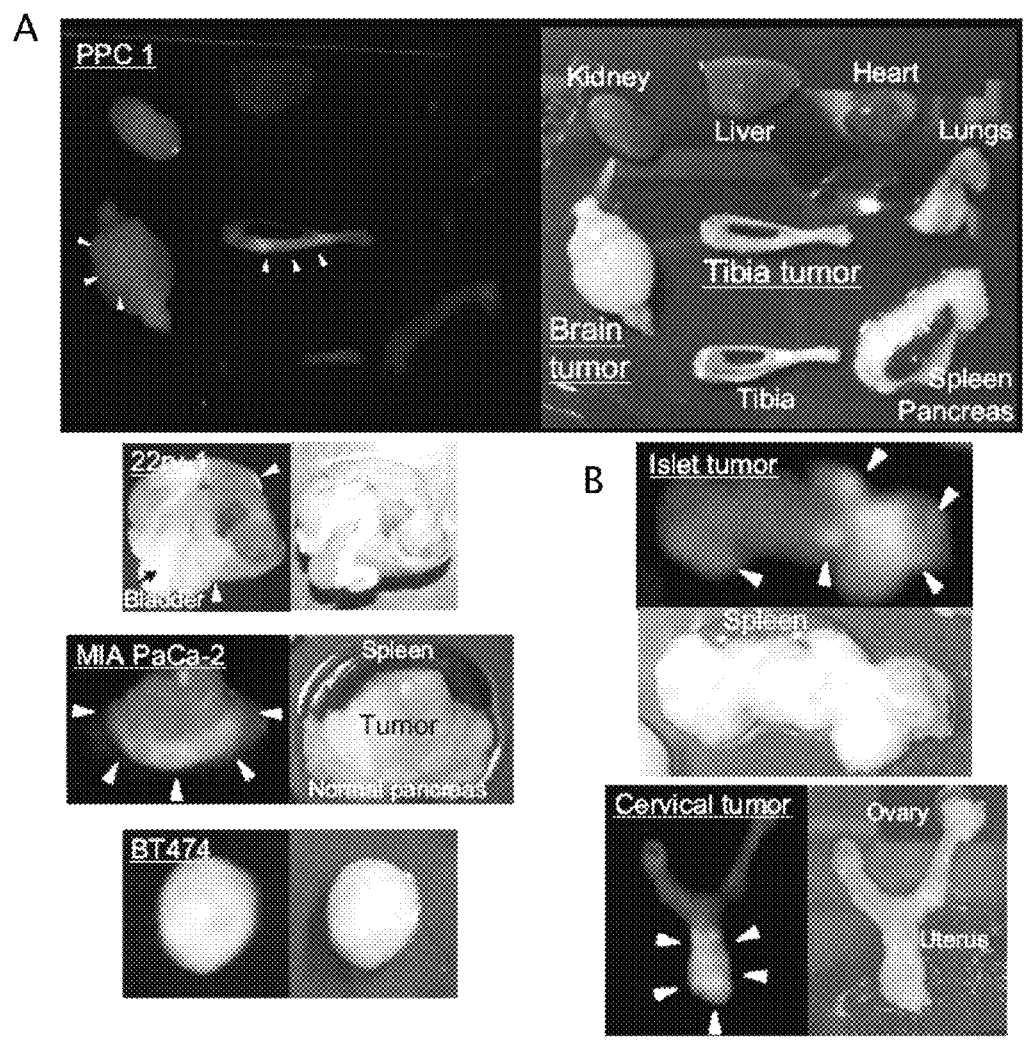
FIGS. 21A and 21B show homing of synthetic iRGD peptide to orthotopic xenografts and spontaneous mouse tumors. Approximately 200 μg of FAM-iRGD in PBS was intravenously administered to mice bearing tumors. The peptides were allowed to circulate for 2 hours and organs were collected and viewed under UV or white light. Arrowheads point to the tumors. a, The tumors were brain and tibia xenografts of a human prostate cancer PPC1 (Zhang et al., Lymphatic zip codes in premalignant lesions and tumors. *Cancer Res.* 66, 5696-5706 (2006)), and orthotopic xenografts of 22rv-1 (Drake et al., Assessing tumor growth and distribution in a model of prostate cancer metastasis using bioluminescence imaging. *Clin. Exp. Metastasis* 22, 674-684 (2005)), a human pancreatic carcinoma MIA PaCa-2 (Sugahara et al., Chondroitin sulfate E fragments enhance CD44 cleavage and CD44-dependent motility in tumor cells. *Cancer Res.* 68, 7191-7199 (2008)), and a human breast cancer BT474 (Rusnak et al., The effects of the novel, reversible epidermal growth factor receptor/ErbB-2 tyrosine kinase inhibitor, GW2016, on the growth of human normal and tumor-derived cell lines in vitro and in vivo. *Mol. Cancer. Ther.* 1, 85-94 (2001)). b, Spontaneous mouse tumors were pancreatic islet tumors of RIP-Tag2 mice (Hanahan, Heritable formation of pancreatic β-cell tumors in transgenic mice expressing recombinant insulin/simian virus 40 oncogenes. *Nature* 315, 115-122 (1985)) and cervical tumors of K14-HPV16 mice (Arbeit et al., Progressive squamous epithelial neoplasia in K14-human papillomavirus type 16 transgenic mice. *J. Virol.* 68, 4358-4368 (1994)).

Forty-eight individual clones were randomly picked for sequencing from phage pools recovered in the final round of ex vivo phage display. Clones that gave unsuccessful sequencing results (less than 5%) were omitted during the analysis. The proportion of each RGD peptide is shown.

iRGD was synthesized as a fluorescein-labeled peptide (FAM-iRGD) and intravenously injected the peptide into tumor-bearing mice. FAM-iRGD accumulated in tumor tissue in each tumor model tested. The tumors, but not normal tissues, were strongly fluorescent under UV light (FIGS. 17A, 17B, and 21). Control peptides produced only minimal tumor fluorescence (FIG. 17B). Co-injecting an excess of unlabelled iRGD peptide greatly reduced the accumulation of FAM-iRGD in tumors, whereas a non-integrin binding (Pierschbacher and Ruoslahti (1984); Ruoslahti (2003)) variant, CRGEKGPDC (iRGE; SEQ ID NO:39), did not have the same effect (FIG. 17C). These results show that iRGD specifically targets tumors and that its RGD motif is critical for the targeting.

Figure 17D:
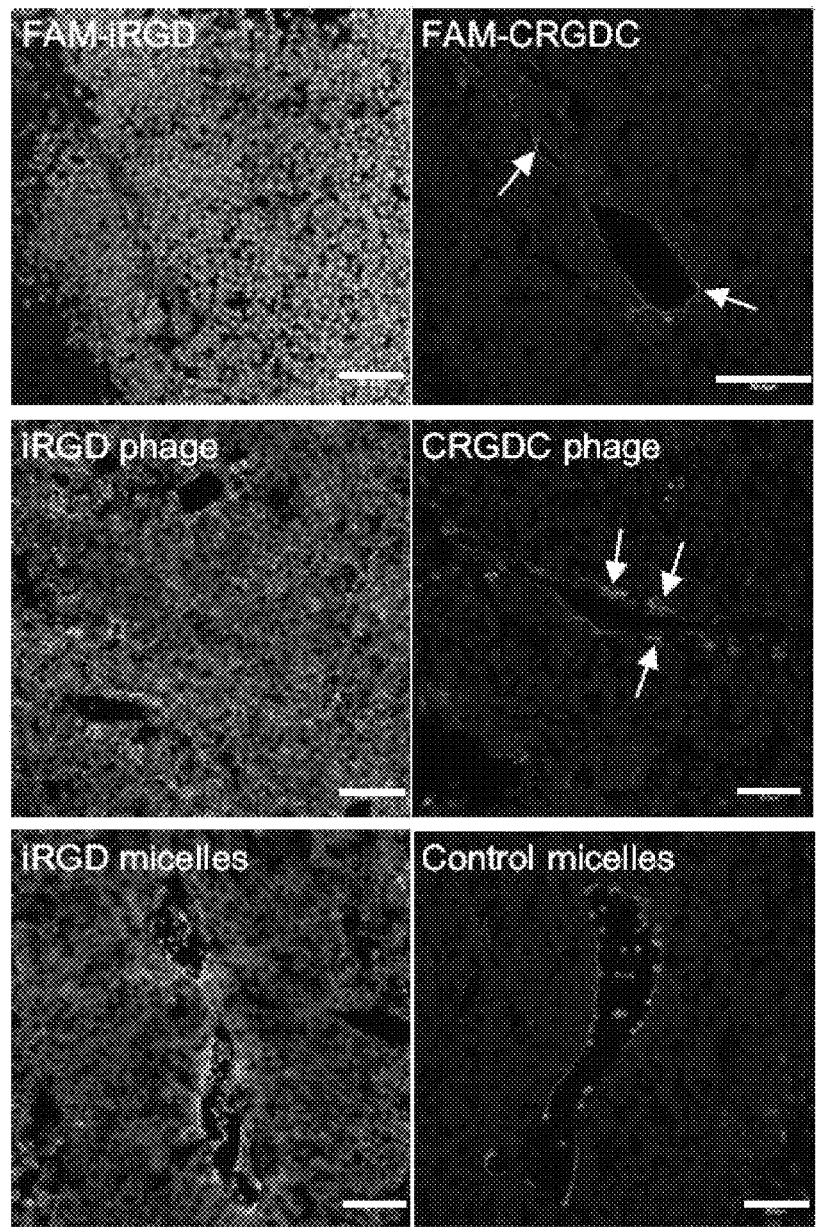
Figure 22:
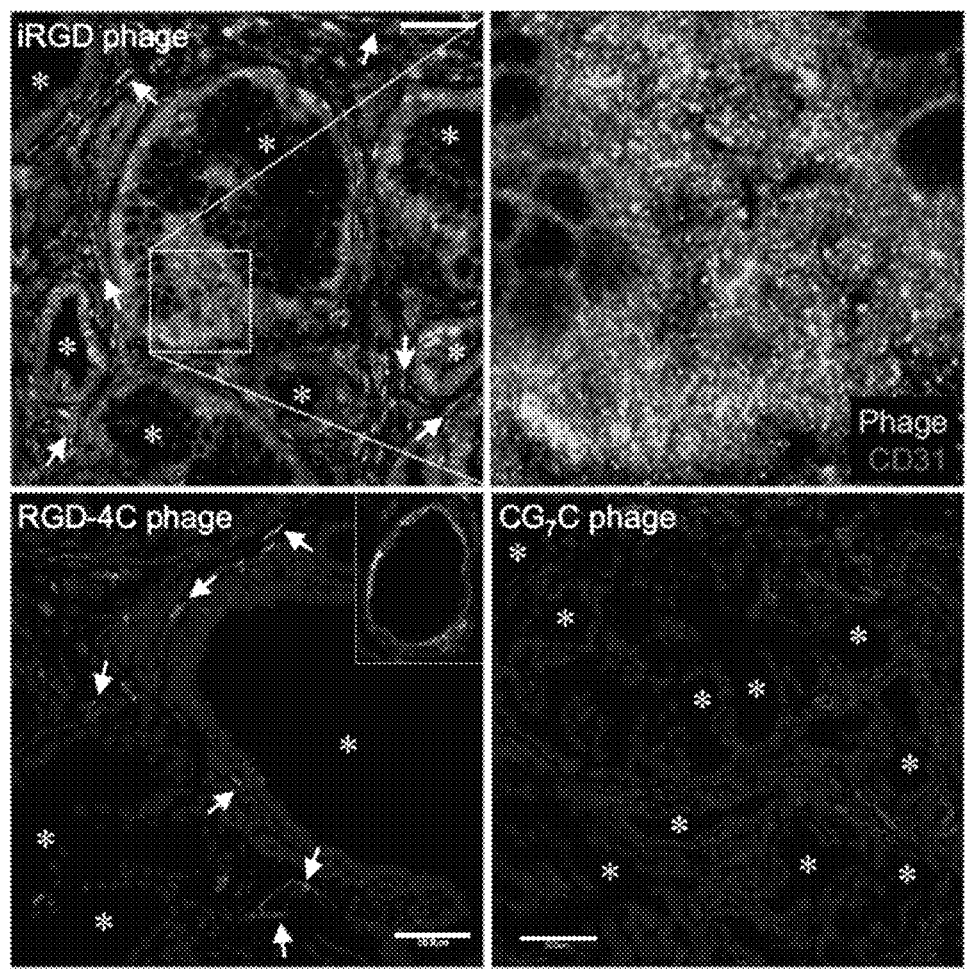
FIG. 22 shows iRGD phage penetrates into the tumor tissue and internalizes into the tumor cells. Confocal images of PDAC tumors from transgenic mice injected with iRGD, RGD-4C, or $CG_7C$ phage. Arrows point to blood vessels positive for phage, and asterisks show the tumor ducts. The upper right panel shows a magnified view of the dotted area in the upper left panel. The inset represents a blood vessel targeted by RGD-4C phage. iRGD phage spreads widely into the tumor parenchyma and internalizes into tumor cells, while RGD-4C phage targets the blood vessels but stays in close association with the vasculature. $CG_7C$ phage showed no tumor homing. Scale bars=50 µm.

Confocal microscopy revealed accumulation of FAM-iRGD peptide in and around tumor vessels and in tumor parenchyma (FIG. 17D), but not in normal tissues. Remarkably, iRGD phage (diameter about 50 nm) and another iRGD-coated nanoparticle, self-assembling micelles (diameter 15-25 nm) (Karmali et al., Targeting of albumin-embedded paclitaxel nanoparticles to tumors. *Nanomedicine* in press (2008); Arleth et al., Detailed structure of hairy mixed micelles formed by phosphatidylcholine and PEGylated phospholipids in aqueous media. *Langmuir* 21, 3279-3290 (2005)), also reached extravascular tumor parenchyma (FIGS. 17D and 22). Two other RGD peptides and corresponding phage, CRGDC (SEQ ID NO:40) and RGD-4C (SEQ ID NO:41), which have a strong affinity for αv integrins (Koivunen et al., Selection of peptides binding to the $\alpha_5\beta_1$ integrin from phage display library. *J. Biol. Chem.* 268, 20205-20210 (1993); Koivunen et al., Phage libraries displaying cyclic peptides with different ring sizes: ligand specificities of the RGD-directed integrins. *Biotechnology (N Y)* 13, 265-270 (1995)), also homed to tumors, but accumulated only in and around tumor blood vessels and did not disperse throughout the interstitium like iRGD (FIGS. 17D and 22).

Figure 17E:
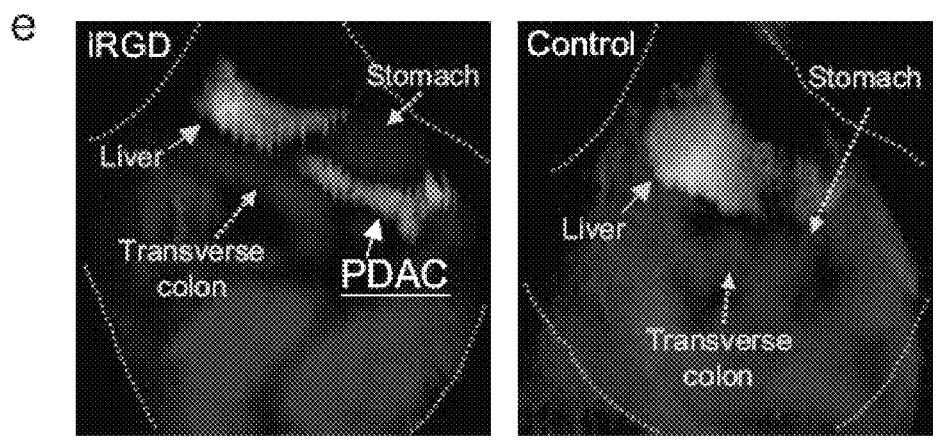

Whole body imaging of mice injected with FAM-iRGD micelles labeled with the near-infrared dye, Cy7, produced a strong and specific signal from the tumors, illustrating the ability of iRGD for tumor targeting (FIG. 17E). The internalizing properties of the iRGD, and its apparent spreading into tumor tissue, prompted study of the mechanisms underlying these unique activities of iRGD.

Figure 18A:
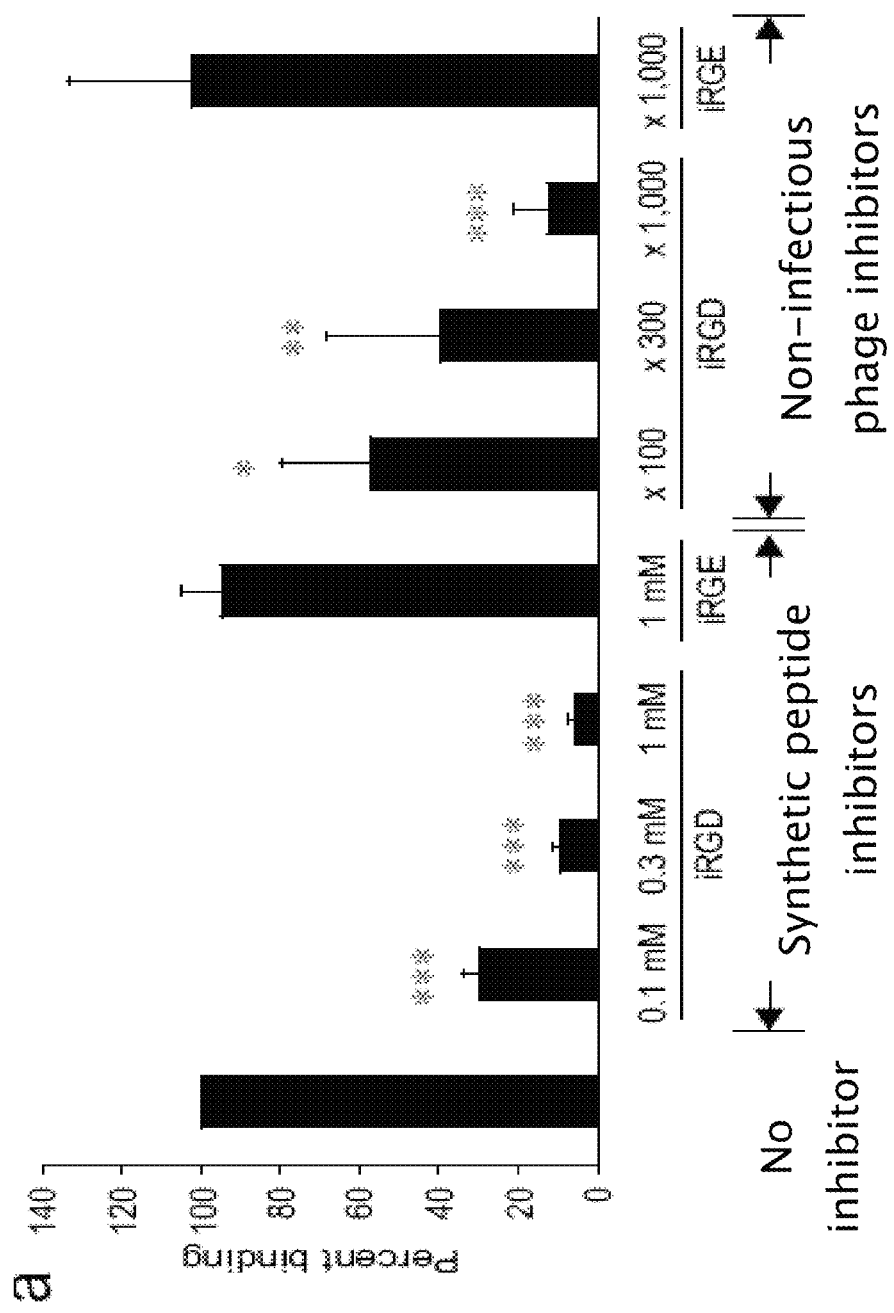
FIGS. 18A-18C show iRGD binds to αv integrins. a, Inhibition of iRGD phage binding to PPC1 prostate cancer cells by synthetic iRGD peptide and its variants, and corresponding non-infectious phage. b, c, Inhibition of iRGD phage binding to PPC1 cells (b) and M21 cells (c) by antibodies against integrins or control mouse IgG. Statistical analysis was performed with ANOVA (a, c) and Student's t-test (b). iRGD phage binding without inhibitors was considered as 100% in a. n=3; error bars, s.d.; single asterisk, p<0.05; double asterisk, p<0.01; triple asterisk, p<0.001.
Figure 18B:
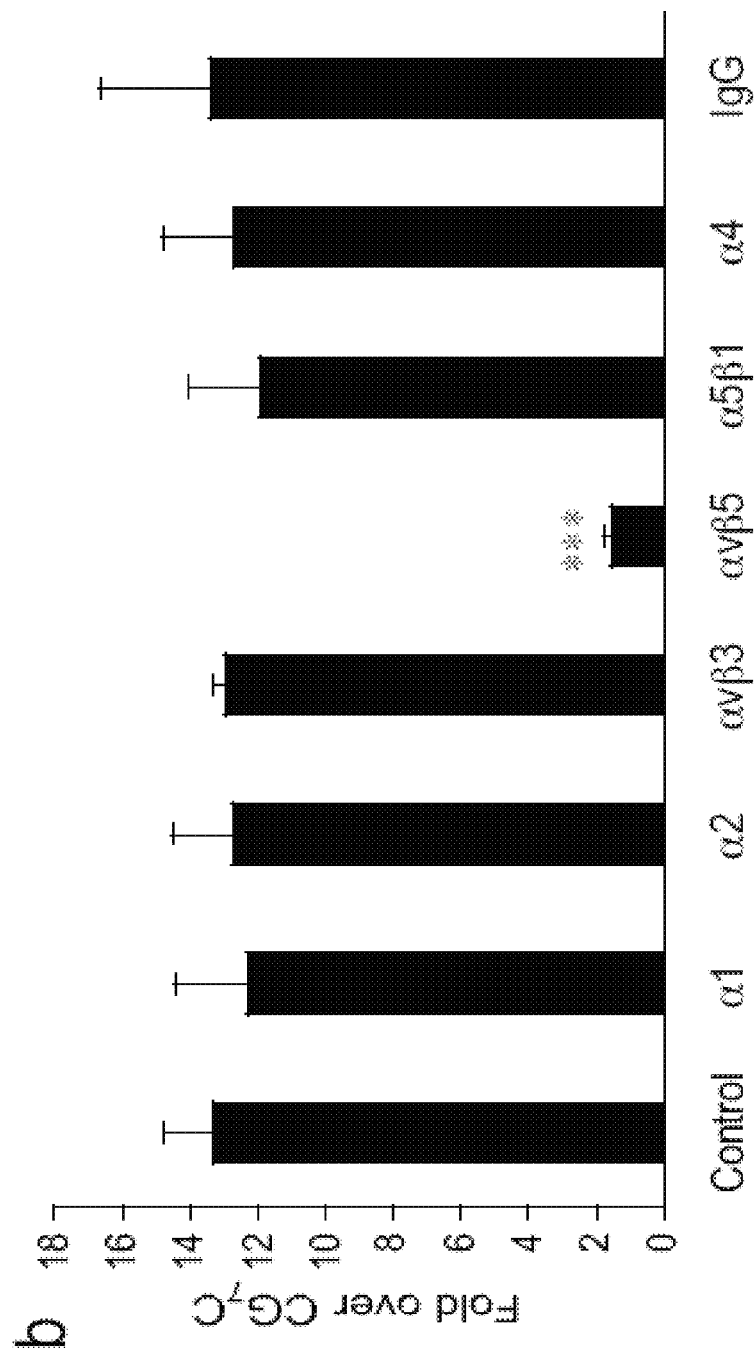
Figure 18C:
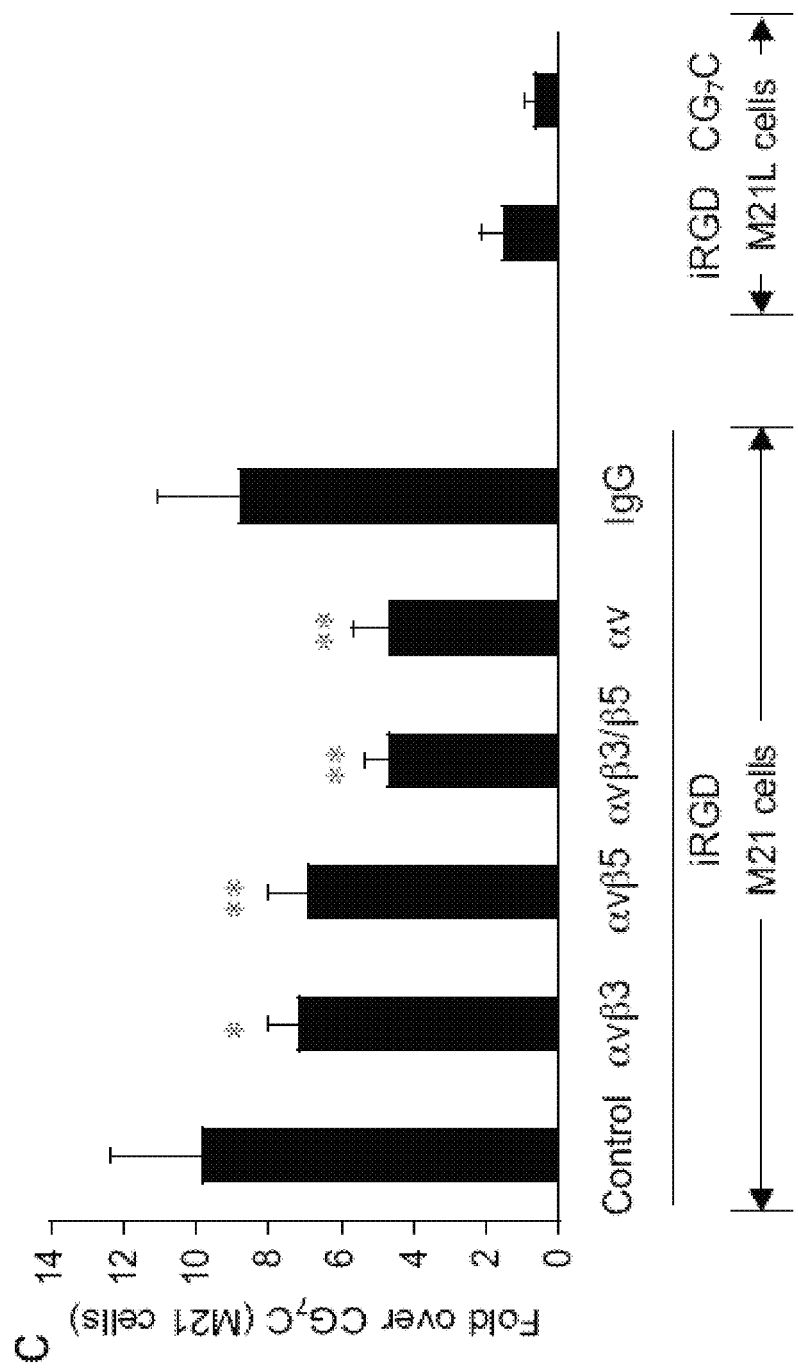
Figure 23:
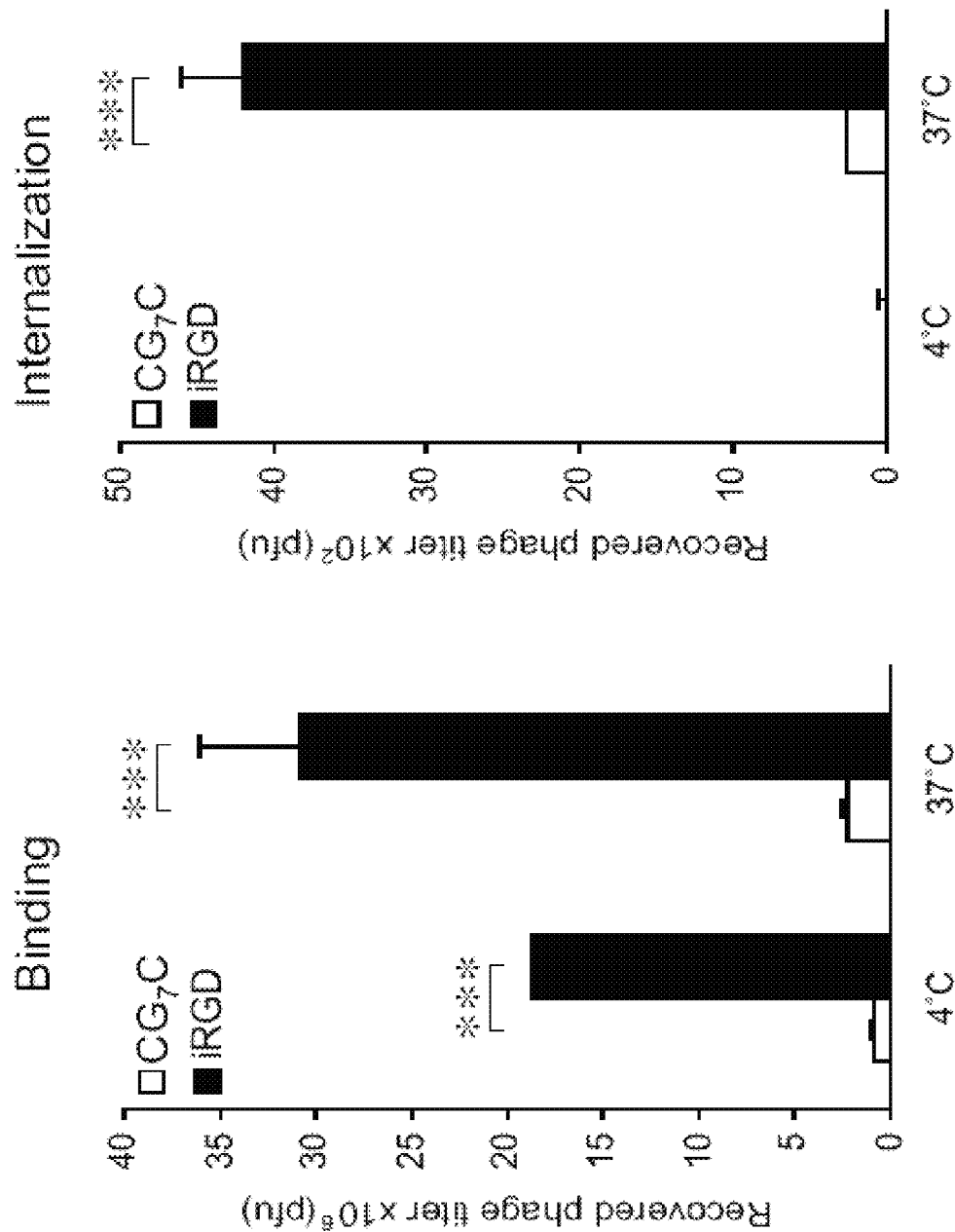
FIG. 23 shows binding and internalization to PPC1 cells of iRGD phage in comparison to $CG_7C$ phage. PPC1 cells were treated with iRGD or $CG_7C$ phage for 1 hour at 4° C. or 37° C. To assess the internalization, the phage that bound to the cell surface were removed by washing the cells with acid buffer before phage titration. Note that the internalization of iRGD phage does not occur at 4° C. Statistical analysis was performed with Student's t-test. n=3, error bars represent s.d.
Figures 24A, 24B:
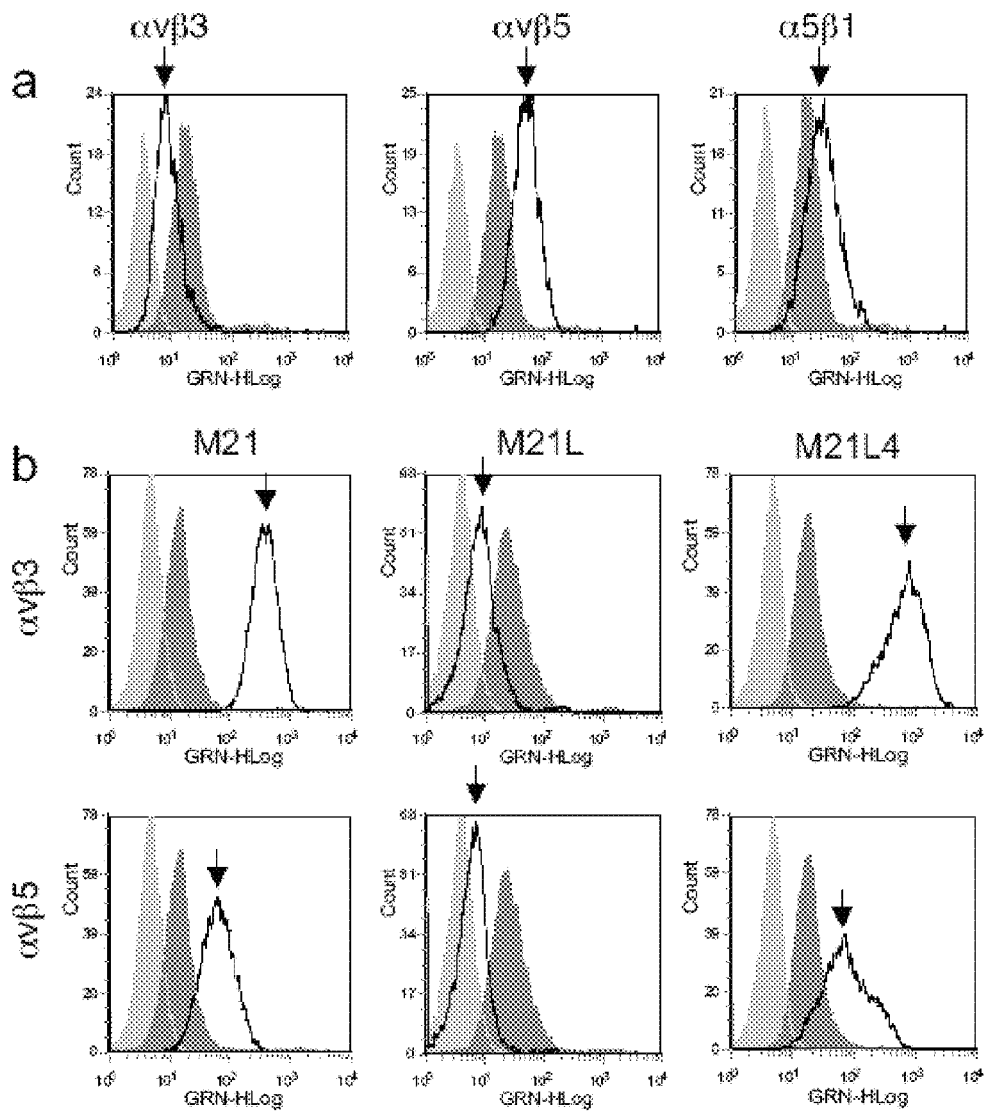
FIGS. 24A and 24B show integrin expression in tumor cells. a, b, Integrin expression in PPC1 (a) and M21 cells (b) analyzed by flow cytometry. The profiles represent the values of unstained cells (light gray), and cells incubated with mouse IgG (dark gray) or appropriate integrin antibodies (unshaded with arrows) as primary antibodies.

Cultured prostate tumor cells bound iRGD phage at 4° C., but did not significantly internalize it, whereas both binding and internalization occurred at 37° C. (FIG. 23). The binding at 4° C. was inhibited in a dose-dependent manner by free iRGD peptide and by non-infectious (UV-inactivated) iRGD phage, but not by non-integrin-binding iRGE peptide or phage (FIG. 18A). The RGD-directed integrins αvβ33, αvβ35, and β5β1, are upregulated in angiogenic endothelial cells and certain tumor cells (Eliceiri and Cheresh (2001); Ruoslahti (2002)). PPC1 cells express βvβ5 and α5β1, but not αvβ3 (FIG. 24A). An anti-αvβ5 antibody almost completely inhibited iRGD phage binding to PPC1 cells, whereas inhibitory antibodies against αvβ3, α5β1, and several other integrins had no effect (FIG. 18B). M21 human melanoma cells (Cheresh and Spiro, Biosynthetic and functional properties of an Arg-Gly-Asp-directed receptor involved in human melanoma cell attachment to vitronectin, fibrinogen, and von Willebrand factor. *J. Biol. Chem.* 262, 17703-17711 (1987)) (FIG. 24B) that express both αvβ3 and αvβ5 bound iRGD, whereas variants lacking expression of these integrins did not, confirming the αv integrin dependency of iRGD binding (FIG. 18C). M21 cell binding was reduced by either anti-αvβ3 or anti-αvβ5 (FIG. 18C), indicating that iRGD recognizes both of these integrins.

Figure 19A:
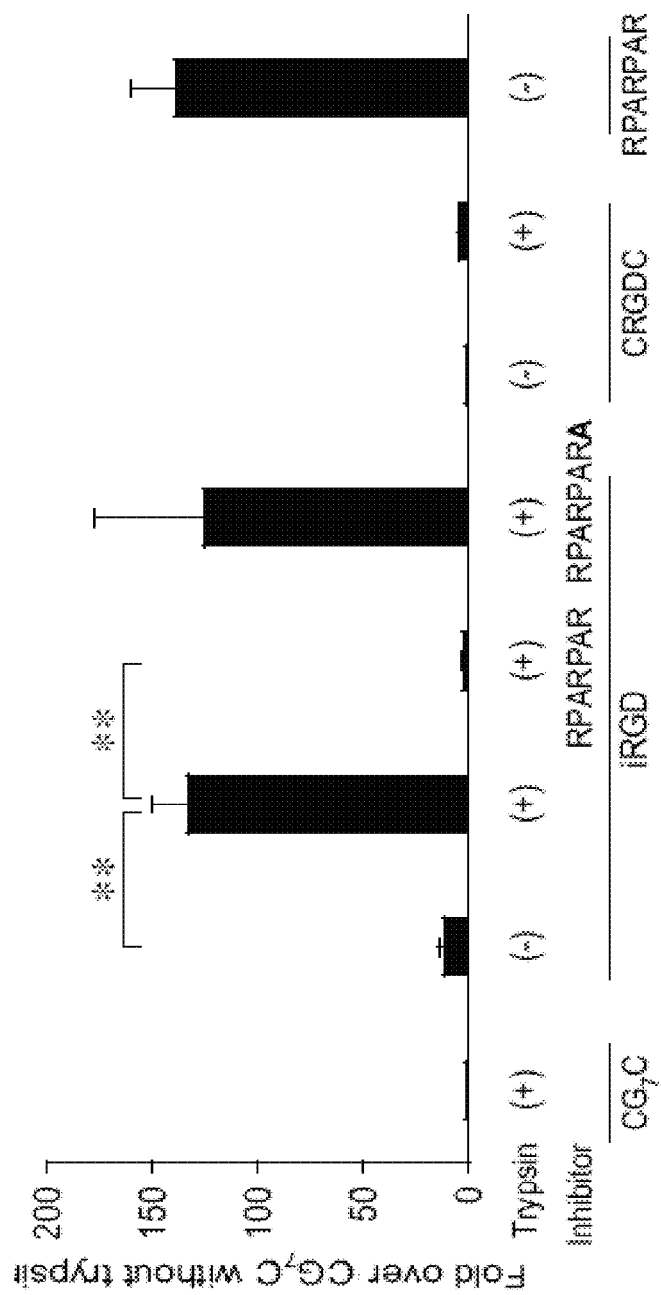
FIGS. 19A-19E show CendR motif in iRGD internalization within tumor cells. a, The internalization of trypsin-treated iRGD phage within PPC1 cells pre-treated or not with non-infectious RPARPAR (SEQ ID NO:44) or RPARPARA (SEQ ID NO:45) phage. b, Inhibition of CRGDK (SEQ ID NO:46) phage binding to PPC1 by synthetic CRGDK (SEQ ID NO:46), RPARPAR (SEQ ID NO:44), and RPARPARA (SEQ ID NO:45) peptides, and corresponding non-infectious phage. c, CRGDK (SEQ ID NO:46) phage binding to PPC1 cells treated with anti-neuropilin-1 blocking antibodies (anti-NRP-1) or control goat-IgG (left panel), and M21 cells transfected with neuropilin-1 cDNA to induce forced expression of neuropilin-1 (NRP-1), vector alone, or without transfection (right panel). d, Inhibition of iRGD and iRGE phage internalization within PPC1 by non-infectious phage displaying the CendR-internalizing peptides RPARPAR (SEQ ID NO:44) and CRGDK (SEQ ID NO:46). e, Dose-dependent inhibition of iRGD phage internalization within PPC1 cells by anti-neuropilin-1 antibodies (anti-NRP-1) to block neuropilin-1 function. Statistical analyses were performed with ANOVA (a, b, d) or Student's t-test (c, e). CRGDK (SEQ ID NO:46) phage binding without inhibitors was considered as 100% in b. n=3; error bars, s.d.; single asterisk, p<0.05; double asterisk, p<0.01; triple asterisk, p<0.001.

A consensus CendR motif, R/KXXR/K (SEQ ID NOs:19, 20, 42, and 43), was shown to mediate neuropilin-1-dependent binding and internalization of peptides into cells. The motif is not active, unless it occupies a C-terminal position in the peptide. iRGD contains a CendR motif, RGDK/R, but this motif is not C-terminal. It was realized that proteolytic processing might be required to activate the CRGDK motif in iRGD. Indeed as shown in FIG. 19A, treatment of iRGD phage with trypsin, which cleaves proteins after arginine and lysine residues, enhanced the binding of iRGD phage to PPC1 cells. Trypsin had no effect on the non-internalizing peptides CRGDC (SEQ ID NO:40) or RGD-4C (SEQ ID NO:41) (not shown). The binding at 4° C. of the trypsin-treated iRGD phage, but not of intact iRGD phage (not shown), was blocked by non-infectious phage expressing a prototypic CendR peptide, RPARPAR (SEQ ID NO:44), but not by phage displaying a peptide in which the CendR motif was disrupted by addition of an alanine residue to the C-terminus (RPARPARA; SEQ ID NO:45).

Figure 25:
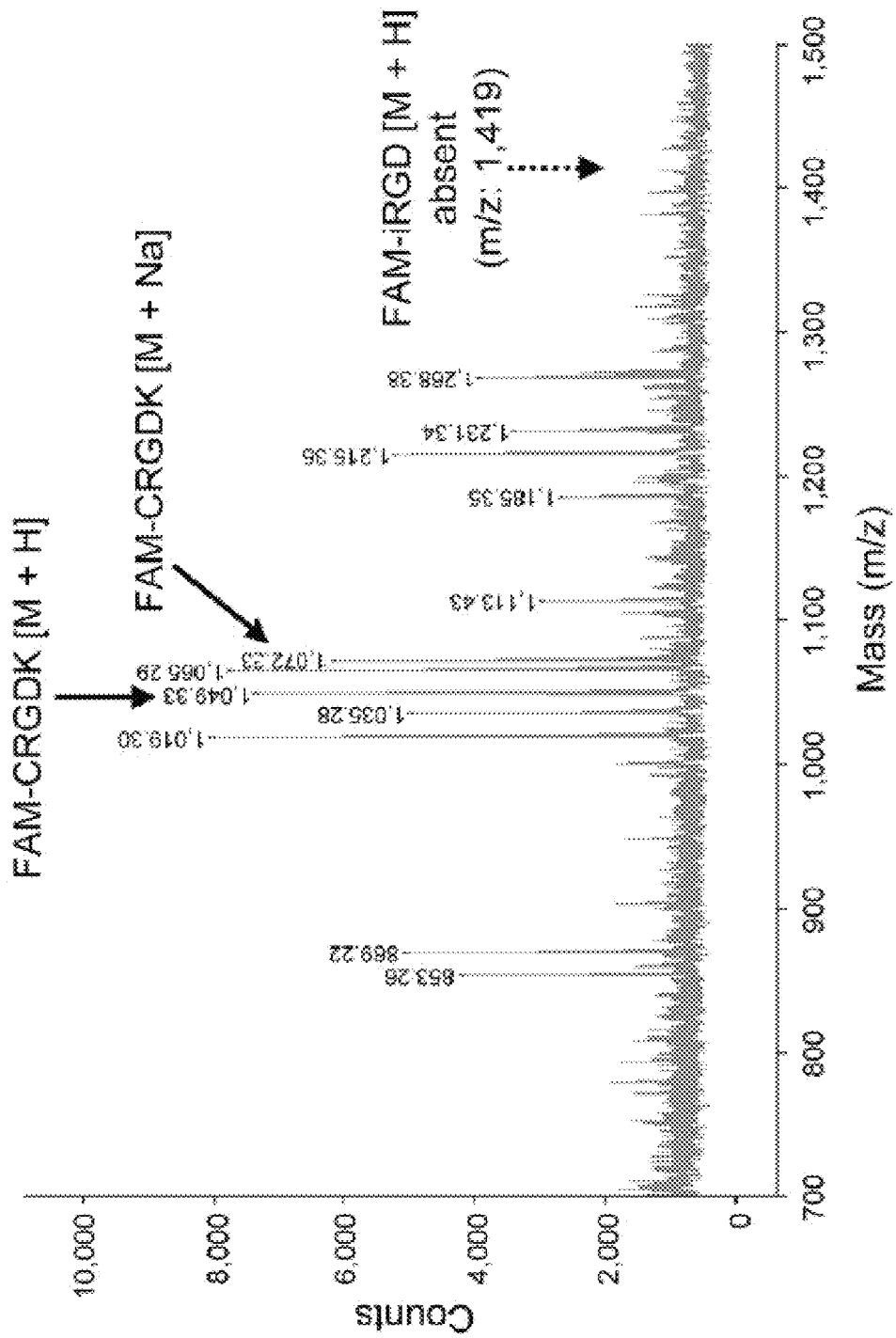
FIG. 25 shows peptide fragments recovered from PPC1 cells treated with FAM-iRGD peptides. PPC1 cells were incubated with FAM-iRGD peptide (FAM at the N-terminus) at 37° C. for 90 min in the presence of the proteasome inhibitor MG132. Peptide fragments were recovered with an anti-FITC affinity column, and analyzed by mass spectrometry. Note the presence of FAM-CRGDK [M+H] (m/z: 1,049) (SEQ ID NO:46) and FAM-CRGDK [M+Na] (m/z: 1,072) (SEQ ID NO:46), and the absence of the full-length FAM-iRGD (m/z: 1,419). No major peptide fragments were recovered from mouse IgG column used as an isotype control for the anti-FITC affinity column, or when a lysate of PPC1 cells that had not been exposed to FAM-iRGD was fractionated on anti-FITC (not shown). An iRGD peptide labeled with FAM at the C-terminus yielded no GPDC-FAM (the 988 mass unit fragment expected from an iRGD cleavage that produces CRGDK (SEQ ID NO:46)) from the cells (not shown). This indicates that the only neuropilin-1-binding N-terminal fragment (CRGDK; SEQ ID NO:46)) internalizes, which could happen if the iRGD peptide is proteolytically cleaved at the K-G bond, and the disulfide bond is reduced, before internalization. Omitting MG132 yielded only peptides smaller than FAM-CRGDK (SEQ ID NO:46) (not shown), indicating that intracellular FAM-CRGDK (SEQ ID NO:46) is degraded in proteasomes.

To determine whether the CendR motif in iRGD is indeed activated by cellular proteases, FAM-iRGD (which carries FAM at its N-terminus) was incubated with PPC1 prostate cancer cells, and isolated intracellular products by affinity chromatography on anti-FITC antibodies. To prevent cytoplasmic proteolysis, while allowing proteolysis at the cell surface, the incubation was done in the presence of a proteasome inhibitor. No intracellular full-length FAM-iRGD was detected, the FAM-CRGDK fragment (SEQ ID NO:46) was recovered (FIG. 25).

Figure 19B:
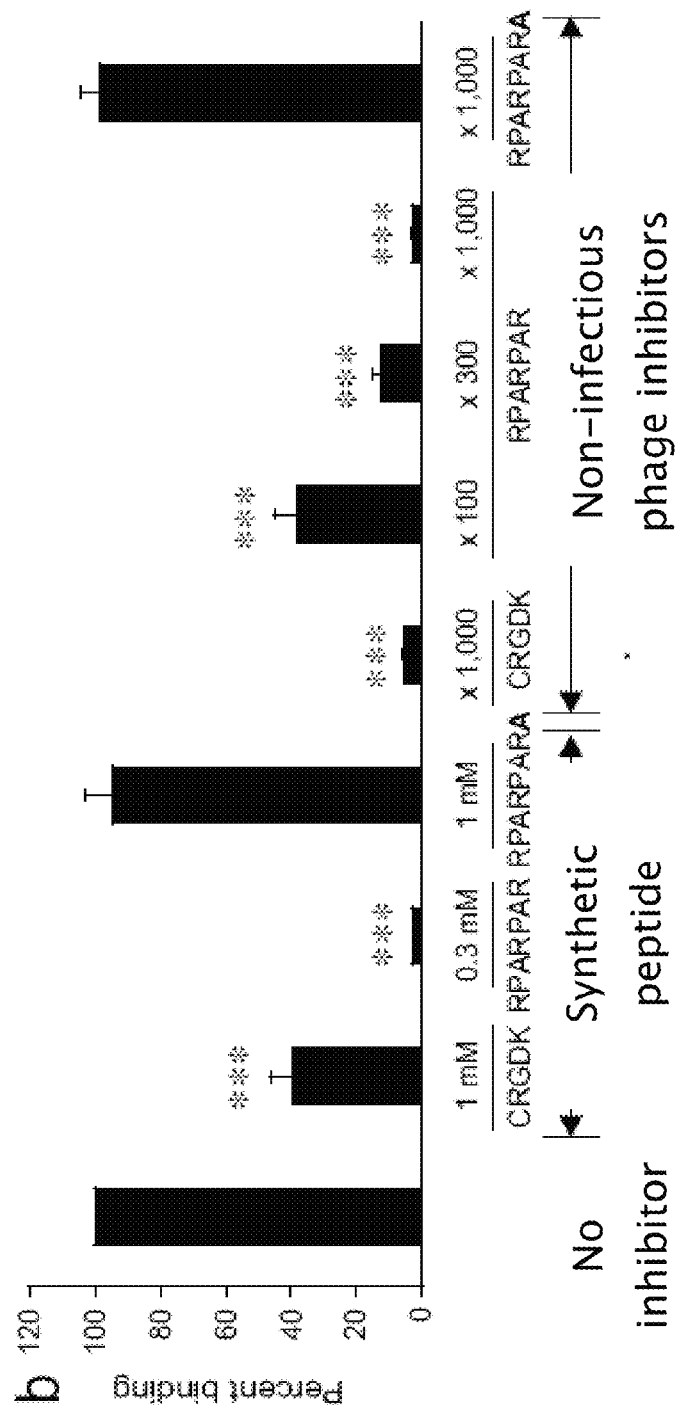
Figures 19C, 19D:
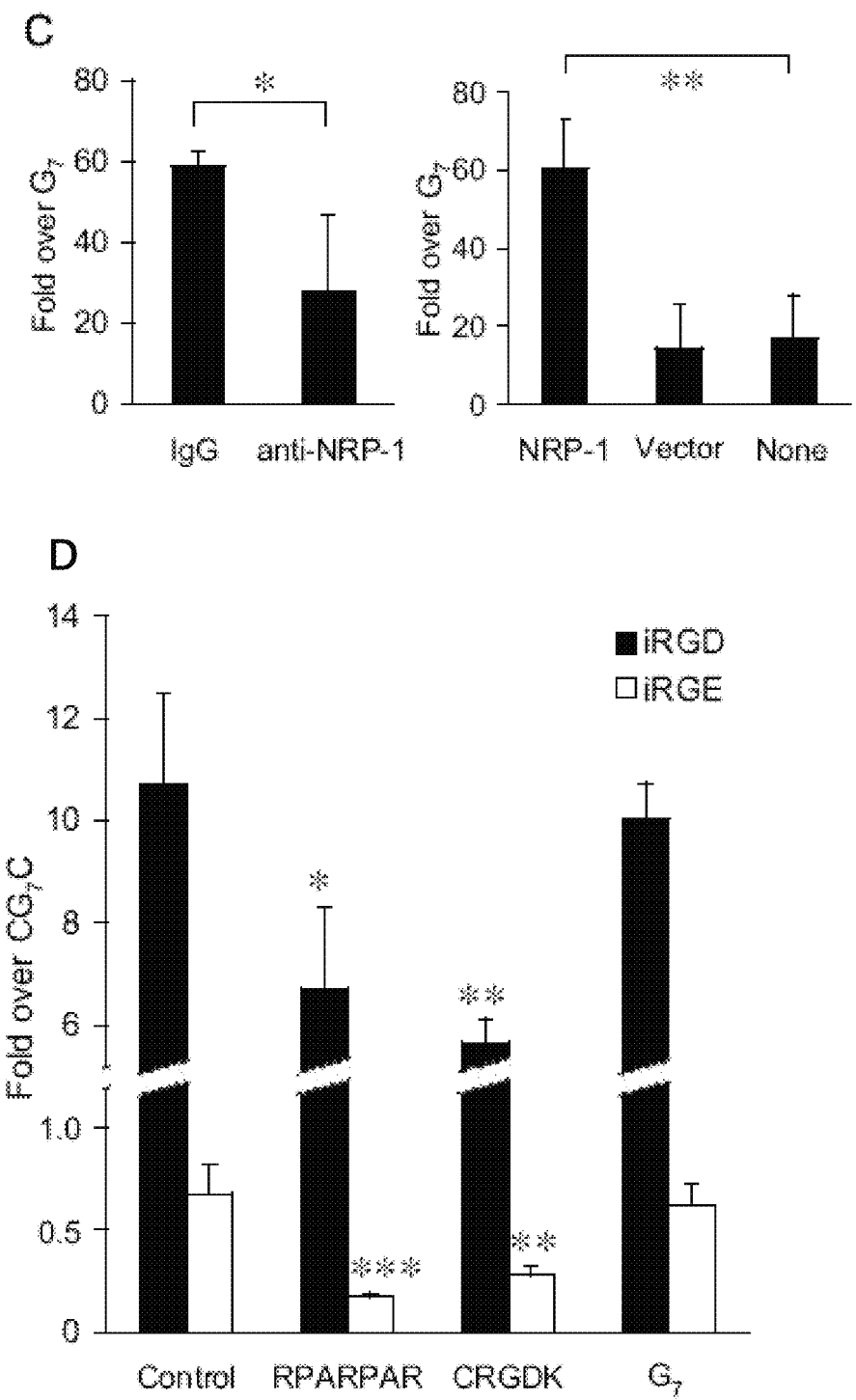
Figure 26A:
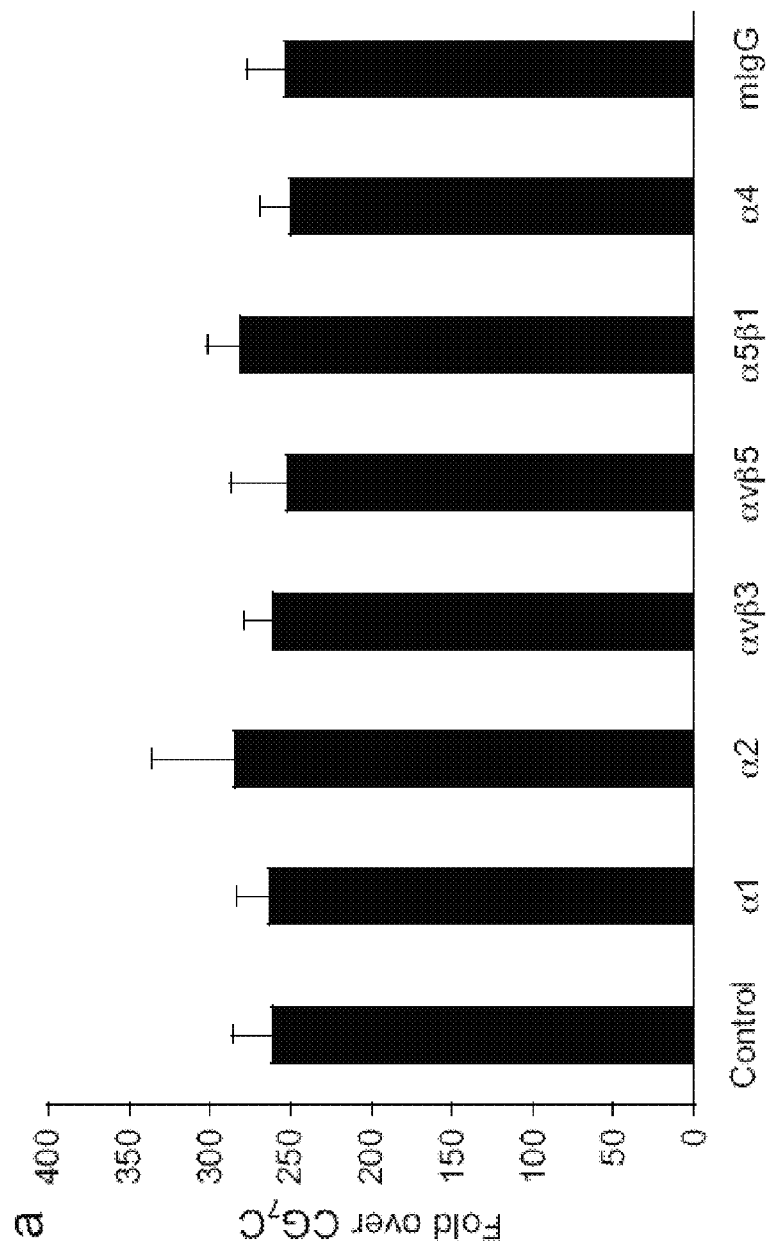
FIGS. 26A and 26B show binding of CRGDK (SEQ ID NO:46) phage to tumor cells in relation to integrin expression. a, Integrin antibodies do not inhibit the binding of CRGDK (SEQ ID NO:46) phage to PPC1 cells. b, CRGDK (SEQ ID NO:46) phage binds similarly to M21 cells with different αv integrin expression levels (refer to FIG. 19B for the αv integrin expression patterns).
Figure 26B:
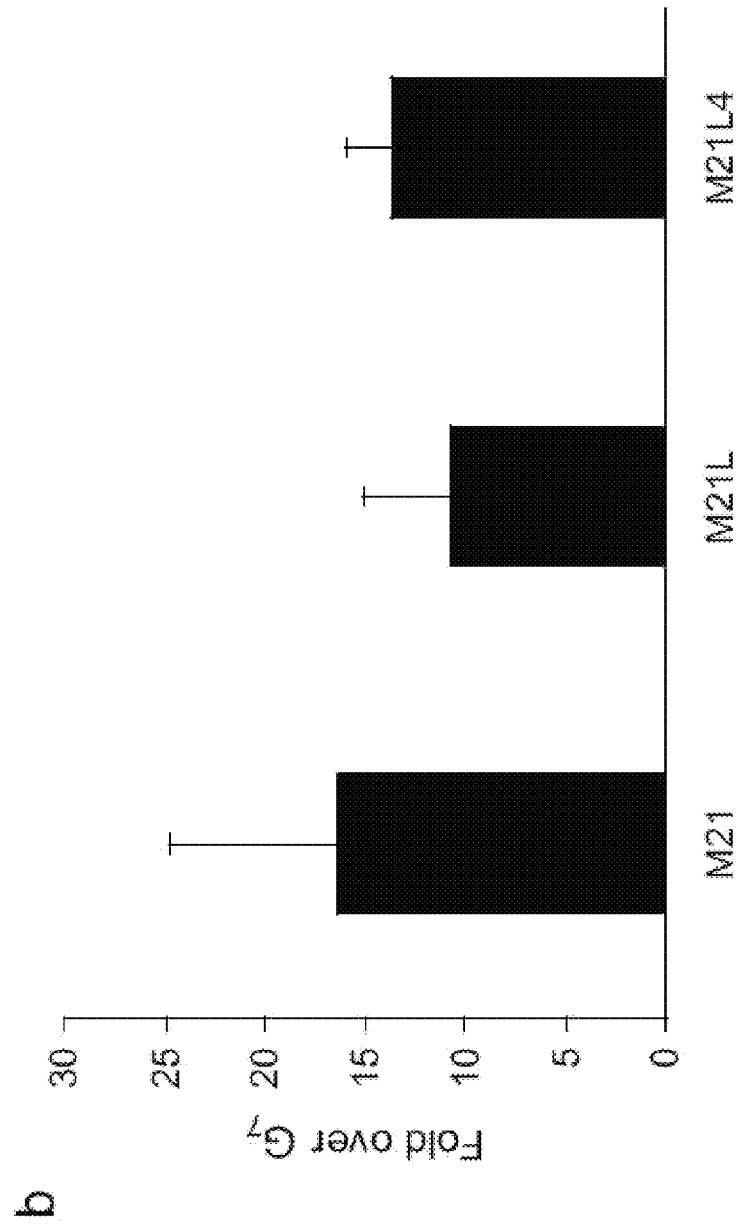
Figure 27:
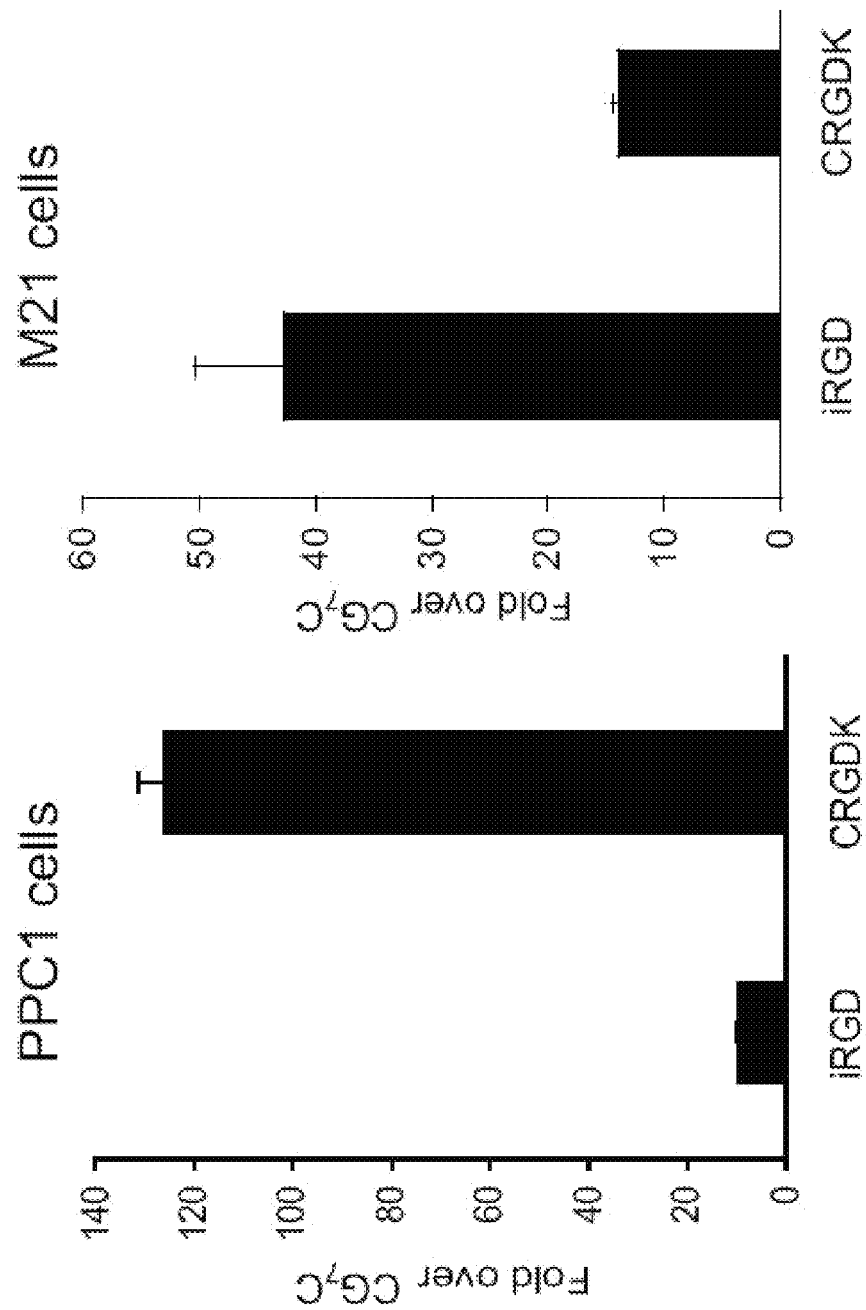
FIG. 27 shows internalization of iRGD and CRGDK (SEQ ID NO:46) phage into PPC1 and M21 cells. Cells were treated with iRGD or CRGDK (SEQ ID NO:46) phage for 1 hour at 37° C. followed by an acid buffer wash to remove the phage that bound to the cell surface. Note that CRGDK (SEQ ID NO:46) phage internalized more efficiently than iRGD phage in PPC1 cells that have high expression of neuropilin-1, whereas it is reversed in M21 cells.

Based on the implication that proteolytically released CRGDK (SEQ ID NO:46) is the active internalizing component of iRGD, phage expressing CRGDK (SEQ ID NO:46) was engineered and it was found that it bound to and was internalized within PPC1 cells. The binding process was not αv integrin-dependent (FIGS. 26A and 26B), but appeared to require the CendR system, as it was dose-dependently inhibited by RPARPAR (SEQ ID NO:44) phage (FIG. 19B). Moreover, an antibody against neuropilin-1, the receptor for CendR peptides, also reduced the binding (FIG. 19C, left panel). CRGDK (SEQ ID NO:46) phage did not substantially bind to or internalize into M21 cells with minimal expression of neuropilin-1 (FIG. 27), but forced expression of neuropilin-1 in these cells, increased the binding (FIG. 19C, right panel) and internalization (not shown) 3.5 fold. These results indicate that the CRGDK (SEQ ID NO:46) (as well as RPARPAR; SEQ ID NO:44) binds to cells and internalize following the CendR pathway.

Figure 19E:
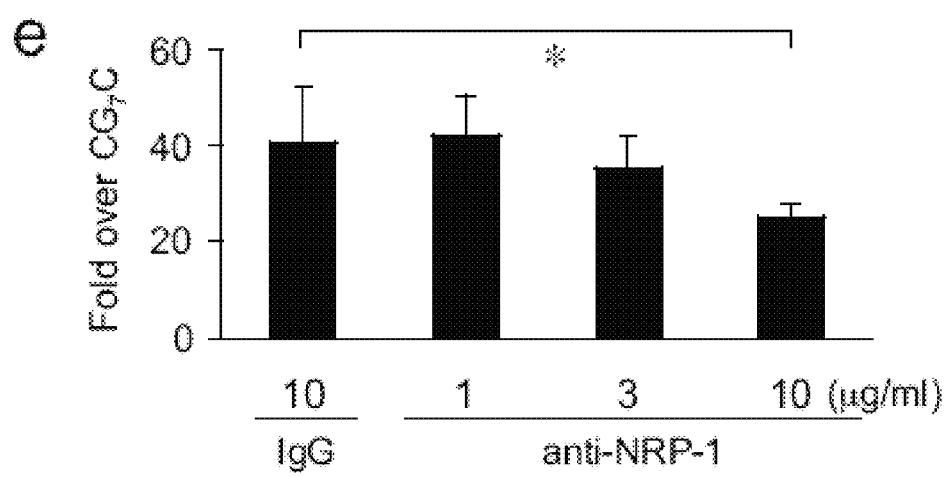

Consistent with the RGDK CendR element (SEQ ID NO:47) being the internalizing sequence in iRGD, CRGDK (SEQ ID NO:46) and RPARPAR (SEQ ID NO:44) phage blocked iRGD phage internalization into PPC1 cells (FIG. 19D). Anti-neuropilin-1 also inhibited the internalization (FIG. 19E), but had little effect on binding of the phage to the cells (not shown). The relative roles of the RGD and RXXK motifs in iRGD was tested by using the iRGE phage, which does not bind to integrins due to the disrupted RGD motif (Pierschbacher and Ruoslahti (1984); Ruoslahti (2003)), but still contains a CendR motif, RXXK. The iRGE phage did internalize within PPC1 cells, and both RPARPAR (SEQ ID NO:44) and CRGDK (SEQ ID NO:46) inhibited the internalization (FIG. 19D), indicating that it follows the CendR internalization pathway. The internalization was far less effective than that of iRGD, presumably because iRGE lacks integrin binding that would concentrate the phage at the cell surface. These results show that iRGD internalizes within cells through the CendR pathway utilizing the RXXK sequence, and that the internalization is facilitated by initial binding to integrins through RGD.

Figures 20A, 20B:
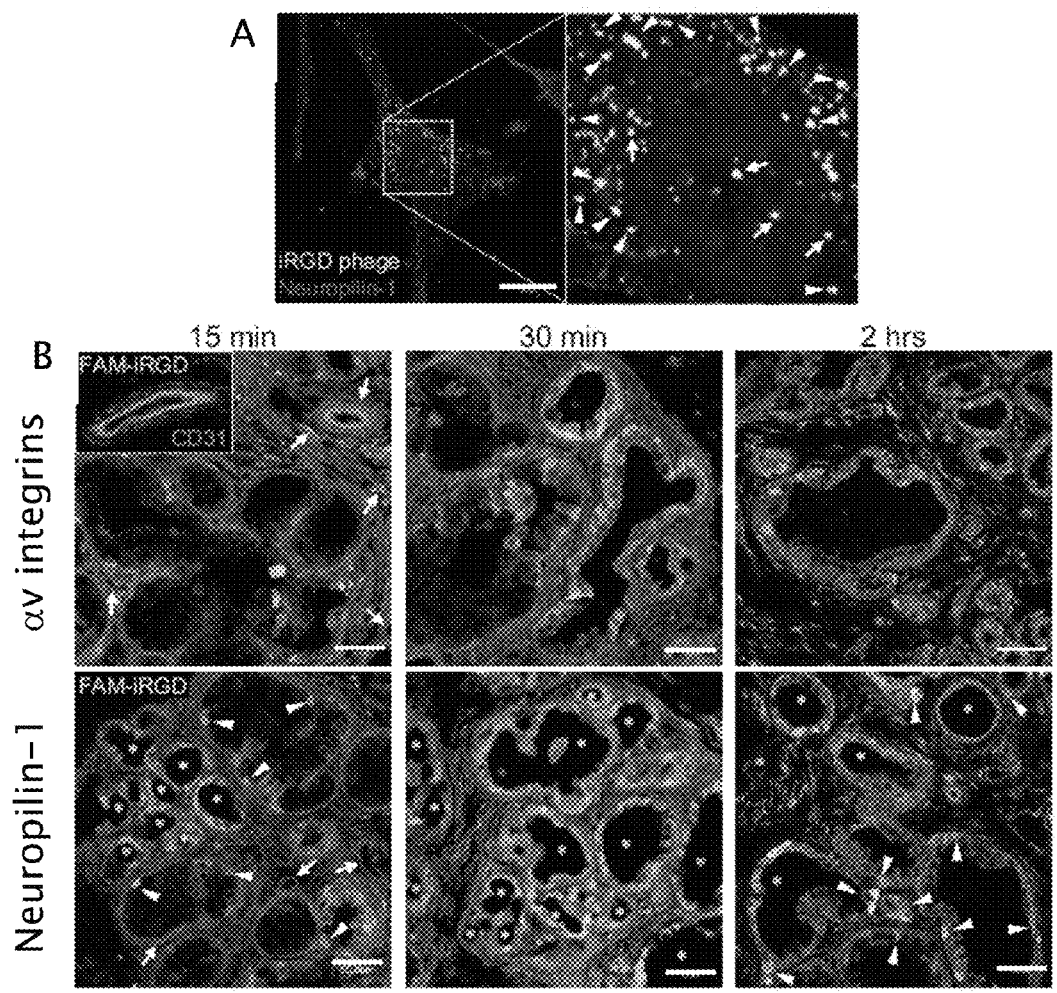
FIGS. 20A and 20B show internalization of iRGD within tumor cells involves neuropilin-1. a, Confocal microscopy images of PPC1 cells incubated with iRGD phage. The cells were stained for phage, neuropilin-1, and nuclei. The right panel is a high magnification view of the dotted area in the left panel. Note that iRGD phage internalizes within PPC1 cells and co-localizes with neuropilin-1 in the perinuclear area (arrowheads) and in the nucleus (arrows). Scale bar=20 μm. b, Time-dependent homing of FAM-iRGD peptide (bright staining primarily around the black areas) in relation to the expression of αv integrins (right panels) and neuropilin-1 (left panels) in PDACs (Bardeesy and DePinho (2002)). The blood vessels targeted by FAM-iRGD were positive for both αv integrins and neuropilin-1 (arrows). The inset shows CD31 staining of the vasculature targeted by FAM-iRGD. In almost all tumor ducts examined, αv integrins were positive. Tumor cells (arrowheads) and tumor ducts (asterisks) also strongly positive for neuropilin-1 were extremely potent in internalizing and retaining FAM-iRGD. Scale bars=50 μm.
Figure 28:
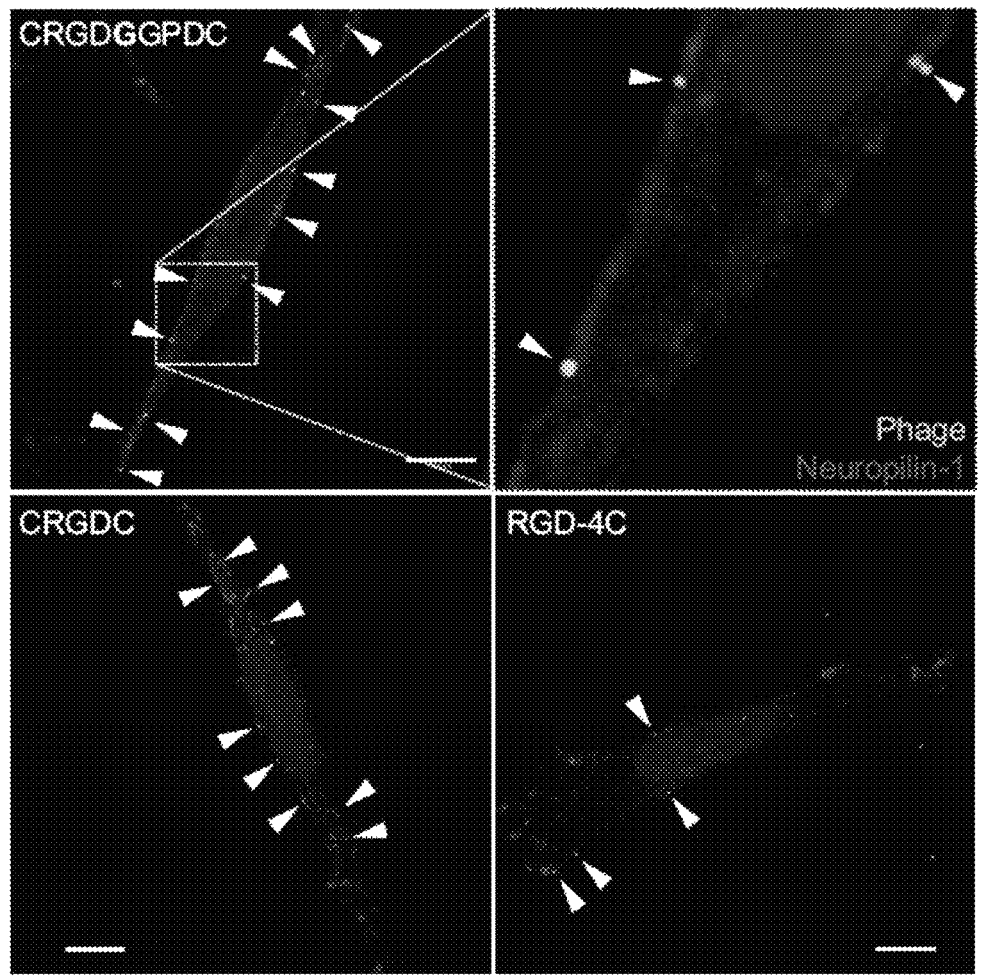
FIG. 28 shows RGD phage that lack a CendR element do not internalize into tumor cells efficiently. Confocal microscopy images of PPC1 cells incubated with T7 phage that express an iRGD phage variant CRGDGGPDC (SEQ ID NO:48), CRGDC (SEQ ID NO:40), or RGD-4C. The cells were stained for phage (arrowed), neuropilin-1 (distal and flanking), and nuclei (central mass). The right panel of CRGDGGPDC (SEQ ID NO:48) phage is a high magnification view of the dotted area in the left panel. Note that the RGD phage bind to the surface of the cells (arrowheads) but do not internalize efficiently into the cells. Scale bars=10 µm.

Confocal microscopy showed that iRGD phage and neuropilin-1 co-localize in the perinuclear area and in the nuclei of cultured cells (FIG. 20A), supporting the involvement of the CendR pathway in the internalization of iRGD to tumor cells. Phage displaying an iRGD variant that lacks the CendR motif (CRGDGGPDC; SEQ ID NO:48), CRGDC (SEQ ID NO:40), or RGD-4C (SEQ ID NO:41) (FIG. 28) did not co-localize with neuropilin-1, nor did they internalize. After intravenous injection of FAM-iRGD peptide into mice bearing de novo PDACs (Bardeesy and DePinho, (2002)), the peptide initially co-localized with tumor vessels and then appeared within tumor cells positive for αv integrins (FIG. 20B, left panels) Importantly, tumor cells strongly positive for neuropilin-1 were particularly effective at accumulating and retaining FAM-iRGD (FIG. 20B, right panels).

Figure 29:
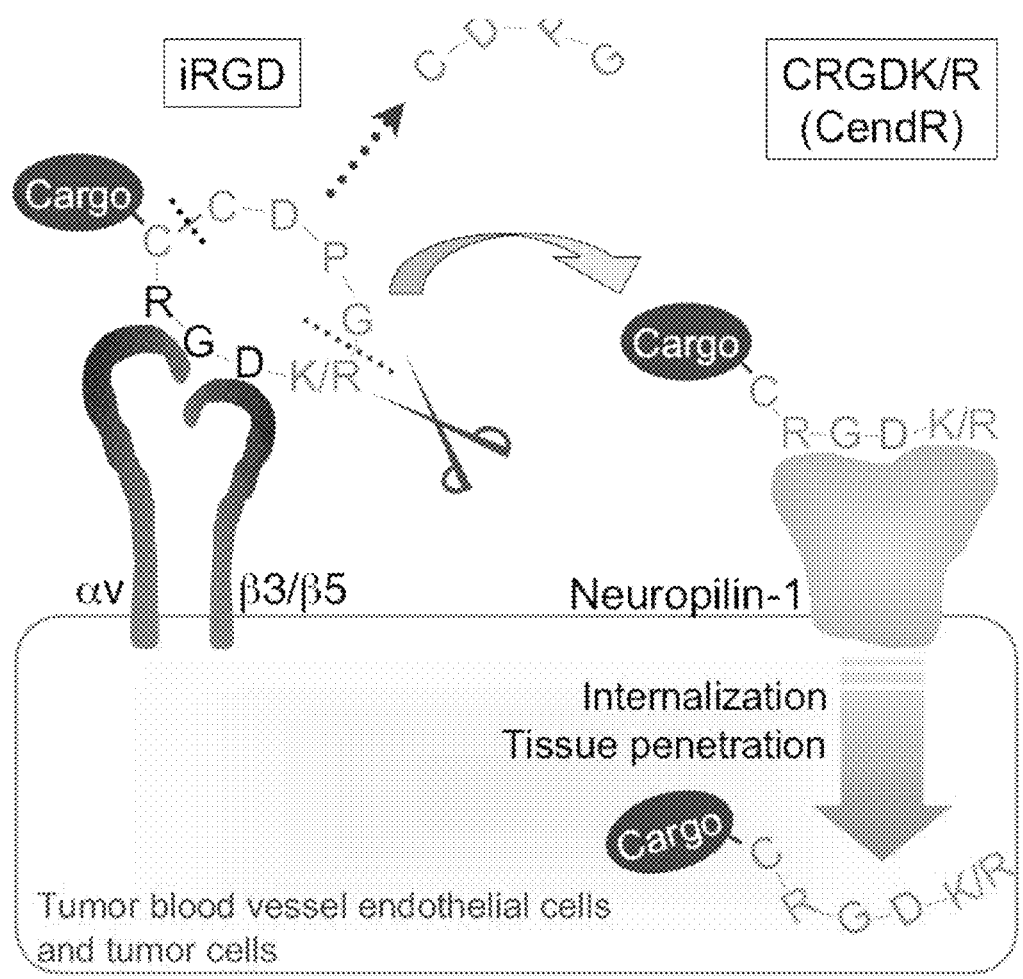
FIG. 29 shows the two step internalization mechanism of iRGD. The iRGD peptide (SEQ ID NO:15) accumulates at the surface of αv integrin-expressing endothelial and other cells in tumors. The RGD motif mediates the integrin binding. The peptide is cleaved by a cell surface-associated protease(s) to expose the cryptic CendR element, RXXK/R (SEQ ID NOs:19 and 20), at the C-terminus (dotted line with scissors) (SEQ ID NOs:46 and 51). The CendR element then mediates binding to neuropilin-1, with resulting internalization into cells. The peptide can carry into cells a cargo, such as a simple chemical or a nanoparticle, provided that the cargo is attached to the N-terminus of the iRGD peptide because the disulfide bond apparently breaks before the peptide is internalized (arrowed dotted line). The discarded peptide is SEQ ID NO:52.

These results delineate a novel multi-step targeting mechanism for iRGD; the intact peptide accumulates at the surface of cells expressing αv integrins, where it is proteolytically cleaved to produce the CendR motif-containing the CRGDK (SEQ ID NO:46) fragment. This fragment then binds to neuropilin-1 and is internalized within the target cells (FIG. 29). This mechanism makes iRGD special: it displays strong tumor specificity, is efficiently internalized within target cells, and penetrates into the tumor tissue. The multiple steps can each add to the tumor specificity of iRGD because the expression of αv integrins and neuropilin-1 is elevated in various tumor types (Eliceiri and Cheresh (2001); Ruoslahti (2002); Pellet-Many et al., Neuropilins: structure, function and role in disease. *Biochem. J.* 411, 211-226 (2008)). The same may be true of the processing protease(s). For example, matriptase, a membrane-bound protease, which preferentially cleaves proteins after a sequence similar to the R/KXXR/K CendR motif, is over-expressed in tumors (Uhland, Matriptase and its putative role in cancer. *Cell Mol. Life. Sci.* 63, 2968-2978 (2006)).

Integrins shuttle from the cell surface to intracellular compartments and back to the cell surface, and certain viral pathogens take advantage of this mechanism in entering into cells (Pellinen and Ivaska, Integrin traffic. *J. Cell Sci.* 119, 3723-3731 (2006)). However, the internalizing ability of iRGD, which requires the CendR pathway, is far more effective than that of conventional RGD peptides that follow the integrin trafficking. The most remarkable result is the tissue-penetrating activity of iRGD which far exceeds what can be accomplished with conventional RGD peptides and their mimics, which only take their payload to tumor vessels (Murphy et al. (2008); Pasqualini et al., αv integrins as receptors for tumor targeting by circulating ligands. *Nature Biotechnol.* 15, 542-546 (1997)). This indicates that the CendR motif is important for penetration into the tumor interstitium, via mechanisms still to be elaborated.

Some previously described tumor-specific, cell-penetrating peptides contain cryptic CendR sequences (Hoffman et al. (2003); Laakkonen et al., A tumor-homing peptide with a targeting specificity related to lymphatic vessels. *Nature Med.* 8, 751-755 (2002); Porkka et al., A fragment of the HMGN2 protein homes to the nuclei of tumor cells and tumor endothelial cells in vivo. *Proc. Natl. Acad. Sci. USA* 99, 7444-7449 (2002); Joyce et al., Stage-specific vascular markers revealed by phage display in a mouse model of pancreatic islet tumorigenesis. *Cancer Cell* 4, 393-403 (2003)). LyP-1 (CGNKRTRGC; SEQ ID NO:49; Laakkonen et al. (2002)) is a 9-amino acid cyclic peptide with a binding site for a specific receptor (Fogal et al., Mitochondrial/cell-surface protein p32/gC1qR as a molecular target in tumor cells and tumor stroma. *Cancer Res.* 68, 7210-7218 (2008)) and a cryptic CendR motif, KRTR (amino acids 4-7 of SEQ ID NO:49). Like iRGD nanoparticles, LyP-1-coated nanoparticles extravasate into tumor tissue within minutes after an intravenous injection (Karmali et al. (2008); Laakkonen et al. (2002); von Maltzahn et al., In vivo tumor cell targeting with "click" nanoparticles. *Bioconjug. Chem.* 19, 1570-1578 (2008)). CendR involvement in the activities of LyP-1 and other homing peptides remains to be studied but seems likely. iRGD and the CendR system can be used to improve cancer targeting and treatment.

1. Methods

Mice were maintained in accordance with institutional guidelines and the animal experiments were approved by the Animal Research Committees at University of California, Santa Barbara and San Francisco. transgenic tumor mice (Bardeesy and DePinho, (2002); Arbeit et al., Progressive squamous epithelial neoplasia in K14-human papillomavirus type 16 transgenic mice. *J. Virol.* 68, 4358-4368 (1994); Hanahan, Heritable formation of pancreatic β-cell tumors in transgenic mice expressing recombinant insulin/simian virus 40 oncogenes. *Nature* 315, 115-122 (1985)) and xenograft tumors generated by injecting BALB/c nude mice (Harlan Sprague Dawley, Indianapolis, Ind.) with $10^6$ human cancer cells orthotopically, intracardiacly or into the brain and tibia were used. T7 phage expressing individual peptides (e.g., iRGE) were produced with T7-Select Phage Display System (EMD Biosciences, Gibbstown, N.J.) according to the manufacturer's instruction. Phage homing studies in vivo and cell binding studies in vitro (Zhang et al., (2006)), immunofluorescence (Karmali et al. (2008)) and flow cytometry (Sugahara et al., Hyaluronan oligosaccharides induce CD44 cleavage and promote cell migration in CD44-expressing tumor cells. *J. Biol. Chem.* 278, 32259-32265 (2003)) were done as described. Whole body imaging was performed 3 hrs after injecting the Cy7-labelled micelles with the Odyssey Infrared Imaging System (LI-COR Biosciences, Lincoln, Nebr.). In phage internalization assays, the cells were treated with $10^9$ plaque forming units (pfu) of phage for 1 hr at 37° C., washed with an acidic buffer (glycine-HCl, pH 2.5) to remove and inactivate phage bound to the cell surface, and lysed for phage titration. Peptide internalization was studied by incubating cells with 20 μM of FAM-labeled peptide for 90 min at 37° C. FAM-iRGD peptide internalized into PPC1 cells was recovered from acid-washed cells by anti-FITC affinity chromatography, and analyzed by mass spectrometry. To inhibit the binding and/or internalization of the phage, synthetic peptides or phage rendered non-infectious by UV-irradiation were added to the cells 20 min before incubation with the test phage. FAM-labeled peptides in tissues were quantified by measuring the fluorescence with Image J software. Student's t-test and one-way analysis of variance (ANOVA) followed by a suitable post hoc t-test were used for statistical analysis (Table 3).

TABLE 3

Statistical significance

| FIG. | Method | p | Value § |
|---|---|---|---|
| 17B | t-test, 2 tailed | ** | p = 0.0028 |
| 17C | t-test, 2 tailed | ** | p = 0.0038 |
| 18A | one way ANOVA | *** | p < 0.0001 |
|  |  | *** | p < 0.0001 |
|  |  | *** | p < 0.0001 |
|  |  | * | p = 0.0298 |
|  |  | ** | p = 0.0059 |
|  |  | *** | p < 0.0001 |
| 18B | t-test, 2 tailed | *** | p < 0.0001 |
| 18C | one way ANOVA | * | p = 0.0458 |
|  |  | ** | p = 0.0030 |
|  |  | ** | p = 0.0012 |
|  |  | ** | p = 0.0012 |
| 19A | one way ANOVA | ** | p = 0.0018 |
|  |  | ** | p = 0.0027 |
| 19B | one way ANOVA | *** | p < 0.0001 |
|  |  | *** | p < 0.0001 |
|  |  | *** | p < 0.0001 |
|  |  | *** | p < 0.0001 |
|  |  | *** | p < 0.0001 |
|  |  | *** | p < 0.0001 |
| 19C | t-test, 2 tailed | * | p = 0.0237 |
|  |  | ** | p = 0.0027 |
| 19D | t-test, 2 tailed | * | p = 0.0403 |
| 19E | one way ANOVA | * | p = 0.0130 |
|  |  | *** | p = 0.0004 |
|  |  | ** | p = 0.0046 |
|  |  | ** | p = 0.0014 |
| 23 | t-test, 2 tailed | *** | p < 0.0001 |
|  |  | *** | p < 0.0001 |
|  |  | *** | p < 0.0001 |

§ The p values correspond to the asterisks from left to right in each figure;
single asterisk, p < 0.05;
double asterisk, p < 0.01;
triple asterisk, p < 0.001.
† n = 3 for all statistical analyses.

i. Tumor Models

Xenografts were created by injecting BALB/c nude mice with $10^6$ human cancer cells orthotopically or into the tibia and brain: prostate cancers PC-3 (Yang et al., A fluorescent orthotopic bone metastasis model of human prostate cancer. *Cancer Res.* 59, 781-786 (1999)), PPC1 (Zhang et al., (2006)), and 22Rv-1 (Drake et al., Assessing tumor growth and distribution in a model of prostate cancer metastasis using bioluminescence imaging. *Clin. Exp. Metastasis* 22, 674-684 (2005)), pancreatic cancer MIA PaCa-2 (Sugahara et al., Chondroitin sulfate E fragments enhance CD44 cleavage and CD44-dependent motility in tumor cells. Cancer Res. 68, 7191-7199 (2008)), and breast cancer BT474 (Rusnak et al., The effects of the novel, reversible epidermal growth factor receptor/ErbB-2 tyrosine kinase inhibitor, GW2016, on the growth of human normal and tumor-derived cell lines in vitro and in vivo. *Mol. Cancer. Ther.* 1, 85-94 (2001)). Disseminated prostate tumors were generated by injecting $10^6$ GFP-PC-3 cells (Yang et al. (1999)) into the left ventricle of the heart. Tumors were monitored with the X-ray system of the Image Station In Vivo FX (Eastman Kodak Company, Rochester, N.Y.) or the Illumatool Bright Light System LT-9900 (Lightools Research, Encinitas, Calif.). Transgenic mice were maintained as described (Bardeesy and DePinho (2002); Arbeit et al. (1994); Hanahan (1985)).

ii. Screening of Phage Libraries

Figures 30A, 30B:
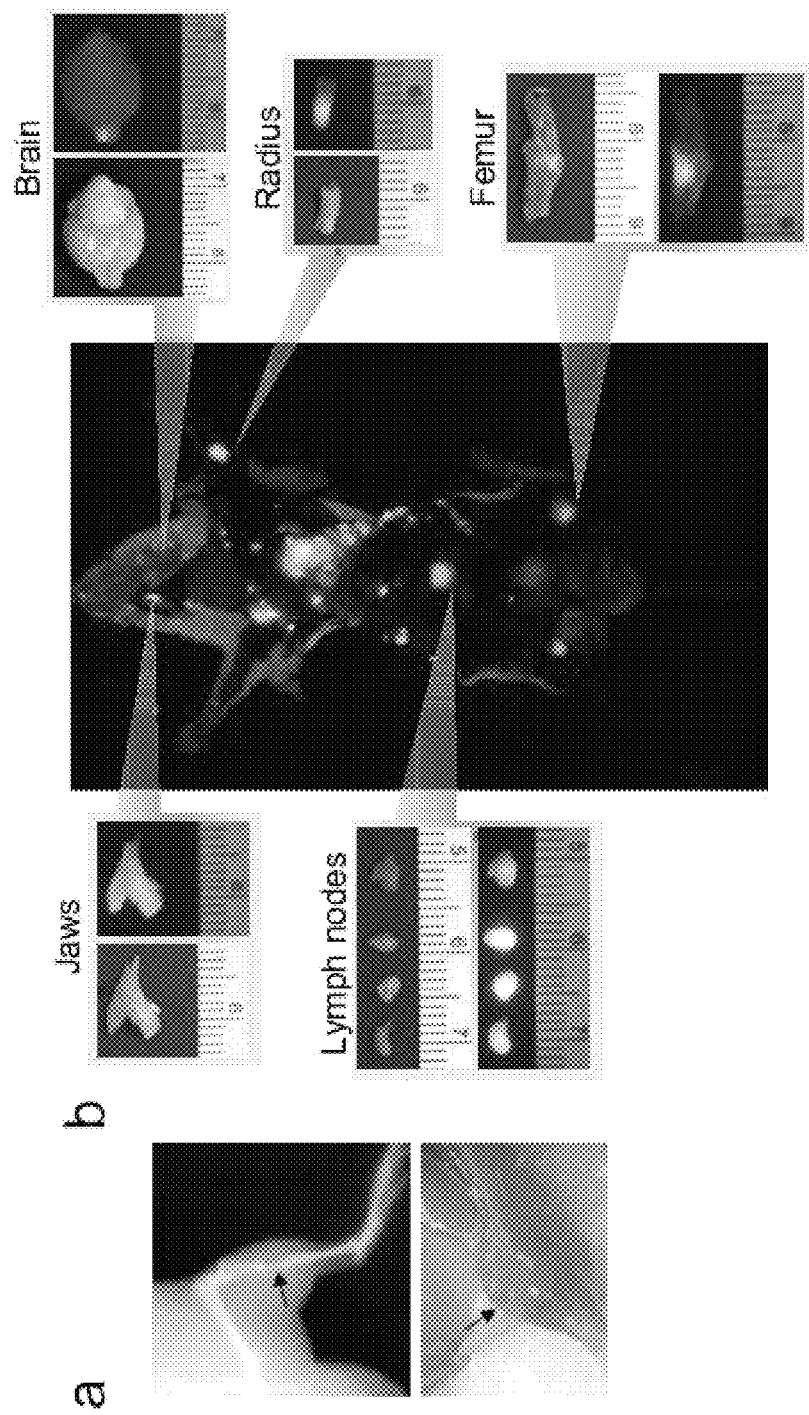
FIGS. 30A-30C show tumors and enrichment data from phage display screening. a, PPC1 tibia xenografts: Upper panel, x-ray picture taken with Image Station In Vivo FX of the area shown in the lower panel. Arrows point to tumors in tibia. b, GFP-PC-3 tumors disseminated from an injection of one million tumor cells into the left ventricle of the heart. The mouse was imaged under UV light using the Illumatool Bright Light System LT-9900. Tumors that grew in the bones (e.g., jaws, radius, femur) were used for the screening. c, An example of the enrichment obtained in successive rounds of phage display screening.
Figure 30C:
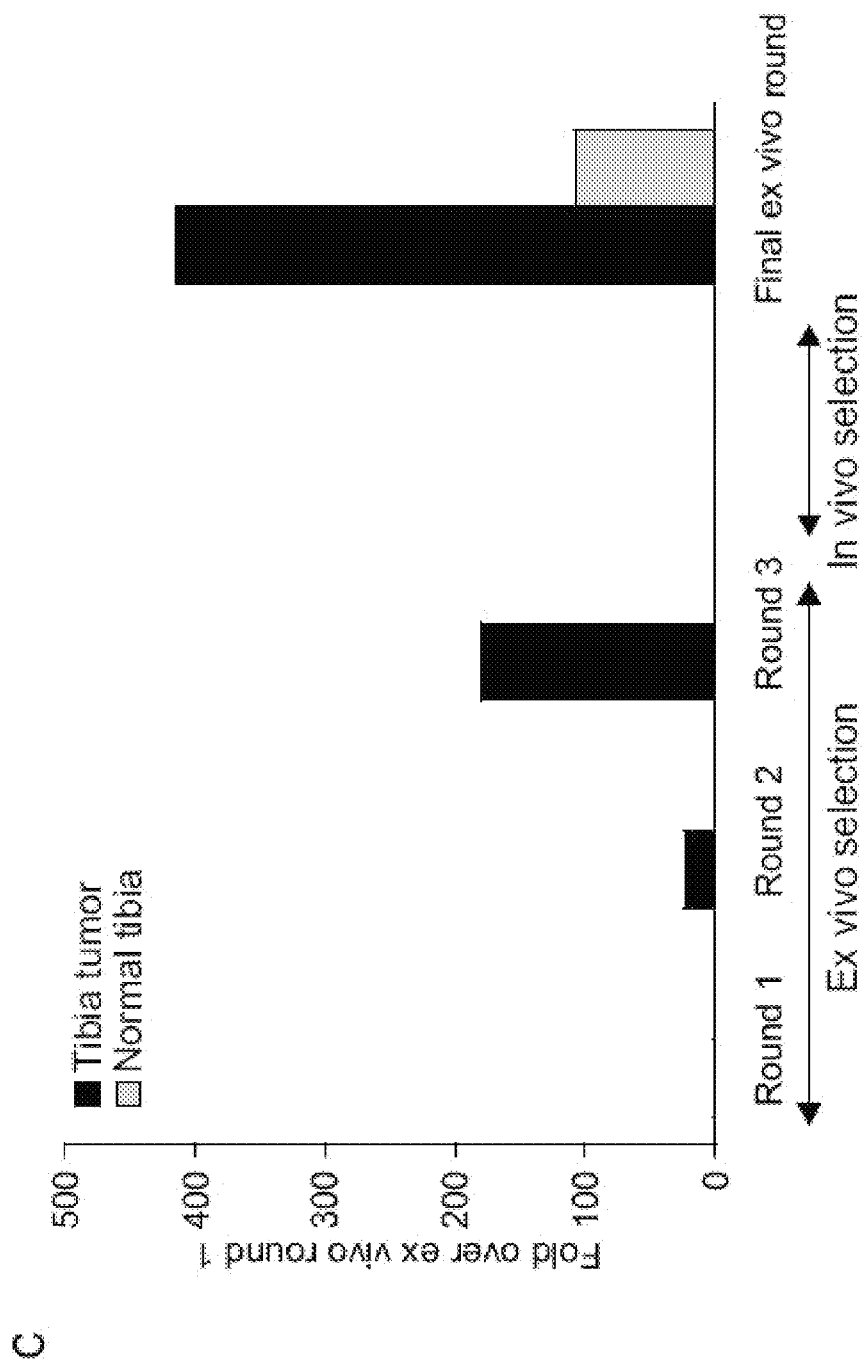

A cyclic $CX_7C$ (C+cysteine; X=any amino acid) peptide library displayed on T7 phage (diversity approximately $10^9$) and a combination of ex vivo and in vivo screenings (Hoffman et al. (2003)) was used. Bone xenografts of PPC1 and PC-3 (FIG. 30A) or disseminated bone tumors of GFP-PC-3 were used (FIG. 30B). Three rounds of ex vivo selection with tumor cell suspensions were followed by one in vivo selection for tumor homing. After a final ex vivo selection, the resulting phage pools bound to tumor-derived cell suspensions 200-400 times more than the original library, and 5 times more than to normal bone marrow-derived cells (FIG. 30C). Individual phage clones were randomly picked up from the phage pools and sequenced.

iii. In Vivo Peptide and Phage Homing

Synthetic peptides labeled with fluorescein (Karmali et al. (2008)) (approximately 200 μg) were intravenously injected into tumor-bearing mice and allowed to circulate for 15 min to 2 hrs. Tissues were collected and observed under UV light (Illumatool Bright Light System LT-9900) or processed for immunofluorescence (Karmali et al. (2008)). To assess phage homing (Zhang et al., (2006)), $10^9$ pfu of T7 phage were intravenously injected into tumor-bearing mice, and allowed to circulate for 15 min. The mice were perfused through the heart with PBS containing 1% BSA and tissues were harvested for immunofluorescence.

iv. Preparation of Micelles

Lipids were purchased from Avanti Polar Lipids (Alabaster, Ala.). DSPE-$PEG_{2,000}$-iRGD(FAM) was prepared by coupling FAM-iRGD peptide bearing a cysteine on its N-terminus to 1,2-distearoyl-sn-glycero-3-phosphoethanolamine-N-maleimide(polyethylene glycol)$_{2,000}$ (DSPE-$PEG_{2,000}$-maleimide) at 1:1 molar ratio at room temperature for 4 hrs. DSPE-$PEG_{2,000}$-FAM was prepared by coupling 1,2-distearoyl-sn-glycero-3-phosphoethanolamine-N-amino(polyethylene glycol)$_{2,000}$ (DSPE-$PEG_{2,000}$-amine) with NHS-Fluorescein (Pierce Biotechnology, Rockford, Ill.) at a 1:1 molar ratio for 1 hr at room temperature. DSPE-$PEG_{2,000}$-Cy7 was prepared similarly using 1,2-distearoyl-sn-glycero-3-phosphoethanolamine-N-amino(polyethylene glycol)$_{2,000}$ and Cy7-NHS ester (GE Healthcare, UK).

DSPE-$PEG_{2,000}$-iRGD(FAM), DSPE-$PEG_{2,000}$-amine, and DSPE-$PEG_{2,000}$-Cy7 in 3:6.7:0.3 molar ratios were dissolved in chloroform/methanol (3:1, v/v). The solvent was evaporated, and the dried lipid film was kept under vacuum for 8 hrs and allowed to swell in PBS for 2 hrs at 60° C. The vial was vortexed and sonicated to produce micelles. The micelles were sequentially filtered through 0.2 μM and 0.1 μM filters, and washed with sterile PBS to remove unreacted peptides. Control Cy7 micelles were prepared using DSPE-$PEG_{2,000}$-FAM in place of DSPE-$PEG_{2,000}$-iRGD(FAM). The micelles were 15-25 nm in diameter as measured in deionized water by dynamic laser light scattering (refractive index, 1.59; viscosity, 0.89) on a Malvern Zetasizer Nano (Malvern, UK).

In vivo Imaging of Micelle-Peptide Conjugates

PDAC mice (Bardeesy and DePinho, (2002)) were injected with 100 μl of 1 mM micelles in PBS. After 3 hrs, the mice were anesthetized, shaved, and subjected to whole body imaging with the Odyssey Infrared Imaging System (LI-COR Biosciences, Lincoln, Nebr.).

v. Immunofluorescence

Tissue sections were processed as described (Karmali et al. (2008)). Cells ($2\times10^5$ cells) were grown on collagen I-coated coverslips (BD Biosciences, San Jose, Calif.) overnight, and incubated with $10^8$ pfu/ml of T7 phage for 30 min. The cells were fixed in 4% paraformaldehyde, and stained with antibodies and DAPI (Molecular Probes, Eugene, Oreg.). The primary antibodies were rat anti-mouse CD31 monoclonal antibody (BD Biosciences), and rabbit anti-human $\alpha v$ integrin (Chemicon, Temecula, Calif.), rabbit anti-human neuropilin-1 (Chemicon), mouse anti-human neuropilin-1 (Miltenyi Biotec, Auburn, Calif.), and rabbit anti-T7 phage polyclonal antibodies. The secondary antibodies, Alexa594 goat antibodies to mouse, rat, and rabbit IgG and Alexa488 donkey anti-rabbit antibody were from Molecular Probes. Cells and tissue sections were examined by confocal microscopy (Fluoview 500, Olympus America, Center Valley, Pa.).

vi. In vitro Phage Binding and Internalization Assays

Suspended cells ($10^6$ cells in DMEM containing 1% BSA) were incubated with $10^8$ pfu/ml of T7 phage for 1 hr at 4° C. The cells were washed 4 times with the binding buffer, lysed with lysogeny broth containing 1% NP-40, and titrated. Phage internalization assays used the same procedure, except that the cells were incubated with phage at 37° C., and that an acidic buffer (500 mM sodium chloride, 0.1 M glycine, 1% BSA, pH 2.5) was substituted for the binding buffer in the second wash. Inhibitors of binding and internalization were added 20 min prior to incubation with phage. Non-infectious phage were prepared by treating phage with UV for 8 min in DMEM containing 1% BSA. The resulting UV-inactivated phage particles expressing about 200 peptides per particle were used as multivalent inhibitors. Free synthetic peptides, mouse antibodies against human $\alpha 1$, $\alpha 2$, $\alpha v \beta 3$, $\alpha v \beta 5$, $\alpha 5 \beta 1$, $\alpha 4$, or $\alpha v$ integrins and integrin subunits (Chemicon), goat anti-rat neuropilin-1 (R&D Systems, Minneapolis, Minn.), with mouse and a goat IgG isotype controls (Abcam) were also tested.

vii. Flow Cytometry

The experiments were performed as described (Sugahara et al., Hyaluronan oligosaccharides induce CD44 cleavage and promote cell migration in CD44-expressing tumor cells. *J. Biol. Chem.* 278, 32259-32265 (2003)) except that 1 mM of $MgSO_4$, $CaCl_2$, and $MnCl_2$ were added to the buffer. The antibodies were the same as in the cell binding assays, and were detected with Alexa488 goat anti-mouse antibody (Molecular Probes). The cells were analyzed with an EasyCyte Plus System (Guava Technologies, Hayward, Calif.).

viii. FAM-iRGD Fragment Isolation

PPC1 cells ($10^7$ cell sin DMEM) were treated with 10 μM carbobenzoxyl-leucinyl-leucinyl-leucinal (MG132, EMD Chemicals, Gibbstown, N.J.) for 30 min at 37° C. to inhibit proteasomes, and incubated with 20 µl of iRGD peptide labeled with FAM at the N-terminus or C-terminus. The cells were washed once with acidic buffer and lysed in MPER (Pierce Biotechnology) containing protease inhibitors (Complete Mini EDTA-free, Roche Applied Science, Indianapolis, Ind.) on ice for 30 min. The sample was centrifuged for 30 min at 12,000 rpm. The supernatant was applied onto an anti-FITC affinity column, and after washing, bound peptides were eluted with glycine-HCl, pH 2.8. The eluate was subjected to mass spectrometry.

E. Example 5

Tissue-Penetrating Delivery of Compounds and Nanoparticles into Tumors

The vasculature in different tissues expresses distinct biochemical signatures, the "vascular zip codes" (Ruoslahti, 2002; Ruoslahti and Rajotte, 2000). Vascular zip codes can serve as targets for docking-based (synaphic) delivery of diagnostics and therapeutics. αv integrins are highly expressed in tumor vasculature, where they can be accessed with peptides containing the RGD integrin recognition motif (Eliceiri and Cheresh, 2001; Pierschbacher and Ruoslahti, 1984; Ruoslahti, 2002, 2003). RGD-based synaphic targeting has been successfully used to deliver drugs, biologicals (Arap et al., 1998; Curnis et al., 2004), imaging agents (Sipkins et al., 1998), viruses (Pasqualini et al., 1997; Wickham, 2000), and nanoparticles (Murphy et al., 2008) to tumor vasculature. However, crossing the vascular wall and penetrating into the tumor parenchyma against the elevated interstitial pressure in tumors remains a major challenge in tumor therapy (Heldin et al., 2004; Jain, 1990).

A consensus R/KXXR/K motif has recently been identified as a mediator of cell and tissue penetration (Teesalu et al., 2009). The receptor for the R/KXXR/K motif was shown to be neuropilin-1. This motif is not active unless it occupies a C-terminal position in the peptide; this position effect is referred to as the C-end Rule (CendR).

The interaction between the CendR motif and neuropilin-1 appears to be a key determinant for penetration of biological barriers. For example, vascular endothelial growth factor-165 and certain semaphorins bind to neuropilin-1 through C-terminal CendR motifs and thereby increase vascular permeability (Acevedo et al., 2008; Jia et al., 2006; Soker et al., 1998; Teesalu et al., 2009). In addition, many viruses possess CendR motifs within their capsid proteins and often require proteolytic cleavage to expose the CendR motif to be infective, a process that requires penetration of biological barriers (Steinhauer, 1999; Teesalu et al., 2009) One such virus, HTLV-1, has been shown to use its CendR motif (KPXR) to bind to and internalize into immune cells in a neuropilin-1 dependent fashion to infect the cells (Lambert et al., 2009).

The tissue-penetrating properties of the CendR system can be used to deliver drugs and nanoparticles into tumor parenchyma, beyond the vascular barrier. Here results obtained with a peptide that combines tumor-homing and CendR-dependent tissue-penetrating properties are reported. The potential of the technology for clinical applications by performing magnetic resonance imaging (MRI) and tumor treatment studies is also examined.

Figure 31:
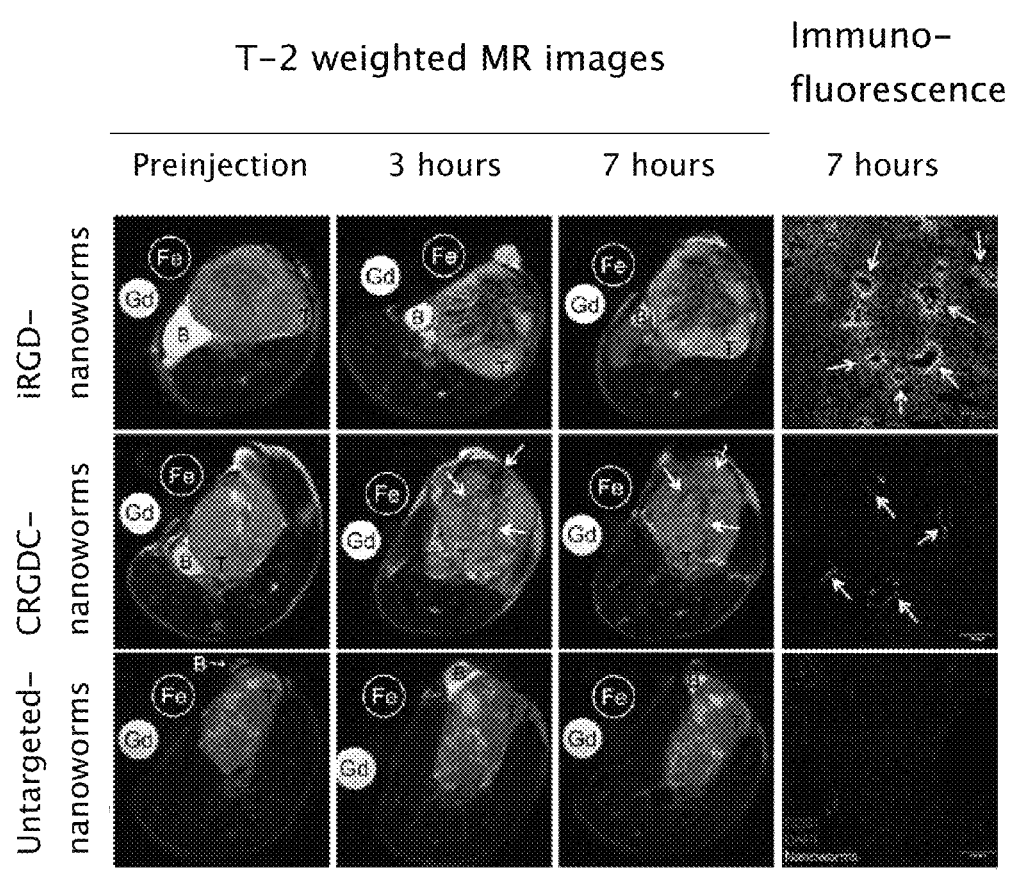
FIG. 31 shows tumor imaging with iRGD-coated iron oxide nanoworms. T2-weighted magnetic resonance images of mice bearing orthotopic 22Rv1 human prostate tumors. The mice were injected intravenously with iron oxide nanoworms coated with iRGD, CRGDC, or no peptide (5 mg/kg of iron). Shown are axial images through the tumors acquired by repeated imaging before the nanoworm injection (Preinjection) and 3 hr or 7 hr after the injection. The orientation of the tumors is slightly different between the time points because the mice were anesthetized for each scan and reintroduced in the MRI instrument. Gadolinium (Gd) was used as a reference for T1 and Feridex (Fe) for T2 imaging agents. Note the wide hypointensity areas indicating the spreading of iRGD nanoworms in the tumor interstitium. CRGDC nanoworms only decreased the intensity of tumor vessels, and the untargeted nanoworms gave no signal in the tumor. Arrows point to the vasculature. T, tumor; B, urinary bladder. The rightmost panels represent the nanoworm distribution in tumor tissue examined by confocal microscopy. Light staining around the vasculature, nanoworms; *, CD31; small gray spheres, DAPI. Scale bars, 100 µm. The images are representative of multiple tumor mice; iRGD nanoworms, n=5; CRGDC nanoworms, n=3; untargeted nanoworms, n=3.

1. Results
   i. iRGD in Tumor Imaging and Treatment
   To demonstrate the use of iRGD relevant to clinical applications, MRI and therapeutic targeting experiments were performed. For MRI, mice bearing 22Rv1 orthotopic xenografts were injected intravenously with iRGD peptide-linked superparamagnetic iron oxide nanoworms (about 80 nm long and 30 nm thick; Park et al., 2009; Simberg et al., 2007). Iron oxide nanoparticles are evidenced as hypointensities in T2-weighted magnetic resonance images (McAteer et al., 2007). In addition to hypointense vascular signals, the iRGD nanoworms gave low intensity regions that spread throughout the tumor, while CRGDC nanoworms only decreased the intensity of the tumor vasculature (FIG. 31, T2-weighted magnetic resonance images). Untargeted nanoworms produced no detectable signal under identical imaging conditions. Confocal microscopy of the tumors confirmed the enhanced tissue penetration of the iRGD nanoworms (FIG. 31, rightmost panels). Both the MRI results and optical imaging (FIG. 17E) indicate that iRGD is capable of delivering diagnostics to tumors and that tumors are more efficiently visualized with this peptide than with conventional RGD peptides.

Figure 32:
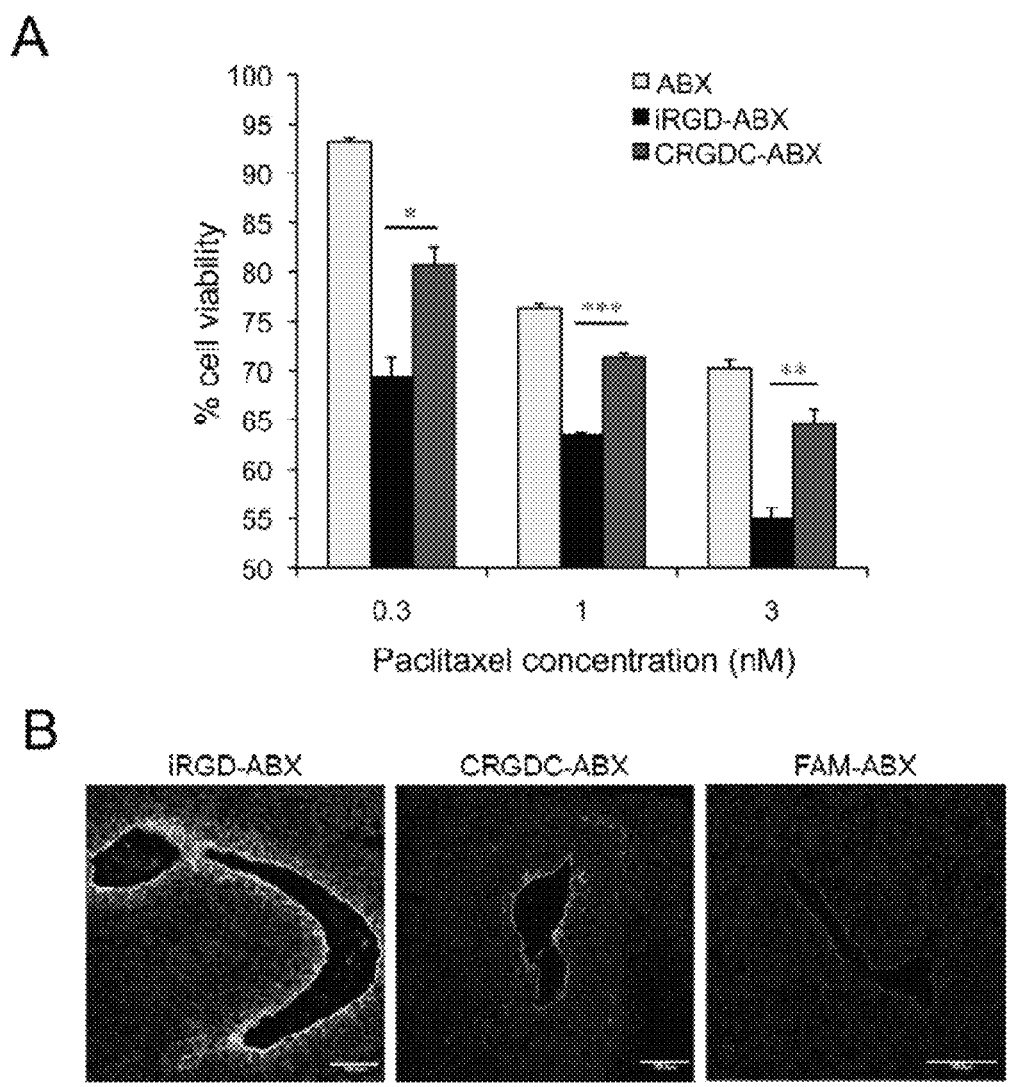
FIGS. 32A and 32B shows cytotoxicity and tumor homing of abraxane conjugates.
Figure 33A:
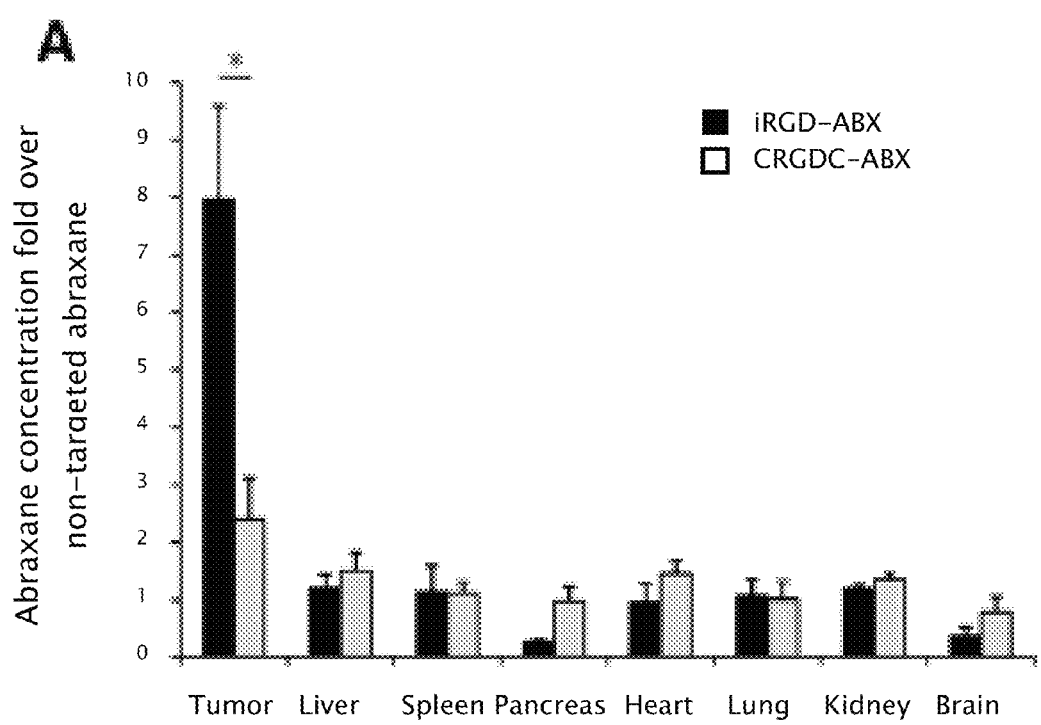
FIGS. 33A-33D show tumor treatment with iRGD-coated nanoparticles.
Figure 33B:
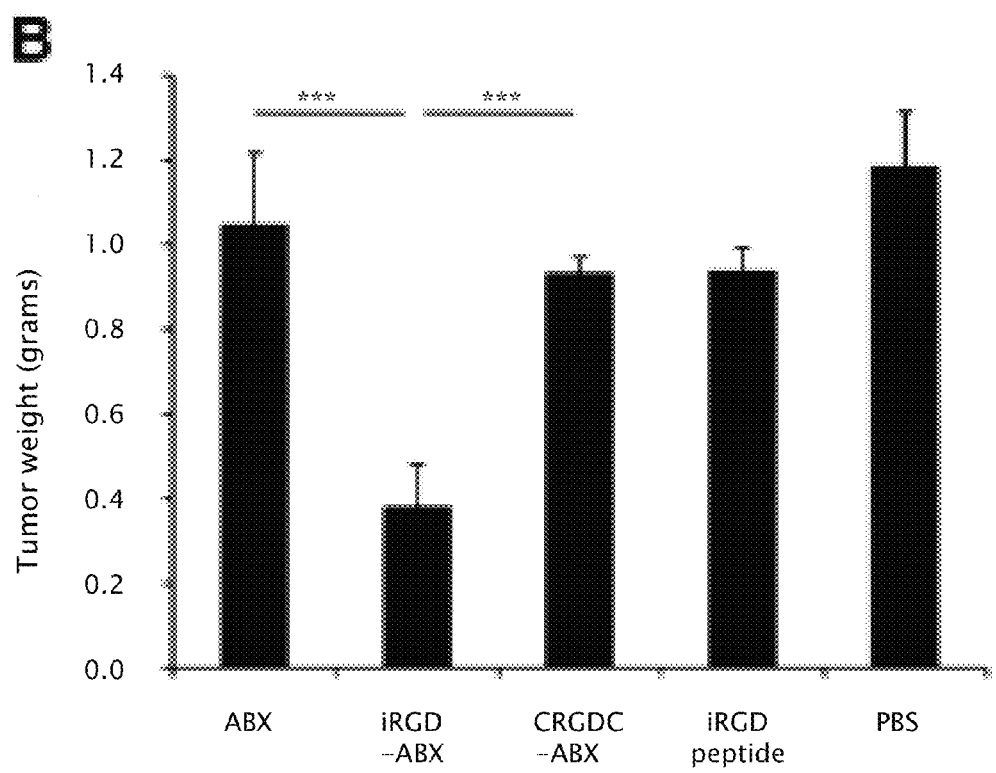
Figure 34A:
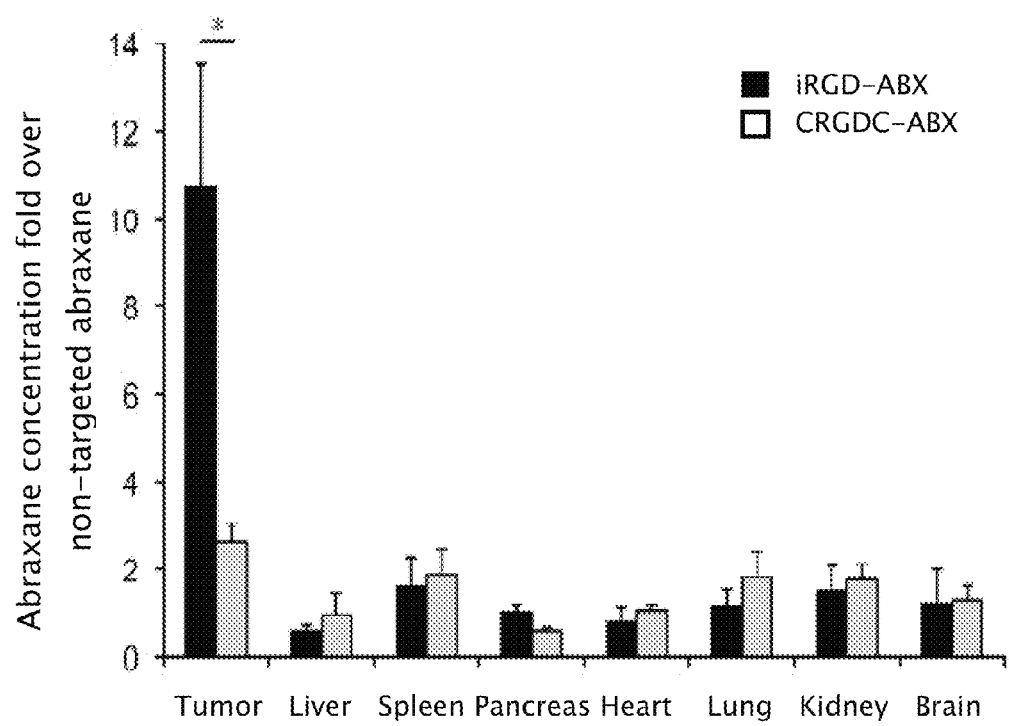
FIGS. 34A and 34B show subcutaneous 22Rv1 tumor treatment with iRGD-coated abraxane. (A) Abraxane quantification in a subcutaneous 22Rv1 xenograft model. Abraxane was intravenously injected into tumor mice 3 hours earlier and captured from tumor extracts with a taxol antibody, followed by detection with a human albumin antibody. N=3 for each group. (B) Mice bearing subcutaneous 22Rv1 xenografts were intravenously injected with peptide-coated abraxanes every other day at 3 mg paclitaxel/kg/injection. The treatment was continued for 12 days. The number of mice per group was 8. Statistical analysis was performed with Student's t-test in (A) and ANOVA in (B). Error bars, s.e.m.; n.s., not significant; single asterisk, $p<0.05$; triple asterisk, $p<0.001$.
Figure 34B:
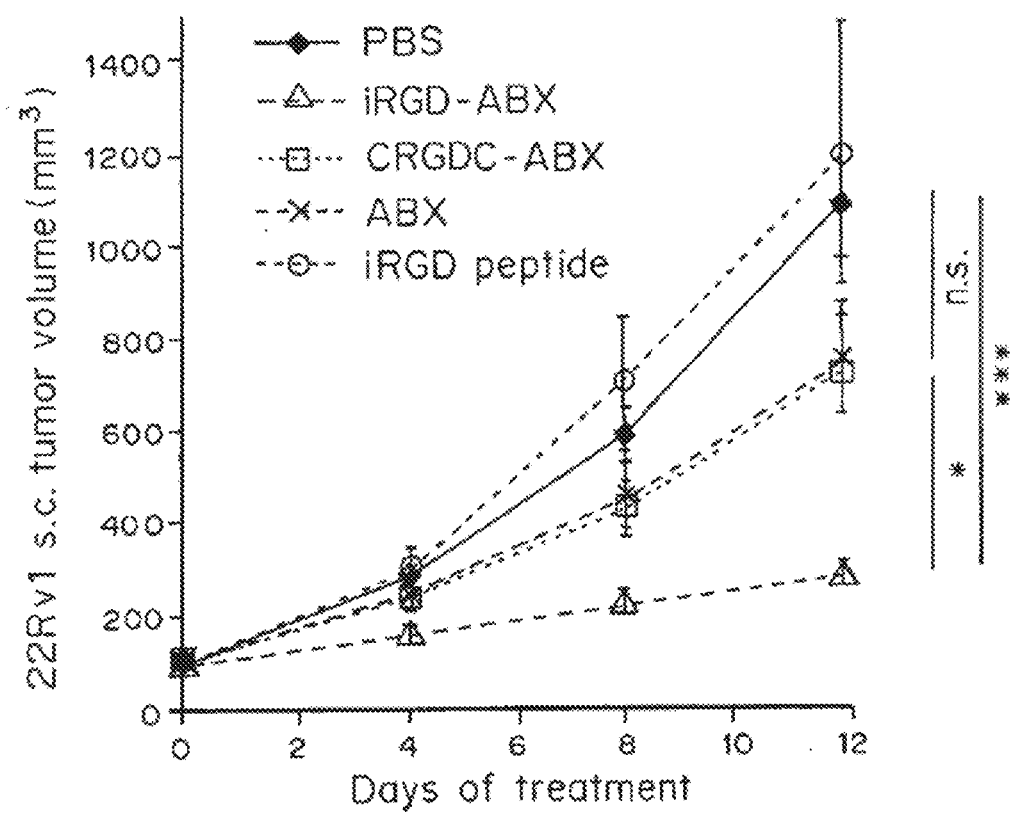

The ability of iRGD to deliver anticancer drugs was investigated by treating mice bearing orthotopic 22Rv1 tumors with iRGD-coated abraxane, a 130 nm nanoparticle consisting of albumin-embedded paclitaxel (Haley and Frenkel, 2008; Karmali et al., 2009). In vitro, iRGD-abraxane inhibited the proliferation of 22Rv1 cells more efficiently than abraxane conjugated with a cyclic RGD peptide without a CendR motif (CRGDC; Koivunen et al, 1993) or abraxane alone (FIG. 32A). Intravenously injected iRGD-abraxane spread more within tumor tissue than the other abraxane formulations (FIG. 32B). Quantification of the drug showed that 8-fold more abraxane accumulated in the tumors from injections of iRGD-abraxane than of nontargeted abraxane (FIG. 33A). CRGDC-abraxane concentration was only about 2-fold higher than that of non-targeted abraxane in the tumors. In line with these results, iRGD-abraxane treatment resulted in significant inhibition of tumor growth at a dose at which untargeted abraxane showed no significant effect (FIG. 33B); the slight reduction in tumor growth in the CRGDC group was not statistically significant. Treatment with the iRGD peptide alone at a dose equivalent to its molar amount in iRGD-abraxane did not affect tumor growth, indicating that the effect of iRGD-abraxane was not due to the disruption of the integrin signaling by the iRGD peptide. An additional treatment study in a subcutaneous 22Rv1 tumor model with time-dependent tumor volume measurements confirmed the treatment data obtained with the orthotopic tumors (FIG. 34B). A similar biodistribution of the abraxane formulations was also observed in the subcutaneous and orthotopic tumors (FIG. 34A).

Figure 33C:
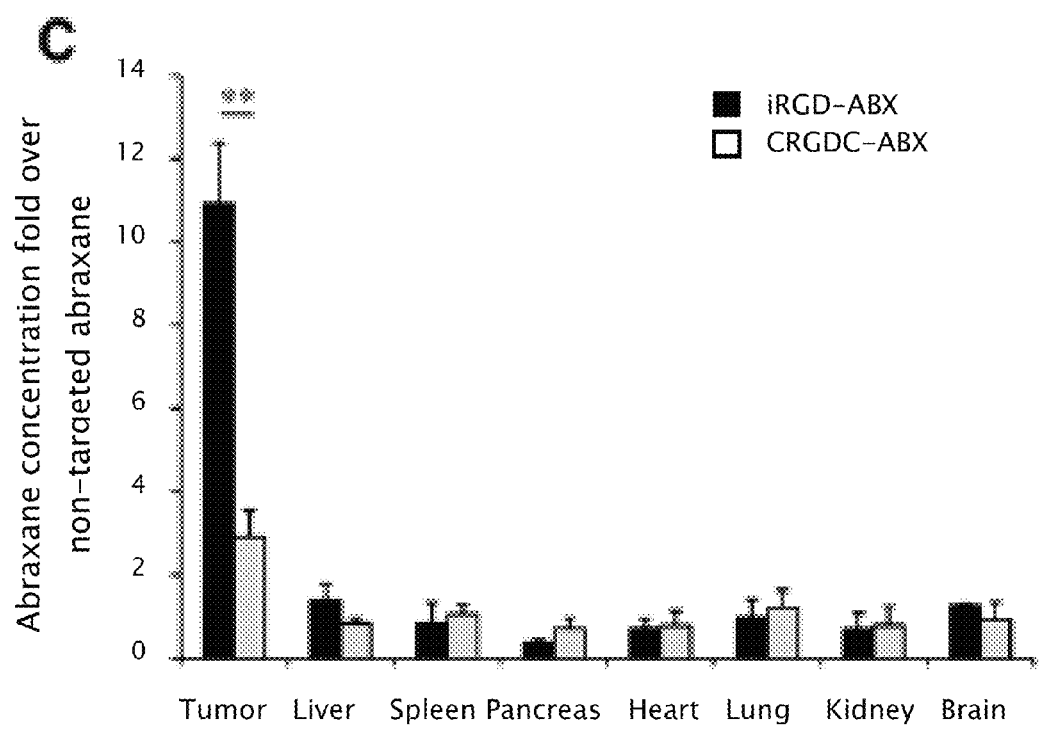
Figure 33D:
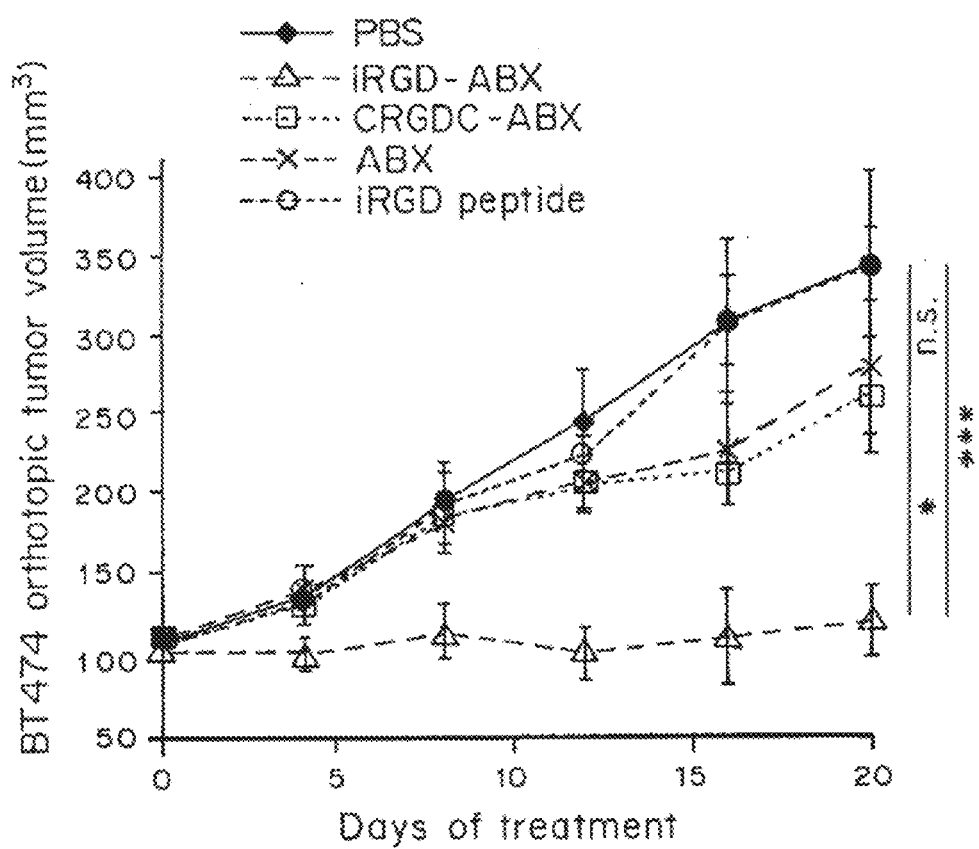
Figure 35:
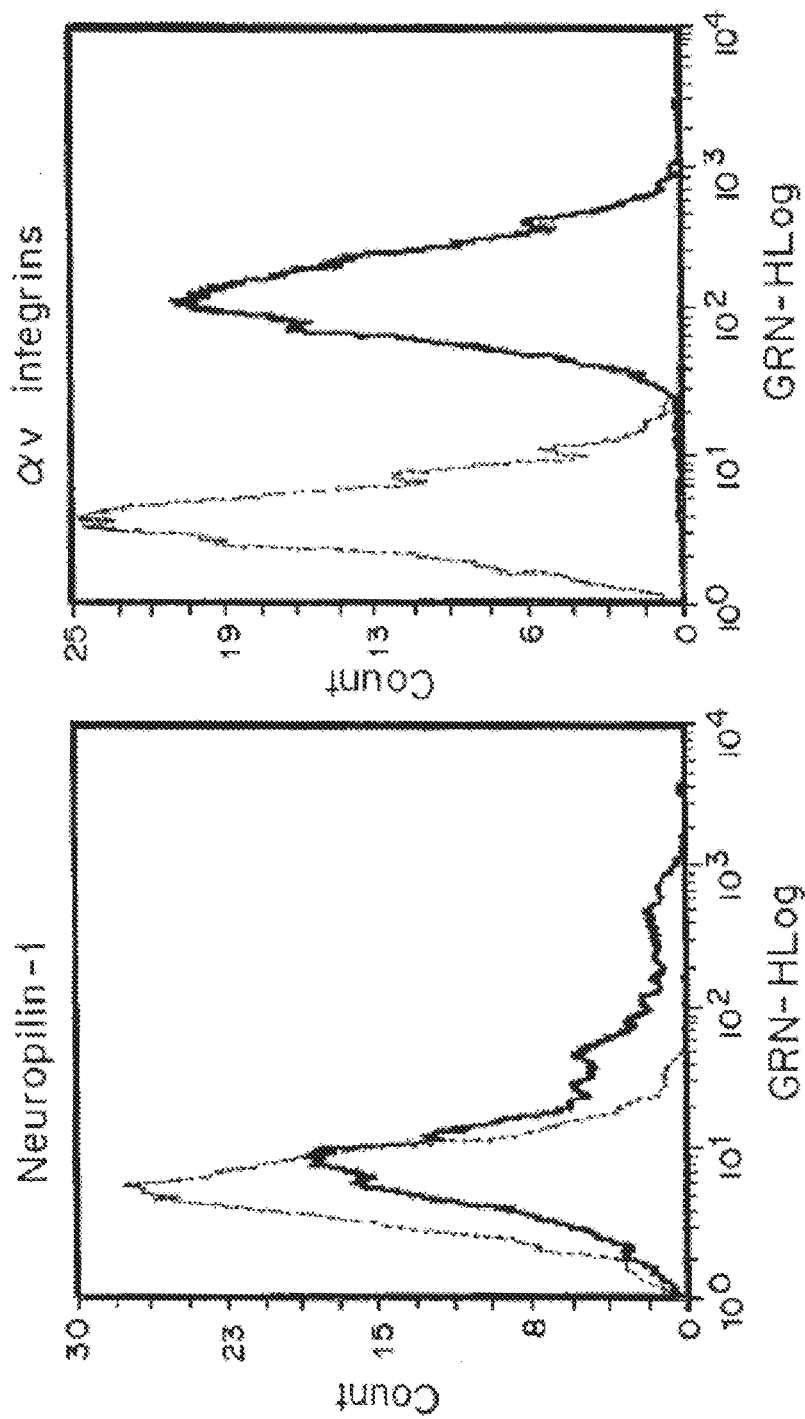
FIG. 35 shows integrin and neuropilin expression on cultured BT474. The expression of αv integrins and neuropilin-1 in cultured BT474 tumor cells were analyzed by flow cytometry. The profiles are from cells incubated with rabbit IgG (gray), an αv-integrin antibody (left, black), or a neuropilin-1 antibody (right, black).
Figure 36:
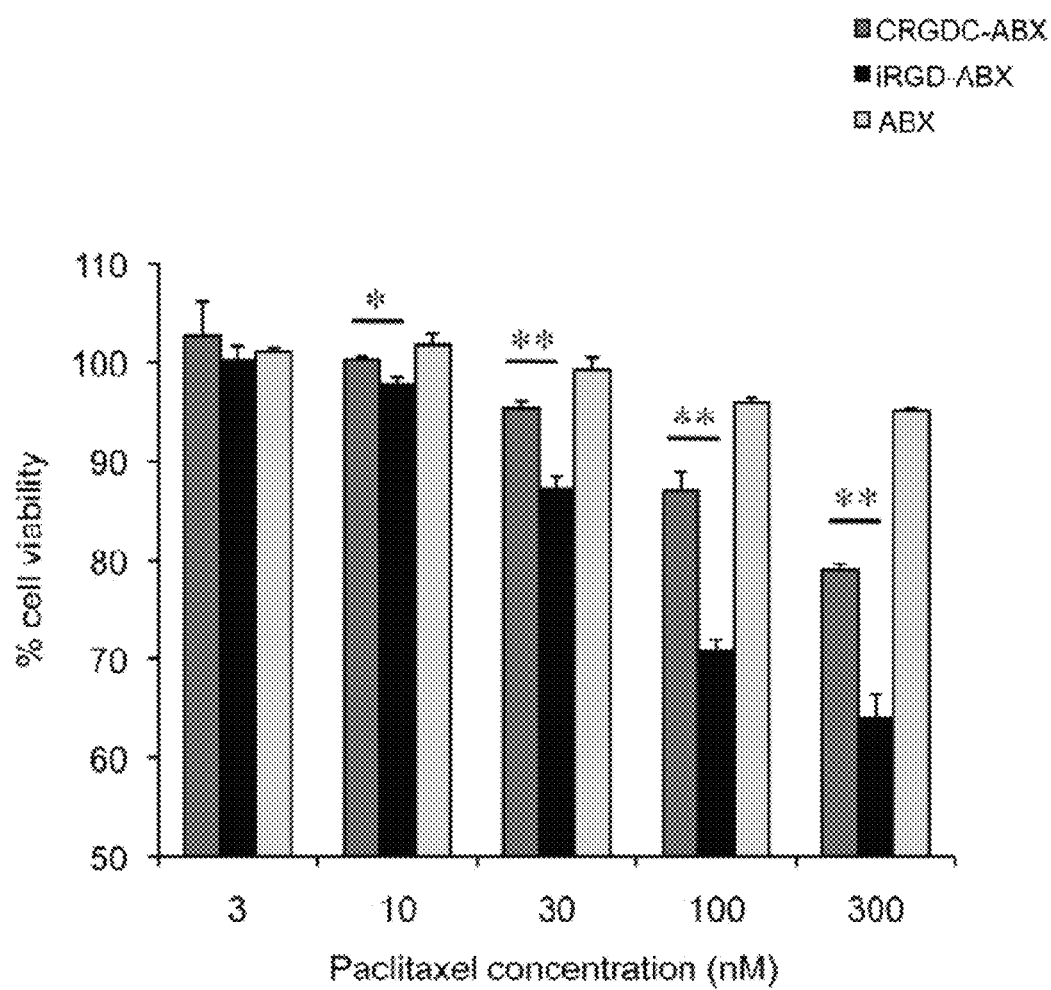
FIG. 36 shows cytotoxicity of abraxane conjugates to cultured BT474 cells. In vitro tumor cell treatment with various abraxane conjugates. Cultured BT474 cells were treated for 30 min at room temperature with non-targeted abraxane (ABX), or abraxane coated with iRGD (iRGD-ABX) or CRGDC (CRGDC-ABX). The cells were incubated for 48 hrs and cell death was quantified by MTT assays (n=3). Note that about 300 fold more abraxane is required to provide similar cell toxicity in the BT474 cells than in 22Rv1 cells (see FIG. 19A). Statistical analyses were performed with Student's t-test. Error bars, s.e.m.; single asterisk, $p<0.05$; double asterisk, $p<0.01$.

The efficacy of iRGD-abraxane in a tumor model unrelated to 22Rv1 was tested. Orthotopic tumors generated with the BT474 human breast cancer cell line, which expresses both αv integrins and neuropilin-1 at the cell surface, were chosen (FIG. 35). In addition, the BT474 cells are more resistant to abraxane (paclitaxel) than 22Rv1 as shown in cytotoxicity assays (FIG. 36). When injected intravenously into the tumor mice, the iRGD-abraxane accumulated in the tumor 11-fold more than nontargeted abraxane and about 4-fold more than the CRGDC-abraxane (FIG. 33C). Despite the resistance of the BT474 cells to paclitaxel, the iRGD abraxane significantly inhibited the tumor growth in vivo (FIG. 33D). The other abraxane formulations or iRGD peptide alone did not show significant effects at the same dose. Together, these results clearly demonstrate the efficacy of iRGD in drug delivery.

2. Discussion

The results in this and other examples herein delineate a technology to deliver diagnostics and therapeutics into the extravascular tumor parenchyma using a unique tumor-specific homing peptide, iRGD.

Several pieces of data support the model that the iRGD peptide follows a multistep tumor-targeting mechanism. First, the affinity of iRGD for αv integrins is in the mid to low nanomolar range, similar to that of RGD peptides previously used in tumor targeting (Koivunen et al., 1993, 1995). Significantly, the proteolytically processed CRGDK fragment identified within the targeted cells has lost most of its affinity to the integrins (about 50- to 150-fold reduction in affinity), which is in agreement with the observation that RGDK peptides lack cell attachment activity (Pierschbacher and Ruoslahti, 1984). Instead, the CRGDK fragment acquires an affinity for neuropilin-1 that is stronger than its residual affinity for αv-integrins. These changes likely facilitate the transfer of CRGDK from integrins to neuropilin-1, and the resulting penetration activities.

The initial recruitment of iRGD to cells surfaces appears to be crucial for its pronounced tumor targeting ability, since the related but non-integrin-binding peptide iRGE showed only modest uptake into cultured cells and was inefficient in targeting tumors in vivo. The presence of the tumor-specific recruitment element RGD distinguishes iRGD from some previously described tumor-targeting peptides. Jiang et al. (2004) have described a design for tumor-homing peptides in which a cationic cell-penetrating peptide is tethered to a negatively charged sequence that blocks the cell-penetrating activity. The tether contains a recognition sequence for a protease known to be elevated in tumors. These authors achieved a 3-fold increase in tumor homing. The greater homing achieved with iRGD (12-fold over a control peptide) is likely due to the RGD-directed specific homing of the intact peptide. In addition, the recruitment of iRGD to the cell surface through the RGD-integrin interaction can be needed for the proteolytic cleavage that triggers the subsequent tumor penetration, as protease inhibitors are generally inactive on cell surfaces, but block proteolysis elsewhere (Hall et al. 1991). The unbiased screening performed in identifying iRGD may also have selected for a protease that is more readily available to cleave an incoming peptide than the proteases with known expression but unknown availability in tumors.

The strong tumor MRI signals provided by iRGD-coated iron oxide nanoworms and the enhanced tumor growth suppression by iRGD-linked abraxane demonstrate that this peptide can be used in tumor targeting.

Several lines of evidence indicate that rapid tumor tissue penetration can involve the so-called vascular permeabilization in the tumor induced by the CendR property of iRGD. Molecules such as vascular endothelial growth factor-165 and some semaphorins that have exposed CendR motifs increase vascular permeability (Jia et al., 2006; Acevedo et al., 2008). In addition, a prototypic CendR peptide, RPARPAR, has recently been demonstrated to induce vascular permeability (Teesalu et al., 2009).

3. Methods i. Magnetic Resonance Imaging

Nude mice bearing 22Rv1 orthotopic human prostate tumors were injected intravenously with superparamagnetic iron oxide nanoworms (Park et al., 2009) coated with iRGD or CRGDC peptides or untargeted nanoworms at a dose of 5 mg/kg of iron. Each animal received nickel liposomes (0.2 μmol of Ni) intravenously 1 hr prior to the nanoworms to increase the half-life of the nanoworms (Simberg et al., 2007). The mice were repeatedly imaged before and 3 and 7 hr after injection of the nanoworms. For each scan, the mice were anesthetized with isofluorane and repositioned into a 30 mm diameter mouse coil. The axial plains were carefully matched to previous scans by measuring the height of the sections and comparing the vascular patterns in the images. Iron-sensitive MRI scans consisting of T2-weighted fast spin-echo were acquired using a 3-Tesla magnetic resonance imager (GE Healthcare). The conditions used were as follows: repetition time/echo time=6.4 s/70 ms, echo train length=32, readout bandwith=±15.6 kHz, in-plane spatial resolution=220 μm, field of view=(3.5 cm)$^2$, slice thickness=1 mm, number of excitation=3. After imaging, tissues of interest were harvested without perfusion and processed for immunofluorescence.

ii. Tumor Treatment Studies

Peptide-conjugated abraxanes were prepared and characterized as described previously (Karmali et al., 2009). For in vitro cytotoxicity studies, 22Rv1 or BT474 cells were seeded in 96 well culture plates ($5 \times 10^4$ cells per well) and incubated overnight. The cells were incubated with various concentrations of the conjugates for 30 min at room temperature and washed with fresh culture media. MTT assays (Invitrogen) to assess cell viability were performed on the cells 48 hr later. For in vivo tumor treatment studies, nude mice bearing 2-week-old 22Rv1 orthotopic xenografts (typically about 250 mm$^3$ in tumor volume) were intravenously injected with the abraxane conjugates. The conjugates were given every other day for 14 days at a paclitaxel equivalent of 3 mg/kg/injection. The iRGD peptide control was administered in an equivalent amount of iRGD in each iRGD-abraxane dose. Mice bearing subcutaneous 22Rv1 tumors were treated similarly for 12 days, and orthotopic BT474 tumors for 20 days. The experiments were terminated according to the guidelines by the Animal Research Committee at the University of California, Santa Barbara. To study the homing pattern of the abraxane conjugates in the 22Rv1 orthotopic tumors, the conjugates were intravenously injected to tumor-bearing mice at a dose of 3 mg/kg and allowed to circulate for 3 hr. The mice were perfused through the heart and tissues of interest were harvested and processed for immunofluorescence.

iii. Immunofluorescence

Tissue sections were processed as described previously (Karmali et al., 2009). The primary antibodies were rat anti-mouse CD31 monoclonal antibody (BD Biosciences) and rabbit anti-human αv integrin (Chemicon), rabbit anti-human neuropilin-1 (Chemicon), mouse anti-human neuropilin-1 (Miltenyi Biotec), and rabbit anti-T7 phage (Teesalu et al., 2009) polyclonal antibodies. The secondary antibodies, Alexa 594 goat antibodies to mouse, rat, and rabbit IgG and Alexa 488 donkey anti-rabbit antibody, were from Molecular Probes. Cells and tissue sections were examined by a Fluoview 500 confocal microscope (Olympus America).

iv. Abraxane Quantification

Mice bearing 22Rv1 or BT474 tumors were intravenously injected with the abraxane conjugates at a paclitaxel equivalent of 9 mg/kg/injection. After 3 hr, the mice were perfused through the heart and tissues of interest were harvested. The tissues were homogenized in cold RIPA buffer (Pierce Biotechnology) containing protease inhibitors (Complete MiniEDTA-free) and kept on ice for 30 min. The samples were then centrifuged for 30 min at 14,000 rpm. The abraxane concentration in the supernatant was quantified with an ELISA: abraxane was captured with a taxol antibody (Novus Biologicals) coated onto a 96 well plate and detected with a human albumin antibody labeled with biotin (US Biological).

v. Optical In Vivo Imaging of Micelle-Peptide Conjugates

PDAC mice were injected with 100 μl of 1 mM micelles in

PBS. After 3 hr, the mice were anesthetized, shaved, and subjected to whole-body imaging with the Odyssey Infrared Imaging System (LI-COR Biosciences).

vi. Flow Cytometry

The experiments were performed as described previously (Sugahara et al., 2003) except that 1 mM of $MgSO_4$, $CaCl_2$, and $MnCl_2$ were added to the buffer containing the integrin antibodies. The antibodies were the same as in the cell binding assays and were detected with an Alexa 488 goat anti-mouse or goat anti-rabbit antibody (Molecular Probes). The cells were analyzed with an Easy-Cyte Plus System (Guava Technologies).

vii. Statistical Analyses

Data were analyzed by two-tailed Student's t test and one-way analysis of variance (ANOVA), followed by suitable post-hoc test.

REFERENCES

Alirol, E., and Martinou, J. C. (2006). Mitochondria and cancer: is there a morphological connection? Oncogene 25, 4706-4716.

Alitalo, K., Mohla, S., and Ruoslahti, E. (2004). Lymphangiogenesis and cancer: meeting report. Cancer Res 64, 9225-9229.

Arap, W., Haedicke, W., Bernasconi, M., Kain, R., Rajotte, D., Krajewski, S., Ellerby, H. M., Bredesen, D. E., Pasqualini, R., and Ruoslahti, E. (2002). Targeting the prostate for destruction through a vascular address. Proc Natl Acad Sci USA 99, 1527-1531.

Arap, W., Pasqualini, R., and Ruoslahti, E. (1998a). Cancer treatment by targeted drug delivery to tumor vasculature in a mouse model. Science 279, 377-380.

Arap, W., Pasqualini, R., and Ruoslahti, E. (1998b). Chemotherapy targeted to tumor vasculature. Curr Opin Oncol 10, 560-565.

Blancato, J., Singh, B., Liu, A., Liao, D. J., and Dickson, R. B. (2004). Correlation of amplification and overexpression of the c-myc oncogene in high-grade breast cancer: FISH, in situ hybridisation and immunohistochemical analyses. Br J Cancer 90, 1612-1619.

Braun, L., Ghebrehiwet, B., and Cossart, P. (2000). gC1q-R/p32, a C1q-binding protein, is a receptor for the In1B invasion protein of *Listeria monocytogenes*. Embo J 19, 1458-1466.

Christian, S., Pilch, J., Akerman, M. E., Porkka, K., Laakkonen, P., and Ruoslahti, E. (2003). Nucleolin expressed at the cell surface is a marker of endothelial cells in angiogenic blood vessels. J Cell Biol 163, 871-878.

Deb, T. B., and Datta, K. (1996). Molecular cloning of human fibroblast hyaluronic acid-binding protein confirms its identity with P-32, a protein co-purified with splicing factor SF2. Hyaluronic acid-binding protein as P-32 protein, co-purified with splicing factor SF2. J Biol Chem 271, 2206-2212.

Dedio, J., Jahnen-Dechent, W., Bachmann, M., and Muller-Esterl, W. (1998). The multiligand-binding protein gC1qR, putative C1q receptor, is a mitochondrial protein. J Immunol 160, 3534-3542.

Degenhardt, K., Mathew, R., Beaudoin, B., Bray, K., Anderson, D., Chen, G., Mukherjee, C., Shi, Y., Gelinas, C., Fan, Y., et al. (2006). Autophagy promotes tumor cell survival and restricts necrosis, inflammation, and tumorigenesis. Cancer Cell 10, 51-64.

Effert, P. J., Bares, R., Handt, S., Wolff, J. M., Bull, U., and Jakse, G. (1996). Metabolic imaging of untreated prostate cancer by positron emission tomography with 18-fluorine-labeled deoxyglucose. J Urol 155, 994-998.

Fantin, V. R., St-Pierre, J., and Leder, P. (2006). Attenuation of LDH-A expression uncovers a link between glycolysis, mitochondrial physiology, and tumor maintenance. Cancer Cell 9, 425-434.

Garber, K. (2006). Energy deregulation: licensing tumors to grow. Science 312, 1158-1159.

Ghebrehiwet, B., Jesty, J., and Peerschke, E. I. (2002). gC1q-R/p33: structure-function predictions from the crystal structure. Immunobiology 205, 421-432.

Ghebrehiwet, B., Lim, B. L., Peerschke, E. I., Willis, A. C., and Reid, K. B. (1994). Isolation, cDNA cloning, and overexpression of a 33-kD cell surface glycoprotein that binds to the globular "heads" of C1q. J Exp Med 179, 1809-1821.

Ghosh, I., Chowdhury, A. R., Rajeswari, M. R., and Datta, K. (2004). Differential expression of Hyaluronic Acid Binding Protein 1 (HABP1)/P32/C1QBP during progression of epidermal carcinoma. Mol Cell Biochem 267, 133-139.

Guarino, R. D., Dike, L. E., Haq, T. A., Rowley, J. A., Pitner, J. B., and Timmins, M. R. (2004). Method for determining oxygen consumption rates of static cultures from microplate measurements of pericellular dissolved oxygen concentration. Biotechnol Bioeng 86, 775-787.

Guo, W. X., Ghebrehiwet, B., Weksler, B., Schweitzer, K., and Peerschke, E. I. (1999). Up-regulation of endothelial cell binding proteins/receptors for complement component C1q by inflammatory cytokines. J Lab Clin Med 133, 541-550.

Gupta, S., Batchu, R. B., and Datta, K. (1991). Purification, partial characterization of rat kidney hyaluronic acid binding protein and its localization on the cell surface. Eur J Cell Biol 56, 58-67.

Herwald, H., Dedio, J., Kellner, R., Loos, M., and Muller-Esterl, W. (1996). Isolation and characterization of the kininogen-binding protein p33 from endothelial cells. Identity with the gC1q receptor. J Biol Chem 271, 13040-13047.

Hirasawa, A., Awaji, T., Xu, Z., Shinoura, H., and Tsujimoto, G. (2001). Regulation of subcellular localization of alpha1-adrenoceptor subtypes. Life Sci 68, 2259-2267.

Hofer, C., Laubenbacher, C., Block, T., Breul, J., Hartung, R., and Schwaiger, M. (1999). Fluorine-18-fluorodeoxyglucose positron emission tomography is useless for the detection of local recurrence after radical prostatectomy. Eur Urol 36, 31-35.

Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer Cell 4, 383-391.

Inoki, K., Zhu, T., and Guan, K. L. (2003). TSC2 mediates cellular energy response to control cell growth and survival. Cell 115, 577-590.

Isidoro, A., Casado, E., Redondo, A., Acebo, P., Espinosa, E., Alonso, A. M., Cejas, P., Hardisson, D., Fresno Vara, J. A., Belda-Iniesta, C., et al. (2005). Breast carcinomas fulfill the Warburg hypothesis and provide metabolic markers of cancer prognosis. Carcinogenesis 26, 2095-2104.

Jain, R. K. (1998). The next frontier of molecular medicine: delivery of therapeutics. Nat Med 4, 655-657.

Jiang, J., Zhang, Y., Krainer, A. R., and Xu, R. M. (1999). Crystal structure of human p32, a doughnut-shaped acidic mitochondrial matrix protein. Proc Natl Acad Sci USA 96, 3572-3577.

Jin, S., DiPaola, R. S., Mathew, R., and White, E. (2007). Metabolic catastrophe as a means to cancer cell death. J Cell Sci 120, 379-383.

Jones, R. G., Plas, D. R., Kubek, S., Buzzai, M., Mu, J., Xu, Y., Birnbaum, M. J., and Thompson, C. B. (2005). AMP-activated protein kinase induces a p53-dependent metabolic checkpoint. Mol Cell 18, 283-293.

Joseph, K., Ghebrehiwet, B., Peerschke, E. I., Reid, K. B., and Kaplan, A. P. (1996). Identification of the zinc-dependent endothelial cell binding protein for high molecular weight kininogen and factor XII: identity with the receptor that binds to the globular "heads" of C1q (gC1q-R). Proc Natl Acad Sci USA 93, 8552-8557.

Joyce, J. A., Laakkonen, P., Bernasconi, M., Bergers, G., Ruoslahti, E., and Hanahan, D. (2003). Stage-specific vascular markers revealed by phage display in a mouse model of pancreatic islet tumorigenesis. Cancer Cell 4, 393-403.

Kaur, I., Voss, S. D., Gupta, R. S., Schell, K., Fisch, P., and Sondel, P. M. (1993). Human peripheral gamma delta T cells recognize hsp60 molecules on Daudi Burkitt's lymphoma cells. J Immunol 150, 2046-2055.

Kerjaschki, D. (2005). The crucial role of macrophages in lymphangiogenesis. J Clin Invest 115, 2316-2319.

Kerjaschki, D., Huttary, N., Raab, I., Regele, H., Bojarski-Nagy, K., Bartel, G., Krober, S. M., Greinix, H., Rosenmaier, A., Karlhofer, F., et al. (2006). Lymphatic endothelial progenitor cells contribute to de novo lymphangiogenesis in human renal transplants. Nat Med 12, 230-234.

Khan, I. U., Wallin, R., Gupta, R. S., and Kammer, G. M. (1998). Protein kinase A-catalyzed phosphorylation of heat shock protein 60 chaperone regulates its attachment to histone 2B in the T lymphocyte plasma membrane. Proc Natl Acad Sci USA 95, 10425-10430.

Kittlesen, D. J., Chianese-Bullock, K. A., Yao, Z. Q., Braciale, T. J., and Hahn, Y. S. (2000). Interaction between complement receptor gC1qR and hepatitis C virus core protein inhibits T-lymphocyte proliferation. J Clin Invest 106, 1239-1249.

Krainer, A. R., Mayeda, A., Kozak, D., and Binns, G. (1991). Functional expression of cloned human splicing factor SF2: homology to RNA-binding proteins, U1 70K, and *Drosophila* splicing regulators. Cell 66, 383-394.

Laakkonen, P., Akerman, M. E., Biliran, H., Yang, M., Ferrer, F., Karpanen, T., Hoffman, R. M., and Ruoslahti, E. (2004). Antitumor activity of a homing peptide that targets tumor lymphatics and tumor cells. Proc Natl Acad Sci USA 101, 9381-9386.

Laakkonen, P., Porkka, K., Hoffman, J. A., and Ruoslahti, E. (2002). A tumor-homing peptide with a targeting specificity related to lymphatic vessels. Nat Med 8, 751-755.

Lee, S. M., Lee, E. J., Hong, H. Y., Kwon, M. K., Kwon, T. H., Choi, J. Y., Park, R. W., Kwon, T. G., Yoo, E. S., Yoon, G. S., et al. (2007). Targeting bladder tumor cells in vivo and in the urine with a peptide identified by phage display. Mol Cancer Res 5, 11-19.

Levine, B. (2007). Cell biology: autophagy and cancer. Nature 446, 745-747.

Liao, D. J., and Dickson, R. B. (2000). c-Myc in breast cancer. Endocr Relat Cancer 7, 143-164.

Lim, B. L., Reid, K. B., Ghebrehiwet, B., Peerschke, E. I., Leigh, L. A., and Preissner, K. T. (1996). The binding protein for globular heads of complement C1q, gC1qR. Functional expression and characterization as a novel vitronectin binding factor. J Biol Chem 271, 26739-26744.

Liu, Y. (2006). Fatty acid oxidation is a dominant bioenergetic pathway in prostate cancer. Prostate Cancer Prostatic Dis 9, 230-234.

Majumdar, M., Meenakshi, J., Goswami, S. K., and Datta, K. (2002). Hyaluronan binding protein 1 (HABP1)/C1QBP/p32 is an endogenous substrate for MAP kinase and is translocated to the nucleus upon mitogenic stimulation. Biochem Biophys Res Commun 291, 829-837.

Maruyama, K., Asai, J., Ii, M., Thorne, T., Losordo, D. W., and D'Amore, P. A. (2007). Decreased macrophage number and activation lead to reduced lymphatic vessel formation and contribute to impaired diabetic wound healing. Am J Pathol 170, 1178-1191.

Maruyama, K., Ii, M., Cursiefen, C., Jackson, D. G., Keino, H., Tomita, M., Van Rooijen, N., Takenaka, H., D'Amore, P. A., Stein-Streilein, J., et al. (2005). Inflammation-induced lymphangiogenesis in the cornea arises from CD 11b-positive macrophages. J Clin Invest 115, 2363-2372.

Matthews, D. A., and Russell, W. C. (1998). Adenovirus core protein V interacts with p32—a protein which is associated with both the mitochondria and the nucleus. J Gen Virol 79 (Pt 7), 1677-1685.

Muta, T., Kang, D., Kitajima, S., Fujiwara, T., and Hamasaki, N. (1997). p32 protein, a splicing factor 2-associated protein, is localized in mitochondrial matrix and is functionally important in maintaining oxidative phosphorylation. J Biol Chem 272, 24363-24370.

Oh, P., Li, Y., Yu, J., Dun, E., Krasinska, K. M., Carver, L. A., Testa, J. E., and Schnitzer, J. E. (2004). Subtractive proteomic mapping of the endothelial surface in lung and solid tumours for tissue-specific therapy. Nature 429, 629-635.

Parle-McDermott, A., McWilliam, P., Tighe, O., Dunican, D., and Croke, D. T. (2000). Serial analysis of gene expression identifies putative metastasis-associated transcripts in colon tumour cell lines. Br J Cancer 83, 725-728.

Peerschke, E. I., Reid, K. B., and Ghebrehiwet, B. (1994). Identification of a novel 33-kDa C1q-binding site on human blood platelets. J Immunol 152, 5896-5901.

Porkka, K., Laakkonen, P., Hoffman, J. A., Bernasconi, M., and Ruoslahti, E. (2002). A fragment of the HMGN2 protein homes to the nuclei of tumor cells and tumor endothelial cells in vivo. Proc Natl Acad Sci USA 99, 7444-7449.

Reef, S., Shifman, O., Oren, M., and Kimchi, A. (2007). The autophagic inducer smARF interacts with and is stabilized by the mitochondrial p32 protein. Oncogene.

Robles-Flores, M., Rendon-Huerta, E., Gonzalez-Aguilar, H., Mendoza-Hernandez, G., Islas, S., Mendoza, V., Ponce-Castaneda, M. V., Gonzalez-Mariscal, L., and Lopez-Casillas, F. (2002). p32 (gC1qBP) is a general protein kinase C(PKC)-binding protein; interaction and cellular localization of P32-PKC complexes in ray hepatocytes. J Biol Chem 277, 5247-5255.

Rozanov, D. V., Ghebrehiwet, B., Postnova, T. I., Eichinger, A., Deryugina, E. I., and Strongin, A. Y. (2002a). The hemopexin-like C-terminal domain of membrane type 1 matrix metalloproteinase regulates proteolysis of a multifunctional protein, gC1qR. J Biol Chem 277, 9318-9325.

Rozanov, D. V., Ghebrehiwet, B., Ratnikov, B., Monosov, E. Z., Deryugina, E. I., and Strongin, A. Y. (2002b). The cytoplasmic tail peptide sequence of membrane type-1 matrix metalloproteinase (MT1-MMP) directly binds to gC1qR, a compartment-specific chaperone-like regulatory protein. FEBS Lett 527, 51-57.

Rubinstein, D. B., Stortchevoi, A., Boosalis, M., Ashfaq, R., Ghebrehiwet, B., Peerschke, E. I., Calvo, F., and Guillaume, T. (2004). Receptor for the globular heads of C1q (gC1q-R, p33, hyaluronan-binding protein) is preferentially expressed by adenocarcinoma cells. Int J Cancer 110, 741-750.

Rubinsztein, D. C., Gestwicki, J. E., Murphy, L. O., and Klionsky, D. J. (2007). Potential therapeutic applications of autophagy. Nat Rev Drug Discov 6, 304-312.

Ruoslahti, E. (2002). Specialization of tumour vasculature. Nat Rev Cancer 2, 83-90.

Schaerer, M. T., Kannenberg, K., Hunziker, P., Baumann, S. W., and Sigel, E. (2001). Interaction between GABA(A) receptor beta subunits and the multifunctional protein gC1q-R. J Biol Chem 276, 26597-26604.

Schledzewski, K., Falkowski, M., Moldenhauer, G., Metharom, P., Kzhyshkowska, J., Ganss, R., Demory, A., Falkowska-Hansen, B., Kurzen, H., Ugurel, S., et al. (2006). Lymphatic endothelium-specific hyaluronan receptor LYVE-1 is expressed by stabilin-1+, F4/80+, CD11b+ macrophages in malignant tumours and wound healing tissue in vivo and in bone marrow cultures in vitro: implications for the assessment of lymphangiogenesis. J Pathol 209, 67-77.

Sengupta, A., Tyagi, R. K., and Datta, K. (2004). Truncated variants of hyaluronan-binding protein 1 bind hyaluronan and induce identical morphological aberrations in COS-1 cells. Biochem J 380, 837-844.

Shaw, R. J. (2006). Glucose metabolism and cancer. Curr Opin Cell Biol 18, 598-608.

Shim, H., Dolde, C., Lewis, B. C., Wu, C. S., Dang, G., Jungmann, R. A., Dalla-Favera, R., and Dang, C. V. (1997). c-Myc transactivation of LDH-A: implications for tumor metabolism and growth. Proc Natl Acad Sci USA 94, 6658-6663.

Simberg, D., Duza, T., Park, J. H., Essler, M., Pilch, J., Zhang, L., Derfus, A. M., Yang, M., Hoffman, R. M., Bhatia, S., et al. (2007). Biomimetic amplification of nanoparticle homing to tumors. Proc Natl Acad Sci USA 104, 932-936.

Singh, B., Soltys, B. J., Wu, Z. C., Patel, H. V., Freeman, K. B., and Gupta, R. S. (1997). Cloning and some novel characteristics of mitochondrial Hsp70 from Chinese hamster cells. Exp Cell Res 234, 205-216.

Soltys, B. J., and Gupta, R. S. (1996). Immunoelectron microscopic localization of the 60-kDa heat shock chaperonin protein (Hsp60) in mammalian cells. Exp Cell Res 222, 16-27.

Soltys, B. J., and Gupta, R. S. (1997). Cell surface localization of the 60 kDa heat shock chaperonin protein (hsp60) in mammalian cells. Cell Biol Int 21, 315-320.

Soltys, B. J., and Gupta, R. S. (1999). Mitochondrial-matrix proteins at unexpected locations: are they exported? Trends Biochem Sci 24, 174-177.

Soltys, B. J., Kang, D., and Gupta, R. S. (2000). Localization of P32 protein (gC1q-R) in mitochondria and at specific extramitochondrial locations in normal tissues. Histochem Cell Biol 114, 245-255.

St Croix, B., Rago, C., Velculescu, V., Traverso, G., Romans, K. E., Montgomery, E., Lal, A., Riggins, G. J., Lengauer, C., Vogelstein, B., and Kinzler, K. W. (2000). Genes expressed in human tumor endothelium. Science 289, 1197-1202.

Stacker, S. A., Achen, M. G., Jussila, L., Baldwin, M. E., and Alitalo, K. (2002). Lymphangiogenesis and cancer metastasis. Nat Rev Cancer 2, 573-583.

Storz, P., Hausser, A., Link, G., Dedio, J., Ghebrehiwet, B., Pfizenmaier, K., and Johannes, F. J. (2000). Protein kinase C [micro] is regulated by the multifunctional chaperon protein p32. J Biol Chem 275, 24601-24607.

Tange, T. O., Jensen, T. H., and Kjems, J. (1996). In vitro interaction between human immunodeficiency virus type 1 Rev protein and splicing factor ASF/SF2-associated protein, p32. J Biol Chem 271, 10066-10072.

van Leeuwen, H. C., and O'Hare, P. (2001). Retargeting of the mitochondrial protein p32/gC1Qr to a cytoplasmic compartment and the cell surface. J Cell Sci 114, 2115-2123.

Wallace, D. C. (2005). Mitochondria and cancer: Warburg addressed. Cold Spring Harb Symp Quant Biol 70, 363-374.

Xu, Q., Schett, G., Seitz, C. S., Hu, Y., Gupta, R. S., and Wick, G. (1994). Surface staining and cytotoxic activity of heat-shock protein 60 antibody in stressed aortic endothelial cells. Circ Res 75, 1078-1085.

Zhang, L., Giraudo, E., Hoffman, J. A., Hanahan, D., and Ruoslahti, E. (2006). Lymphatic zip codes in premalignant lesions and tumors. Cancer Res 66, 5696-5706.

Zhang, Y., Qi, H., Taylor, R., Xu, W., Liu, L. F., and Jin, S. (2007). The Role of Autophagy in Mitochondria Maintenance: Characterization of Mitochondrial Functions in Autophagy-Deficient S. cerevisiae Strains. Autophagy 3, 337-346.

Jain, Vascular and interstitial barriers to delivery of therapeutic agents in tumors, Cancer Metastasis Rev, 1990, 9: 253-266.

Ferrara and Alitalo, Clinical applications of angiogenic growth factors and their inhibitors, Nat Med, 1999, 5: 1359-1364.

Hanahan and Weinberg, The hallmarks of cancer, Cell, 2000, 100: 57-70.

Ruoslahti, Specialization of tumor vasculature, Nat Rev Cancer, 2002, 2: 83-90.

Arap et al., Cancer treatment by targeted drug delivery to tumor vasculature in a mouse model, Science, 1998, 279: 377-380.

Hoffman et al., Progressive vascular changes in a transgenic mouse model of squamous cell carcinoma, Cancer Cell, 2003, 4: 383-391.

Joyce et al., Stage-specific vascular markers revealed by phage display in a mouse model of pancreatic islet tumorigenesis, Cancer Cell, 2003, 4: 393-403.

Laakkonen et al., A tumor-homing peptide with a targeting specificity related to lymphatic vessels, Nat Med, 2002, 8: 751-755.

Pilch et al., Peptides selected for binding to clotted plasma accumulate in tumor stroma and wounds, Proc Natl Acad Sci USA, 2006, 103: 2800-2804.

Ruoslahti et al., Vascular homing peptides with cell-penetrating properties, Curr Pharm Des, 2005, 11: 3655-3660.

Simberg et al., Biomimetic amplification of nanoparticle homing to tumors, Proc Natl Acad Sci USA, 2007, 104: 932-936.

Zhang et al., Lymphatic zip codes in premalignant lesions and tumors, Cancer Res, 2006, 66: 5696-5706.

Dvorak et al., Regulation of extravascular coagulation by microvascular permeability, Science, 1985, 227: 1059-1061.

Ghebrehiwet et al., Isolation, cDNA cloning, and overexpression of a 33-kD cell surface glycoprotein that binds to the globular "heads" of C1q, J Exp Med, 1994, 179: 1809-1821.

Fogal et al., Mitochondrial/Cell surface protein p32/gC1qR as a molecular target in tumor cells and tumor stroma. Cancer Research 2008, 68: 7210-7218.

Akerman et al., Nanocrystal targeting in vivo, Proc Natl Acad Sci USA, 2002, 99: 12617-12621.

Von Maltzahn et al., In vivo Tumor Cell Targeting with "Click" Nanoparticles, Bioconjugate Chem., 2008, in press.

Gradishar et al., Phase III trial of nanoparticle albumin-bound paclitaxel compared with polyethylated castor oil-based paclitaxel in women with breast cancer, J Clin Oncol, 2005, 23: 7794-7803.

Laakkonen et al., Antitumor activity of a homing peptide that targets tumor lymphatics and tumor cells, Proc Natl Acad Sci USA, 2004, 101: 9381-9386.

Desai et al., Increased antitumor activity, intratumor paclitaxel concentrations, and endothelial cell transport of cremophor-free, albumin-bound paclitaxel, ABI-007, compared with cremophor-based paclitaxel, Clin Cancer Res, 2006, 12: 1317-1324.

Arleth et al., Detailed structure of hairy mixed micelles formed by phosphatidylcholine and PEGylated phospholipids in aqueous media, Langmuir, 2005, 21: 3279-3290.

Tu and Tirrell, Bottom-up design of biomimetic assemblies, Adv Drug Deliv Rev, 2004, 56: 1537-1563.

Rosenberg et al., T7Select® Phage Display System: A powerful new protein display system based on bacteriophage T7, iNnovations, 1996, 6.

Park et al., Magnetic iron oxide nanoworms for tumor targeting and imaging., Adv. Mater., 2008, 20: 1630-1635.

Le et al., Hypoxic gene expression and metastasis, Cancer Metastasis Rev, 2004, 23: 293-310.

Subarsky and Hill, The hypoxic tumour microenvironment and metastatic progression, Clin Exp Metastasis, 2003, 20: 237-250.

Sullivan and Graham, Hypoxia-driven selection of the metastatic phenotype, Cancer Metastasis Rev, 2007, 26: 319-331.

Langel, Cell-penetrating peptides: Processes and Applications., CRC Press: Boca Raton, Fla. 2002.

Zorko and Langel, Cell-penetrating peptides: mechanism and kinetics of cargo delivery, Adv Drug Deliv Rev, 2005, 57: 529-545.

Vives, Present and future of cell-penetrating peptide mediated delivery systems: "is the Trojan horse too wild to go only to Troy?" J Control Release, 2005, 109: 77-85.

Heldin et al., High interstitial fluid pressure—an obstacle in cancer therapy, Nat Rev Cancer, 2004, 4: 806-813.

| Sequences | |
|---|---|
| SEQ ID NO: 1 | CGNKRTRGC |
| SEQ ID NO: 2 | GNKRTRG |
| SEQ ID NO: 3 | CREKA |
| SEQ ID NO: 4 | CRVRTRSGC |
| SEQ ID NO: 5 | ARALPSQRSR |
| SEQ ID NO: 6 | $_D$(KLAKLAK)$_2$ |
| SEQ ID NO: 7 | CNRRTKAGC |
| SEQ ID NO: 8 | TEGDKAFVEFLTDEIKEE |
| SEQ ID NO: 9 | TDGDKAFVDFLSDEIKEE |
| SEQ ID NO: 10 | GGATGAGGTTGGACAAGAAGA |
| SEQ ID NO: 11 | CCCAATATCGTGGTTGATGTTATAA |
| SEQ ID NO: 12 | GGATGAGGTTGGACAGGAGGA |
| SEQ ID NO: 13 | CGQKRTRGC |
| SEQ ID NO: 14 | Cys-Gly-Gly-Gly-Gly-Gly-Gly-Gly-Cys |
| SEQ ID NO: 15 | CRGDKGPDC |
| SEQ ID NO: 16 | CRGDRGPDC |
| SEQ ID NO: 17 | CRGDKGPEC |
| SEQ ID NO: 18 | CRGDRGPEC |
| SEQ ID NO: 19 | RXXK |
| SEQ ID NO: 20 | RXXR |
| SEQ ID NO: 21 | CRGDKTTNC |
| SEQ ID NO: 22 | CRGDHAGDC |
| SEQ ID NO: 23 | CRGDHGVEC |
| SEQ ID NO: 24 | CGRGDNLPC |
| SEQ ID NO: 25 | CGRGDNLAC |
| SEQ ID NO: 26 | CEKRGDNLC |
| SEQ ID NO: 27 | CEKRGDSVC |
| SEQ ID NO: 28 | CSGRGDSLC |
| SEQ ID NO: 29 | CGKRGDSIC |
| SEQ ID NO: 30 | CTGRGDALC |
| SEQ ID NO: 31 | CRGDSAC |
| SEQ ID NO: 32 | CRGDKGENC |
| SEQ ID NO: 33 | CGRGDSPDC |
| SEQ ID NO: 34 | CRGDKHADC |
| SEQ ID NO: 35 | CRGDHAANC |
| SEQ ID NO: 36 | CRGDAGINC |
| SEQ ID NO: 37 | CGRGDMPSC |
| SEQ ID NO: 38 | CEKRGDSLC |
| SEQ ID NO: 39 | CRGEKGPDC |
| SEQ ID NO: 40 | CRGDC |
| SEQ ID NO: 41 | RGDCCCC |
| SEQ ID NO: 42 | KXXR |
| SEQ ID NO: 43 | KXXK |
| SEQ ID NO: 44 | RPARPAR |
| SEQ ID NO: 45 | RPARPARA |
| SEQ ID NO: 46 | CRGDK |
| SEQ ID NO: 47 | RGDK |
| SEQ ID NO: 48 | CRGDGGPDC |
| SEQ ID NO: 49 | CGNKRTRGC |
| SEQ ID NO: 50 | CRDGC |
| SEQ ID NO: 51 | CRGDR |
| SEQ ID NO: 52 | GPDC |

We claim:

1. A method of treating cancer, the method comprising: administering to a subject having cancer a composition comprising a homing compound coupled to a paclitaxel-loaded albumin nanoparticle, wherein the homing compound is a LyP-1 peptide, wherein the subject is identified as having a cancer associated with gC1g/p32 receptor.

2. The method of claim 1, wherein the composition further comprises a second homing compound coupled to the nanoparticle, wherein the second homing compound is a CREKA peptide.

3. The method of claim 1 further comprising administering to the subject a second composition comprising a second homing compound coupled to a paclitaxel-loaded albumin nanoparticle.

4. A method of identifying a subject as having a cancer associated with gC1q/p32 receptor, wherein the identification is accomplished by bringing into contact a cancer of the subject and a composition that selectively interacts with gC1q/p32 receptor; and detecting interaction between gC1q/p32 receptor and the composition that selectively interacts with gC1q/p32 receptor, thereby detecting the presence or level of gC1q/p32, wherein the presence or level of gC1q/p32 receptor identifies the subject as having a cancer associated with a gC1q/p32 receptor.

5. The method of claim 4, wherein the composition that selectively interacts with gC1q/p32 receptor is a LyP-1 composition, wherein the LyP-1 composition comprises a moiety linked to a LyP-1 peptide.

6. The method of claim 4, wherein the level of the composition that selectively interacts with gC1q/p32 receptor interacting with gC1q/p32 receptor is detected.

7. The method of claim 4, wherein the level of gC1q/p32 receptor in the subject is compared to a previous measurement in the same subject.

8. The method of claim 4, wherein the level of gC1q/p32 receptor in the subject is compared to a control level or standard level.

9. The method of claim 5, wherein the moiety is a detectable agent, a polypeptide, a nucleic acid molecule, or a small molecule.

10. The method of claim 4, wherein the composition that selectively interacts with gC1q/p32 receptor comprises a virus.

11. The method of claim 4, wherein the composition that selectively interacts with gC1q/p32 receptor comprises a phage.

12. The method of claim 9, wherein the detectable agent is a radionuclide, a small molecule, a fluorophore, fluorescein, rhodamine, indium-111, technetium-99, carbon-11, carbon-13, or a combination thereof.

13. The method of claim 11, wherein the LyP-1 peptide comprises SEQ ID NO:1, SEQ ID NO:13, or a variant of SEQ ID NO:1 or SEQ ID NO:13 with one or more conservative amino acid substitutions.

14. The method of claim 13, wherein the LyP-1 peptide consists essentially of SEQ ID NO:1 or SEQ ID NO:13.

15. The method of claim 13, wherein the LyP-1 peptide is SEQ ID NO:1, SEQ ID NO:13, or a variant of SEQ ID NO:1 or SEQ ID NO:13 with one or more conservative amino acid substitutions.

16. The method of claim 13, wherein the LyP-1 peptide is SEQ ID NO:1 or SEQ ID NO:13.

17. The method of claim 1, wherein the composition further comprises a therapeutic moiety.

18. The method of claim 17, wherein the therapeutic moiety targets a DNA-associated process.

19. The method of claim 17, wherein the therapeutic moiety is selected from the group consisting of a cytotoxic agent, an alkylating agent, an anti-tumor antibiotic, a sequence-selective agent, and an anti-angiogenic agent.

20. A composition comprising a homing compound coupled to a paclitaxel-loaded albumin nanoparticle, wherein the homing compound is a LyP-1 peptide.

21. The method of claim 19, wherein the cytotoxic agent is selected from the group consisting of cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

22. The method of claim 13, wherein the variant of SEQ ID NO:1 or SEQ ID NO:13 has one, two or three conservative amino acid substitution.

23. The method of claim 22, wherein the variant of SEQ ID NO:1 or SEQ ID NO:13 has one conservative amino acid substitution.

24. The method of claim 1, wherein the homing compound is a LyP-1 peptide, wherein the LyP-1 peptide comprises SEQ ID NO:1 or SEQ ID NO:13.

25. The method of claim 13, wherein the variant of SEQ ID NO:1 comprises CANKRTRGC, CGDKRTRGC, CGNRRTRGC, CGNKKTRGC, CGNKRSRGC, CGNKRTKGC, or CGNKRTRAC.

26. The method of claim 13, wherein the variant of SEQ ID NO:13 comprises CAQKRTRGC, CGQRRTRGC, CGQKKTRGC, CGQKRSRGC, CGQKRTKGC, or CGQKRTRAC.

* * * * *

UNITED STATES PATENT AND TRADEMARK OFFICE
CERTIFICATE OF CORRECTION

PATENT NO. : 8,753,604 B2
APPLICATION NO. : 12/646168
DATED : June 17, 2014
INVENTOR(S) : Erkki Ruoslahti, Venkata Kotamraju and Priya Karmali It is certified that error appears in the above-identified patent and that said Letters Patent is hereby corrected as shown below:

In the Specification

In Column 1, Lines 16 through 21, please replace:
"This invention was made with government support under National Cancer Institute grants CA119335, CA124427, CA115410, CA104898; National Heart, Lung and Blood Institute grant HL080718; and MRSEC Program of the National Science Foundation under Award DMR05-20415. The government has certain rights in the invention."

With:
--This invention was made with government support under CA115410, CA119335, HL080718, CA124427, and CA104898 awarded by the National Institutes of Health. The government has certain rights in the invention.--

Signed and Sealed this
Sixteenth Day of May, 2023

Katherine Kelly Vidal
*Director of the United States Patent and Trademark Office*